(12) United States Patent
DeCrescenzo et al.

(10) Patent No.: US 6,747,027 B1
(45) Date of Patent: *Jun. 8, 2004

(54) THIOL SULFONAMIDE METALLOPROTEASE INHIBITORS

(75) Inventors: Gary DeCrescenzo, St. Charles, MO (US); Zaheer S. Abbas, Chesterfield, MO (US); John N. Freskos, Clayton, MO (US); Daniel P. Getman, Chesterfield, MO (US); Robert M. Heintz, Ballwin, MO (US); Brent V. Mischke, Defiance, MO (US); Joseph J. McDonald, Ballwin, MO (US)

(73) Assignee: Pharmacia Corporation, St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/898,175

(22) Filed: Jul. 22, 1997

Related U.S. Application Data

(60) Provisional application No. 60/022,040, filed on Jul. 22, 1996.

(51) Int. Cl.[7] ............... A61K 31/4965; A61K 31/535; A61K 31/40; A61K 31/18
(52) U.S. Cl. ............... 514/238.2; 514/255.03; 514/237.8; 514/327; 514/331; 514/336; 514/357; 514/424; 514/428; 514/454; 514/466; 514/432; 514/533; 514/538; 514/603; 514/604; 544/160; 544/398; 544/399; 544/400; 546/216; 546/232; 546/233; 546/235; 546/280.4; 546/338
(58) Field of Search ............... 514/237.8, 255.03, 514/331, 238.2, 327, 336, 357, 424, 428, 454, 466, 432, 533, 538, 603, 604; 544/160, 398, 399, 400; 546/232, 233, 235, 216, 280.4, 338; 548/542, 569; 549/390, 443, 28; 560/12, 13; 564/83, 89

(56) References Cited

U.S. PATENT DOCUMENTS

| | | | |
|---|---|---|---|
| 4,595,700 A | 6/1986 | Donald et al. | 514/616 |
| 5,451,676 A | 9/1995 | Whittaker et al. | 546/118 |
| 5,472,978 A | 12/1995 | Baker et al. | 514/443 |
| 5,475,138 A | 12/1995 | Pal et al. | 564/342 |
| 5,599,994 A | 2/1997 | Pal et al. | 564/355 |
| 6,013,649 A | 1/2000 | Freskos et al. | |
| 6,297,247 B1 * | 10/2001 | Ortwine et al. | 514/255.03 |

FOREIGN PATENT DOCUMENTS

| | | | | |
|---|---|---|---|---|
| EP | 1 081 137 A1 | 3/2001 | ......... | C07D/211/96 |
| GB | 2 263 109 A | 7/1993 | | |
| WO | WO 90/05719 | 5/1990 | ......... | C07C/323/62 |
| WO | WO 93/20047 | 10/1993 | ......... | C07C/317/44 |
| WO | WO 94/02466 | 2/1994 | | |
| WO | WO 94/24140 | 10/1994 | | |
| WO | WO 95/04720 | 2/1995 | | |
| WO | WO 95/09841 | 4/1995 | ......... | C07C/323/60 |
| WO | WO 95/12389 | 5/1995 | | |
| WO | WO 95/13064 | 5/1995 | | |
| WO | WO 95/29892 | 11/1995 | ....... | C07D/207/327 |
| WO | WO 96/06074 | 2/1996 | ......... | C07C/259/06 |
| WO | WO 96/11209 | 4/1996 | | |
| WO | WO 97/05865 | 2/1997 | | |
| WO | WO 97/20824 | 6/1997 | | |
| WO | WO 97/24117 | 7/1997 | ......... | A61K/31/19 |
| WO | WO 97/49679 | 12/1997 | ......... | C07C/317/44 |
| WO | WO 98/38859 | 9/1998 | ......... | A01N/37/28 |
| WO | WO 98/39329 | 9/1998 | ......... | C07D/413/12 |
| WO | WO 99/09000 | 2/1999 | ......... | C07C/235/00 |
| WO | WO 99/25687 | 5/1999 | ......... | C07D/211/66 |
| WO | WO 00/46221 | 8/2000 | ......... | C07D/405/12 |
| WO | WO 00/50396 | 8/2000 | ......... | C07D/211/66 |
| WO | WO 00/59874 | 10/2000 | ......... | C07D/259/06 |
| WO | WO 00/69819 | 11/2000 | ......... | C07D/211/16 |
| WO | WO 00/69821 | 11/2000 | ......... | C07D/211/66 |

OTHER PUBLICATIONS

Gearing et al., *Nature*, 370:555–557 (1994).
McGeehan et al., *Nature*, 370:558–561 (1994).
Mitchell et al., *J. Clin. Invest.*, 97:761–768 (1996).
Reboul et al., *J. Clin. Invest.*, 97:2011–2019 (1996).
Kenyon et al., *Investigative Ophthalmology & Visual Science*, 37:1625–1632 (Jul. 1996).
El-Nagger, A.M., *Chemical Abstracts*, 100:701 (1984), Abstract No. 100:139602z.
Ibrahim, T.M., *Chemical Abstracts*, 123:1196 (1995), Abstract No. 123:28592lu.
Vriesema, B.K., *J. Org. Chem.*, 49:110–113 (1984).

* cited by examiner

*Primary Examiner*—Peter O'Sullivan
(74) *Attorney, Agent, or Firm*—Harness, Dickey & Pierce, P.L.C.

(57) ABSTRACT

This invention is directed to proteinase (protease) inhibitors, and more particularly to thiol sulfonamide inhibitors for matrix metalloproteinase 13(MMP-13), compositions of proteinase inhibitors, intermediates for the syntheses of proteinase inhibitors, processes for the preparation of proteinase inhibitors and processes for treating pathological conditions associated with pathological matrix metalloproteinase activity related to MMP-13.

26 Claims, No Drawings

THIOL SULFONAMIDE METALLOPROTEASE INHIBITORS

CROSS-REFERENCE TO RELATED PATENT APPLICATIONS

This patent claims priority to U.S. Provisional Patent Application Serial No. 60/022,040 (filed Jul. 22, 1996). The entire text of each of the above patent applications is hereby incorporated by reference into this patent.

TECHNICAL FIELD

This invention is directed to proteinase (protease) inhibitors, and more particularly to thiol sulfonamide inhibitors for matrix metalloproteinases, compositions of proteinase inhibitors, intermediates for the syntheses of proteinase inhibitors, processes for the preparation of proteinase inhibitors and processes for treating pathological conditions associated with pathological matrix metalloproteinase activity.

BACKGROUND OF THE INVENTION

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals makeup, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason leads to a number of disease states. Inhibition of the enzymes responsible loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function are the zinc metalloproteinases (metalloproteases).

The metalloprotease enzymes are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14). MMP is an abbreviation or acronym representing the term Matrix Metalloprotease with the attached numerals providing differentiation between specific members of the MMP group.

The uncontrolled breakdown of connective tissue by metalloproteases is a feature of many pathological conditions. Examples include rheumatoid arthritis, osteoarthritis, septic arthritis; corneal, epidermal or gastric ulceration; tumor metastasis, invasion or angiogenesis; periodontal disease; proteinuria; Alzheimers Disease; coronary thrombosis and bone disease. Defective injury repair processes also occur. This can produce improper wound healing leading to weak repairs, adhesions and scarring. These latter defects can lead to disfigurement and/or permanent disabilities as with post-surgical adhesions.

Matrix metalloproteases are also involved in the biosynthesis of tumor necrosis factor (TNF), and inhibition of the production or action of TNF and related compounds is an important clinical disease treatment mechanism. TNF-α, for example, is a cytokine that at present is thought to be produced initially as a 28 kD cell-associated molecule. It is released as an active, 17 kD form that can mediate a large number of deleterious effects in vitro and in vivo. For example, TNF can cause and/or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects such as post-ischemic reperfusion injury, congestive heart failure, hemorrhage, coagulation, hyperoxic alveolar injury, radiation damage and acute phase responses like those seen with infections and sepsis and during shock such as septic shock and hemodynamic shock. Chronic release of active TNF can cause cachexia and anorexia. TNF can be lethal.

TNF-α convertase is a metalloproteinase involved in the formation of active TNF-α. Inhibition of TNF-α convertase inhibits production of active TNF-α. Compounds that inhibit both MMPs activity have been disclosed in WIPO International Publication Nos. WO 94/24140, WO 94/02466 and WO 97/20824. There remains a need for effective MMP and TNF-α convertase inhibiting agents. Compounds that inhibit MMPs such as collagenase, stromelysin and gelatinase have been shown to inhibit the release of TNF (Gearing et al. *Nature* 376, 555–557 (1994), McGeehan et al., *Nature* 376, 558–561 (1994)).

MMPs are involved in other biochemical processes in mammals as well. Included is the control of ovulation, post-partum uterine involution, possibly implantation, cleavage of APP (β-Amyloid Precursor Protein) to the amyloid plaque and inactivation of $\alpha_1$-protease inhibitor ($\alpha_1$-PI). Inhibition of these metalloproteases permits the control of fertility and the treatment or prevention of Alzheimers Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases and diseases of aging such as loss of skin or organ stretch and resiliency.

Inhibition of selected MMPs can also be desirable in other instances. Treatment of cancer and/or inhibition of metastasis and/or inhibition of angiogenesis are examples of approaches to the treatment of diseases wherein the selective inhibition of stromelysin, gelatinase, or collagenase III are the relatively most important enzyme or enzymes to inhibit especially when compared with collagenase I (MMP-1). A drug that does not inhibit collagenase I can have a superior therapeutic profile. Osteoarthritis, another prevalent disease wherein it is believed that cartilage degradation in inflamed joints is at least partially caused by MMP-13 released from cells such as stimulated chrondrocytes, may be best treated by administration of drugs one of whose modes of action is inhibition of MMP-13. See, for example, Mitchell et al., *J. Clin. Invest.*, 97:761–768 (1996) and Reboul et al., *J. Clin. Invest.*, 97:2011–2019 (1996).

Inhibitors of metalloproteases are known. Examples include natural biochemicals such as tissue inhibitor of metalloproteinase (TIMP), α₂-macroglobulin and their analogs or derivatives. These are high molecular weight protein molecules that form inactive complexes with metalloproteases. A number of smaller peptide-like compounds that inhibit metalloproteases have been described. Mercaptoamide peptidyl derivatives have shown ACE inhibition in vitro and in vivo. Angiotensin converting enzyme (ACE) aids in the production of angiotensin II, a potent pressor substance in mammals and inhibition of this enzyme leads to the lowering of blood pressure. Thiol group-containing amide or peptidyl amide-based metalloprotease (MMP) inhibitors are known as is shown in, for example, WO95/12389, WO96/11209 and U.S. Pat. No. 4,595,700.

It is recognized that a compound that inhibits a known member of the MMP group of enzymes can inhibit members in that group and also new, yet to be discovered, enzymes. Therefore, the skilled person will presume that the novel inhibitors of this invention can be useful in the treatment of the diseases in which known and new MMP enzymes are implicated.

SUMMARY OF THE INVENTION

The present invention is directed to a process for treating a mammal having a condition associated with pathological matrix metalloprotease (MMP) activity, as well as to molecules that particularly inhibit the activity of MMP-13.

Briefly, therefore, one embodiment of the present invention is directed to a process for treating a mammal having a condition associated with pathological matrix metalloprotease activity that comprises administering a metalloprotease inhibitor in an effective amount to a host having such a condition. The administered enzyme inhibitor corresponds in structure to one of formulae (I), (II) or (III), below

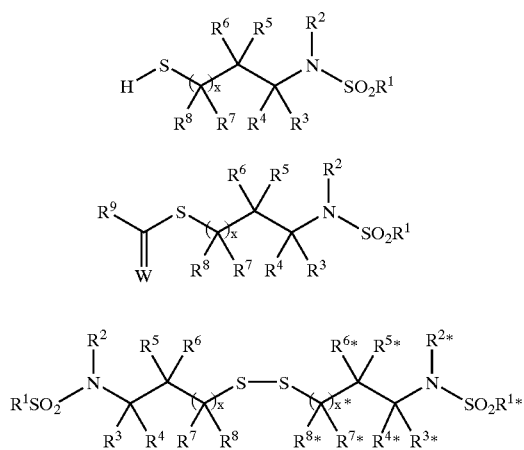

where x represents 0, 1 or 2, and W is oxygen or sulfur.

A contemplated $R^9$ group is an alkyl, aryl, alkoxy, cycloalkyl, aryloxy, aralkoxy, aralkyl, aminoalkyl, heteroaryl and N-monosubstituted or N,N-disubstituted aminoalkyl group wherein the substituent(s) on the nitrogen are selected from the group consisting of alkyl, aryl, aralkyl, cycloalkyl, aralkoxycarbonyl, alkoxycarbonyl, and alkanoyl, or wherein the nitrogen and two substituents attached thereto form a 5- to 8-membered heterocyclic or heteroaryl ring.

A contemplated $R^1$ group is linked to the $SO_2$ portion of an inhibitor and is an alkyl, cycloalkyl, heterocycloalkyl, aralkanoylalkyl, arylcarbonylalkyl, hydroxyalkyl, alkanoylalkyl, aralkylaryl, aryloxyalkylaryl, aralkoxyaryl, arylazoaryl, arylhydrazinoaryl, haloalkyl, alkylthioaryl, arylthioalkyl, alkylthioaralkyl, aralkylthioalkyl, or aralkylthioaryl group, the sulfoxide or sulfone of any of those thio substituents, alkylthioalkyl, and preferably aryl and heterocyclic (heteroaryl) rings such as aralkyl, heteroaralkyl, aralkoxyalkyl, aryloxyalkyl, as well as a fused ring structure comprising two or three 5- or 6-membered aryl rings that can be carbocyclic or heterocyclic rings. The aryl (carbocyclic) and heteroaryl substituents of $R^1$ are themselves unsubstituted or substituted with one or two substituents independently selected from among halo, $C_1$–$C_{10}$ alkyl, $C_1$–$C_{10}$ alkoxy, nitro, cyano, perfluoroalkyl, trifluoromethylalkyl, hydroxy, thiol, hydroxycarbonyl, aryloxy, arylthio, arylamino, aralkyl, arylcarboxamido, heteroarylcarboxamido, azoaryl, azoheteroaryl, aryl, heteroaryloxy, heteroarylthio, heteroarylamino, heteroaralkyl, cycloalkyl, heterocyclooxy, heterocyclothio, heterocycloamino, cycloalkyloxy, cycloalkylthio, cycloalkylamino, heteroaralkoxy, heteroaralkylthio, heteroaralkylamino, aralkoxy, aralkylthio, aralkylamino, heterocyclic, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, alkanoylamino, arylcarbonylamino, aralkanoylamino, heteroarylcarbonylamino, heteroaralkanoylamino, and N-monosubstituted or N,N-disubstituted aminoalkyl wherein the substituent(s) on the nitrogen are selected from the group consisting of alkyl, aryl, aralkyl, cycloalkyl, aralkoxycarbonyl, alkoxycarbonyl, and alkanoyl, or wherein the nitrogen and two substituents attached thereto together form a 5- to 8-membered heterocyclo or heteroaryl ring.

A contemplated $R^2$ substituent can be hydrogen (hydrido), an alkyl, aryl, aralkyl, heteroaryl, heteroaralkyl, alkynylalkyl, alkenylalkyl, thioalkyl, cycloalkyl, cycloalkylalkyl, heterocycloalkylalkyl, alkoxyalkyl, aralkoxyalkyl, aminoalkyl, alkoxyalkoxyalkyl, aryloxyalkyl, hydroxyalkyl, hydroxycarbonylalkyl, hydroxycarbonylaralkyl, or N-monosubstituted or N,N-disubstituted aminoalkyl group wherein the substituent(s) on the nitrogen are selected from the group consisting of alkyl, aralkyl, cycloalkyl and alkanoyl, or wherein $R^2$ and the nitrogen to which it is bonded and another substituent (i.e., $R^2$ and $R^4$, or $R^2$ and $R^6$ or $R^2$ and $R^8$) together form a 4- to 8-membered heterocyclo or heteroaryl ring.

Contemplated $R^3$ and $R^4$ groups are independently selected. Those substituents can be hydrogen (hydrido), an alkyl, cycloalkyl, cycloalkylalkyl, alkoxyalkyl, hydroxyalkyl, aryloxyalkyl, aralkoxyalkyl, aralkyl, aryl, heteroaryl, heteroaralkyl, hydroxycarbonylalkyl, alkoxycarbonylalkyl, aralkoxycarbonylalkyl, hydroxycarbonyl, alkoxycarbonyl, perfluoroalkyl, trifluoromethylalkyl, thioalkyl, alkylthioalkyl, arylthioalkyl, aralkylthioalkyl, heteroaralkylthioalkyl, or a sulfoxide or sulfone of any of the thio substituents, aminocarbonyl, aminocarbonylalkyl, N-monosubstituted or N,N-disubstituted aminocarbonyl or aminocarbonylalkyl group wherein the substituent(s) on the nitrogen are independently selected from among alkyl, aralkyl, cycloalkyl and alkanoyl, or wherein the nitrogen and two substituents attached thereto together form a 5- to 8-membered heterocyclo or heteroaryl ring that can contain one additional heteroatom, or $R^2$ and $R^4$ together with the atoms to which they are attached form a 4- to 8-membered ring (as above), or $R^3$ and $R^4$ together with the atom to which they are attached form a 3- to 8-membered ring or $R^4$ and $R^8$ together with the atoms to which they are attached form a 5- to 8-membered ring.

$R^5$ and $R^6$ substituents are also independently selected. $R^5$ and $R^6$ substituents can be a substituent that constitutes $R^3$ and $R^4$, or $R^6$ and $R^4$ together with atoms to which they are attached form a 4- to 8-membered ring, or $R^6$ and $R^2$ together with the atoms to which they are attached form a 5- to 8-membered ring (as above), or $R^6$ and $R^8$ together with the atoms to which they are attached form a 4- to 8-membered ring, or $R^5$ and $R^6$ together with atom to which they are attached form a 3- to 8-membered ring.

Contemplated $R^7$ and $R^8$ substituents are also independently selected. $R^7$ and $R^8$ substituents can also be a substituent that constitutes $R^3$ and $R^4$, or $R^8$ and $R^2$ together with the atoms to which they are attached form a 6- to 8-membered ring (as above), or $R^7$ and $R^8$ together with the atom to which they are attached form a 3- to 8-membered ring, or $R^8$ and $R^4$ together with the atom to which they are attached form a 5- to 8-membered ring (as above), or $R^8$ and $R^6$ together with the atoms to which they are attached form a 4- to 8-membered ring (as above).

A provision to the above definitions is that no carbon atom is geminally substituted with more than one sulfhydryl group. Additionally, a starred substituent "R" groups and "x" of formula III are the same as or different from the unstarred "R" groups and "x".

The present invention is also directed to a more preferred sub-set of molecules of formulas I, II, and III, above. Here, x is zero so that the mercapto group is bonded directly to the carbon atom that bears the $R^5$ and $R^6$ substituent radicals, which are themselves both hydrido, as is $R^3$. Here, also, $R^2$ is other than hydrogen (hydrido) unless $R^1$ is phenylazophenyl, $R^1$ is an aryl, substituted aryl, heteroaryl, or substituted heteroaryl group containing one 5- or 6-membered ring; i.e. $R^1$ is not a fused aryl ring or heteroaryl group, and a compound of formula III is a homodimer. These preferred compounds are depicted by formulas Ia, IIa, and IIIa, below, and the substituent "R" groups and W are as otherwise defined before.

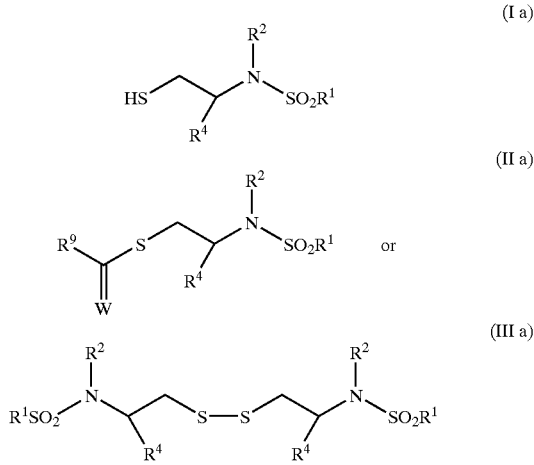

In most preferred practice, a contemplated inhibitor compound constitutes another sub-set of the compounds of formulas I, II and III. Here, $R^3$, $R^5$ and $R^6$ are again hydrido, the $SO_2$-linked $R^1$ substituent is a 4-substituted phenyl group ($PhR^{11}$), and W is O. These most preferred compounds are depicted by formulas Ib, IIb and IIIb, below.

Specifics of the depicted "R" groups are discussed hereinafter.

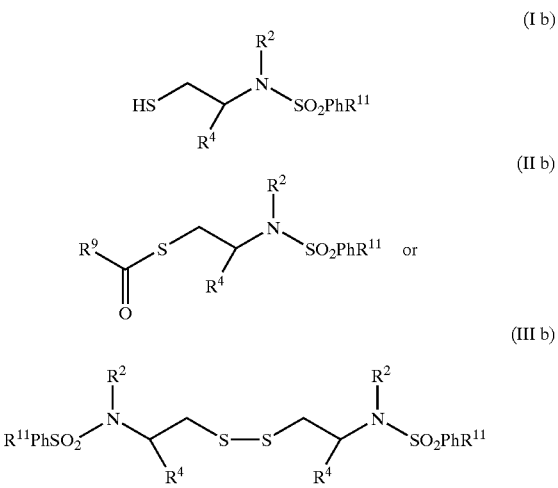

Yet another aspect of the invention is directed to a matrix metalloprotease inhibitor corresponding to formula IV, below,

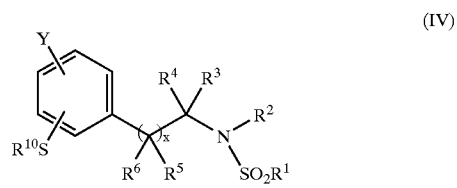

where $R^{10}$ is hydrogen (hydrido) or —C(O)—$R^9$, and $R^1$, $R^2$, $R^3$, $R^4$, $R^5$, $R^6$, $R^9$ and x are as defined above, and Y represents hydrogen, halogen, alkyl, alkoxy, nitro, cyano, carboxy or amino.

Among the several benefits and advantages of the present invention are the provision of compounds and compositions effective as inhibitors of matrix metalloproteinase activity, the provision of such compounds and compositions that are effective for the inhibition of metalloproteinases implicated in diseases and disorders involving uncontrolled breakdown of connective tissue.

More particularly, a benefit of this invention is the provision of a compound and composition effective for inhibiting metalloproteinases, particularly MMP-13, associated with pathological conditions such as, for example, rheumatoid arthritis, osteoarthritis, septic arthritis, corneal, epidermal or gastric ulceration, tumor metastasis, invasion or angiogenesis, periodontal disease, proteinuria, Alzheimer's Disease, coronary thrombosis and bone disease.

An advantage of the invention is the provision of a method for preparing such compositions. Another benefit is the provision of a method for treating a pathological condition associated with abnormal matrix metalloproteinase activity.

Another advantage is the provision of compounds, compositions and methods effective for treating such pathological conditions by selective inhibition of a metalloproteinase, MMP-13, associated with such conditions with minimal side effects resulting from inhibition of other proteinases whose activity is necessary or desirable for normal body function.

Still further benefits and advantages of the invention will be apparent to the skilled worker from the disclosure that follows.

DESCRIPTION OF THE PREFERRED EMBODIMENTS

In accordance with the present invention, it has been discovered that certain thiol sulfonamides are effective for inhibition of matrix metalloproteinases ("MMPs") believed to be associated with uncontrolled or otherwise pathological breakdown of connective tissue. In particular, it has been found that these certain thiol sulfonamides are effective for inhibition of collagenase III (MMP-13), which can be particularly destructive to tissue if present or generated in abnormal quantities or concentrations, and thus exhibit a pathological activity.

Moreover, it has been discovered that many of these thiol sulfonamides are selective in the inhibition of MMP-13, as well as other MMPs associated with diseased conditions without excessive inhibition of other collagenases essential to normal bodily function such as tissue turnover and repair. More particularly, it has been found that particularly preferred the thiol sulfonamides of the invention are particularly active in inhibiting of MMP-13, while being selective for MMP-13, in having a limited or minimal effect on MMP-1. This point is discussed in detail hereinafter and is illustrated in several examples.

One embodiment of the present invention is directed to a process for treating a mammal having a condition associated with pathological matrix metalloprotease activity. That process comprises administering a metalloprotease inhibitor in an effective amount to a host having such a condition. The administered enzyme inhibitor corresponds in structure to one of formulas (I), (II) or (III), below

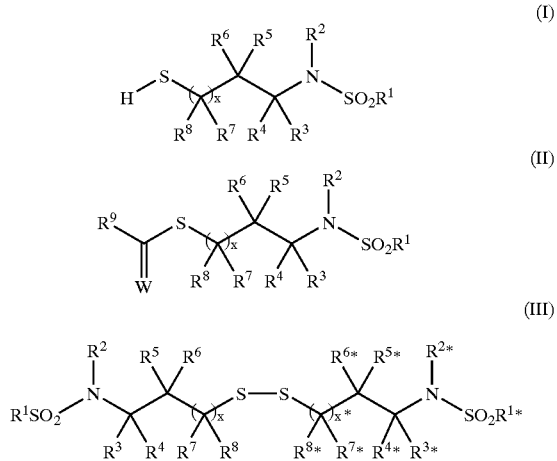

where x represents 0, 1 or 2, and W is oxygen or sulfur.

A contemplated $R^9$ group is an alkyl, aryl, alkoxy, cycloalkyl, aryloxy, aralkoxy, aralkyl, aminoalkyl, heteroaryl and N-monosubstituted or N,N-disubstituted aminoalkyl group wherein the substituent(s) on the nitrogen are selected from the group consisting of alkyl, aryl, aralkyl, cycloalkyl, aralkoxycarbonyl, alkoxycarbonyl, and alkanoyl, or wherein the nitrogen and two substituents attached thereto form a 5- to 8-membered heterocyclo or heteroaryl ring.

A contemplated $R^1$ group is linked to the $SO_2$ portion of an inhibitor and is an alkyl, cycloalkyl, heterocycloalkyl, aralkanoylalkyl, arylcarbonylalkyl, hydroxyalkyl, alkanoylalkyl, aralkylaryl, aryloxyalkylaryl, aralkoxyaryl, arylazoaryl, arylhydrazinoaryl, haloalkyl, alkylthioaryl, arylthioalkyl, alkylthioaralkyl, aralkylthioalkyl, or aralkylthioaryl group, the sulfoxide or sulfone of any of those thio substituents, alkylthioalkyl, and preferably aryl (carbocyclicaryl) and heteroaryl rings such as aralkyl, heteroaralkyl, aralkoxyalkyl, aryloxyalkyl, as well as a fused ring structure comprising two or three 5- or 6-membered aryl rings that can be carbocyclic or heterocyclic rings. The aryl and heteroaryl substituents of which $R^1$ can be comprised are unsubstituted or preferably substituted with one (preferably) or two substituents independently selected from among halo, $C_1$–$C_{10}$ alkyl, $C_1$–$C_{10}$ alkoxy, nitro, cyano, perfluoroalkyl, trifluoromethylalkyl, hydroxy, thiol, hydroxycarbonyl, aryloxy, arylthio, arylamino, aralkyl, arylcarboxamido, heteroarylcarboxamido, azoaryl, azoheteroaryl, aryl, heteroaryloxy, heteroarylthio, heteroarylamino, heteroaralkyl, cycloalkyl, heterocyclooxy, heterocyclothio, heterocycloamino, cycloalkyloxy, cycloalkylthio, cycloalkylamino, heteroaralkoxy, heteroaralkylthio, heteroaralkylamino, aralkoxy, aralkylthio, aralkylamino, heterocyclic, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, alkanoylamino, arylcarbonylamino, aralkanoylamino, heteroarylcarbonylamino, heteroaralkanoylamino, and N-monosubstituted or N,N-disubstituted aminoalkyl wherein the substituent(s) on the nitrogen are selected from the group consisting of alkyl, aryl, aralkyl, cycloalkyl, aralkoxycarbonyl, alkoxycarbonyl, and alkanoyl, or wherein the nitrogen and two substituents attached thereto together form a 5- to 8-membered heterocyclo or heteroaryl ring.

A contemplated $R^2$ substituent can be hydrogen (hydrido), an alkyl, aryl, aralkyl, heteroaryl, heteroaralkyl, alkynylalkyl, alkenylalkyl, thioalkyl, cycloalkyl, cycloalkylalkyl, heterocycloalkylalkyl, alkoxyalkyl, aralkoxyalkyl, aminoalkyl, alkoxyalkoxyalkyl, aryloxyalkyl, hydroxyalkyl, hydroxycarbonylalkyl, hydroxycarbonylaralkyl, or N-monosubstituted or N,N-disubstituted aminoalkyl group wherein the substituent(s) on the nitrogen are selected from the group consisting of alkyl, aralkyl, cycloalkyl and alkanoyl, or wherein $R^2$ and the nitrogen to which it is bonded and another substituent (i.e., $R^2$ and $R^4$, or $R^2$ and $R^6$, or $R^2$ and $R^8$) together form a 4- to 8-membered heterocyclo or heteroaryl ring.

Contemplated $R^3$ and $R^4$ groups are independently selected. Those substituents can be hydrogen (hydrido), an alkyl, cycloalkyl, cycloalkylalkyl, alkoxyalkyl, hydroxyalkyl, aryloxyalkyl, aralkoxyalkyl, aralkyl, aryl, heteroaryl, heteroaralkyl, hydroxycarbonylalkyl, alkoxycarbonylalkyl, aralkoxycarbonylalkyl, hydroxycarbonyl, alkoxycarbonyl, perfluoroalkyl, trifluoromethylalkyl, thioalkyl, alkylthioalkyl, arylthioalkyl, aralkylthioalkyl, heteroaralkylthioalkyl, or a sulfoxide or sulfone of any of the thio substituents, aminocarbonyl, aminocarbonylalkyl, N-monosubstituted or N,N-disubstituted aminocarbonyl or aminocarbonylalkyl group wherein the substituent(s) on the nitrogen are independently selected from among alkyl, aralkyl, cycloalkyl and alkanoyl, or wherein the nitrogen and two substituents attached thereto together form a 5- to 8-membered heterocyclo or heteroaryl ring that can contain one additional heteroatom, or $R^2$ and $R^4$ together with the atoms to which they are attached form a 4- to 8-membered ring (as above), or $R^3$ and $R^4$ together with the atom to which they are attached form a 3- to 8-membered ring, or $R^4$ and $R^6$ together with the atoms to which they are attached form a 4- to 8-membered ring, or $R^4$ and $R^8$ together with the atoms to which they are attached form a 5- to 8-membered ring.

$R^5$ and $R^6$ substituents are also independently selected. $R^5$ and $R^6$ substituents can be a substituent that constitutes $R^3$ and $R^4$. Alternatively, $R^6$ and $R^4$ together with atoms to which they are attached form a 4- to 8-membered ring, or $R^6$ and $R^2$ together with the atoms to which they are attached form a 5- to 8-membered ring (as above), or $R^6$ and $R^8$ together with the atoms to which they are attached form a 4- to 8-membered ring, or $R^5$ and $R^6$ together with atom to which they are attached form a 3- to 8-membered ring.

Contemplated $R^7$ and $R^8$ substituents are also independently selected. $R^7$ and $R^8$ substituents can also be a substituent that constitutes $R^3$ and $R^4$. Alternatively, $R^8$ and $R^2$ together with the atoms to which they are attached form a 6- to 8-membered ring (as above), or $R^7$ and $R^8$ together with the atom to which they are attached form a 3- to 8-membered ring, or $R^8$ and $R^4$ together with the atom to which they are attached form a 5- to 8-membered ring (as above), or $R^8$ and $R^6$ together with the atoms to which they are attached form a 4- to 8-membered ring (as above).

A provision to the above definitions is provided that no carbon atom is geminally substituted with more than one sulfhydryl group. In addition, starred substituent "R" groups and "x" of formula III are the same as or different from the unstarred "R" groups and "x".

In generally increasing order of preference, the following paragraphs summarize the substituents which may most advantageously constitute each of $R^1$ through $R^{10}$, as well as W and x.

$R^1$ represents an aryl-$C_1$–$C_{10}$-alkyl or heteroaryl-$C_1$–$C_{10}$-alkyl, wherein the aryl or heteroaryl ring can optionally be substituted by one or more of the following substituents: $C_1$–$C_{10}$ alkyl, $C_1$–$C_{10}$ alkoxy, aryloxy, heteroaryloxy, aryl, heteroaryl, aralkoxy, heteroaralkoxy, $C_1$–$C_{10}$ alkylthio, arylthio, heteroarylthio.

$R^1$ represents a single aryl or heteroaryl ring, wherein the single aryl or heteroaryl ring can optionally be substituted by one or more of the following substituents: $C_1$–$C_6$ alkyl, $C_1$–$C_6$ alkoxy, arylcarboxamido, heteroarylcarboxamido, arylazo, heteroarylazo, aryloxy, heteroaryloxy, aryl, heteroaryl, aralkoxy, heteroaralkoxy, $C_1$–$C_6$ alkylthio, arylthio, heteroarylthio in which each ring-containing substituent itself contains a single ring.

$R^1$ represents a 6-membered aryl ring, wherein the aryl ring can optionally be substituted in the para-position (4-position) by one of the following substituents: $C_1$–$C_6$ alkyl, $C_1$–$C_6$ alkoxy, arylcarboxamido, heteroarylcarboxamido, arylazo, heteroarylazo, aryloxy, heteroaryloxy, aryloxy, heteroaryloxy, aryl, heteroaryl, aralkoxy, heteroaralkoxy, $C_1$–$C_6$ alkylthio, arylthio, heteroarylthio in which each ring-containing substituent itself contains a single ring.

$R^1$ represents a 6-membered aryl ring, wherein the aryl ring is substituted in the para-position by $C_1$–$C_6$ alkyl, $C_1$–$C_6$ alkoxy arylcarboxamido, arylazo, aryloxy, arylthio and aryl in which each ring-containing substituent itself contains a single ring.

$R^1$ represents phenyl, wherein the phenyl ring is substituted in the para-position by n-propyl, n-butyl, n-pentyl, n-hexyl, isobutyl, isoamyl, ethoxy, n-propyloxy, n-butoxy, n-pentyloxy, n-hexyloxy, isobutoxy, phenoxy, thiophenoxy (phenylthio), phenyl, azophenyl or benzamido, in which the para-substituted $R^1$ phenyl substituent can itself optionally contain a meta- or para-substituent, or both containing one atom or a chain of no more than five atoms other than hydrogen.

$R^2$ Preferences:

$R^2$ represents hydrogen, $C_1$–$C_6$ alkyl, aralkyl, heteroaralkyl, cycloalkylalkyl having 4–8 carbons in the ring and 1–3 carbons in the alkyl chain, heterocycloalkylalkyl in which 4–8 atoms are in the ring, one or two of which atoms can be nitrogen, oxygen or sulfur and in which the alkyl chain contains 1–3 carbons, $C_1$–$C_5$ alkyl substituted by hydroxycarbonyl, amino, mono-substituted amino and di-substituted amino, wherein the substituents on nitrogen are chosen from $C_1$–$C_4$ alkyl, aralkyl, $C_5$–$C_8$ cycloalkyl and $C_1$–$C_6$ alkanoyl groups, or wherein the two substituents and the nitrogen to which they are attached when taken together form a 5- to 8-membered heterocyclo or heteroaryl ring.

$R^2$ represents hydrogen, $C_1$–$C_6$ alkyl, aralkyl, heteroaralkyl, cycloalkylalkyl having 4–8 carbons in the ring and 1–3 carbons in the alkyl chain, heterocycloalkylalkyl in which 4–8 atoms are in the ring, one or two of which atoms can be nitrogen, oxygen or sulfur and in which the alkyl chain contains 1–3 carbons.

$R^2$ represents hydrogen or $C_1$–$C_6$ alkyl.

$R^2$ represents hydrogen, methyl, ethyl, n-propyl, n-butyl, isobutyl.

$R^2$ represents carbocyclic aralkyl or heteroaralkyl as discussed above.

$R^2$ represents benzyl, 2-pyridylmethyl, 3-pyridylmethyl, 4-pyridylmethyl, 2-thiazolylmethyl, 4-thiazolylmethyl, 5-thiazolylmethyl.

$R^2$ represents cycloalkylalkyl having 4–8 carbons in the ring and 1–3 carbons in the alkyl chain, heterocycloalkylalkyl in which 4–8 atoms are in the ring, one or two of which atoms can be nitrogen, oxygen or sulfur and in which the alkyl chain contains 1–3 carbons.

$R^2$ represents cyclopropylmethyl, cyclopentylmethyl, cyclohexylmethyl.

$R^2$ represents alkyl substituted by hydroxycarbonyl, amino, mono-substituted amino and di-substituted amino, wherein the substituents on the amino nitrogen are chosen from $C_1$–$C_6$ alkyl, aralkyl, $C_5$–$C_8$ cycloalkyl and $C_1$–$C_6$ alkanoyl, or wherein the two substituents and the nitrogen to which they are attached when taken together form a 5- to 8-membered heterocyclo or heteroaryl ring containing zero or one additional hetero atoms that are nitrogen, oxygen or sulfur.

$R^2$ represents $C_1$–$C_5$ alkyl substituted by hydroxycarbonyl.

$R^2$ represents 5-pentanoic acid, 4-n-butanoic acid, 3-propanoic acid or 2-ethanoic acid.

$R^2$ represents hydrido, $C_1$–$C_6$ alkyl, $C_2$–$C_4$ alkyl substituted by amino, mono-substituted amino or di-substituted amino, wherein the substituents on nitrogen are chosen from $C_1$–$C_6$ alkyl, aralkyl, $C_5$–$C_8$ cycloalkyl and $C_1$–$C_6$ alkanoyl, or wherein the two substituents and the nitrogen to which they are attached when taken together form a 5- to 8-membered heterocyclo or heteroaryl ring containing zero or one additional hetero atoms that are nitrogen, oxygen or sulfur, a $C_1$–$C_4$ alkylaryl or $C_1$–$C_4$ alkylheteroaryl group having a single ring.

$R^2$ represents methyl, 2-aminoethyl, 3-aminopropyl, 4-aminobutyl, N,N-dimethyl-2-aminoethyl, 2-(4-morpholino)ethyl, 2-(1-piperidino)ethyl, 2-(1-pyrrolidino) ethyl.

$R^3$ and $R^4$ Preferences:

$R^3$ and $R^4$ independently represent hydrogen, hydroxycarbonyl, aminocarbonyl, $C_1$–$C_6$ alkyl, aralkyl, aryl, heteroaryl, $C_5$–$C_8$ cycloalkyl, heteroaralkyl, cycloalkylalkyl having 4–8 carbons in the ring and 1–3 carbons in the alkyl chain.

$R^3$ is hydrido, and $R^4$ is hydroxycarbonyl, aminocarbonyl or $C_1$–$C_6$ alkyl.

$R^3$ and $R^4$ independently represents hydrogen, aminocarbonyl, methyl.

$R^3$ is hydrido and $R^4$ represents methyl.

$R^3$ is hydrido and $R^4$ represents hydroxycarbonyl or aminocarbonyl.

$R^3$ represents hydrido and $R^4$ represents aminocarbonyl (carbamyl) or methyl.

$R^5$ and $R^6$ Preferences:

$R^5$ and $R^6$ independently represent hydrogen (hydrido), hydroxycarbonyl, aryl, heteroaryl, $C_1$–$C_6$ alkyl.

$R^5$ and $R^6$ are both hydrido.

$R^7$ and $R^8$ Preferences:

$R^7$ and $R^8$ independently represent hydrogen, hydroxycarbonyl, $C_1$–$C_6$ alkyl.

x Preferences:

x is preferably zero.

W is preferably oxygen (O).

$R^9$ Preferences:

$R^9$ represents $C_1$–$C_6$ alkyl, aryl, $C_1$–$C_6$ alkoxy, heteroaryl, amino $C_1$–$C_6$ alkyl, N-monosubstituted amino $C_1$–$C_6$ alkyl and N,N-disubstituted amino $C_1$–$C_6$ alkyl, wherein the substituents on nitrogen are chosen from $C_1$–$C_6$ alkyl, aralkyl, $C_5$–$C_8$ cycloalkyl and $C_1$–$C_6$ alkanoyl, or wherein the two substituents and the nitrogen to which they are attached when taken together form a 5- to 8-membered heterocyclo or heteroaryl ring.

$R^9$ represents $C_1$–$C_6$ alkyl, $C_5$–$C_8$ cycloalkyl, aryl, $C_1$–$C_6$ alkoxy, heteroaryl, amino $C_1$–$C_6$ alkyl, N-monosubstituted amino $C_1$–$C_6$ alkyl and N,N-disubstituted amino $C_1$–$C_6$ alkyl, wherein the substituents on nitrogen are chosen from $C_1$–$C_6$ alkyl, aralkyl, $C_5$–$C_8$ cycloalkyl and $C_1$–$C_6$ alkanoyl, or wherein the two substituents and the nitrogen to which they are attached when taken together form a 5- to 8-membered heterocyclo or heteroaryl ring.

$R^9$ represents $C_1$–$C_6$ alkyl, $C_1$–$C_6$ alkoxy, a single-ringed aryl or heteroaryl.

$R^9$ represents methyl, ethyl, n-propyl, n-butyl, isopropyl, isobutyl.

$R^9$ represents a 3- to 8-membered cycloalkyl ring.

$R^9$ represents cyclohexyl and cyclopentyl.

$R^9$ represents aryl or heteroaryl.

$R^9$ represents phenyl, 2-pyridyl, 3-pyridyl, 4-pyridyl, thiophene-2-yl, 3-thiophene-3-yl.

$R^9$ represents $C_1$–$C_6$ alkoxy.

$R^9$ represents methoxy and ethoxy.

Starred substituents, $R^*$, and $x^*$ are preferably the same as unstarred substituents, R, and x so that a compound of formula III is homodimer.

In particularly preferred practice, an $SO_2$-linked $R^1$ substituent is an aryl or heteroaryl group that is a 5- or 6-membered single-ring, and is itself substituted with one other single-ringed aryl or heteroaryl group or, with an alkyl or alkoxy group containing an umbranched chain of 3 to about 7 carbon atoms, a phenoxy group, a thiophenoxy [$C_6H_5$—S—] group, a phenylazido [$C_6H_5$—$N_2$—] group or a benzamido [—NHC(O)$C_6H_5$] group. The $SO_2$-linked single-ringed aryl or heteroaryl $R^1$ group is substituted at its own 4-position when a 6-membered ring and at its own 3-position when a 5-membered ring.

The $R^1$ group's substituent single-ringed aryl or heteroaryl, phenoxy, thiophenoxy, phenylazo or benzamido group is unsubstituted or can itself be substituted at the 4-position when a 6-membered ring or the 3-position when a 5-membered ring. The 4- and 3-positions of rings discussed here are numbered from the sites of substituent bonding as compared to formalized ring numbering positions used in heteroaryl nomenclature. Here, single atoms such as halogen moieties or substituents that contain one to a chain of about five atoms other than hydrogen such as $C_1$–$C_4$ alkyl, $C_1$–$C_4$ alkoxy or carboxyethyl groups can be used. Exemplary substituted $SO_2$-linked $R^1$ substituents include biphenyl, 4-phenoxyphenyl, 4-thiophenoxyphenyl, 4-butoxyphenyl, 4-pentylphenyl, 4-(4'-dimethylaminophenyl)azophenyl, and 2-[(2-pyridyl)-5-thienyl].

When examined along its longest chain of atoms, an $R^1$ substituent including its own substituent has a total length of greater than a saturated chain of four carbon atoms and less than a saturated chain of about 18 and preferably about 12 carbon atoms, even though many more atoms may be present in ring structures or substituents. This length requirement is discussed further below.

Looked at more generally, and aside from specific moieties from which it is constructed, a particularly preferred $R^1$ radical (group or moiety) has a length greater than that of an butyl group. Such an $R^1$ radical also has a length that is less than that of a stearyl (octadecyl) group. That is to say that a particularly preferred $R^1$ is a radical having a length greater than that of a saturated four carbon chain, and shorter than that of a saturated eighteen carbon chain, and more preferably, a length greater than that of a pentyl group and less than that of a lauryl group.

The radical chain lengths are measured along the longest linear atom chain in the radical, and each atom in the chain, e.g. oxygen or nitrogen, is presumed to be carbon for ease in calculation. Such lengths can be readily determined by using published bond angles, bond lengths and atomic radii, as needed, to draw and measure a staggered chain, or by building models using commercially available kits whose bond angles, lengths and atomic radii are in accord with accepted, published values. Radical lengths can also be determined somewhat less exactly by assuming that all atoms have bond lengths saturated carbon, that unsaturated bonds have the same lengths as saturated bonds and that bond angles for unsaturated bonds are the same as those for saturated bonds, although the above-mentioned modes of measurement are preferred.

In addition, a particularly preferred $R^1$ group when rotated about an axis drawn through the $SO_2$-bonded 1-position and the 4-position of a 6-membered ring or the $SO_2$-bonded position and substituent-bonded 3- or 5-position of a 5-membered ring defines a three-dimensional volume whose widest dimension has the width of about one phenyl ring to about three phenyl rings in a direction transverse to that axis to rotation.

As a consequence of these length and width requirements, $R^1$ substituents such as 4-(phenyl)phenyl[biphenyl], 4-(4'-methoxyphenyl)phenyl, 4-(phenoxy)phenyl, 4-(thiophenyl)phenyl[4-(phenylthio)phenyl], 4-(azophenyl)phenyl and 4-(benzamido)phenyl are particularly preferred $R^1$ substituents.

One sub-set of particularly preferred MMP-13 inhibitor compounds useful in a before-described process has structures depicted by formulas Ia, IIa and IIIa, below.

(Ia)

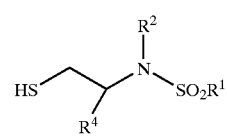

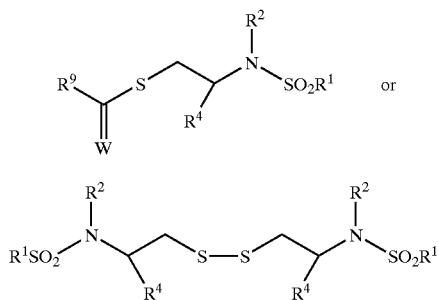

(IIa)

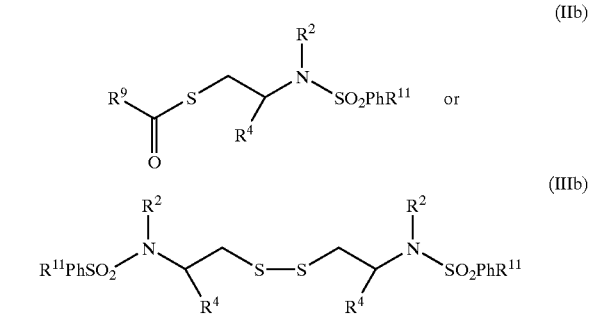

(IIb)

(IIIa)

(IIIb)

In a particularly preferred compound of the above structural formulas, the configuration about the $R^4$-containing carbon atom is that of a naturally-occurring amino acid. The substituent groups are discussed below for these compounds.

An $R^1$ group represents a single aryl or heteroaryl ring, wherein the single aryl ring is unsubstituted or can optionally be substituted by one or more of the following substituents: $C_1$–$C_6$ alkyl, $C_1$–$C_6$ alkoxy, aryloxy, heteroaryloxy, aryl, heteroaryl, aralkoxy, heteroaralkoxy, $C_1$–$C_6$ alkylthio, arylthio, heteroarylthio in which each ring-containing substituent itself contains a single ring.

A single-ringed aryl or heteroaryl group is 5- or 6-membered, and is itself preferably substituted at its own 4-position when a 6-membered ring and at its own 3-position when a 5-membered ring with a substituent selected from the group consisting of one other single-ringed aryl or hetroaryl group, an alkyl or alkoxy group containing an umbranched chain of 3 to about 7 carbon atoms, a phenoxy group, a thiophenoxy group, a phenylazo group or a benzamido group.

$R^2$ represents hydrido, $C_1$–$C_6$ alkyl, $C_2$–$C_4$ alkyl substituted by amino, mono-substituted amino or di-substituted amino, wherein the substituents on nitrogen are chosen from $C_1$–$C_6$ alkyl, aralkyl, $C_5$–$C_8$ cycloalkyl and $C_1$–$C_6$ alkanoyl, or wherein the two substituents and the nitrogen to which they are attached when taken together form a 5- to 8-membered heterocyclo or heteroaryl ring containing zero or one additional hetero atoms that are nitrogen, oxygen or sulfur, a $C_1$–$C_4$ alkylaryl or $C_1$–$C_4$ alkylheteroaryl group having a single ring.

An $R^4$ group is hydroxyxcarbonyl, aminocarbonyl or $C_1$–$C_6$ alkyl.

W is sulfur or oxygen, but preferably oxygen (O).

An $R^9$ group represents a $C_1$–$C_6$ alkyl group, $C_1$–$C_6$ alkoxy group, or a single-ringed carbocyclic aryl or heteroaryl group.

A most preferred MMP-13 inhibitor sub-set of compounds useful in a before-described process also preferably has the configuration of a naturally-occurring amino acid, and corresponds to the structures depicted by formulas Ib, IIb and IIIb, below.

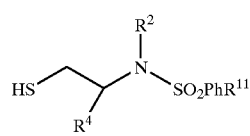

(Ib)

The substituents of these most preferred MMP-13 inhibitor compounds are as follows:

An $R^4$ group is $C_1$–$C_6$ alkyl, and particularly methyl, or aminocarbonyl [—C(O)NH$_2$].

An $R^2$ group is $C_1$–$C_6$ alkyl and particularly methyl, a $C_2$–$C_3$ alkyl cycloamino group having five or six atoms in the ring and zero or one additional heteroatom that is oxygen or nitrogen, and $C_1$–$C_4$ alkyl single-ringed aryl or heteroaryl, wherein the single heteroaryl ring contains one or two nitrogen atoms. Exemplary most preferred substituents in addition to methyl include 2-(4-morpholino)ethyl, 2-(1-piperidino)ethyl, 2-(1-pyrrolidino)ethyl and (3-pyridyl)methyl. Hydrogen (hydrido) can also be a most preferred $R^2$ group as is discussed below.

The sulfonyl group (—SO$_2$—) of a most preferred sub-set of inhibitor compounds is linked to a phenyl group (Ph), which itself is substituted at the 4-position by a substituent denominated $R^{11}$ that together with the phenyl group is referred to as PhR$^{11}$. A 4-substituted phenyl group substituent, $R^{11}$, can be $C_3$–$C_8$ alkoxy such as butoxy, $C_3$–$C_8$ alkyl such as pentyl, as well as phenoxy, thiophenoxy (phenylthio), benzamido, phenylazo or phenyl.

An $R^{11}$ 6-membered ring-containing substituent group can itself also be substituted in a 3-(meta) or 4-(para-) position, or both, with a halogen (fluorine, chlorine, bromine or iodine), a $C_1$–$C_4$ alkoxy group such as methoxy or isopropoxy, a $C_1$–$C_4$ alkyl group such as methyl, a two or three carbon-containing carboxyl group such as carboxymethyl or carboxyethyl an amine, or a mono- or di-$C_1$–$C_4$ alkyl-substituted amine such as dimethyl amino. A 3,4-methylenedioxy substituent is a contemplated 3,4-substituent, whereas methyl is a contemplated 3-substituent. A substituent of such a $R^{11}$ ring para substituent has one atom or a longest chain of up to five atoms, excluding hydrogen.

$R^9$ represents a $C_1$–$C_6$ alkyl group, a $C_1$–$C_6$ alkoxy group, a single-ringed carbocyclic aryl or heteroaryl group, and more particularly, a phenyl, 2-pyridyl, 3-pyridyl, 4-pyridyl, thiophene-2-yl, 3-thiophene-3-yl, methyl, ethyl, methoxy or ethoxy group.

With respect to compounds of the formula

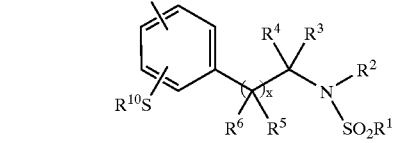

(IV)

$R^{10}$ is hydrogen (hydrido) or —C(O)—$R^9$, and $R^1$, $R^2$, $R^3$, $R^4$, $R^5$, $R^6$, $R^9$ and x are as defined above, and Y represents hydrogen, halogen, alkyl, alkoxy, nitro, cyano, carboxy or amino.

In particularly preferred and most preferred practice, the substituent "R" groups and x are as they have been previously described in regard to formulas Ia–IIIa and Ib–IIIb, respectively, except that $R^3$ and $R^4$ are both hydrido in most preferred compounds. Additionally, x is zero so that $R^5$ and $R^6$ and the carbon to which they are bonded are absent, Y is hydrogen, and the sulfur atom bonded to the depicted phenyl ring is linked ortho to the sulfonamide-bearing carbon atom. It is thus seen that particularly preferred and most preferred compounds of formula IV constitute compounds of formulas I and II in which x is one, and the $R^6$ and $R^8$ substituents together with the atoms to which they are attached form a 6-membered, aromatic ring.

A particularly or most preferred $R^1$ group is a radical having a length greater than that of a saturated four carbon chain, and shorter than that of a saturated eighteen carbon chain. When rotated about an axis drawn through the $SO_2$-bonded $R^1$ group 1-position and the 4-position of a 6-membered ring or the $SO_2$-bonded position and substituent-bonded 3- or 5-position of a 5-membered $R^1$ ring, the substituent defines a three-dimensional volume whose widest dimension has the width of about one phenyl ring to about three phenyl rings in a direction transverse to that axis to rotation.

More specifically, an $SO_2$-linked $R^1$ substituent is an aryl or heteroaryl group that is a 5- or 6-membered single-ring, and is itself substituted with one other single-ringed aryl or heteroaryl group or, with an alkyl or alkoxy group containing an umbranched chain of 3 to about 7 carbon atoms, a phenoxy group, a thiophenoxy [$C_6H_5$—S—] group, a phenylazido [$C_6H_5$—$N_2$—] group or a benzamido [—NHC(O)$C_6H_5$] group. The $SO_2$-linked single-ringed aryl or heteroaryl $R^1$ group is substituted at its own 4-position when a 6-membered ring and at its own 3-position when a 5-membered ring $R^2$ represents hydrido, $C_1$–$C_6$ alkyl, $C_2$–$C_4$ alkyl substituted by amino, mono-substituted amino or di-substituted amino, wherein the substituents on nitrogen are chosen from $C_1$–$C_6$ alkyl, aralkyl, $C_5$–$C_8$ cycloalkyl and $C_1$–$C_6$ alkanoyl, or wherein the two substituents and the nitrogen to which they are attached when taken together form a 5- to 8-membered heterocyclo or heteroaryl ring containing zero or one additional hetero atoms that are nitrogen, oxygen or sulfur, a $C_1$–$C_4$ alkylaryl or $C_1$–$C_4$ alkylheteroaryl group having a single ring.

An $R^3$ group is hydrido, and $R^4$ is hydroxyxcarbonyl, aminocarbonyl or $C_1$–$C_6$ alkyl. Again, $R^3$ and $R^4$ are both hydrido in most preferred compounds.

An $R^9$ group represents $C_1$–$C_6$ alkyl, $C_1$–$C_6$ alkoxy, a single-ringed carbocyclic aryl or heteroaryl, and more particularly, phenyl, 2-pyridyl, 3-pyridyl, 4-pyridyl, thiophene-2-yl, 3-thiophene-3-yl, methyl, ethyl, methoxy and ethoxy.

Particularly preferred and most preferred compounds correspond to formulas IVa, IVb, IVc and IVd that are shown below:

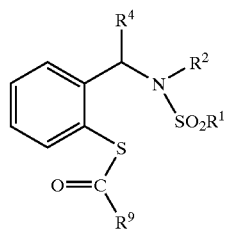

(IVa)

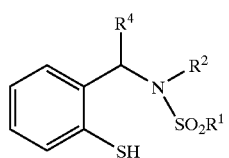

(IVb)

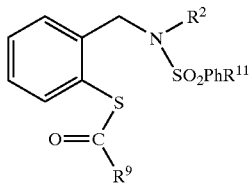

(IVc)

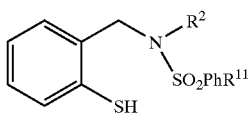

(IVd)

The compounds described herein are useful in a process described herein in that such compounds can inhibit the activity of MMP-13. A particularly preferred compound inhibits the enzyme with an $IC_{50}$ value of about 1000 nm or less in the in vitro assay discussed hereinafter. A most preferred compound exhibits an $IC_{50}$ value in that assay of about 20 nm or less, with some compounds exhibiting values of about 1 nm or less.

In addition, while being highly active against MMP-13, selectivity of inhibitory activity toward MMP-1 is also exhibited by many of these particularly preferred and most preferred compounds. That is, many compounds exhibit little or no inhibition in the in vitro assay against MMP-1 so that $IC_{50}$ values are often found to be several thousand to greater than 10,000 nm toward MMP-1. Exemplary ratios of $IC_{50}$ values toward MMP-1 and MMP-13 ($IC_{50}$ MMP-1/$IC_{50}$ MMP-13) can range from about 5 to about 20,000, with most preferred compounds exhibiting ratios of about 500 to about 20,000. Inhibition data for several exemplary compounds are provided in a table hereinafter.

A contemplated inhibitor compound is used for treating a host mammal such as a mouse, rat, rabbit, dog, horse, primate such as a monkey, chimpanzee or human that has a condition associated with pathological matrix metalloprotease activity.

Also contemplated is use of a contemplated metalloprotease inhibitor compound in the treatment of a disease state that can be affected by the activity of metalloproteases TNF-α convertase. Exemplary of such disease states are the acute phase responses of shock and sepsis, coagulation responses, hemorrhage and cardiovascular effects, fever and inflammation, anorexia and cachexia.

In treating a disease condition associated with pathological matrix metalloproteinase activity, a contemplated MMP inhibitor compound can be used in the form of an amine salt derived from an inorganic or organic acid. Exemplary salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Also, a basic nitrogen-containing group can be quaternized with such agents as lower alkyl halides, such as methyl, ethyl, propyl, and butyl chloride, bromides, and iodides; dialkyl sulfates like dimethyl, diethyl, dibuytl, and diamyl sulfates, long chain halides such as decyl, lauryl, myristyl and stearyl chlorides, bromides and iodides, aralkyl halides like benzyl and phenethyl bromides, and others to provide enhanced water-solubility. Water or oil-soluble or dispersible products are thereby obtained as desired. The salts are formed by combining the basic compounds with the desired acid.

Other compounds useful in this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

Total daily dose administered to a host mammal in single or divided doses can be in amounts, for example, for 0.001 to 30 mg/kg body weight daily and more usually 0.01 to 10 mg. Dosage unit compositions can contain such amounts or submultiples thereof to make up the daily dose. A suitable dose can be administered, in multiple sub-doses per day. Multiple doses per day can also increase the total daily dose should this be desired by the person prescribing the drug.

The dosage regimen for treating a disease condition with a compound and/or composition of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

A compound useful in the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Reminqton's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

Certain compounds of this invention can serve as prodrugs to other compounds of this invention. Prodrugs are drugs that can be chemically converted in vivo or in vitro by biological systems into an active derivative or derivatives. An example from this invention are drugs of formula II (IIa or IIb) where the acyl group is hydrolyzed to a compound of formula I (or Ia or Ib). An additional example is where a disulfide of this invention is reduced to its thiol product or, in some cases, converted into an active mixed disulfide.

Table 1 through Table 80, below, show several series of compounds useful in this invention. Each case, class or group of compounds is illustrated by a generic formula, or formulae, followed by a series of preferred moieties or groups that constitute various substituents that can be attached at the position clearly shown in the generic structure. The generic symbols, e.g., $R^1$, $R^2$ and the like, are as defined before, except that $R^3$ of the following tables corresponds to particularly and must preferred $R^4$ discussed previously. This system is well known in the chemical communication arts and is widely used in scientific papers and presentations. For example in Table 1, $R^2$ is the variable group with the structural variables that can substitute for $R^2$ shown in the balance of the table. There are 40 $R^2$ groups (including hydrogen) shown that are used to represent, in a non-limiting manner, 40 distinct compounds. In a similar manner, Table 43 for example, illustrates a compound with a generic structure containing two variable groups. The groups are $R^1$ and $R^2$. Thus, this example shows a matrix of 12 $R^1$ groups and 10 $R^2$ groups (including hydrogen) that represent 120 non-limiting compounds of this invention that can be prepared.

TABLE 1

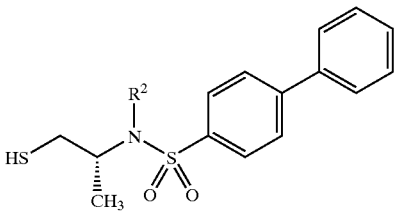

—$R^2$

| —H | 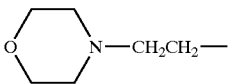 | 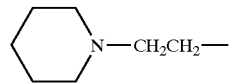 |
|---|---|---|
| —$CH_3$ | | |
| —$CH_2CH_3$ | 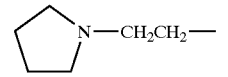 | 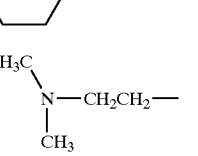 |
| —$CH_2CH_2CH_3$ | | |
| —$CH_2CH_2CH_2CH_3$ | 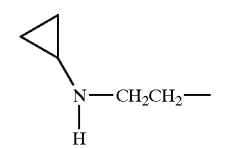 | 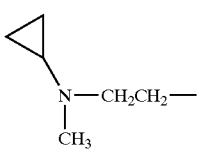 |
| —$CH_2CH_2CH_2CH_2CH_3$ | | |
| —$CH_2CH_2CH_2CH_2CH_2CH_3$ | 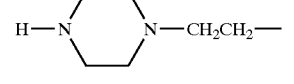 | 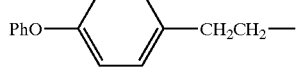 |
| —$CH_2Ph$ | | |
| —$CH_2CH_2Ph$ | 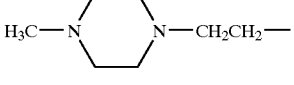 | 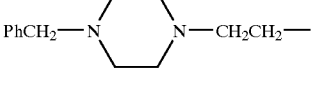 |
| —$CH_2CH(CH_3)_2$ | | |
| —$CH_2CF_3$ | 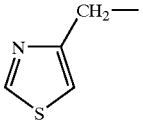 | 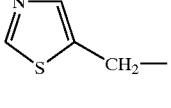 |
| —$CH_2CH_2OCH_3$ | | |
| —$CH_2CH_2OH$ | 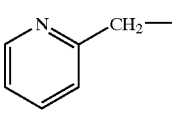 | 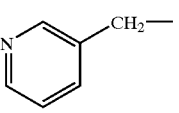 |
| —$CH_2CO_2H$ | | |
| —$CH_2CH_2CO_2H$ | 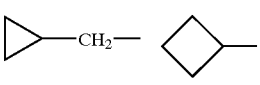 | 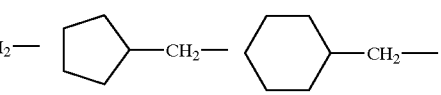 |
| —$CH_2CH_2CH_2CO_2H$ | | |

TABLE 1-continued
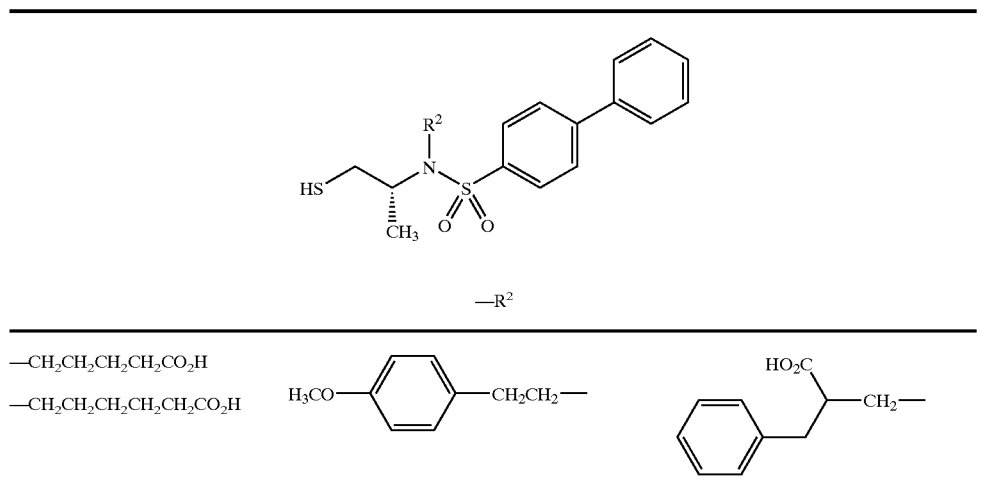
| —R² | | | |
|---|---|---|---|
| —CH₂CH₂CH₂CH₂CO₂H | H₃CO—⟨⟩—CH₂CH₂— | HO₂C—CH(CH₂Ph)—CH₂— | |
| —CH₂CH₂CH₂CH₂CH₂CO₂H | | | |
TABLE 2
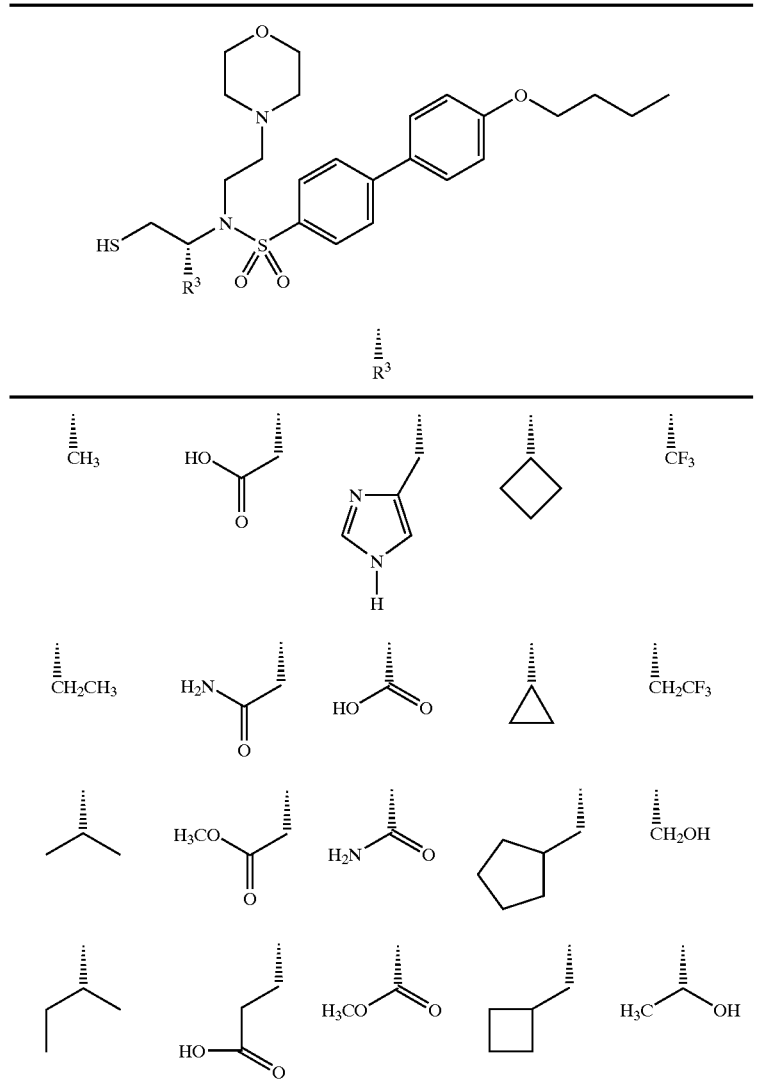

TABLE 2-continued
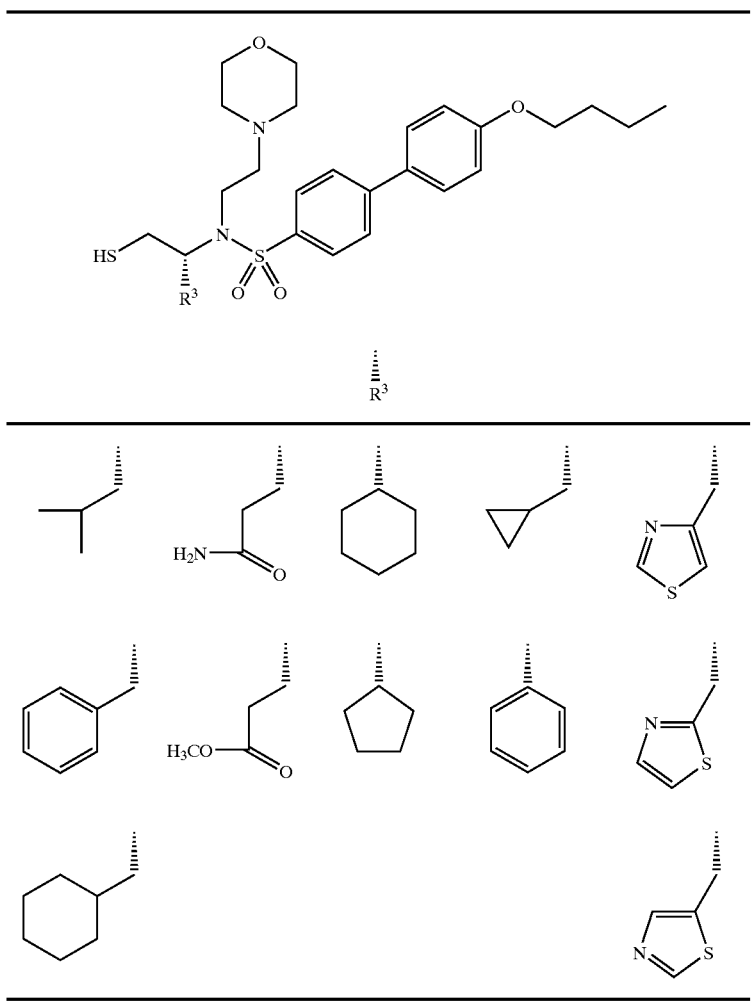
TABLE 3
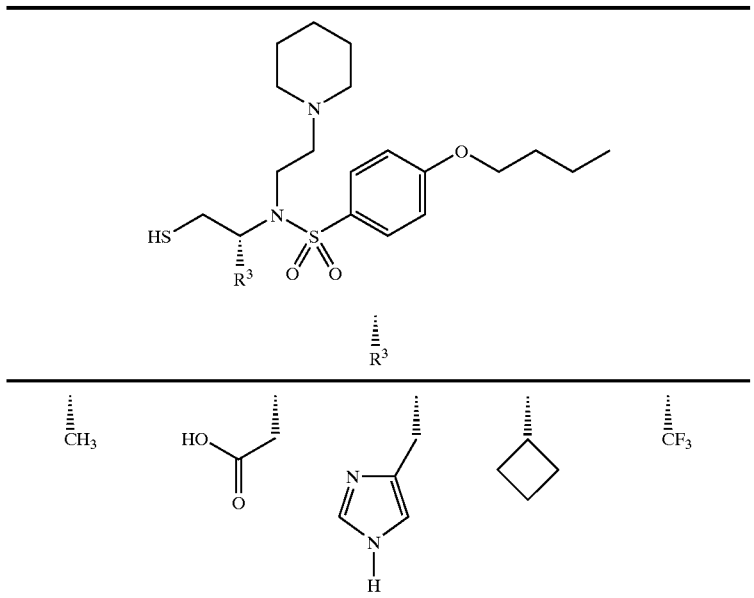

TABLE 3-continued
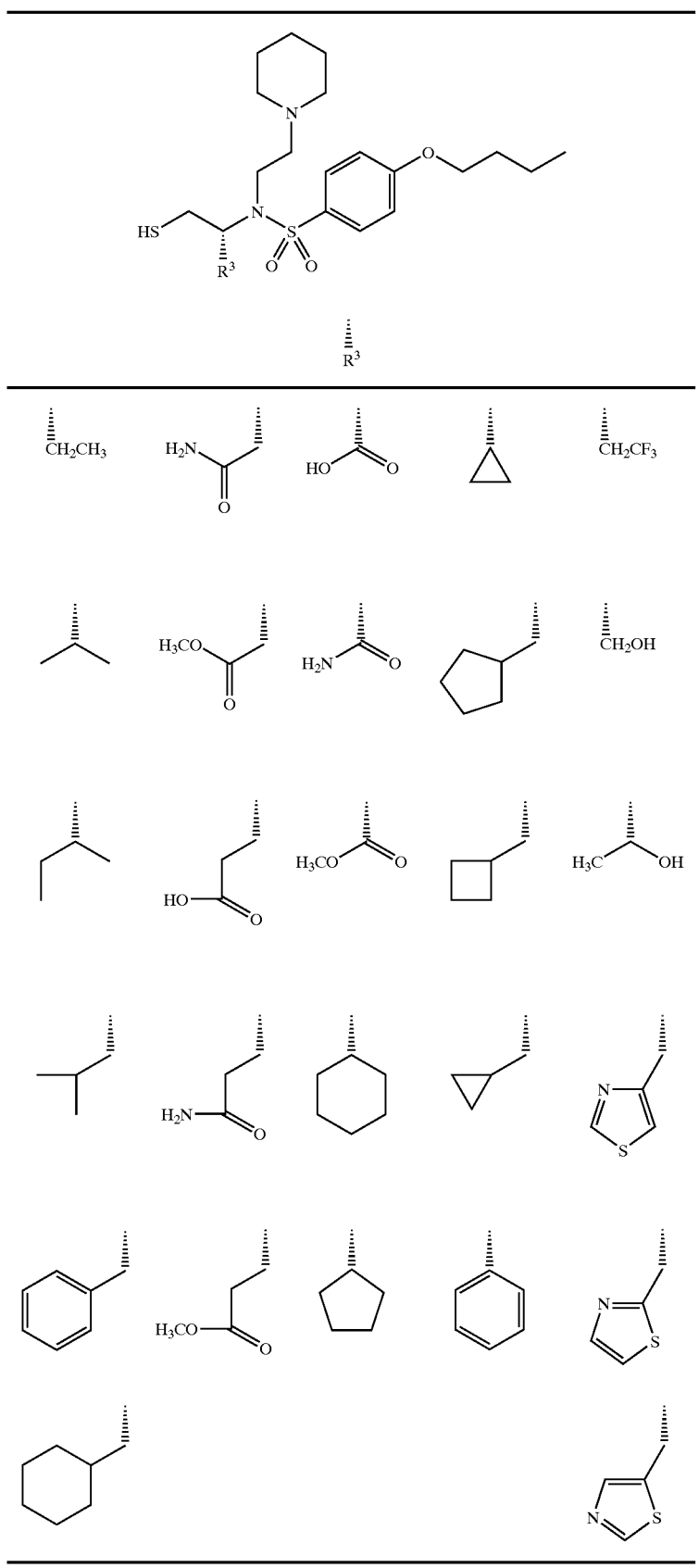

TABLE 4
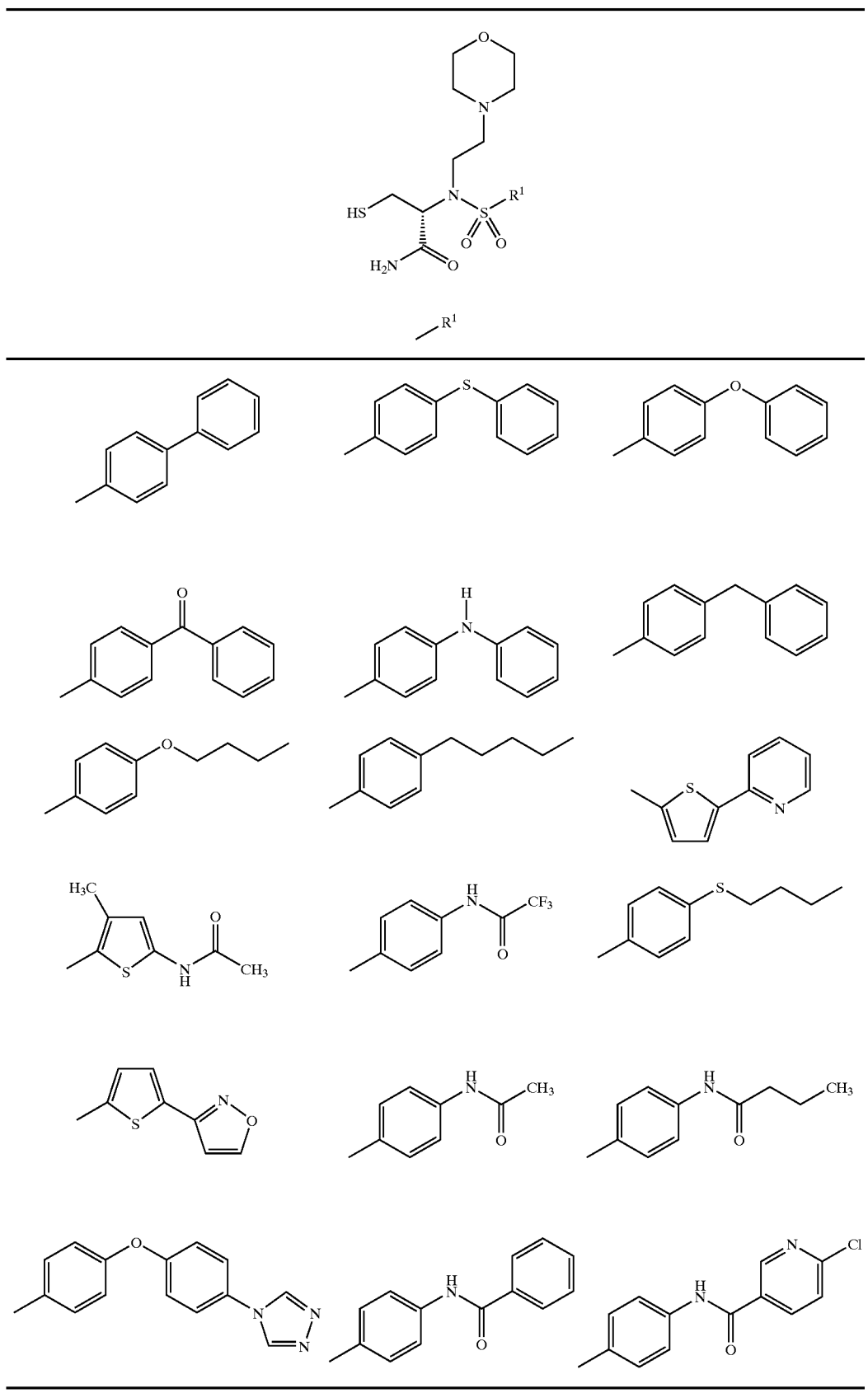

TABLE 5
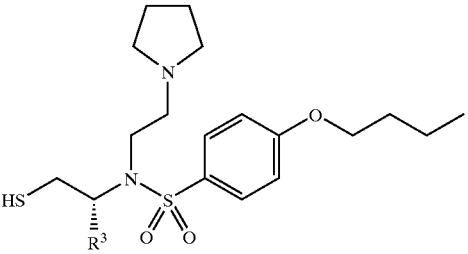

TABLE 6

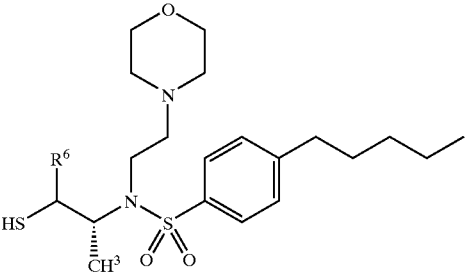

| R⁶ | | | | |
|---|---|---|---|---|
| CH₃ | CH₂COOH | CH₂-(1H-imidazol-4-yl) | cyclobutyl | CF₃ |
| CH₂CH₃ | CH₂C(O)NH₂ | CH₂CH₂COOH | cyclopropyl | CH₂CF₃ |
| CH₂CH(CH₃)₂ | CH₂C(O)OCH₃ | CH₂C(O)NH₂ | CH₂-cyclopentyl | CH₂OH |
| CH(CH₃)CH₂CH₃ | CH₂CH₂COOH | CH₂C(O)OCH₃ | CH₂-cyclobutyl | CH(CH₃)OH |
| CH₂C(CH₃)₃ | CH₂CH₂C(O)NH₂ | CH₂-cyclohexyl | CH₂-cyclopropyl | CH₂-(thiazol-4-yl) |
| CH₂-phenyl | CH₂CH₂C(O)OCH₃ | CH₂-cyclopentyl | CH₂-phenyl | CH₂-(thiazol-2-yl) |
| CH₂-cyclohexyl | | CH(CH₃)CO₂H | | CH₂-(thiazol-5-yl) |

TABLE 7
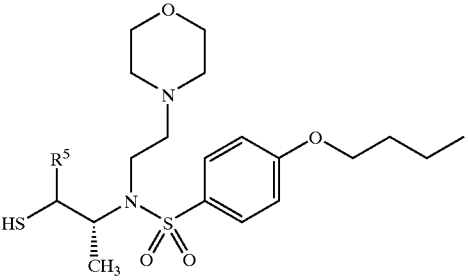

TABLE 8
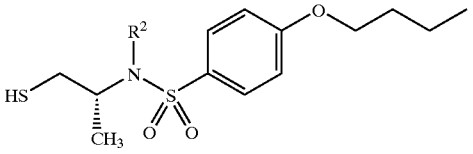
—R²
| | | |
|---|---|---|
| —H | 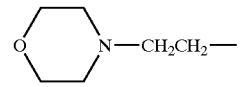 | 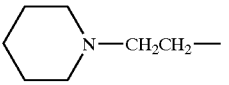 |
| —CH₃ | | |
| —CH₂CH₃ | 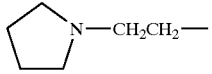 | 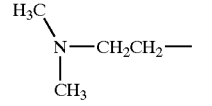 |
| —CH₂CH₂CH₃ | | |
| —CH₂CH₂CH₂CH₃ | 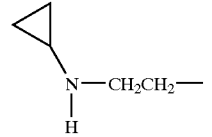 | 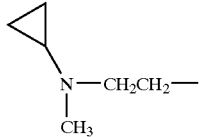 |
| —CH₂CH₂CH₂CH₂CH₃ | | |
| —CH₂CH₂CH₂CH₂CH₂CH₃ | 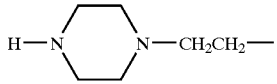 | 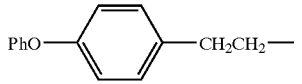 |
| —CH₂Ph | | |
| —CH₂CH₂Ph | 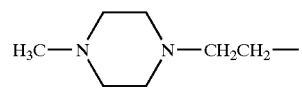 | 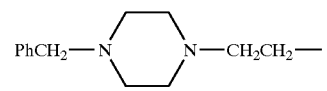 |
| —CH₂CH(CH₃)₂ | | |
| —CH₂CF₃ | 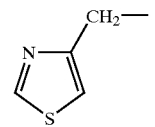 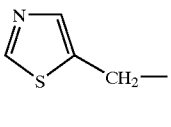 | 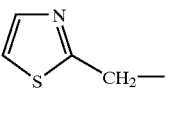 |
| —CH₂CH₂OCH₃ | | |
| —CH₂CH₂OH | 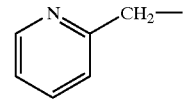 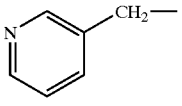 | 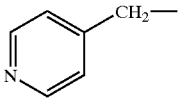 |
| —CH₂CO₂H | | |
| —CH₂CH₂CO₂H |    |  |
| —CH₂CH₂CH₂CO₂H | | |
| —CH₂CH₂CH₂CH₂CO₂H | 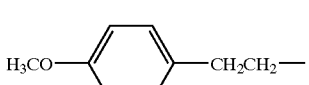 | 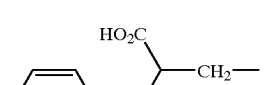 |
| —CH₂CH₂CH₂CH₂CH₂CO₂H | | |

TABLE 9

[Structure: morpholine-CH2CH2-N(SO2-C6H4-O-C6H5)-CH(R3)-CH2-SH]

| R³ | | | | |
|---|---|---|---|---|
| CH₃ | HOOC-CH₂- | imidazol-4-ylmethyl | cyclobutyl | CF₃ |
| CH₂CH₃ | H₂N-C(O)-CH₂- | HOOC-CH₂CH₂- | cyclopropyl | CH₂CF₃ |
| isobutyl | H₃CO-C(O)-CH₂- | H₂N-C(O)-CH₂CH₂- | cyclopentylmethyl | CH₂OH |
| sec-butyl | HOOC-CH₂CH₂- | H₃CO-C(O)-CH₂CH₂- | cyclobutylmethyl | CH(CH₃)OH |
| isobutyl | H₂N-C(O)-CH₂CH₂CH₂- | cyclohexyl | cyclopropylmethyl | thiazol-4-ylmethyl |
| benzyl | H₃CO-C(O)-CH₂CH₂CH₂- | cyclopentyl | phenyl | thiazol-2-ylmethyl |
| cyclohexylmethyl | | | | thiazol-5-ylmethyl |

TABLE 10

[Structure: piperidine-CH2CH2-N(SO2-C6H4-O-C6H5)-CH(R3)-CH2-SH]

R3 groups:

| | | | | |
|---|---|---|---|---|
| CH3 | HOOC-CH2- | imidazol-4-yl-CH2- | cyclobutyl | CF3 |
| CH2CH3 | H2N-C(O)-CH2- | HOOC-CH2CH2- | cyclopropyl | CH2CF3 |
| isopropyl | H3CO-C(O)-CH2- | H2N-C(O)-CH2CH2- | cyclopentyl-CH2- | CH2OH |
| sec-butyl | HOOC-CH2CH2- | H3CO-C(O)-CH2CH2- | cyclobutyl-CH2- | CH3-CH(OH)- |
| isobutyl | H2N-C(O)-CH2CH2CH2- | cyclohexyl | cyclopropyl-CH2- | thiazol-4-yl-CH2- |
| benzyl | H3CO-C(O)-CH2CH2CH2- | cyclopentyl | phenyl | thiazol-2-yl-CH2- |
| cyclohexyl-CH2- | | | | thiazol-5-yl-CH2- |

TABLE 11
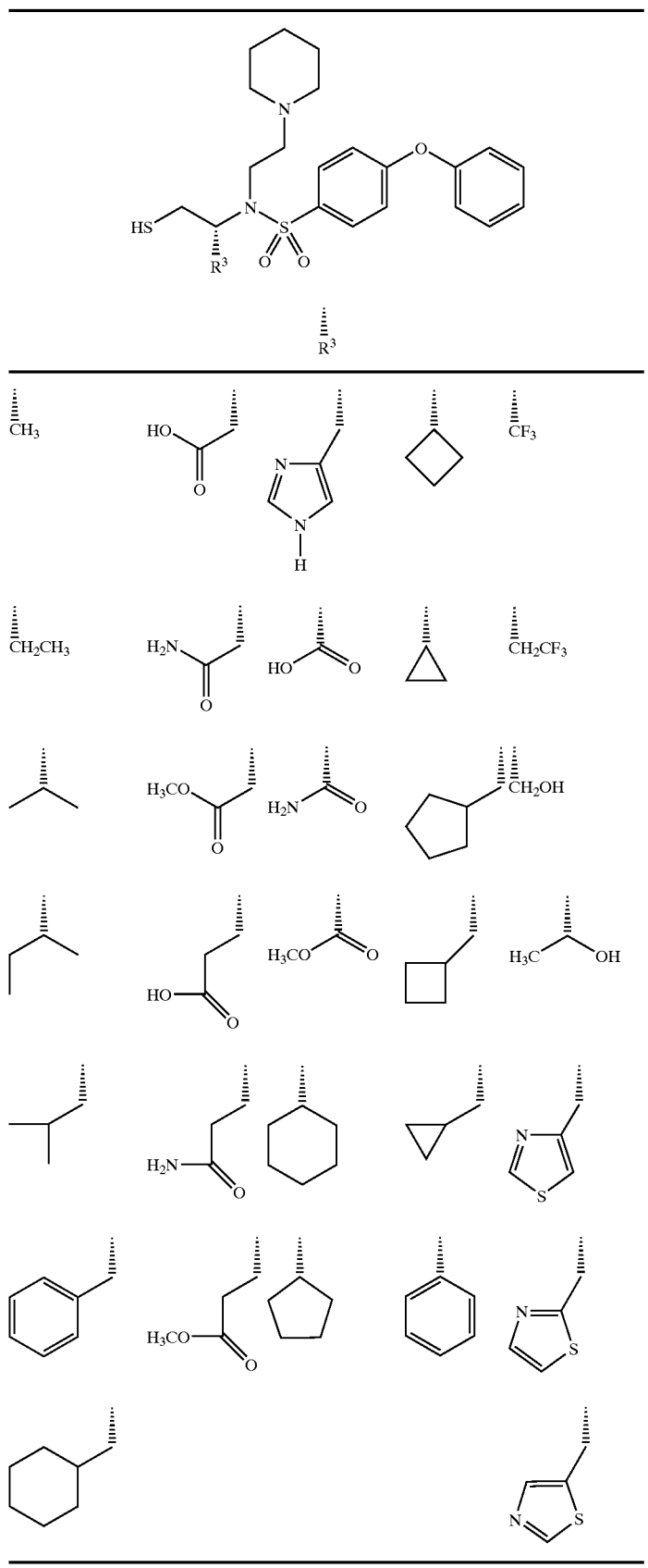

TABLE 12
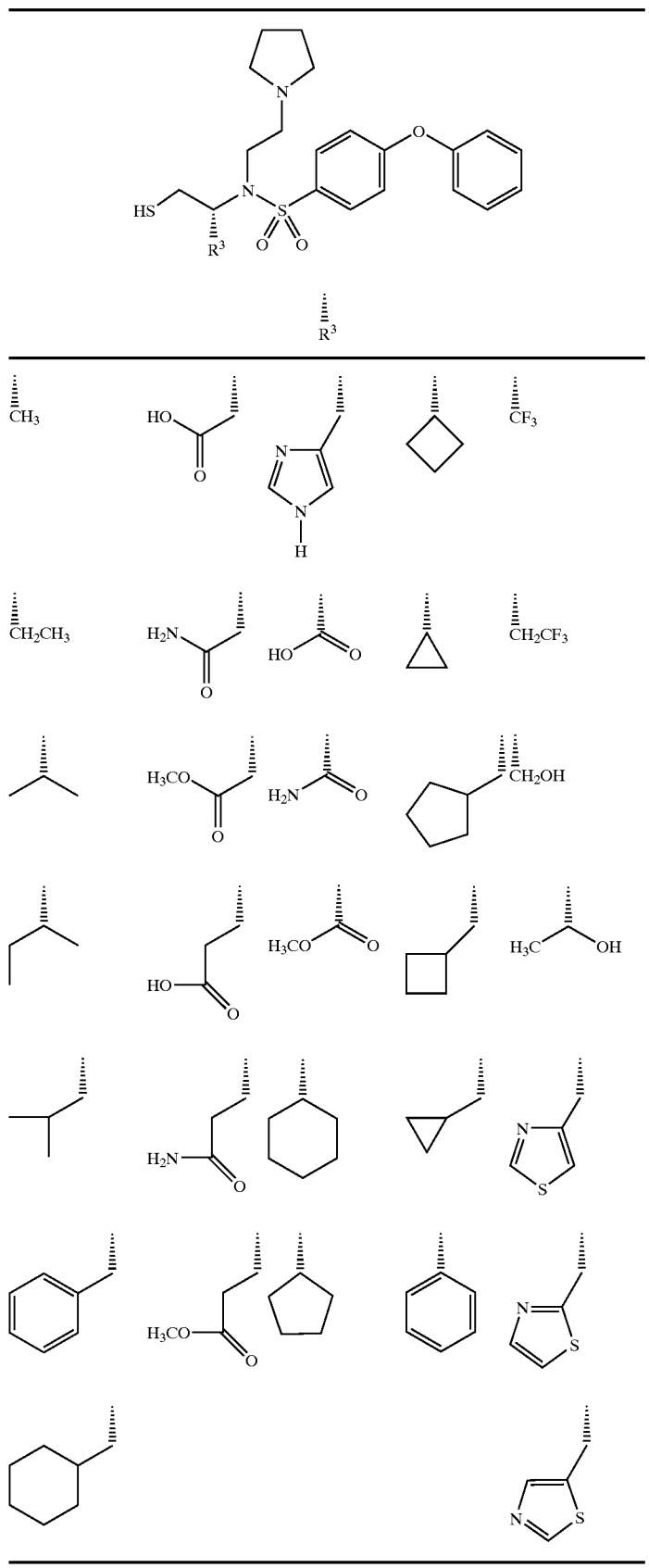

TABLE 13
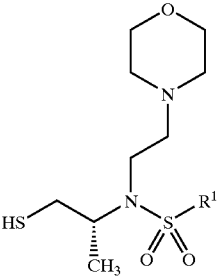
—R¹
| 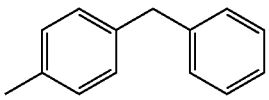 | 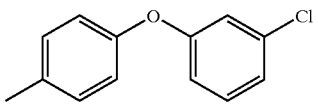 | 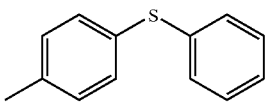 |
| --- | --- | --- |
| 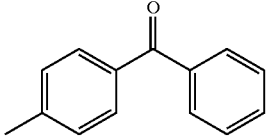 | 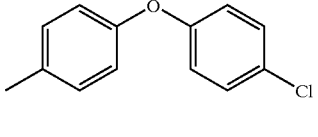 | 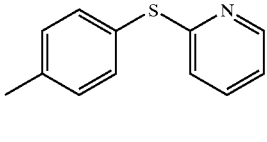 |
| 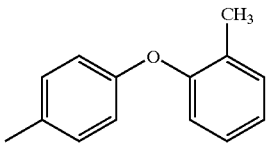 | 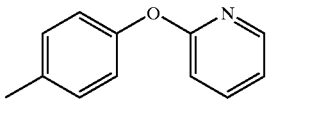 | 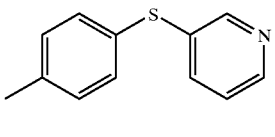 |
| 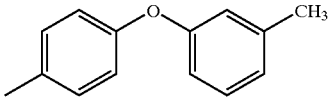 | 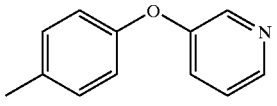 | 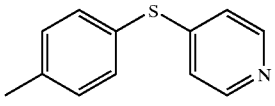 |
| 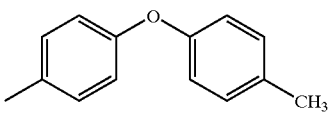 | 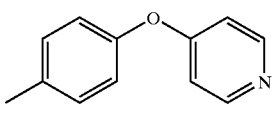 | 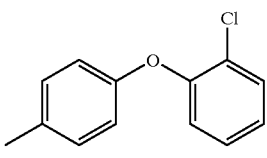 |
| 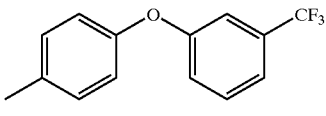 | 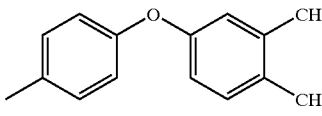 | 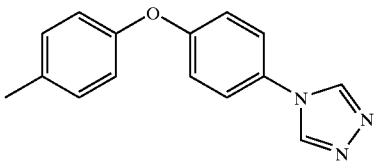 |

TABLE 14
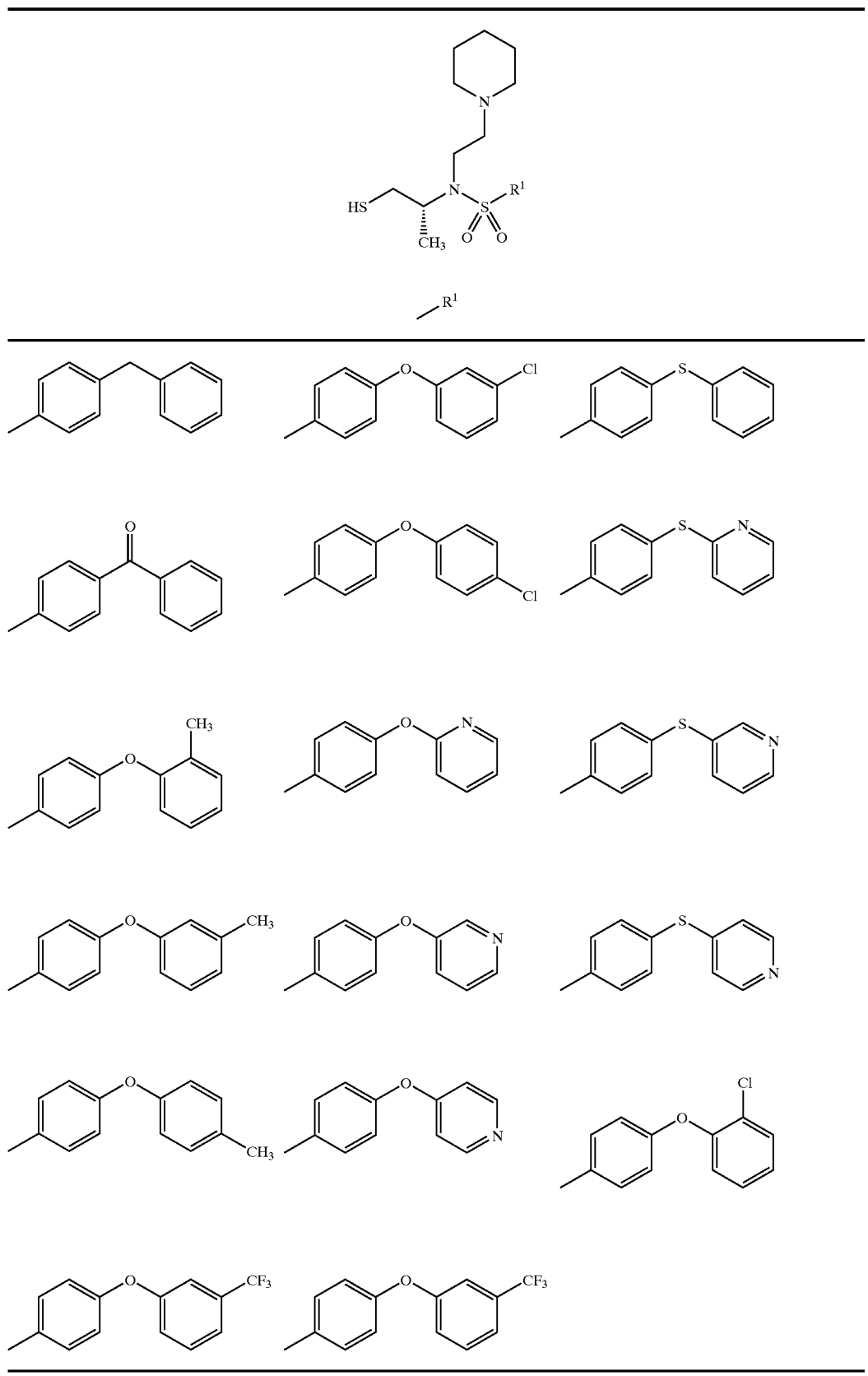

TABLE 15
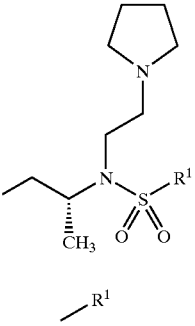
—R¹
| | | |
|---|---|---|
| 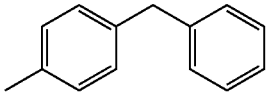 | 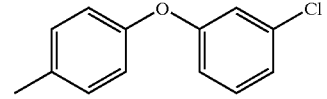 | 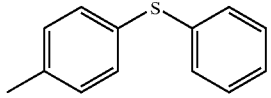 |
| 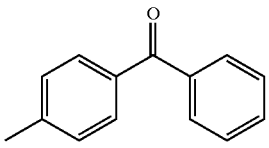 | 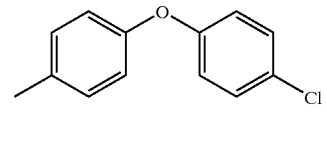 | 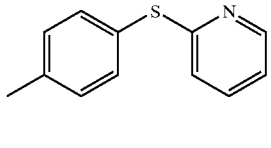 |
| 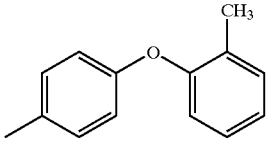 | 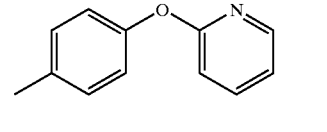 | 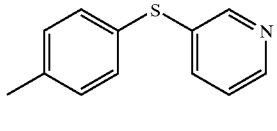 |
| 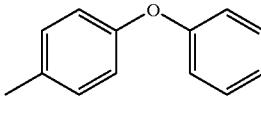 | 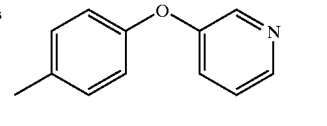 | 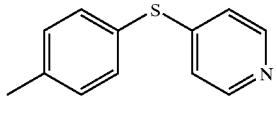 |
| 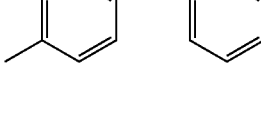 | 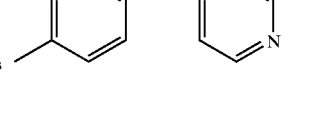 | 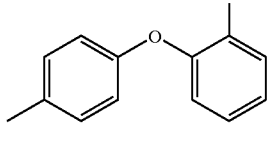 |
| 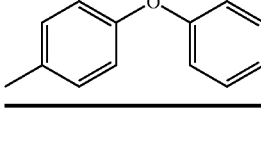 | 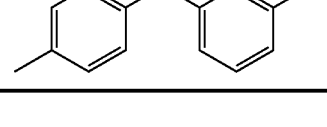 | |
TABLE 16
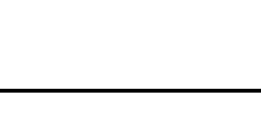
—R²
| | | |
|---|---|---|
| —H<br>—CH₃ | 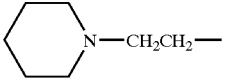 | 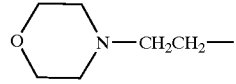 |

TABLE 16-continued

[Structure: 4-phenoxyphenylsulfonyl group attached to N(R²) of a chiral (S)-configured carbon bearing CH₃ and CH₂SH]

| —R² | | |
|---|---|---|
| —CH₂CH₃<br>—CH₂CH₂CH₃ | pyrrolidin-1-yl—CH₂CH₂— | (CH₃)₂N—CH₂CH₂— |
| —CH₂CH₂CH₂CH₃<br>—CH₂CH₂CH₂CH₂CH₃ | cyclopropyl-NH—CH₂CH₂— | cyclopropyl-N(CH₃)—CH₂CH₂— |
| —CH₂CH₂CH₂CH₂CH₂CH₃<br>—CH₂Ph | cyclopropyl-NH—CH₂CH₂— | cyclopropyl-N(CH₃)—CH₂CH₂— |
| —CH₂CH₂Ph<br>—CH₂CH(CH₃)₂ | H—N(piperazinyl)N—CH₂CH₂— | PhO—C₆H₄—CH₂CH₂— |
| —CH₂CF₃<br>—CH₂CH₂OCH₃ | H₃C—N(piperazinyl)N—CH₂CH₂— | PhCH₂—N(piperazinyl)N—CH₂CH₂— |
| —CH₂CH₂OH | thiazol-4-yl—CH₂— | thiazol-5-yl—CH₂— | thiazol-2-yl—CH₂— |
| —CH₂CO₂H | pyridin-2-yl—CH₂— | pyridin-3-yl—CH₂— | pyridin-4-yl—CH₂— |
| —CH₂CH₂CO₂H | cyclopropyl-CH₂— | cyclobutyl-CH₂— | cyclopentyl-CH₂— | cyclohexyl-CH₂— |
| —CH₂CH₂CH₂CO₂H | H₃CO—C₆H₄—CH₂CH₂— | HO₂C-CH(CH₂Ph)-CH₂— |
| —CH₂CH₂CH₂CH₂CO₂H<br>—CH₂CH₂CH₂CH₂CH₂CO₂H | | |

TABLE 17
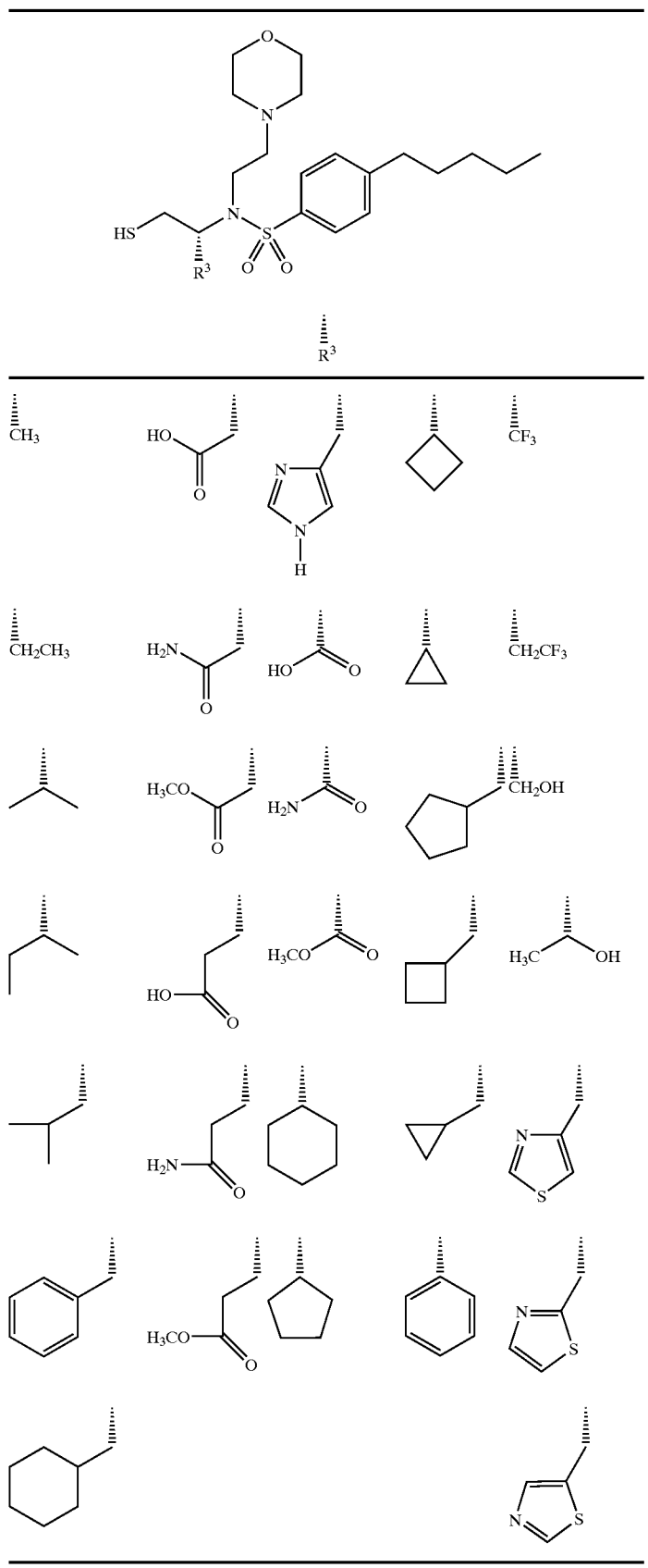

TABLE 18
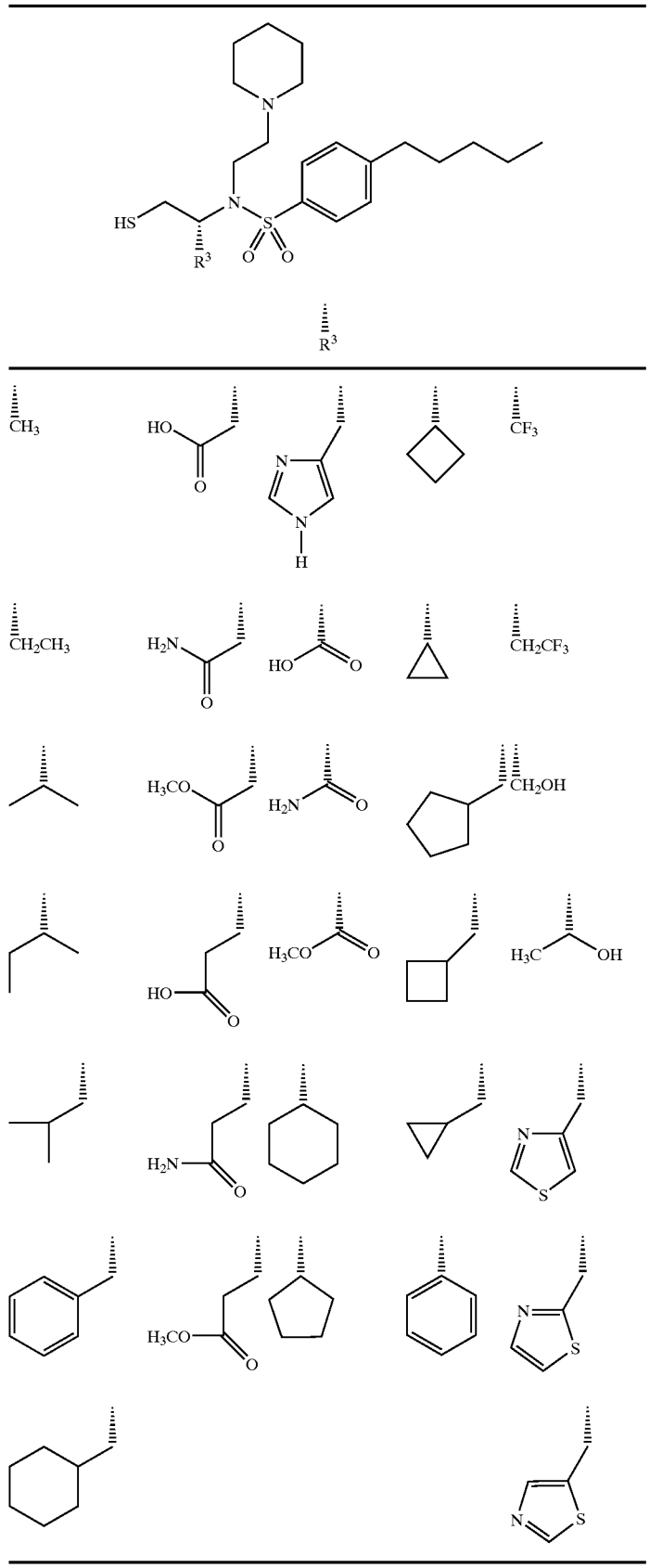

TABLE 19
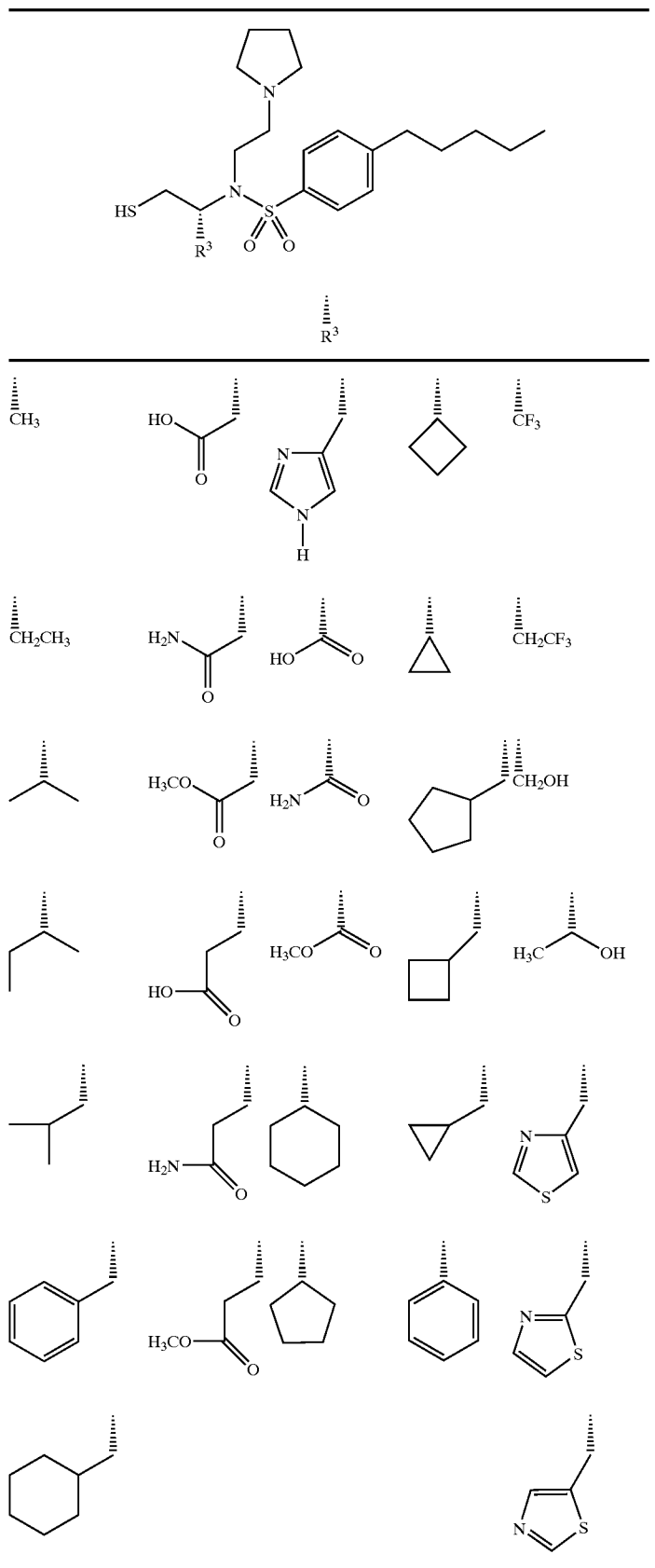

TABLE 20
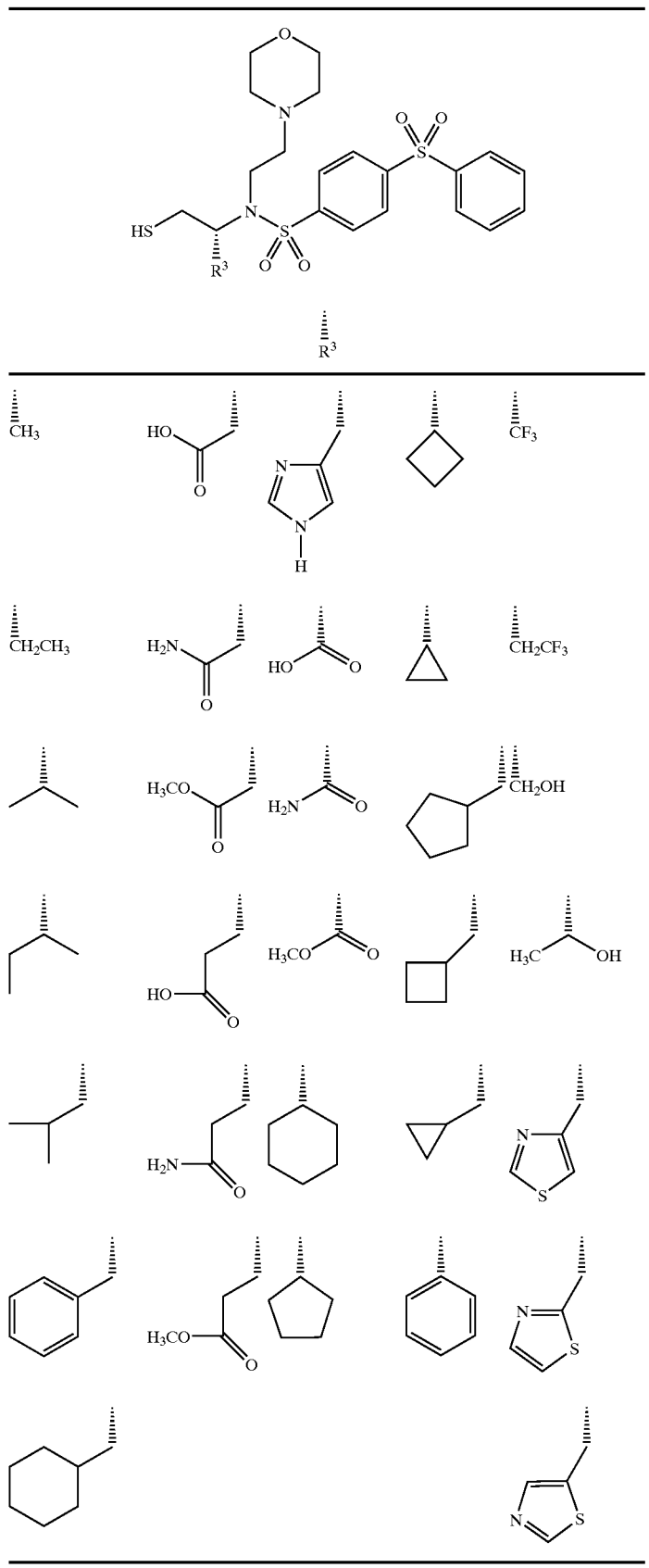

TABLE 21
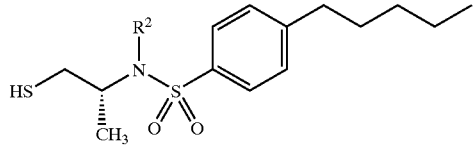
—R²
| —H | | |
|---|---|---|
| —CH₃ | 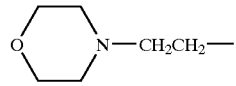 | 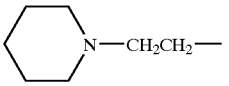 |
| —CH₂CH₃ | | |
| —CH₂CH₂CH₃ |  | 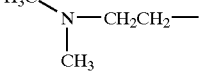 |
| —CH₂CH₂CH₂CH₃ | | |
| —CH₂CH₂CH₂CH₂CH₃ | 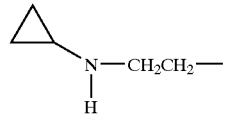 | 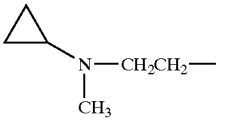 |
| —CH₂CH₂CH₂CH₂CH₂CH₃ | | |
| —CH₂Ph | 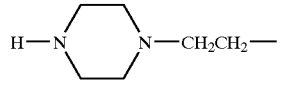 | 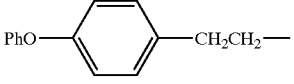 |
| —CH₂CH₂Ph | | |
| —CH₂CH(CH₃)₂ | 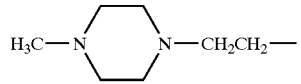 | 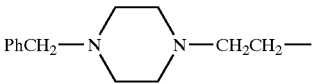 |
| —CH₂CF₃ | | |
| —CH₂CH₂OCH₃ | 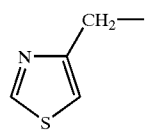 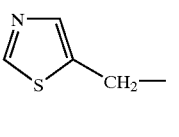 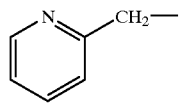 | |
| —CH₂CH₂OH | | |
| —CH₂CO₂H | 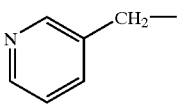 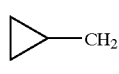 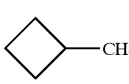 | |
| —CH₂CH₂CO₂H | | |
| —CH₂CH₂CH₂CO₂H | 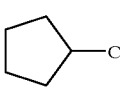 | |
| —CH₂CH₂CH₂CH₂CO₂H | | |
| —CH₂CH₂CH₂CH₂CH₂CO₂H | 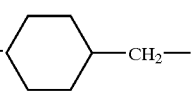 | 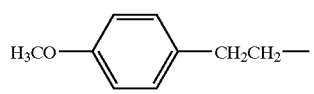 |

TABLE 22
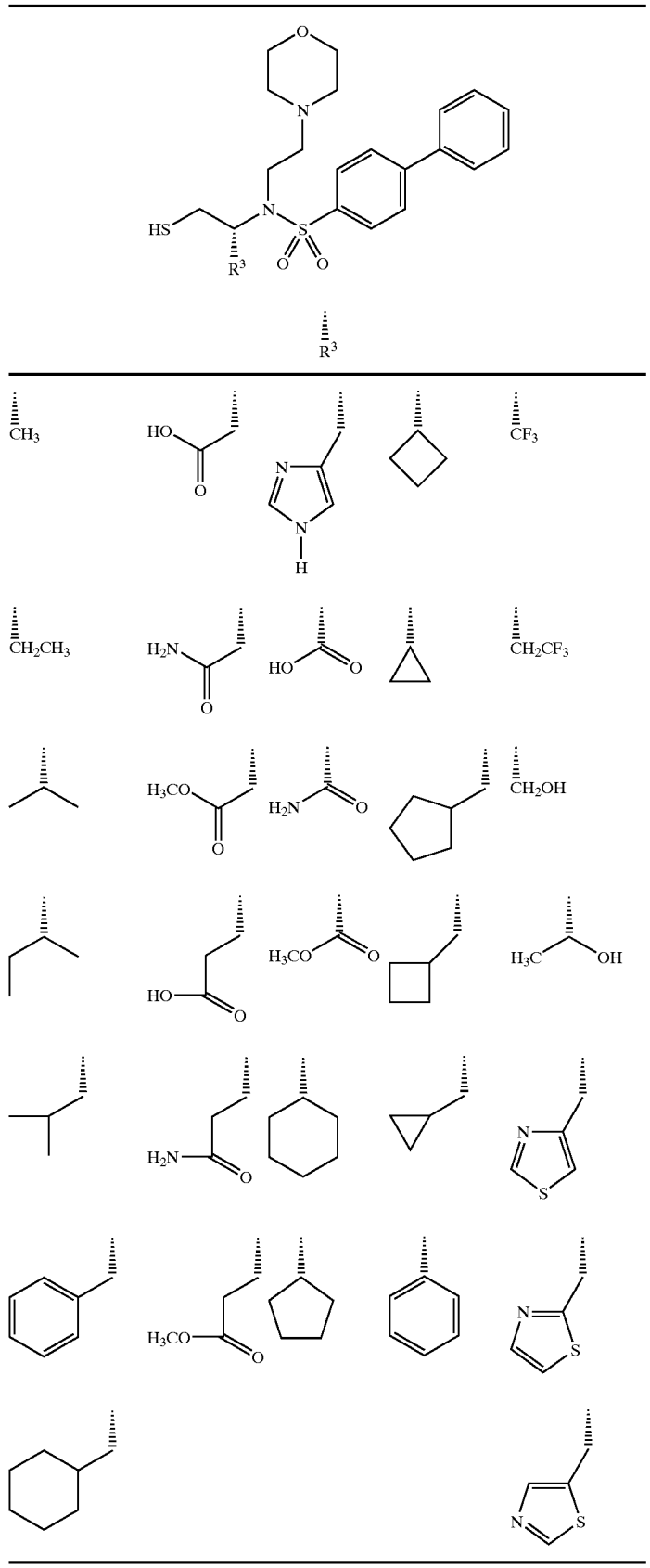

TABLE 23
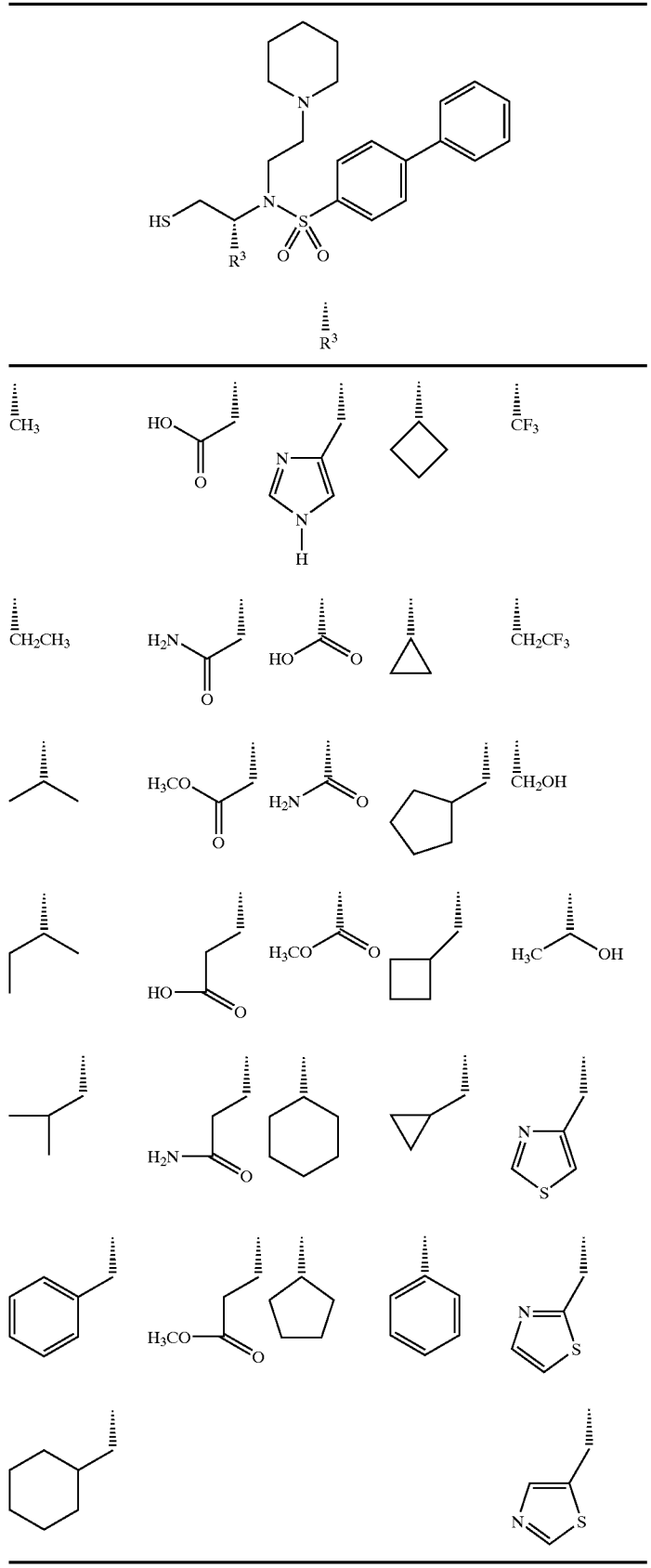

TABLE 24
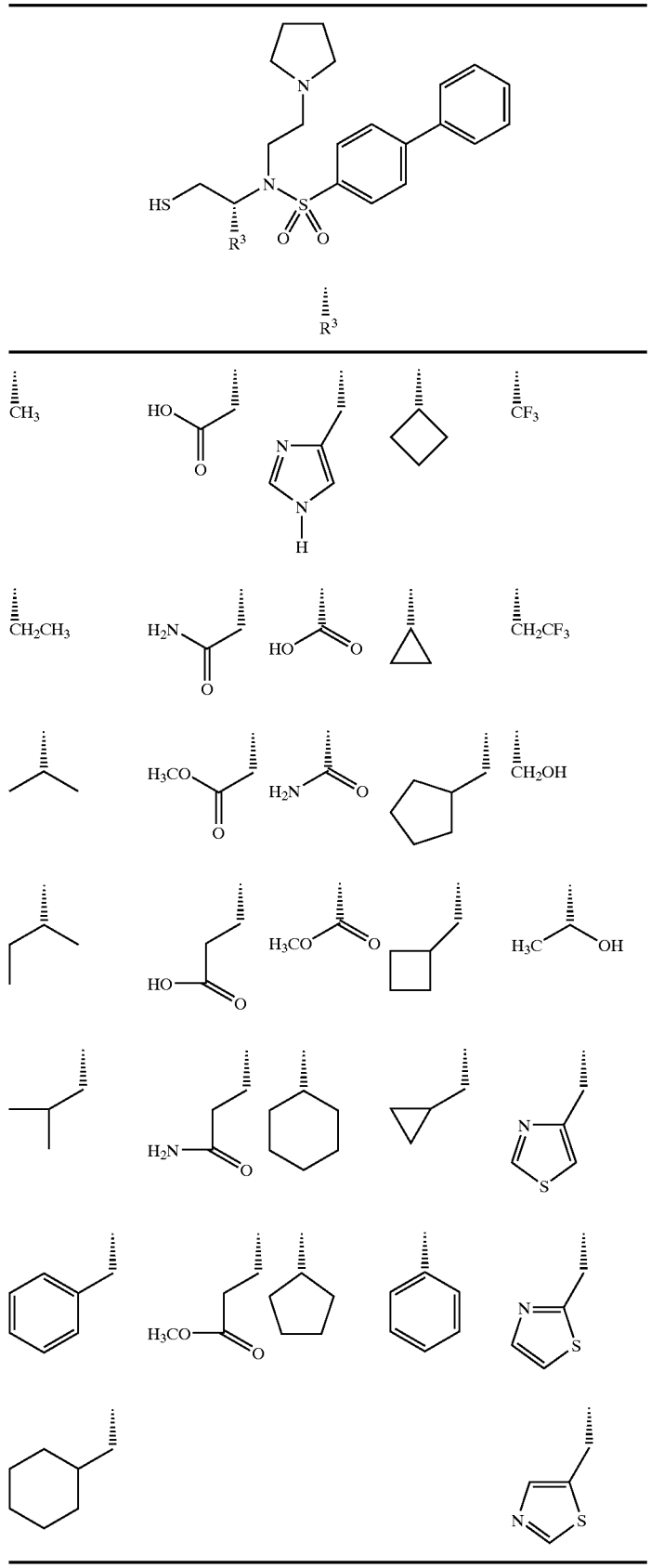

TABLE 25
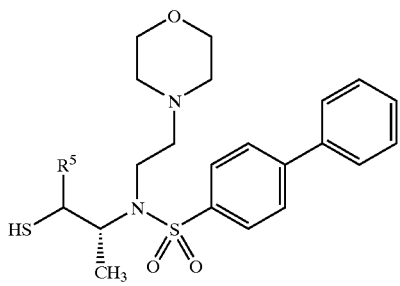

TABLE 26

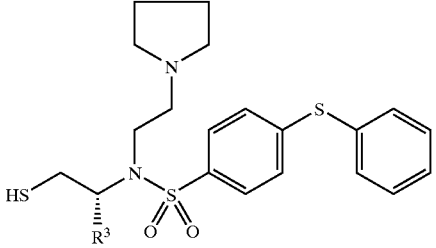

| R³ | | | | |
|---|---|---|---|---|
| CH₃ | HOOC-CH₂- | imidazol-4-ylmethyl | cyclobutyl | CF₃ |
| CH₂CH₃ | H₂NCO-CH₂- | HOOC- (cyclopropyl-CH-) | cyclopropyl | CH₂CF₃ |
| iPr | H₃COOC-CH₂- | H₂NCO- | cyclopentylmethyl | CH₂OH |
| sec-Bu | HOOC-CH₂CH₂- | H₃COOC-CH₂- (cyclobutylmethyl) | cyclobutylmethyl | CH(OH)CH₃ |
| iBu | H₂NCO-CH₂CH₂- | piperidin-1-yl | cyclopropylmethyl | thiazol-4-ylmethyl |
| benzyl | H₃COOC-CH₂CH₂- | cyclopentyl | phenyl | thiazol-2-ylmethyl |
| cyclohexylmethyl | | | | thiazol-5-ylmethyl |

TABLE 27
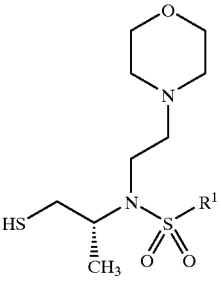

TABLE 28
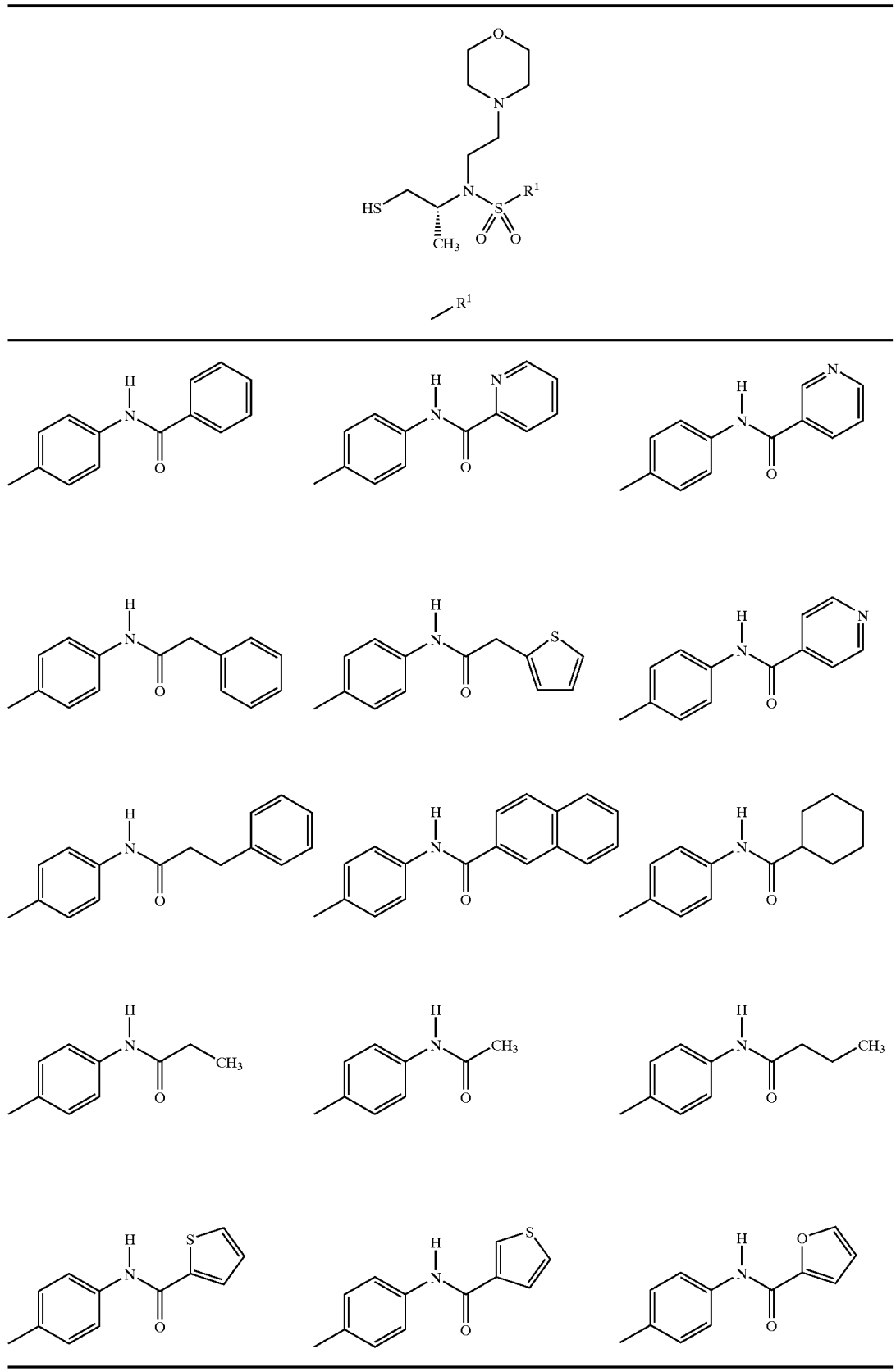

TABLE 29
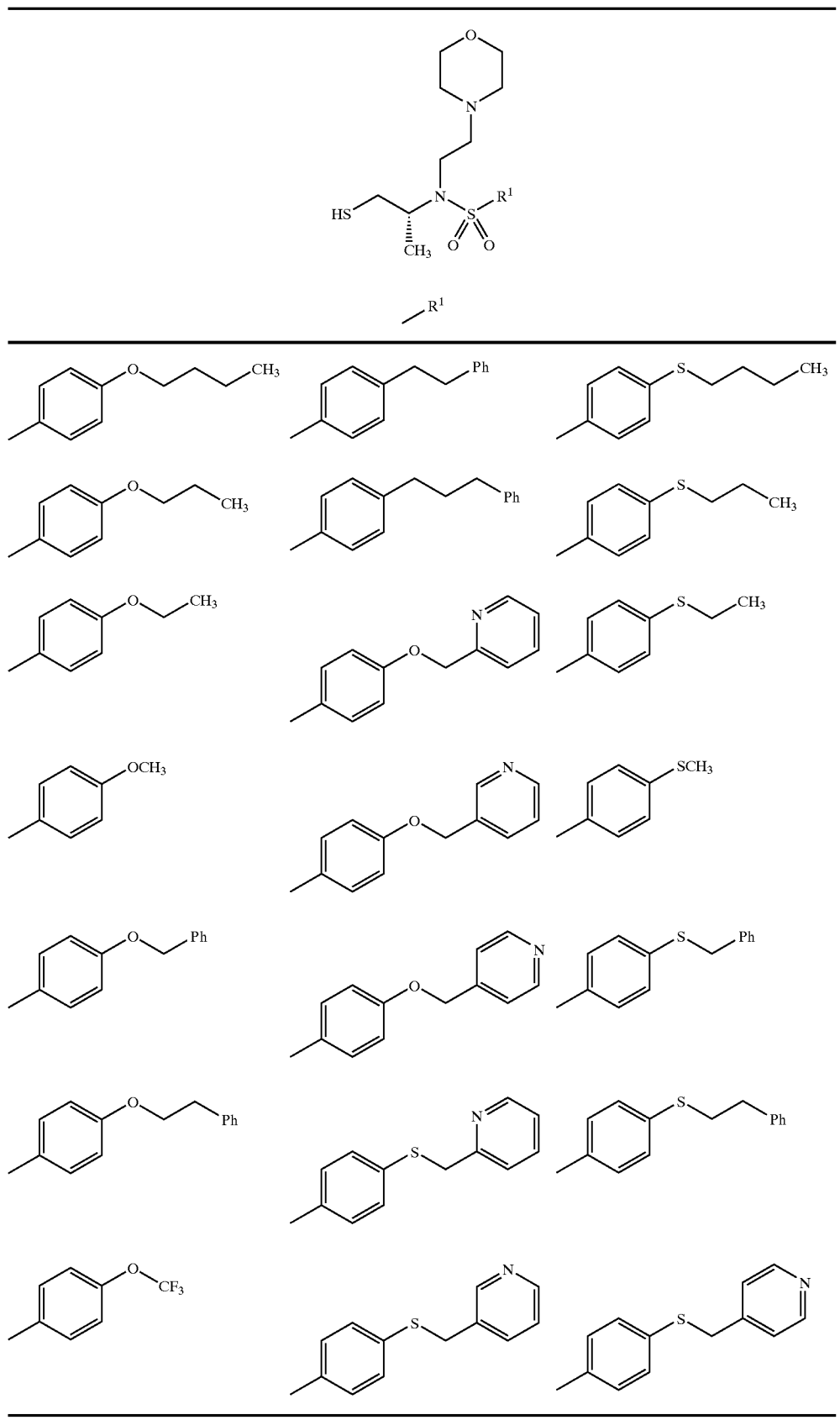

TABLE 30
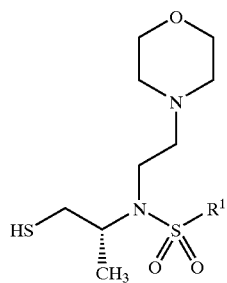
—R¹
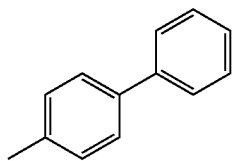
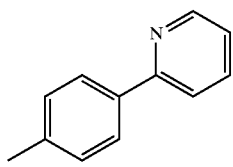 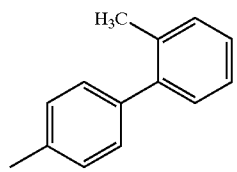 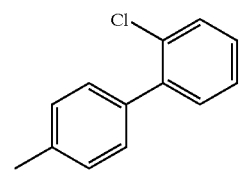 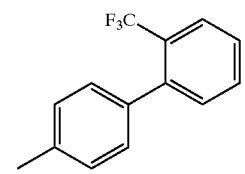
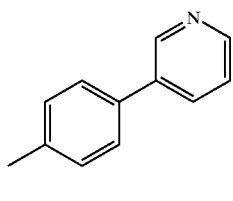 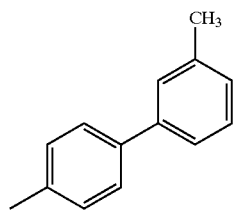 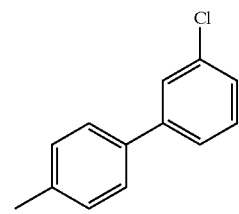 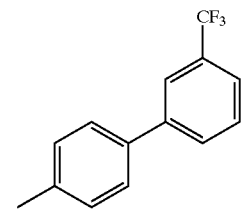
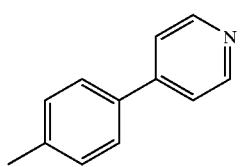 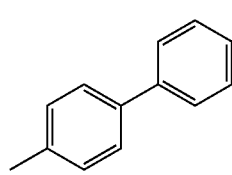 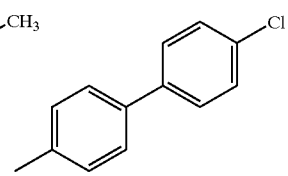 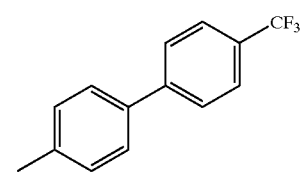
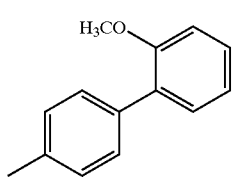 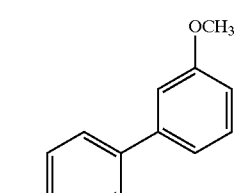 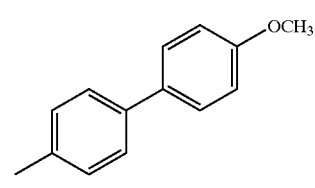

TABLE 31
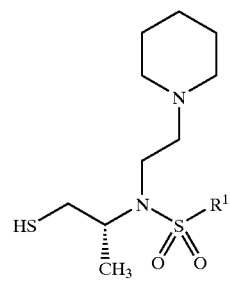
—R¹
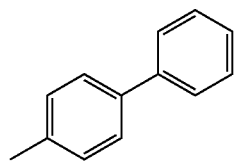
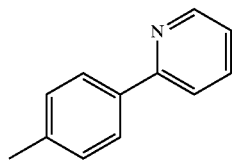 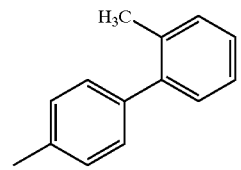 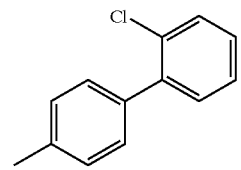 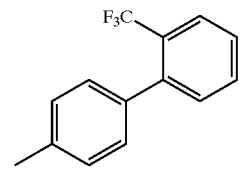
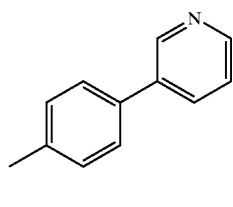 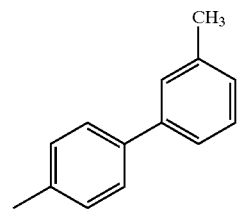 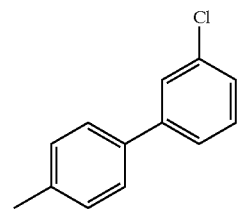 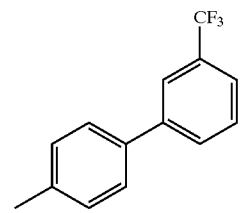
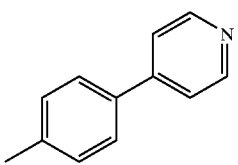 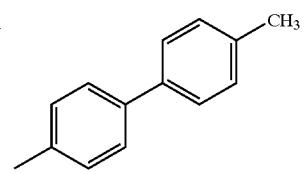 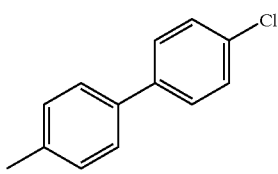 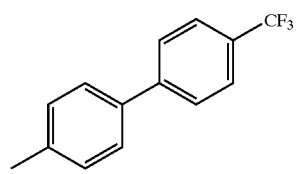
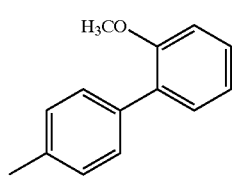 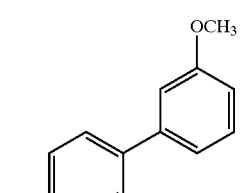 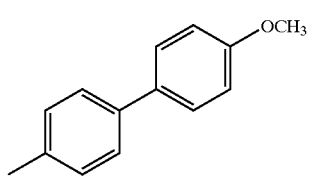

TABLE 32
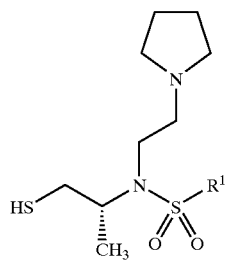
—R¹
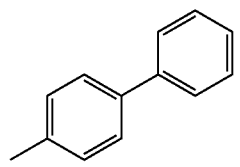
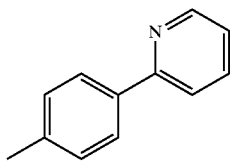 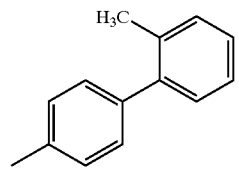 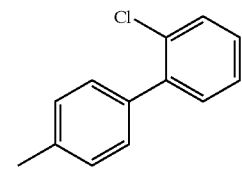 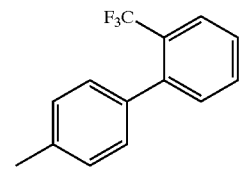
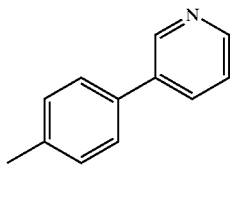 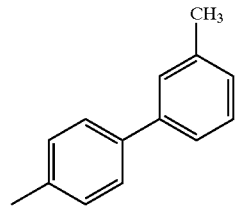 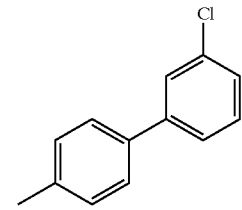 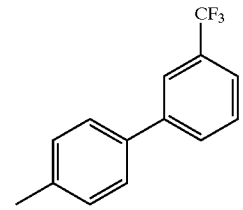
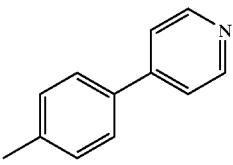 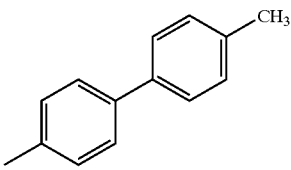 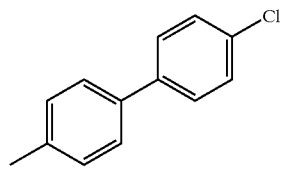 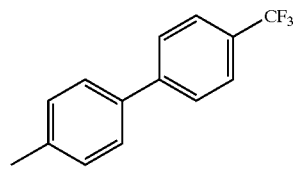
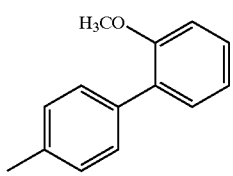 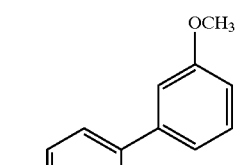 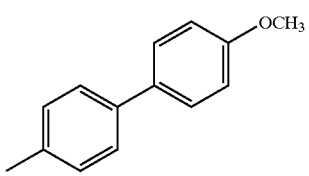

TABLE 33
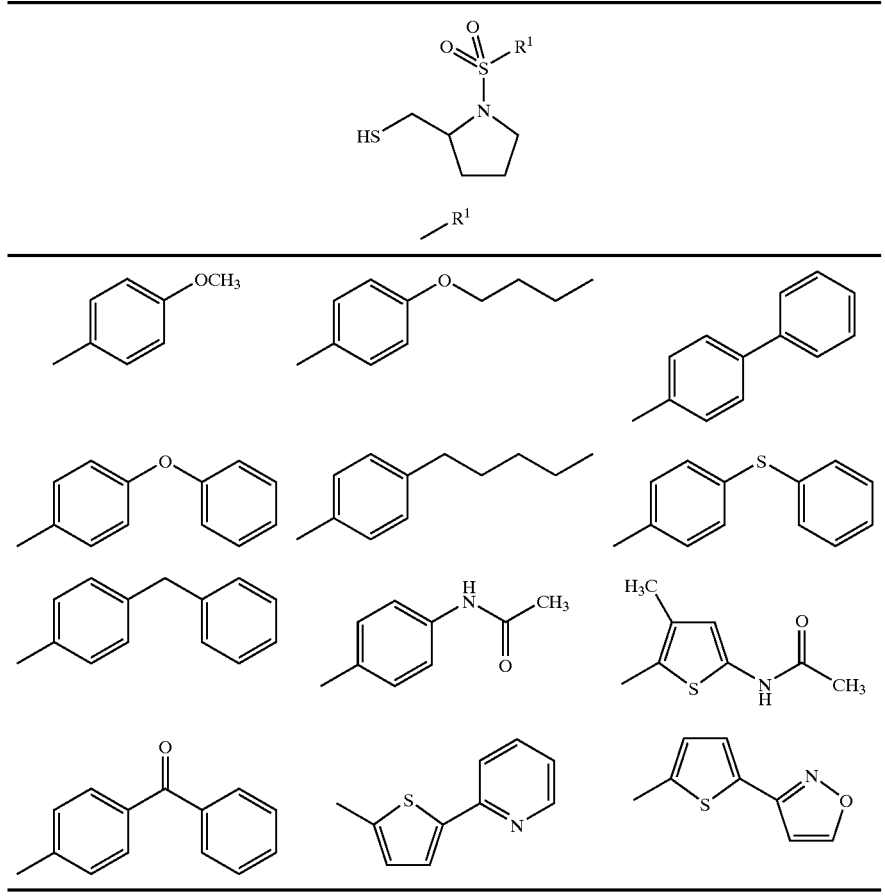
TABLE 34
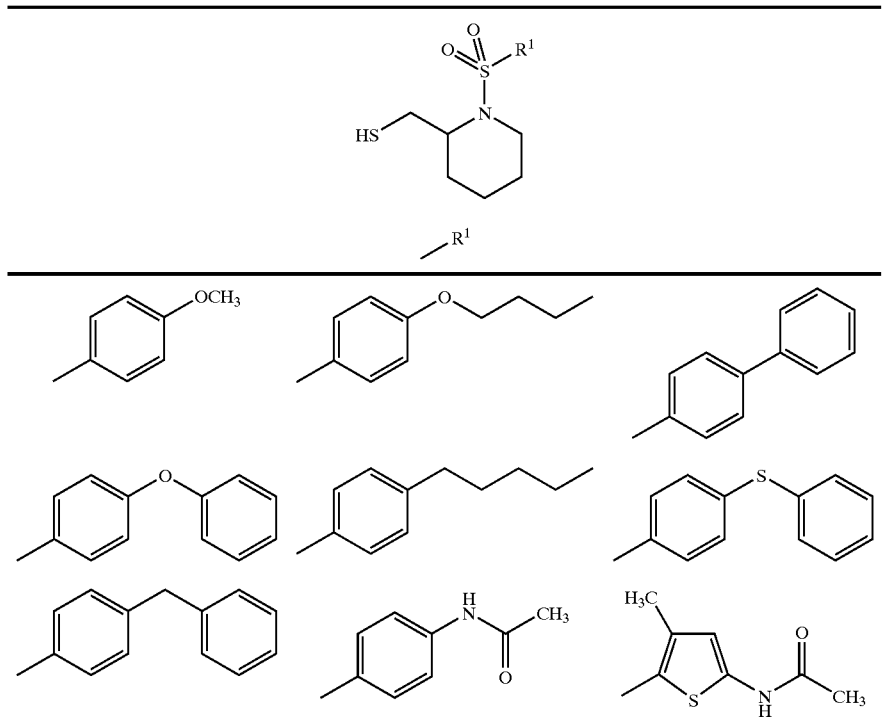

TABLE 34-continued
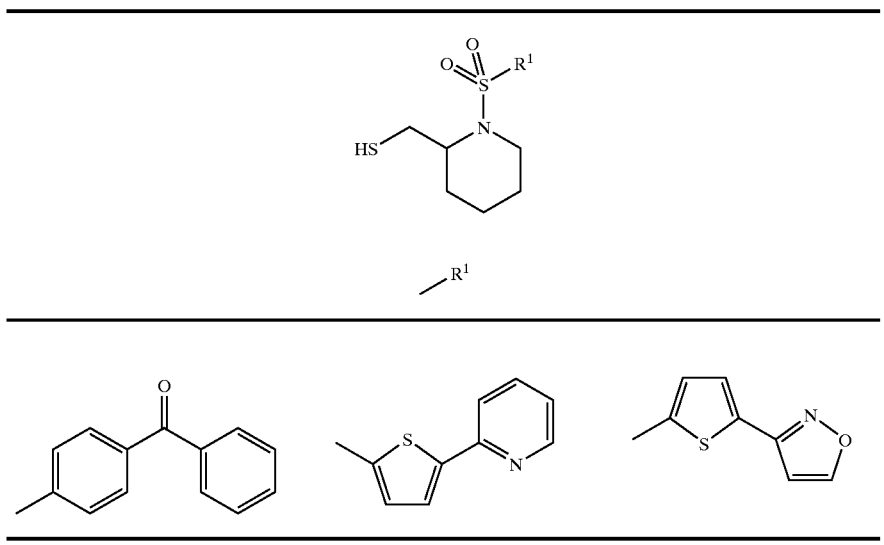
TABLE 35
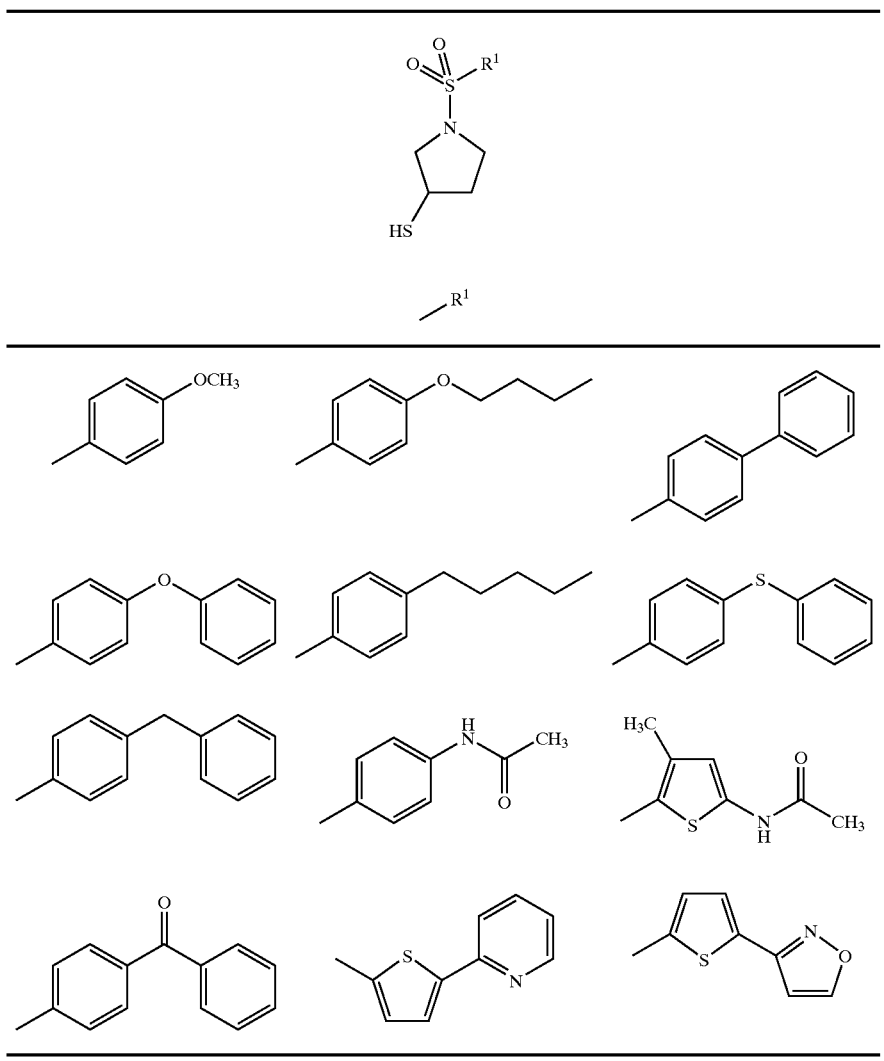

TABLE 36
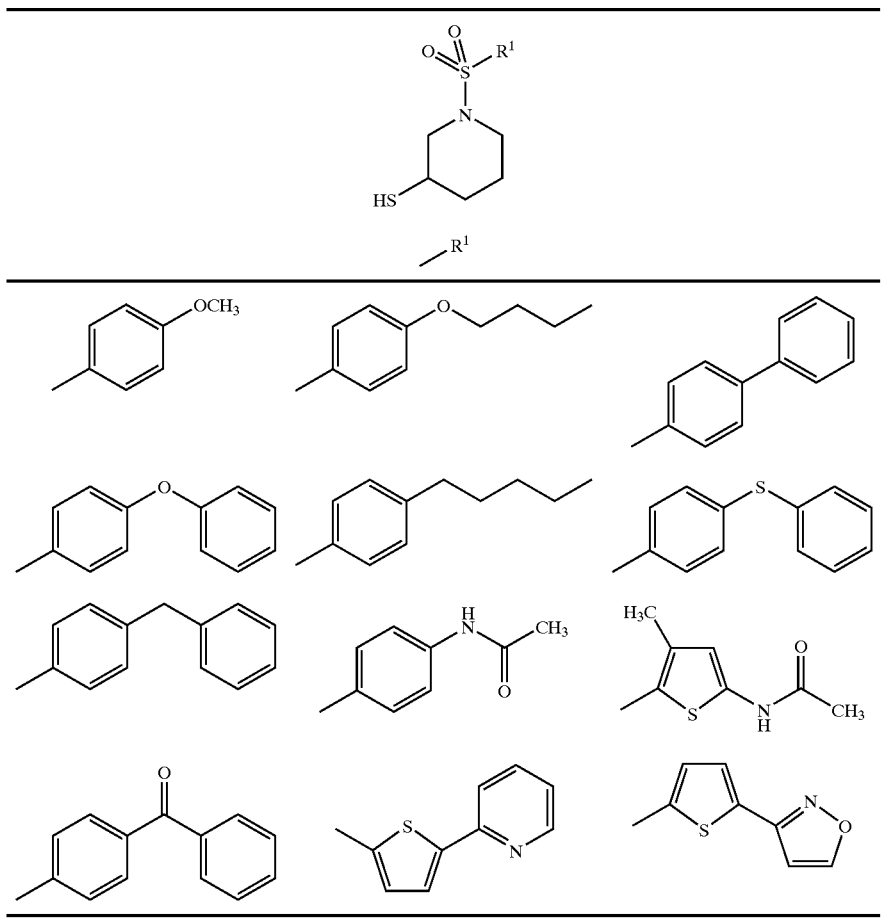
TABLE 37
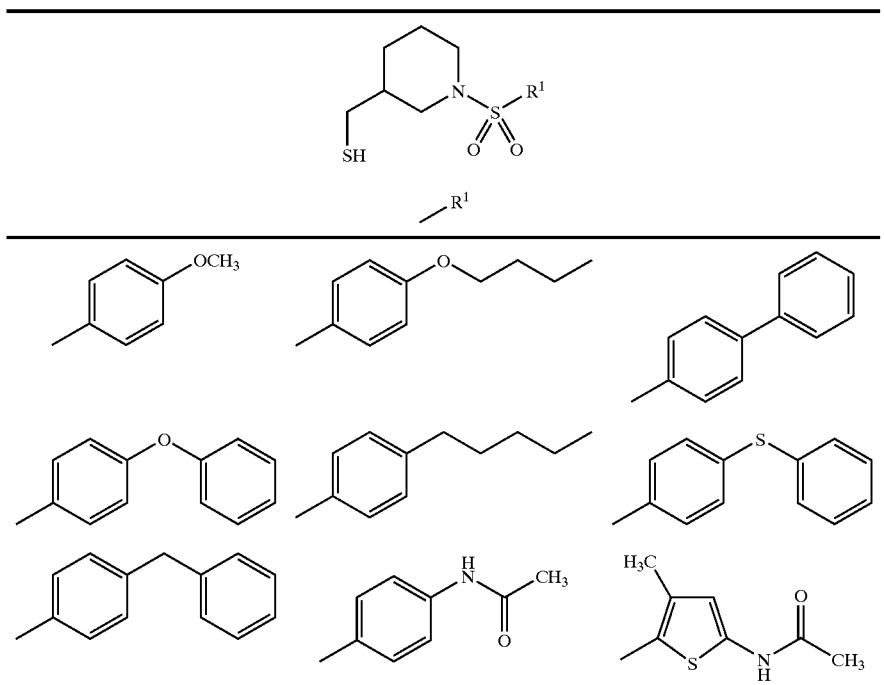

TABLE 37-continued
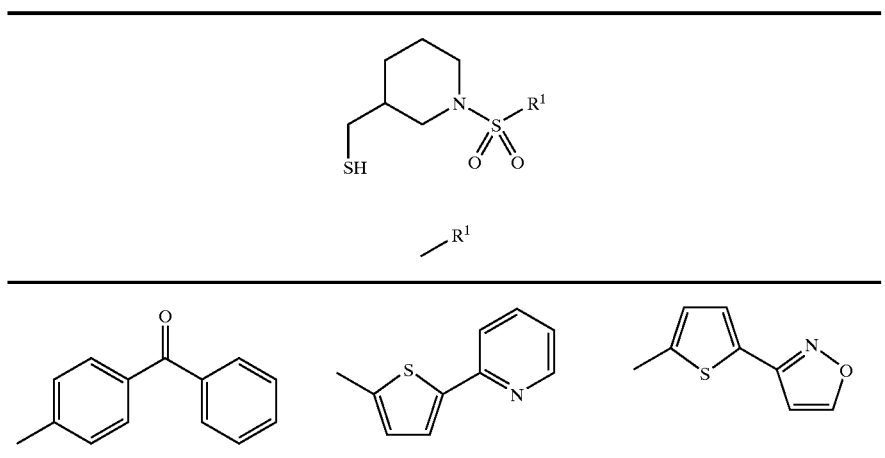
TABLE 38
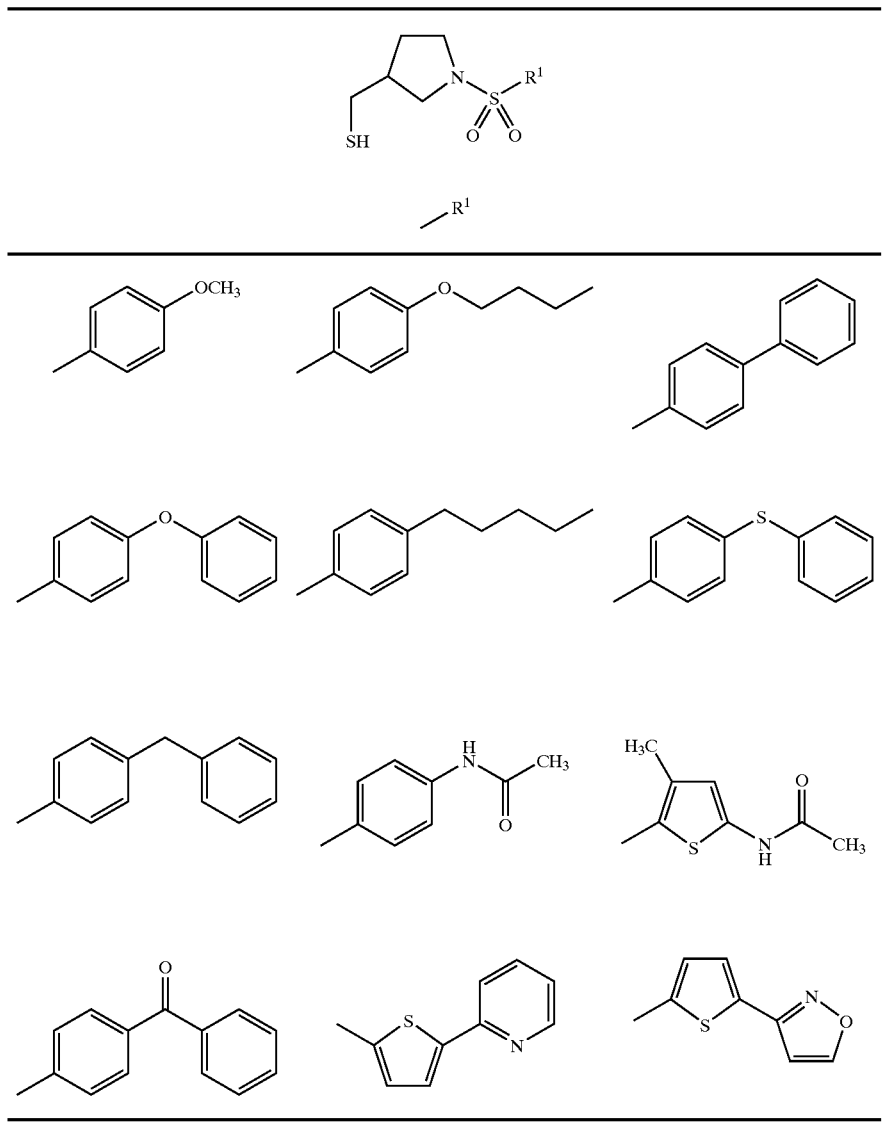

TABLE 39
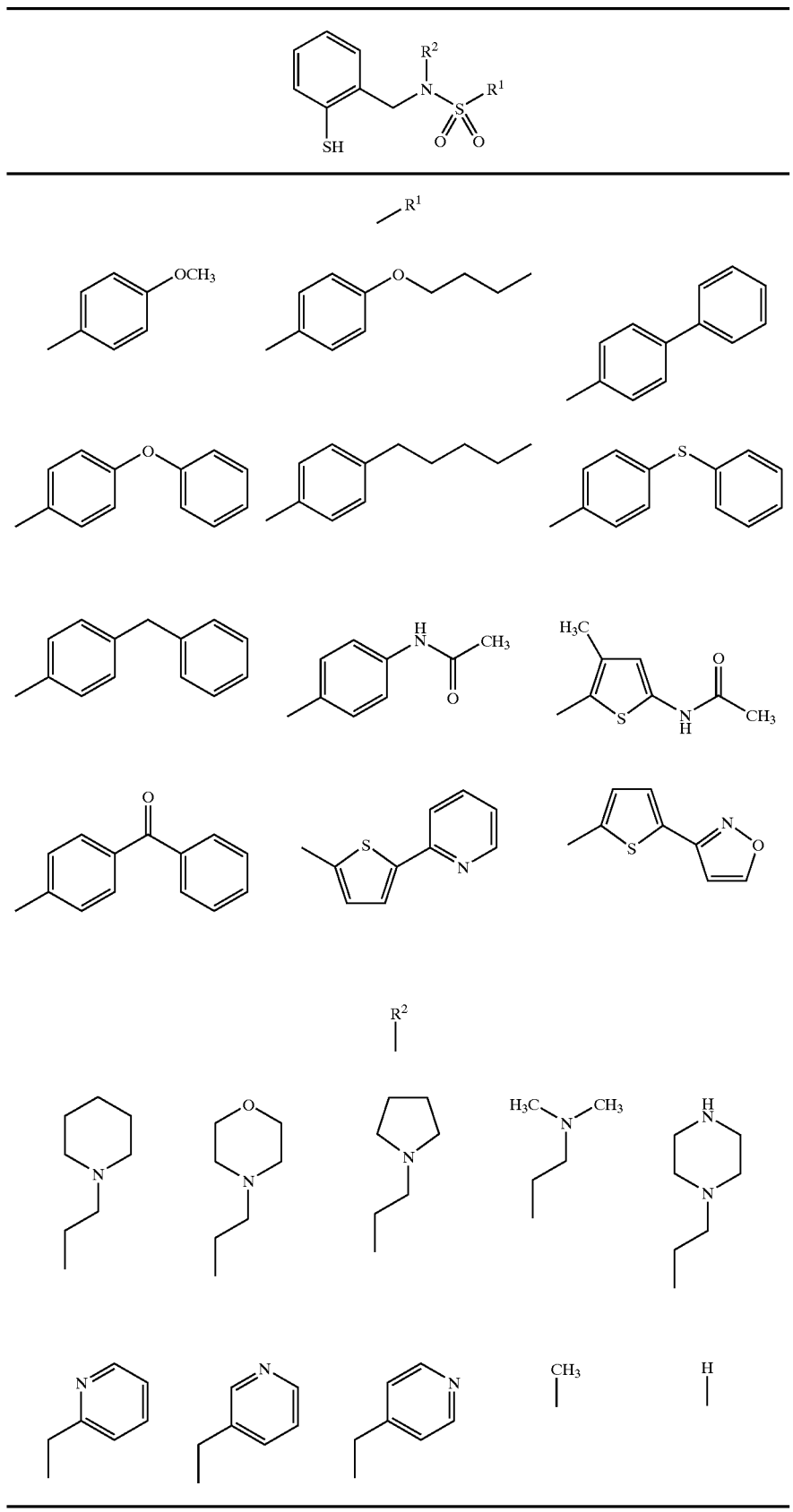

TABLE 40
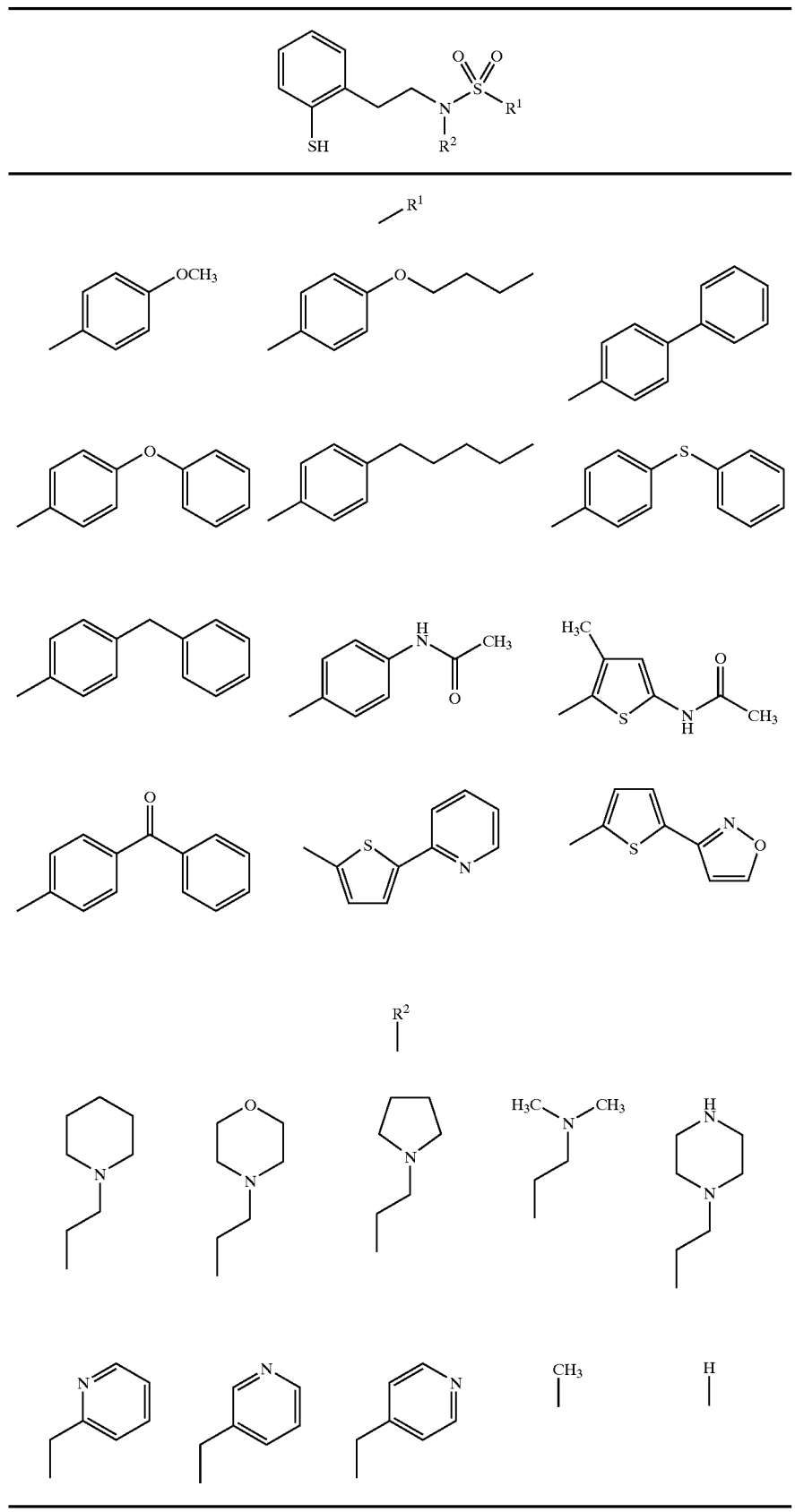

TABLE 41
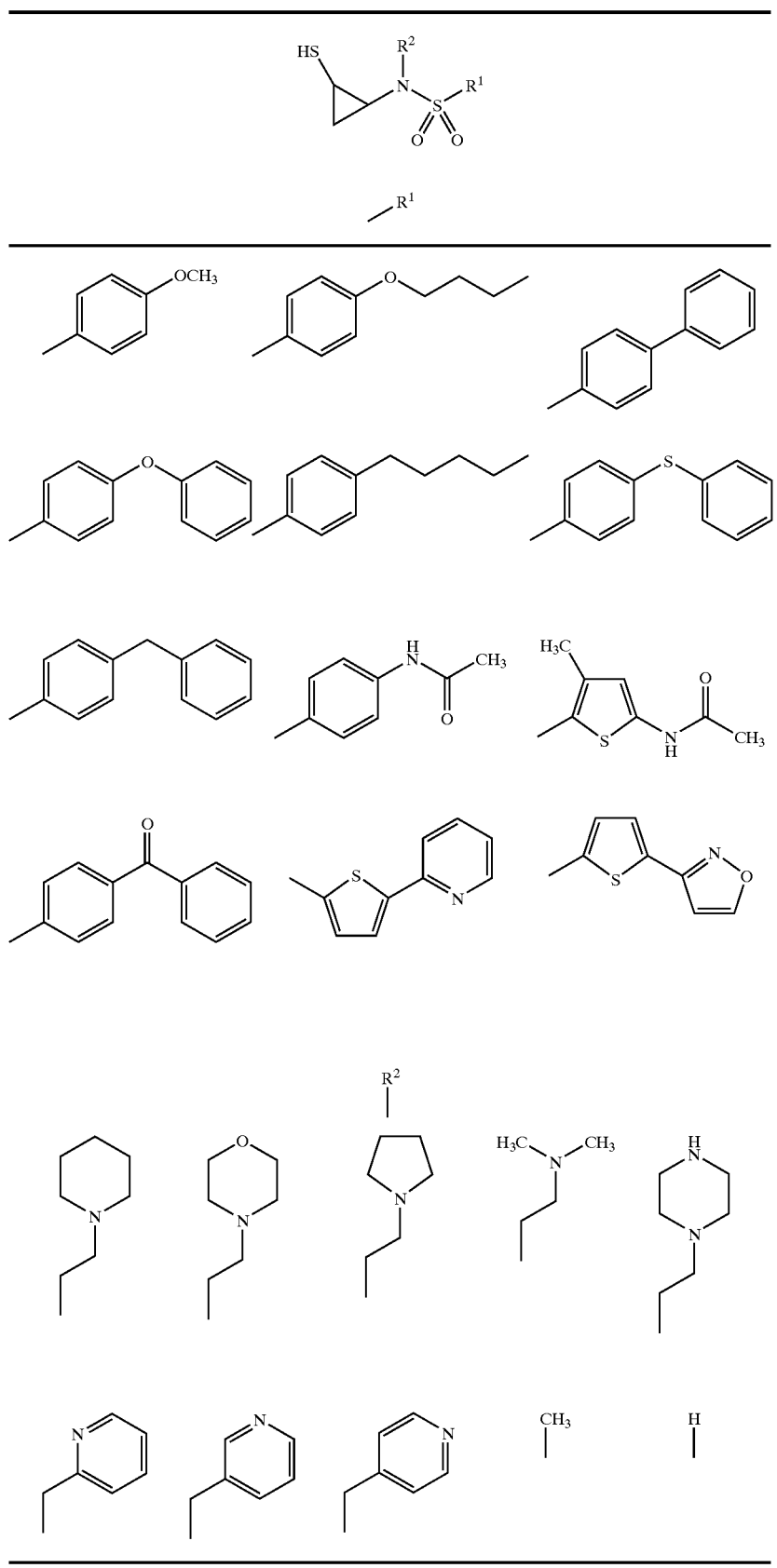

TABLE 42
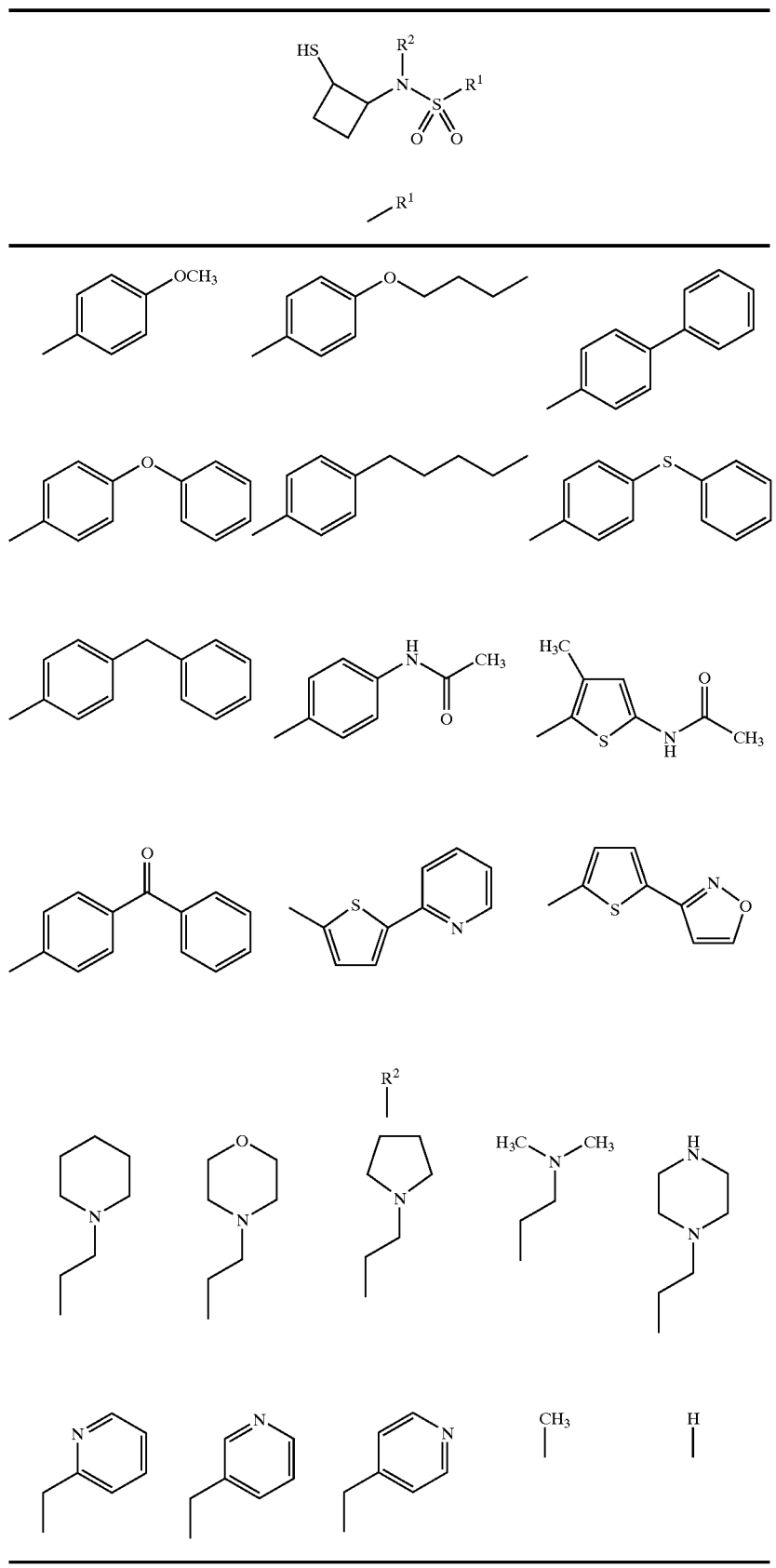

TABLE 43
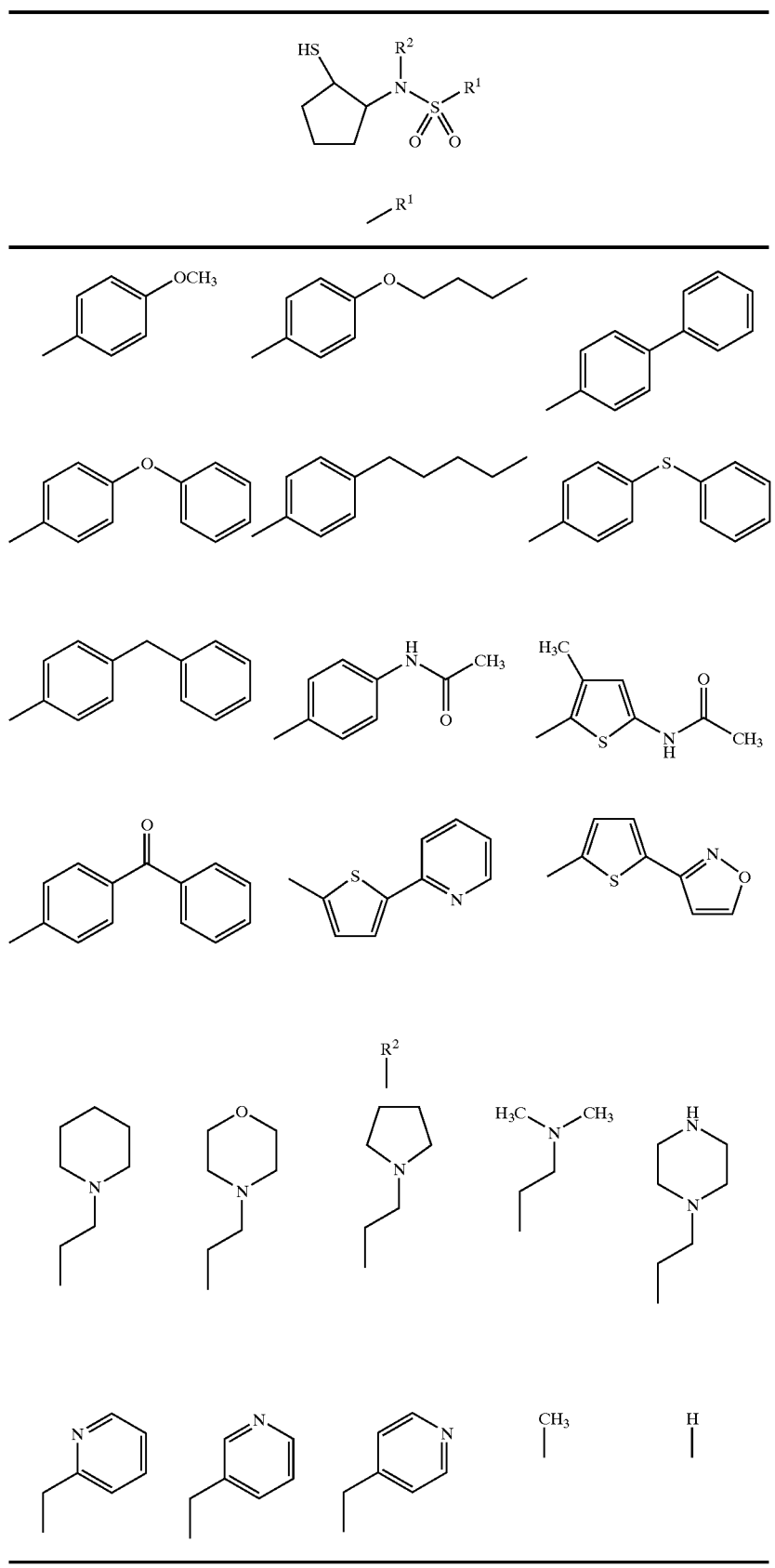

TABLE 44
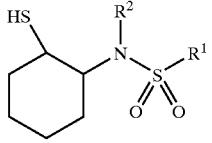
| —R¹ |
|---|
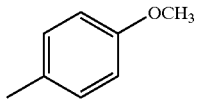
R²
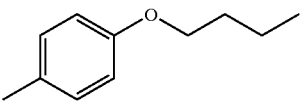
TABLE 45
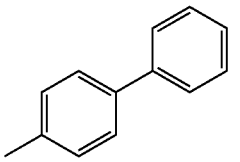

TABLE 45-continued
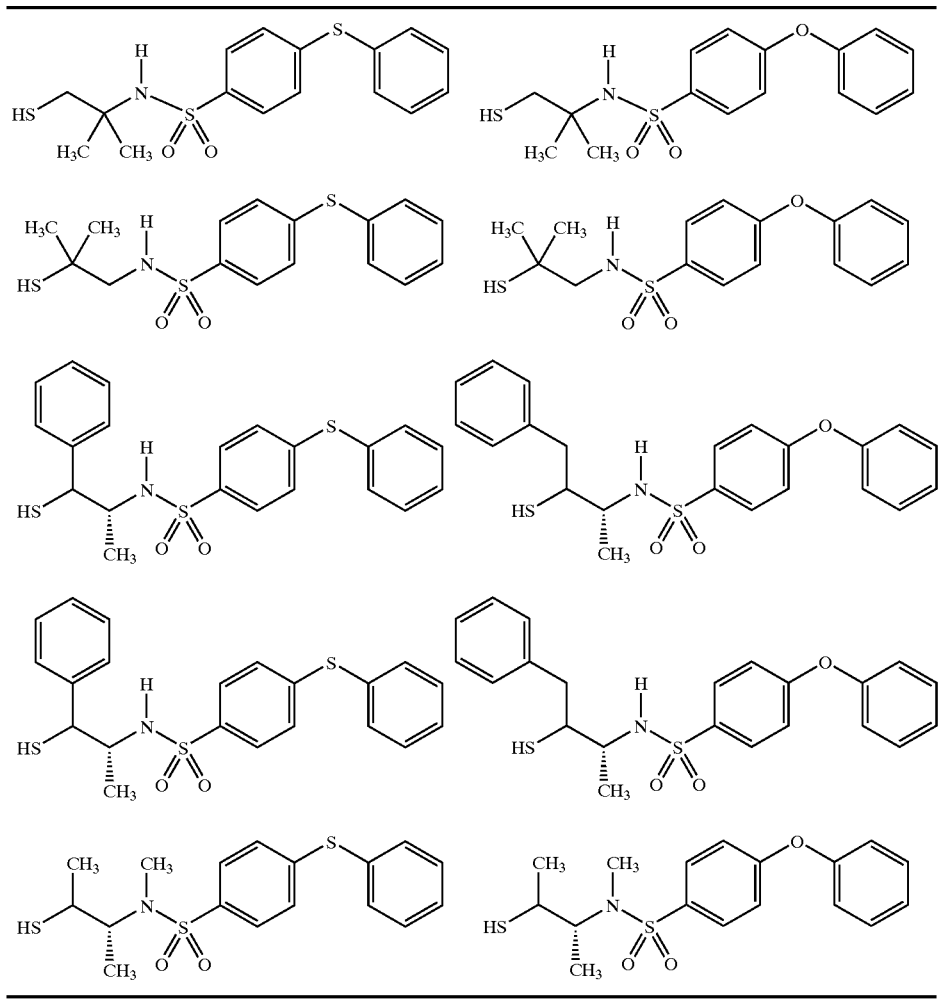
TABLE 46
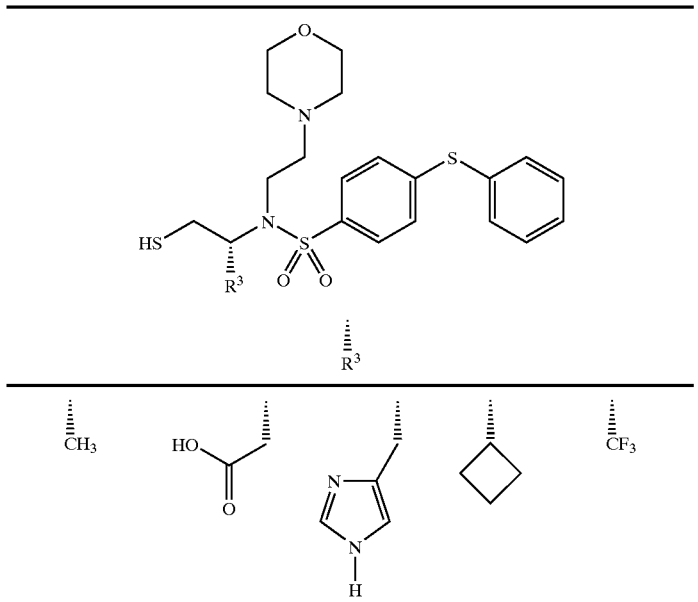

TABLE 46-continued
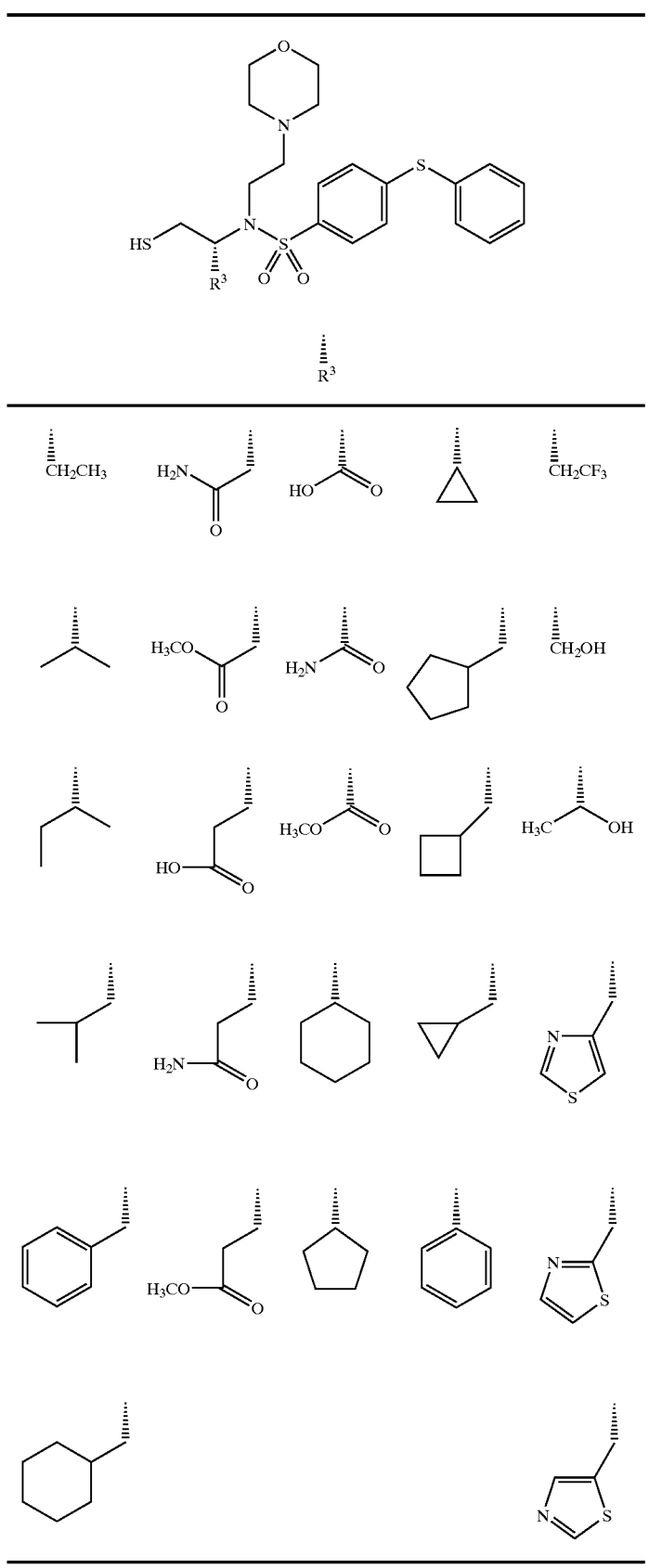

TABLE 47
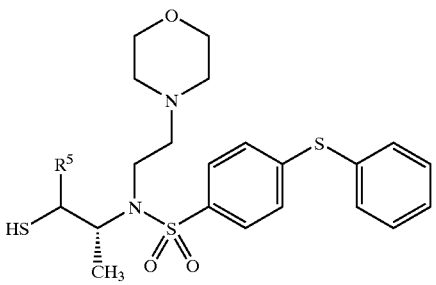
| R⁵ | | | | | |
|---|---|---|---|---|---|

TABLE 48
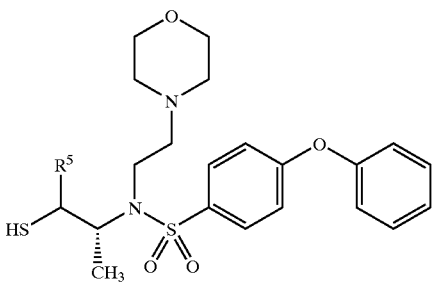
| R⁵ | | | | | |
|---|---|---|---|---|---|

TABLE 49

[Structure: 4-(phenylthio)-N-[(R)-1-mercapto-2-propyl]-N-R²-benzenesulfonamide]

| —R² | | |
|---|---|---|
| —H | | |
| —CH₃ | morpholino-CH₂CH₂— | piperidino-CH₂CH₂— |
| —CH₂CH₃ | | H₃C,CH₃-N—CH₂CH₂— |
| —CH₂CH₂CH₃ | pyrrolidino-CH₂CH₂— | (dimethylamino)ethyl |
| —CH₂CH₂CH₂CH₃ | | |
| —CH₂CH₂CH₂CH₂CH₃ | cyclopropyl-NH—CH₂CH₂— | cyclopropyl-N(CH₃)—CH₂CH₂— |
| —CH₂CH₂CH₂CH₂CH₂CH₃ | | |
| —CH₂Ph | H-piperazino-CH₂CH₂— | PhO-C₆H₄—CH₂CH₂— |
| —CH₂CH₂Ph | | |
| —CH₂CH(CH₃)₂ | H₃C-piperazino-CH₂CH₂— | PhCH₂-piperazino-CH₂CH₂— |
| —CH₂CF₃ | thiazol-4-yl-CH₂— | thiazol-5-yl-CH₂— | thiazol-2-yl-CH₂— |
| —CH₂CH₂OCH₃ | | | |
| —CH₂CH₂OH | pyridin-2-yl-CH₂— | pyridin-3-yl-CH₂— | pyridin-4-yl-CH₂— |
| —CH₂CO₂H | | | |
| —CH₂CH₂CO₂H | cyclopropyl-CH₂— | cyclobutyl-CH₂— | cyclopentyl-CH₂— | cyclohexyl-CH₂— |
| —CH₂CH₂CH₂CO₂H | | | | |
| —CH₂CH₂CH₂CH₂CO₂H | H₃CO-C₆H₄-CH₂CH₂— | HO₂C-CH(CH₂Ph)— |
| —CH₂CH₂CH₂CH₂CH₂CO₂H | | |

TABLE 50
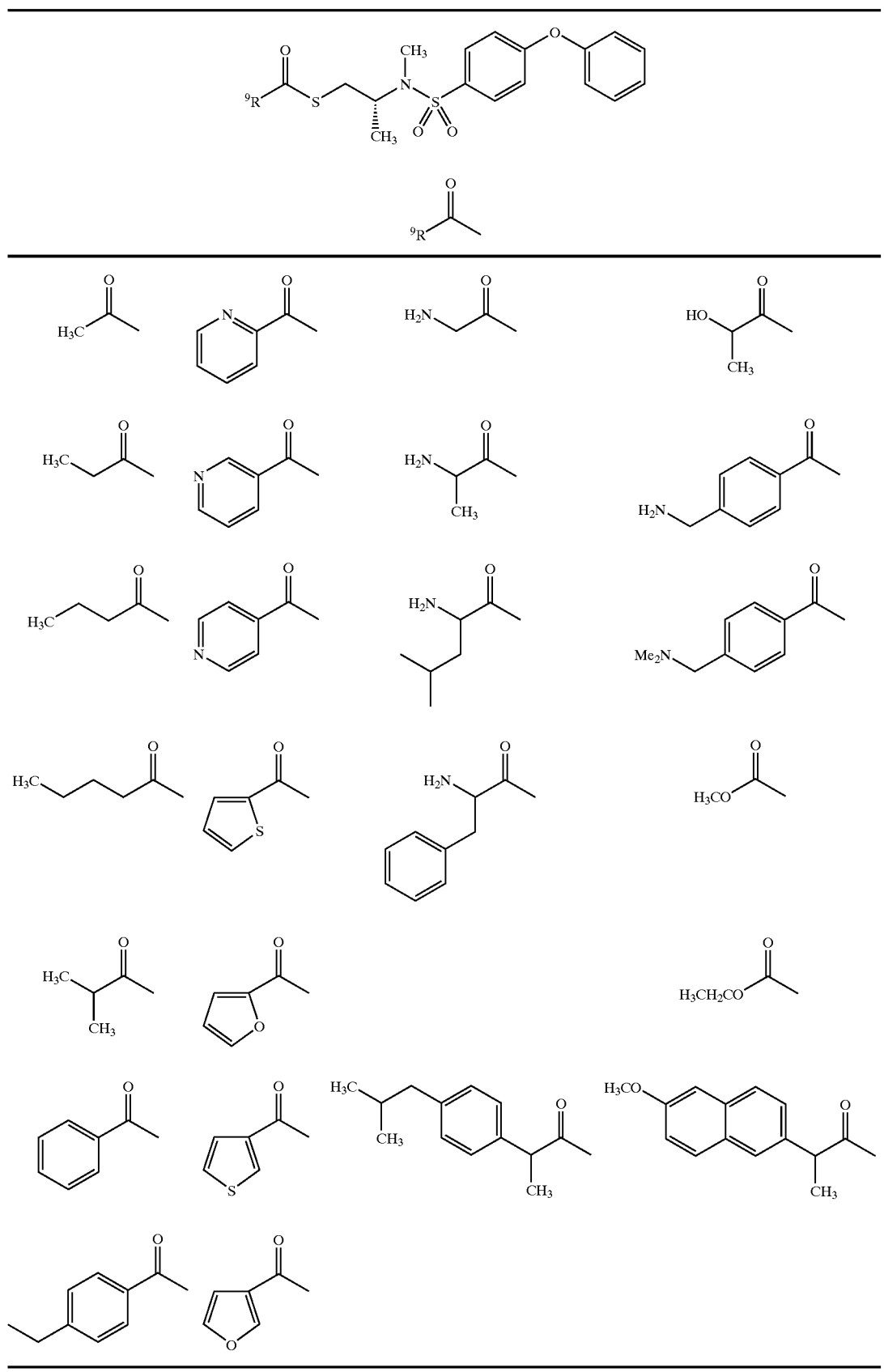

TABLE 51
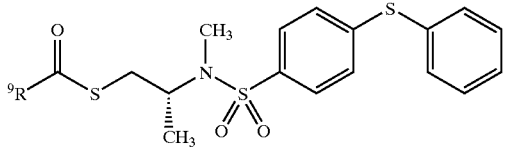

TABLE 52

TABLE 53
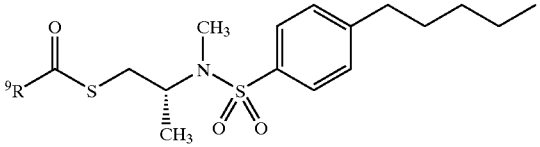

TABLE 54
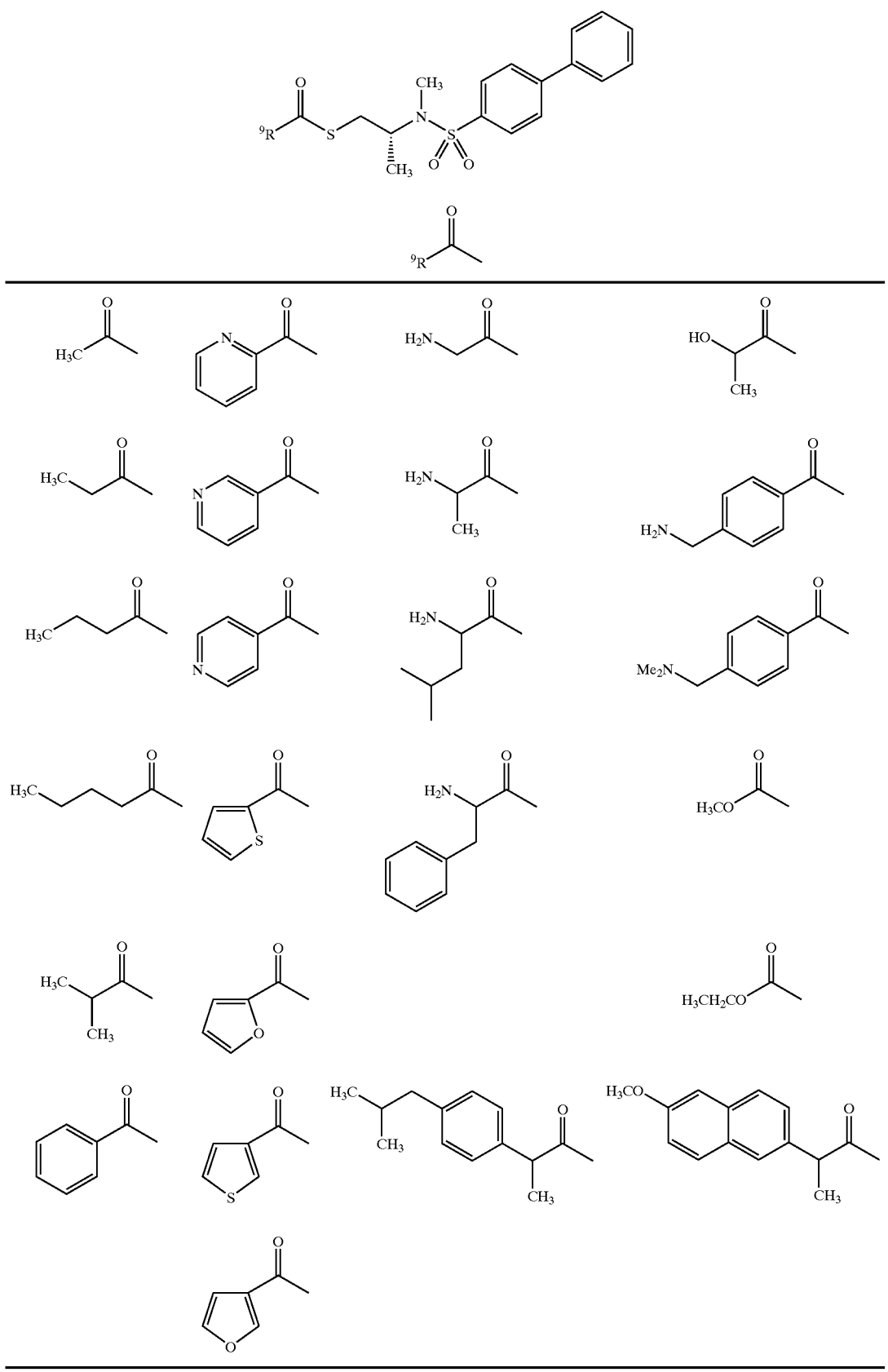

TABLE 55
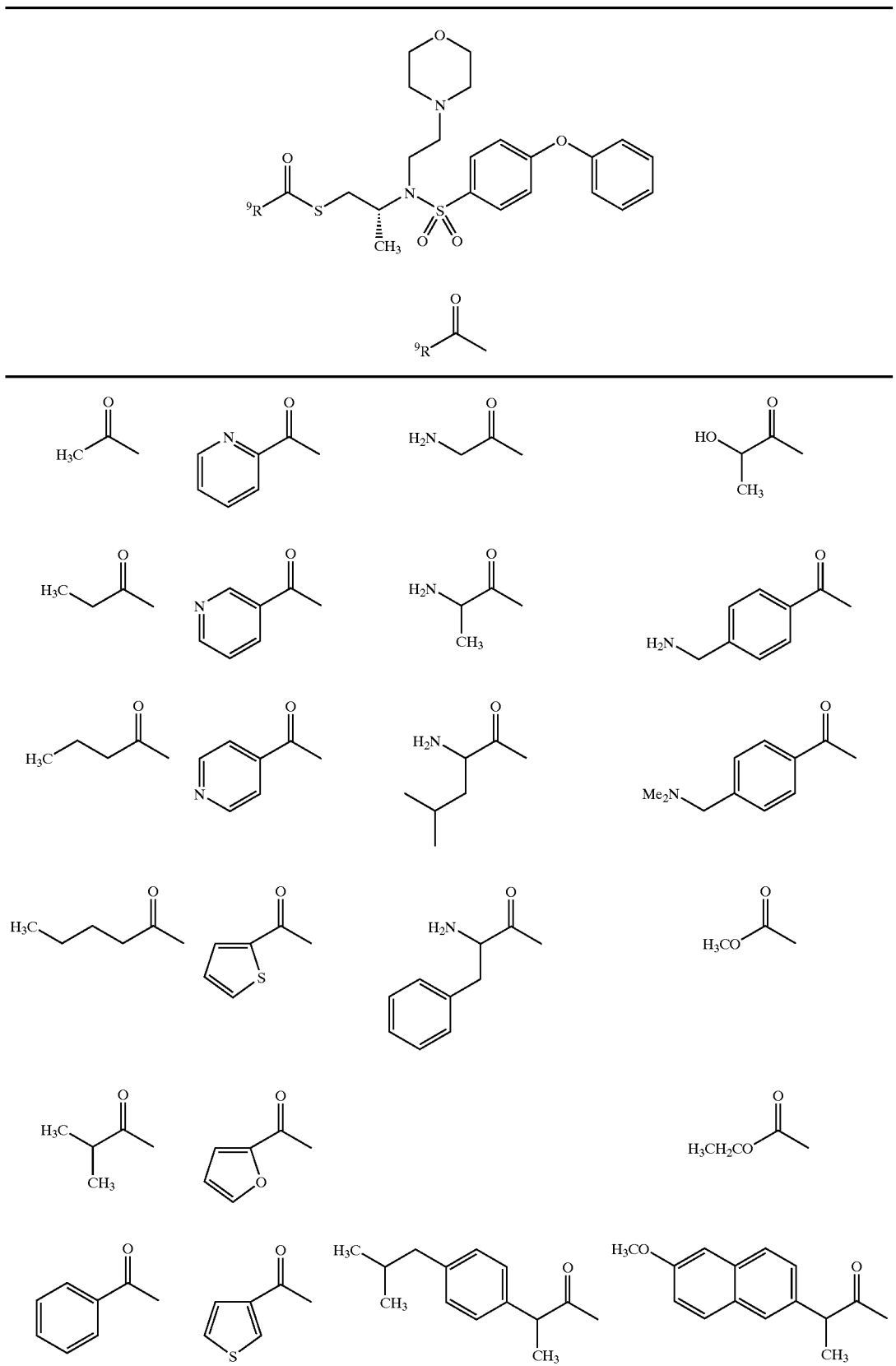

TABLE 55-continued
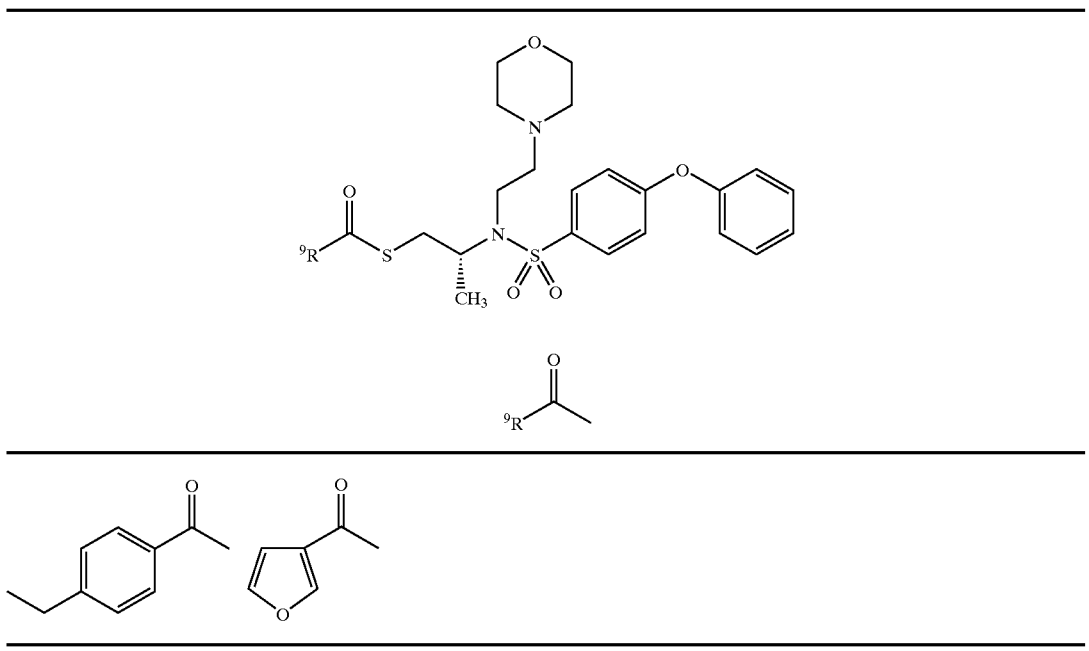
TABLE 56
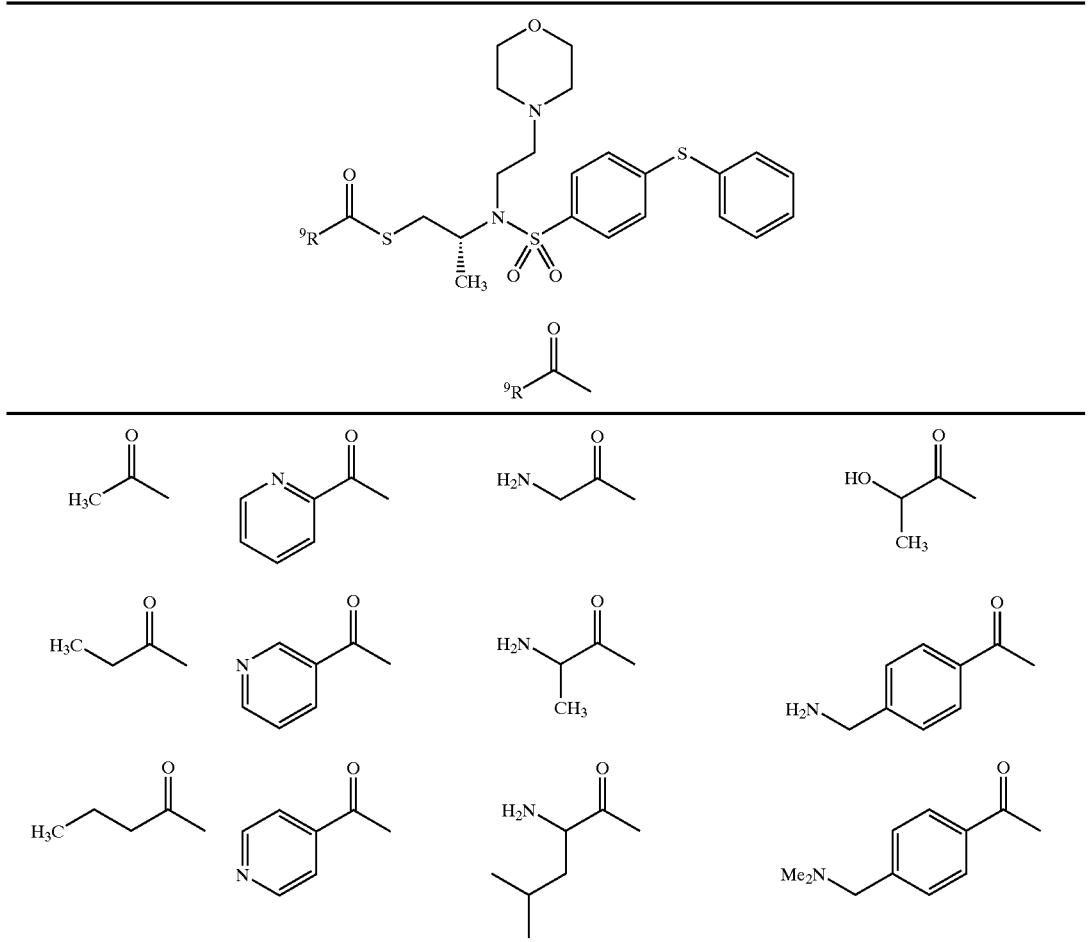

TABLE 56-continued
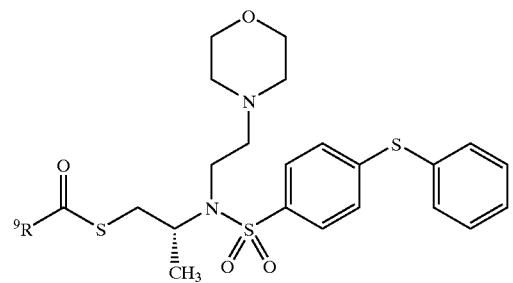
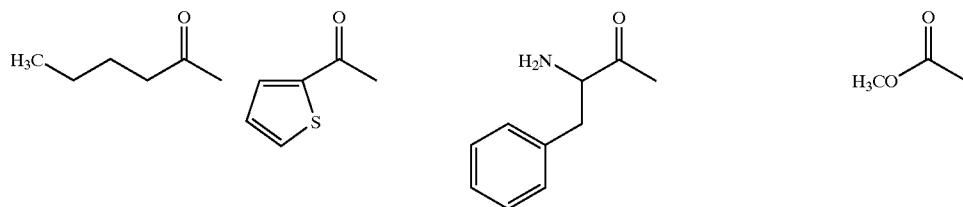
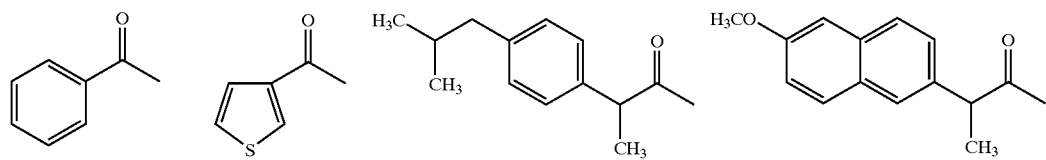
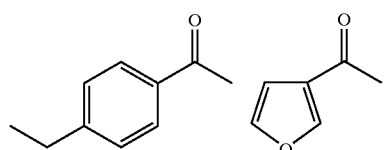

TABLE 57
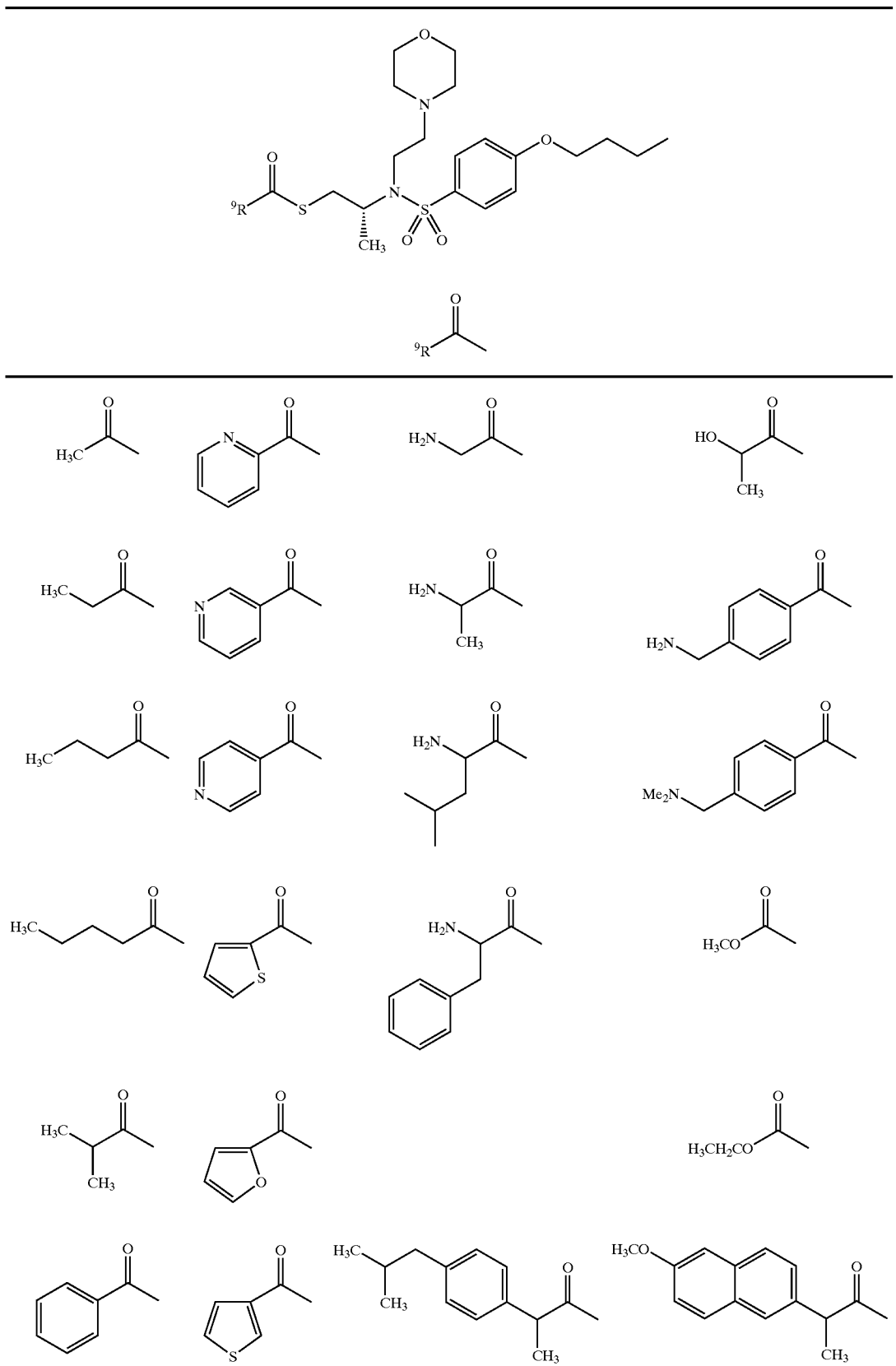

TABLE 57-continued
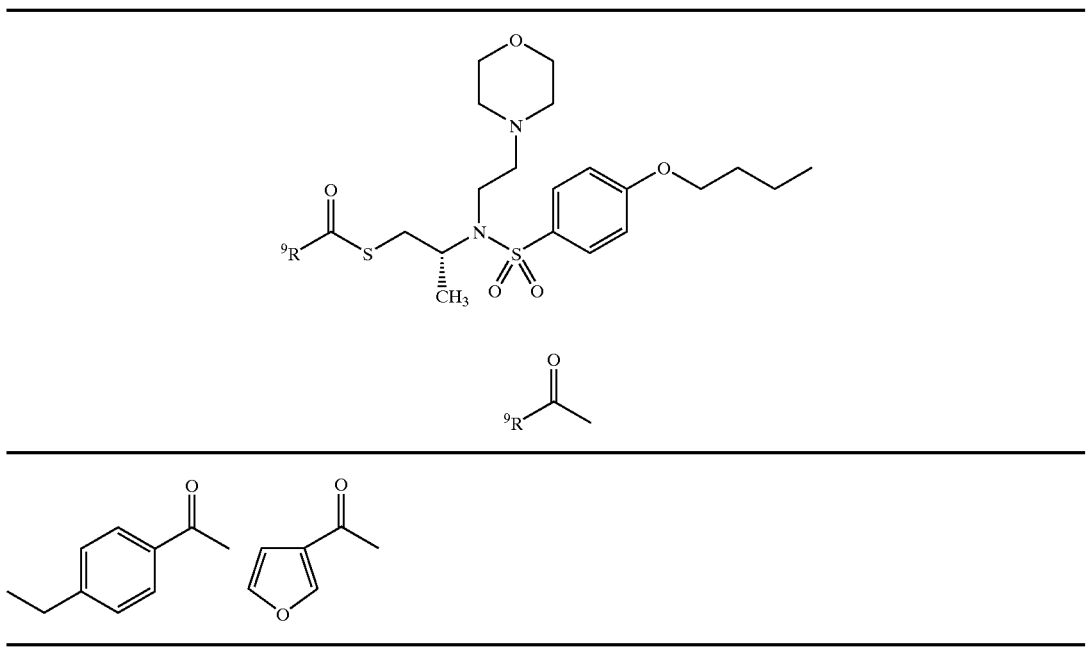
TABLE 58
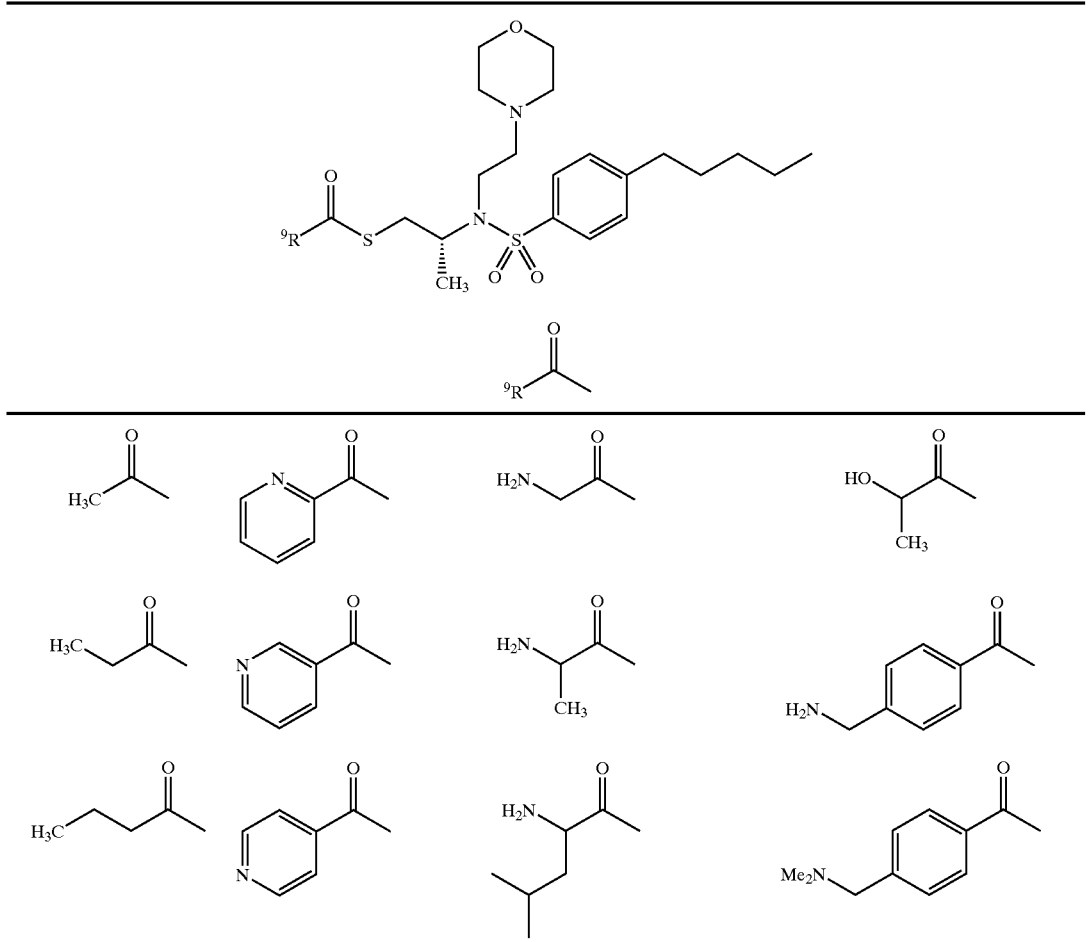

TABLE 58-continued
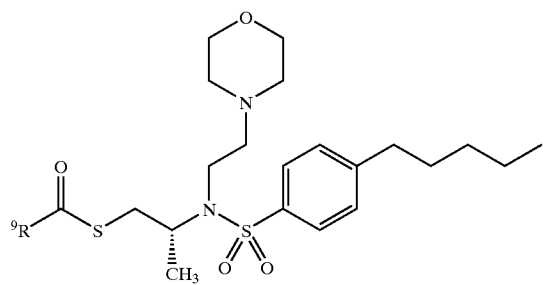
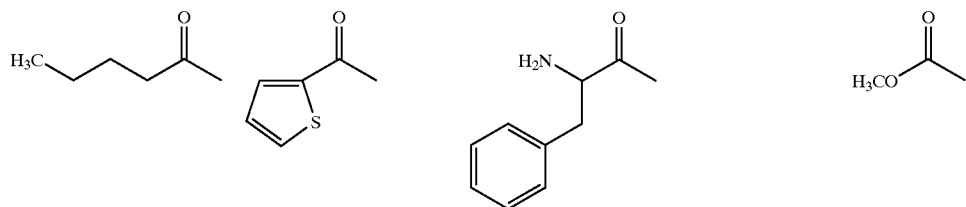
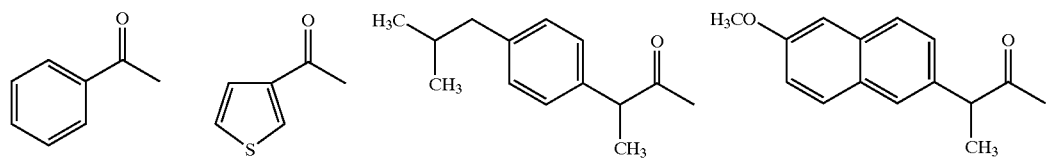
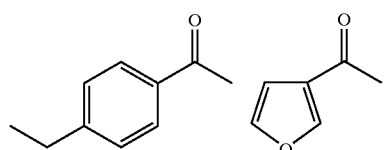

TABLE 59
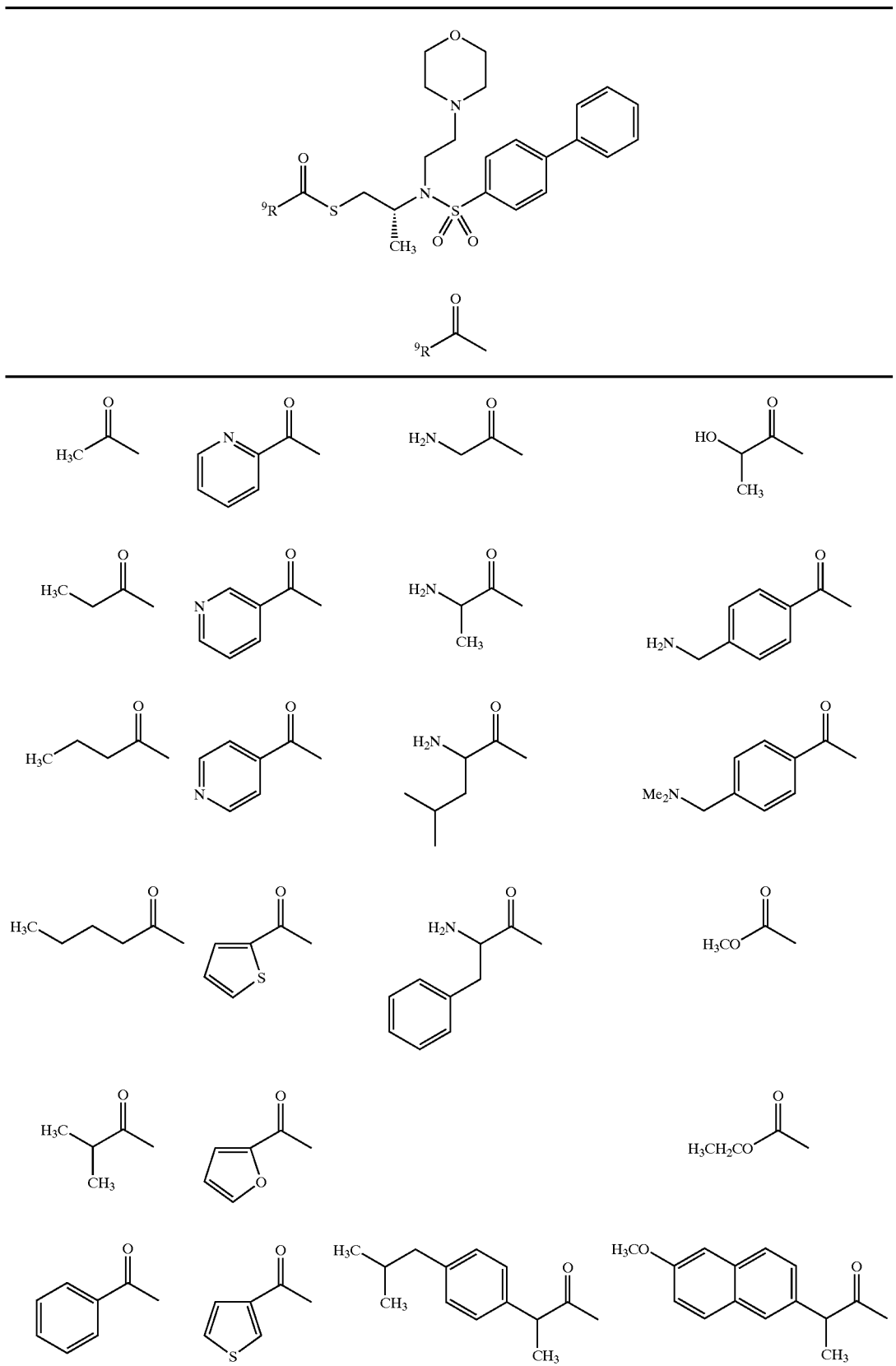

TABLE 59-continued
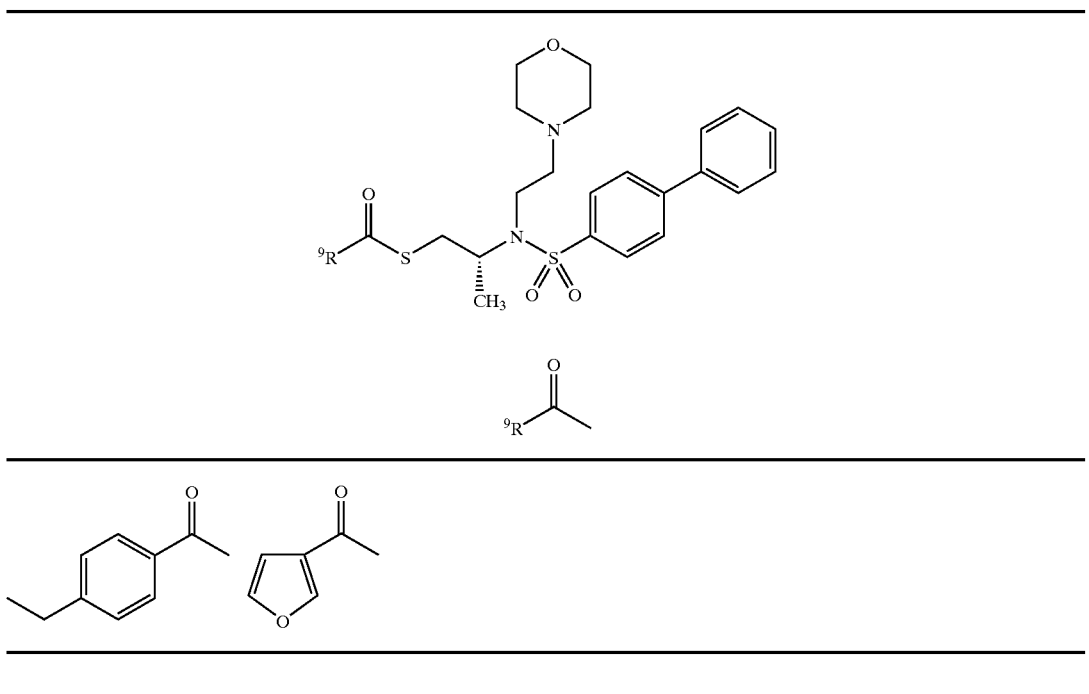
TABLE 60
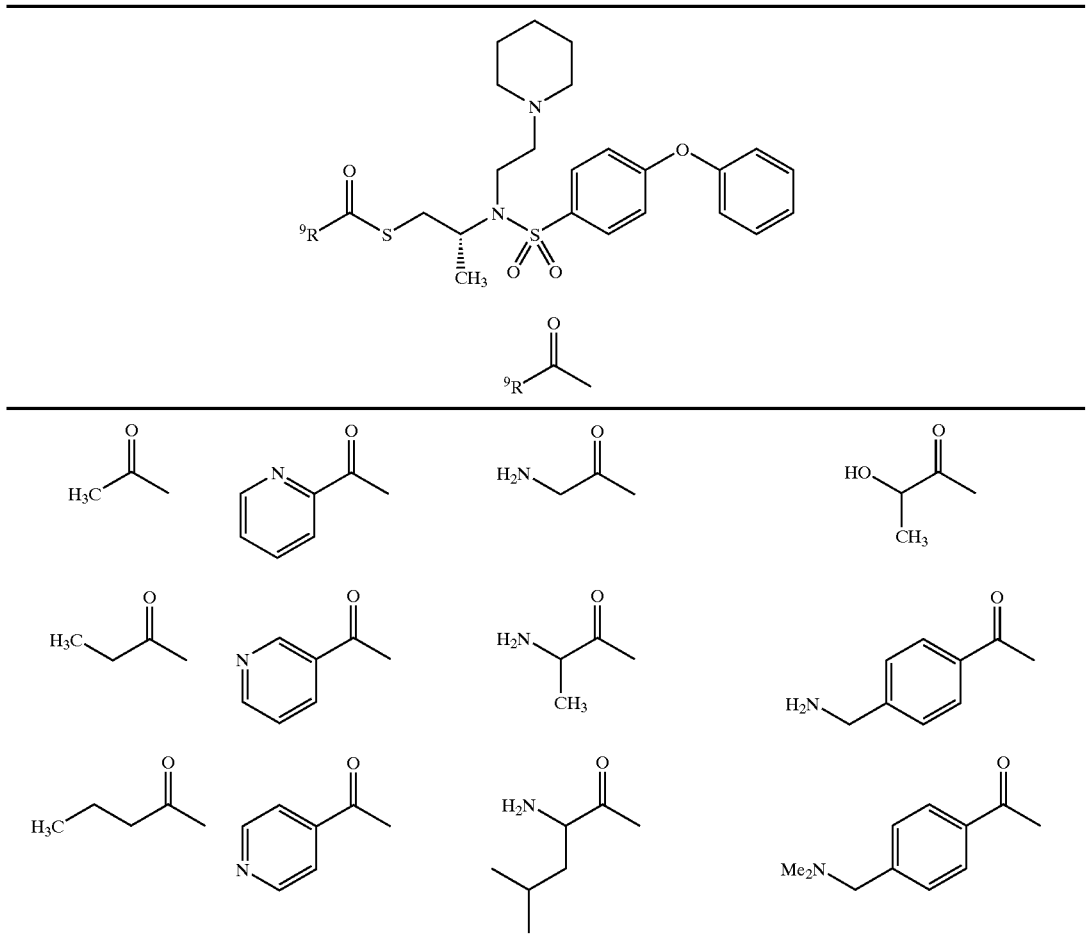

TABLE 60-continued
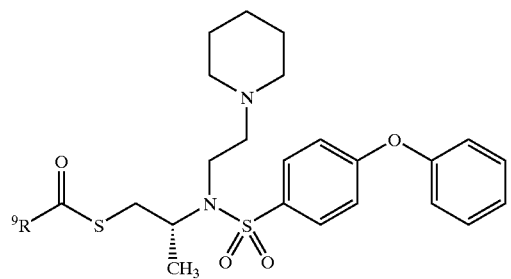
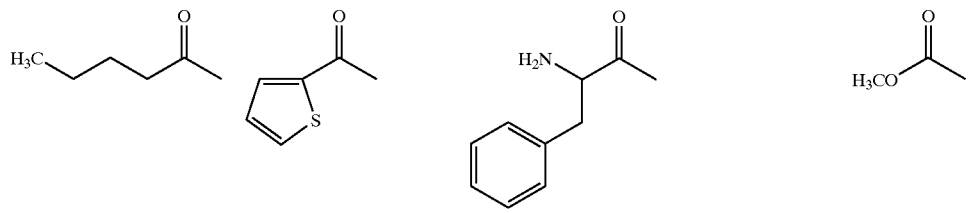
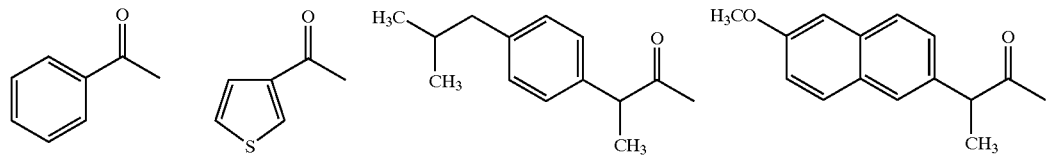
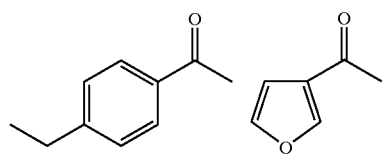

TABLE 61
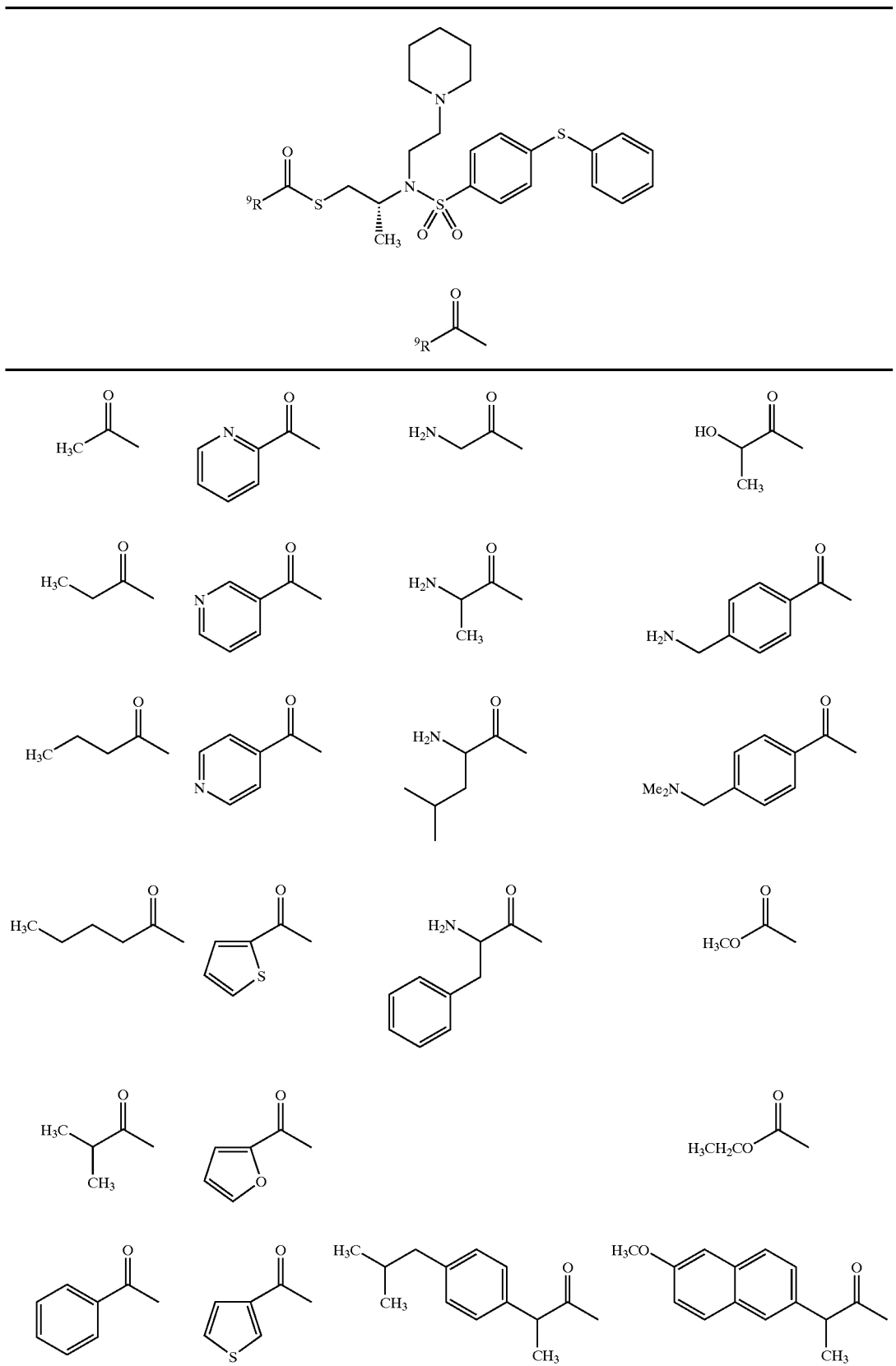

TABLE 61-continued
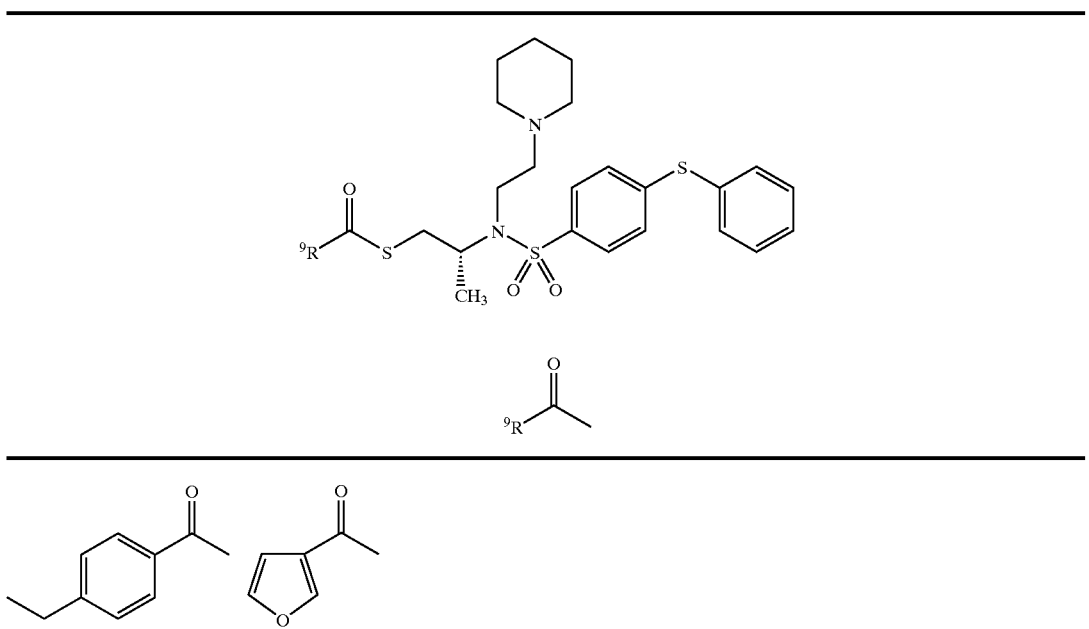
TABLE 62
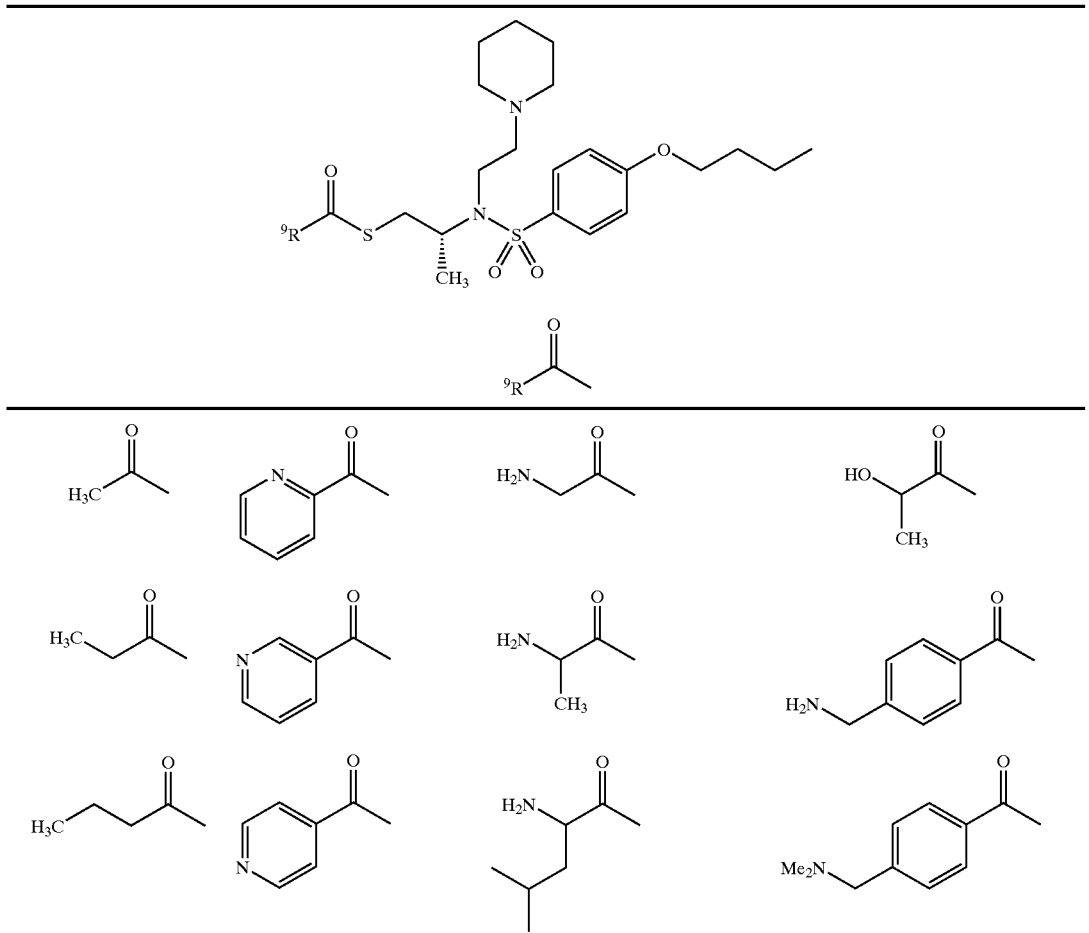

TABLE 62-continued
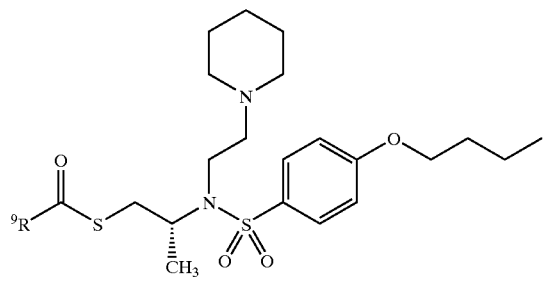
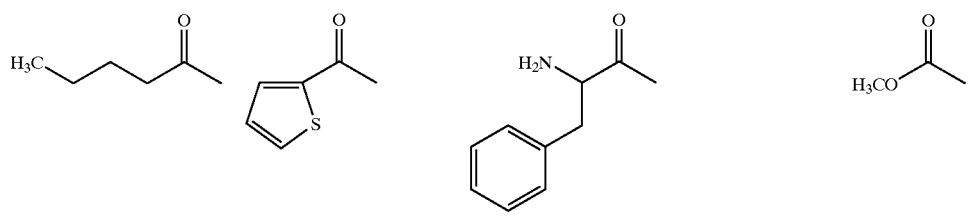
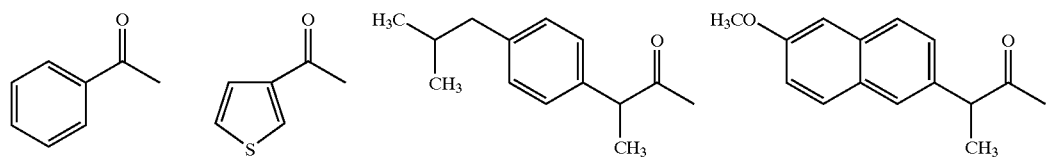
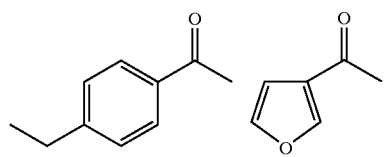

TABLE 63
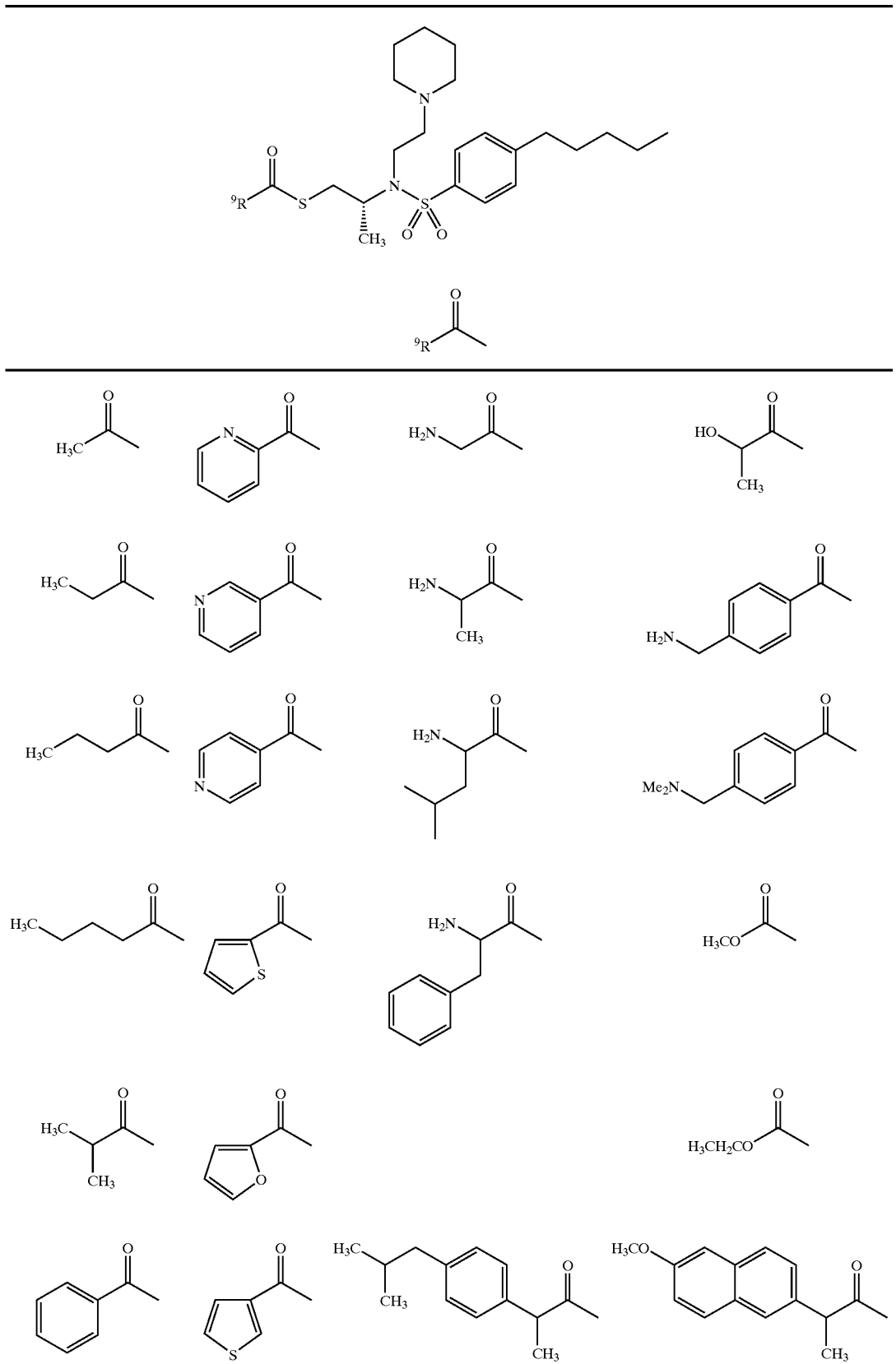

TABLE 63-continued
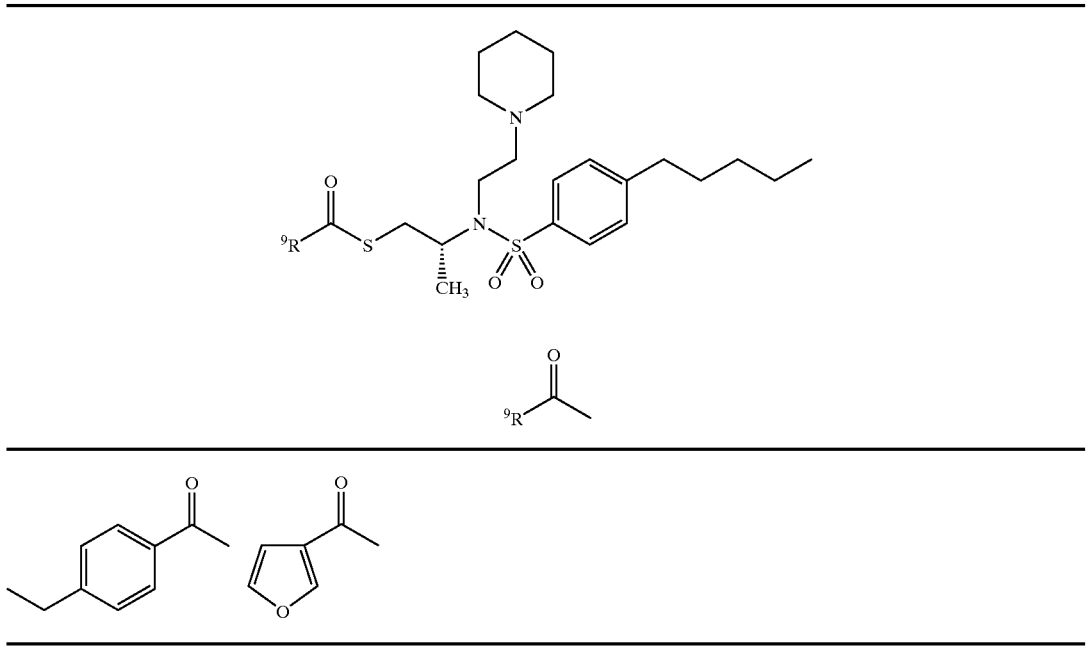
TABLE 64
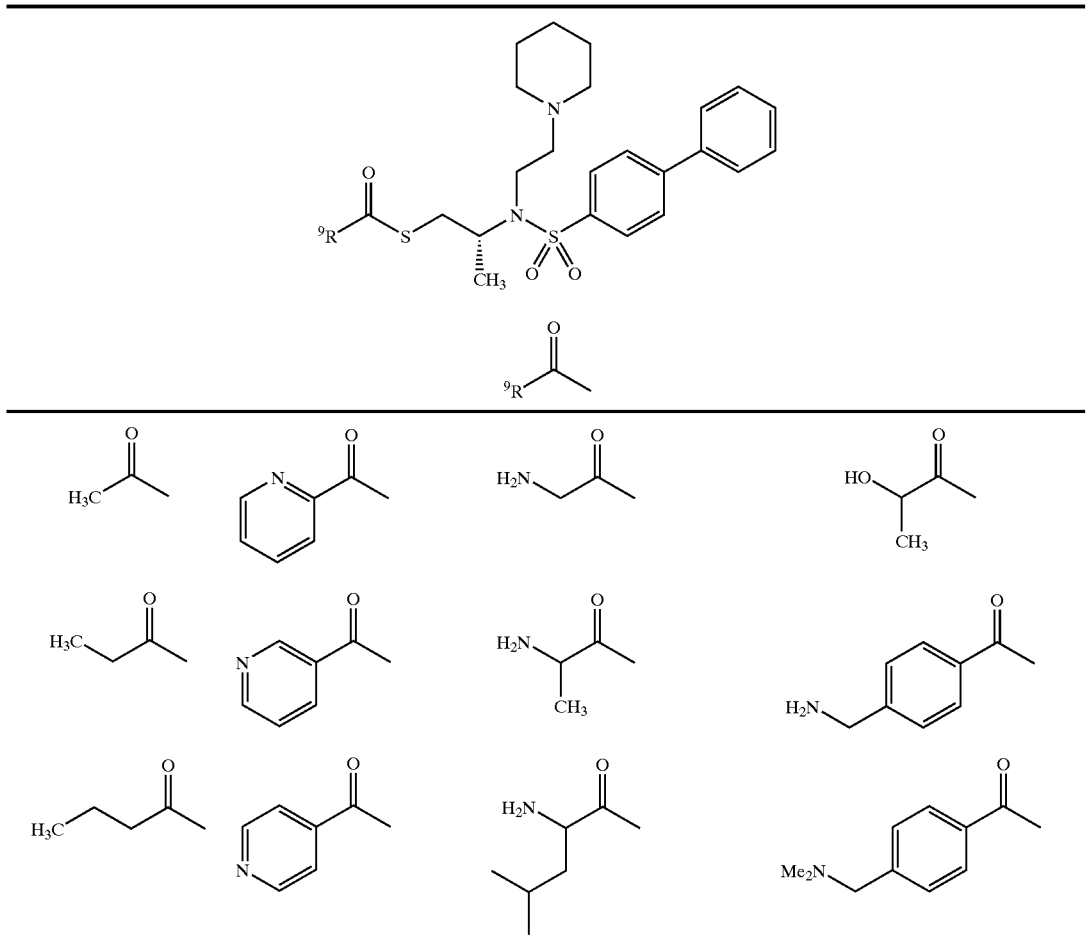

TABLE 64-continued
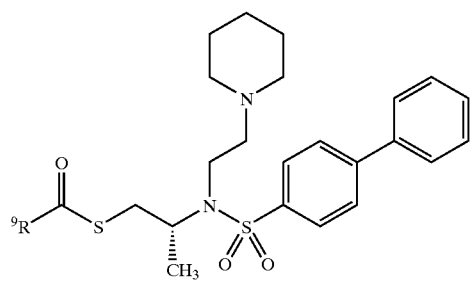
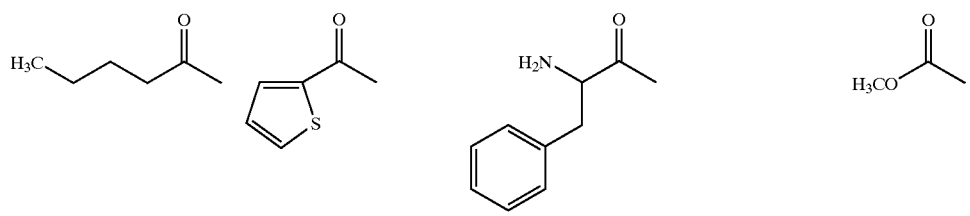
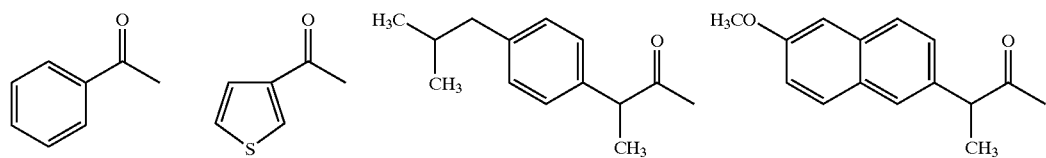
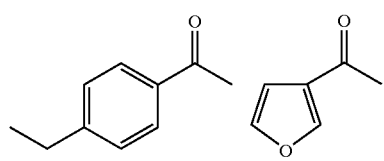

TABLE 65
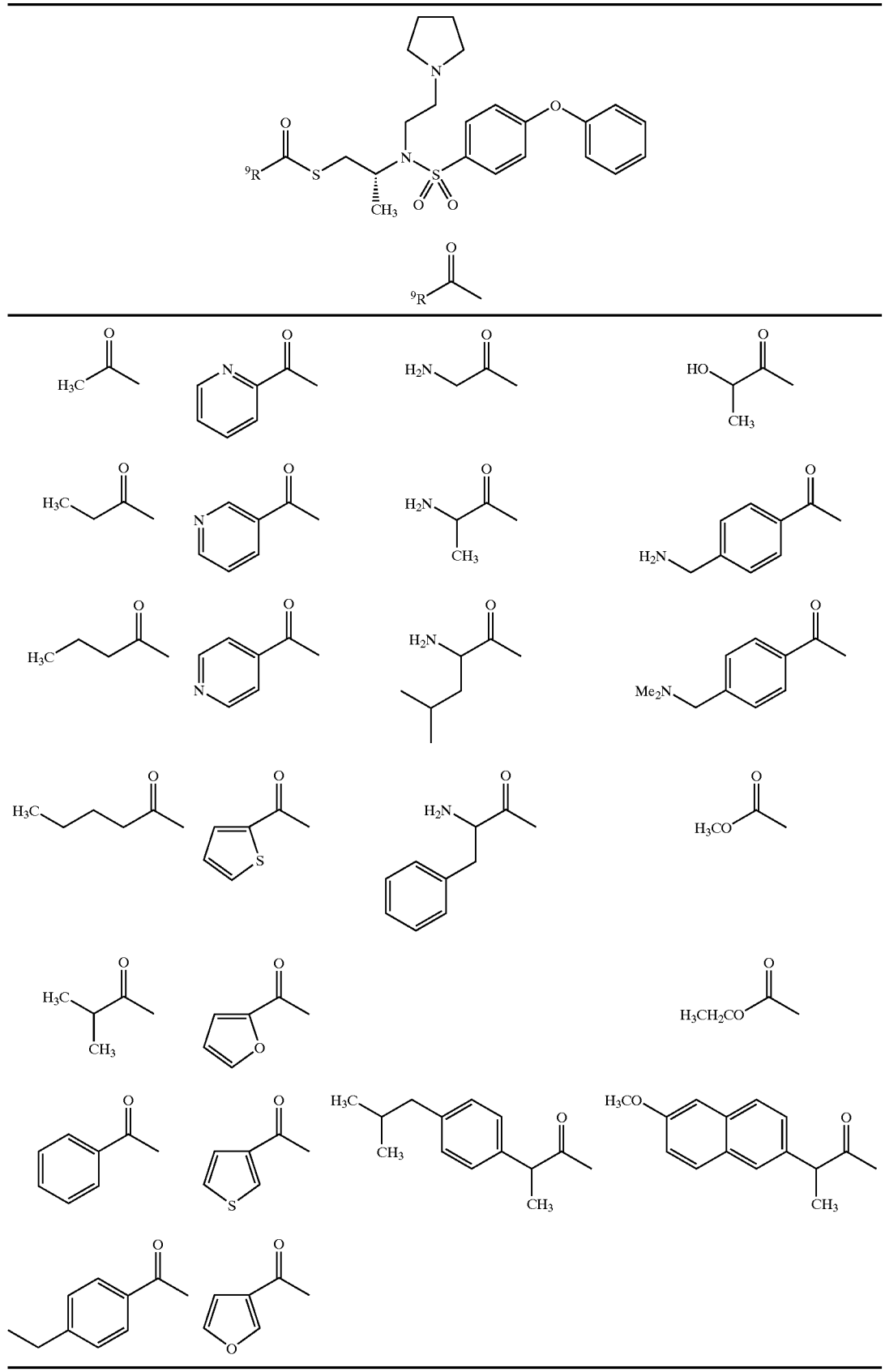

TABLE 66
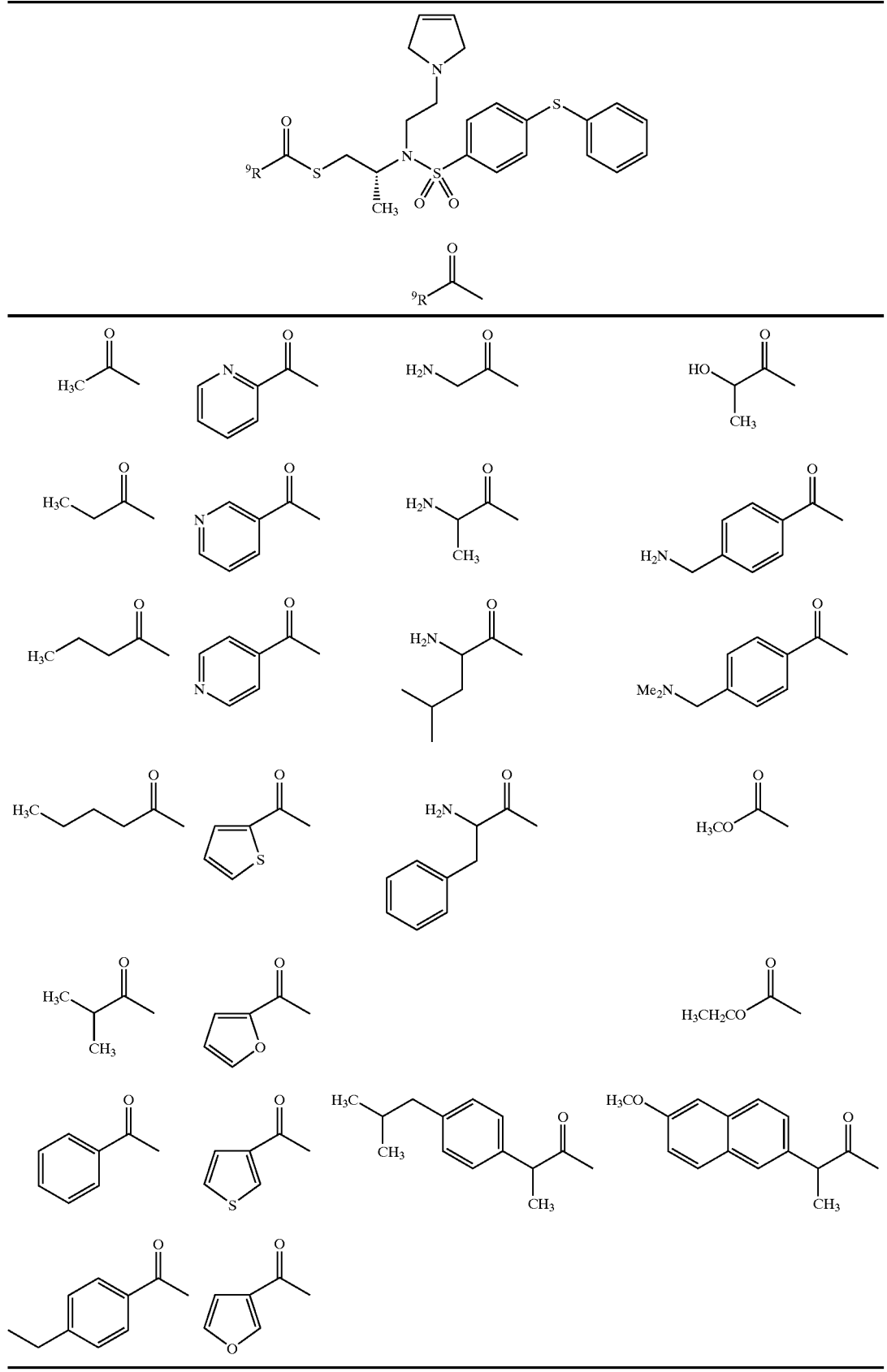

TABLE 67
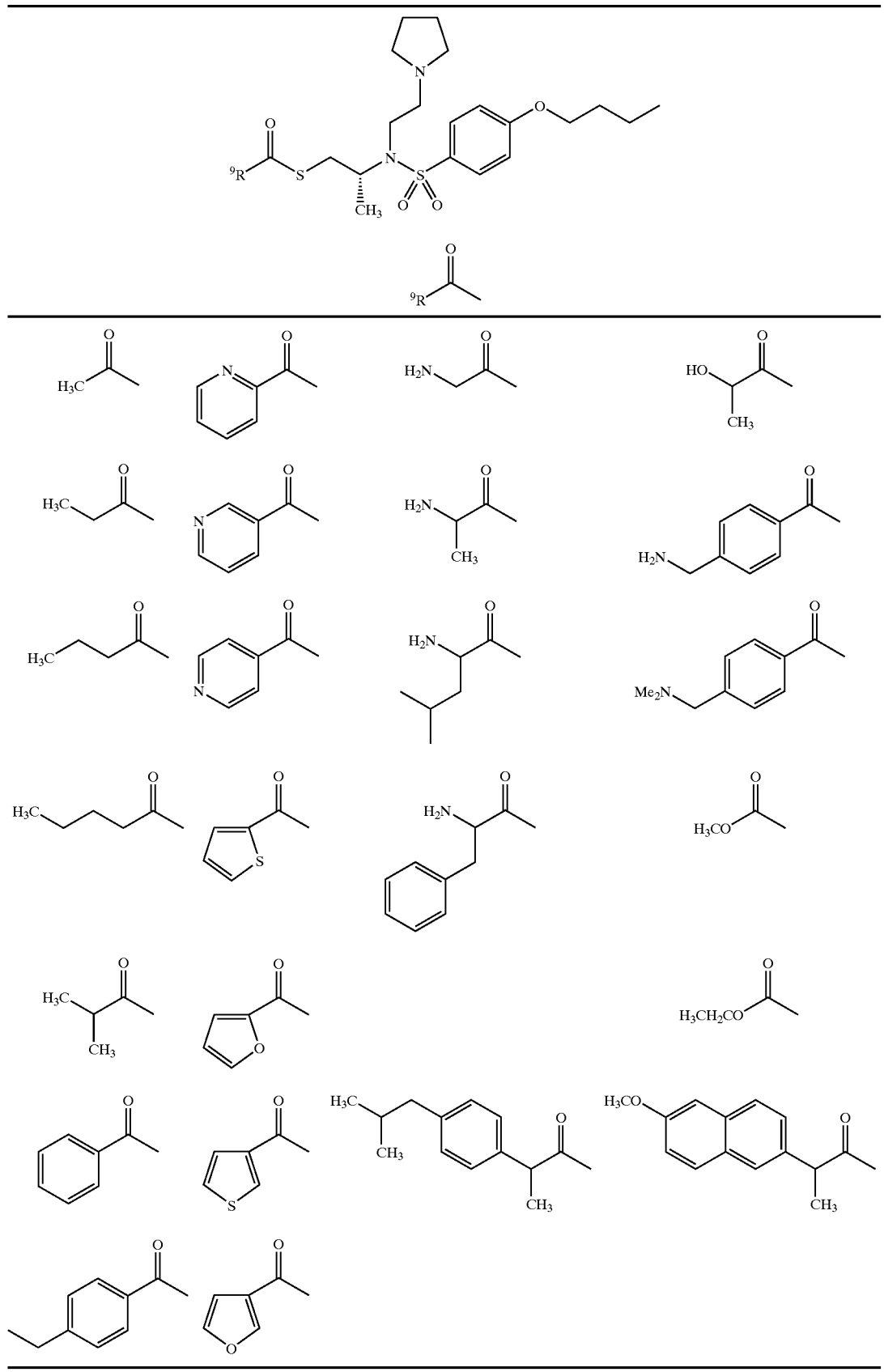

TABLE 68
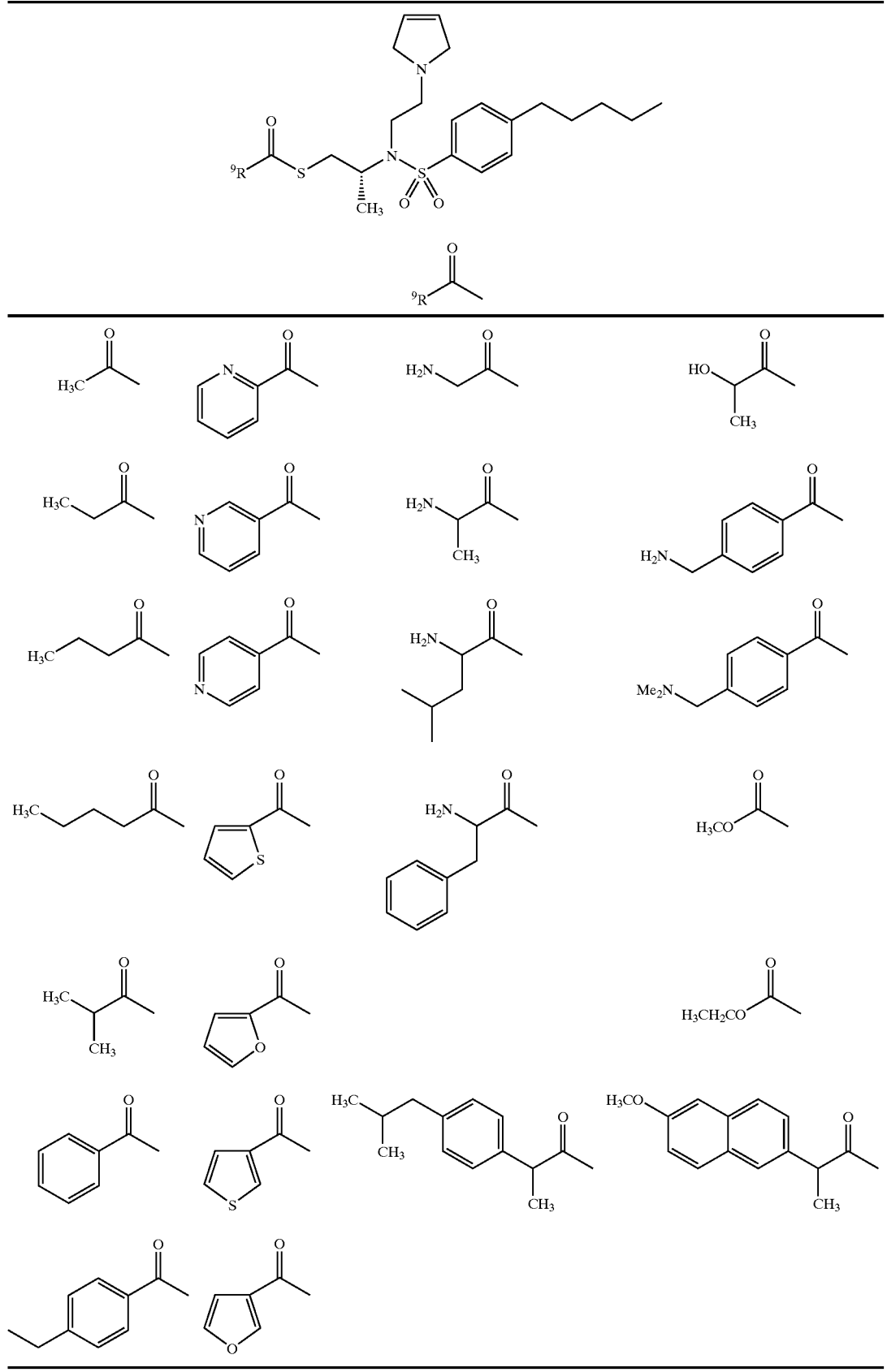

TABLE 69
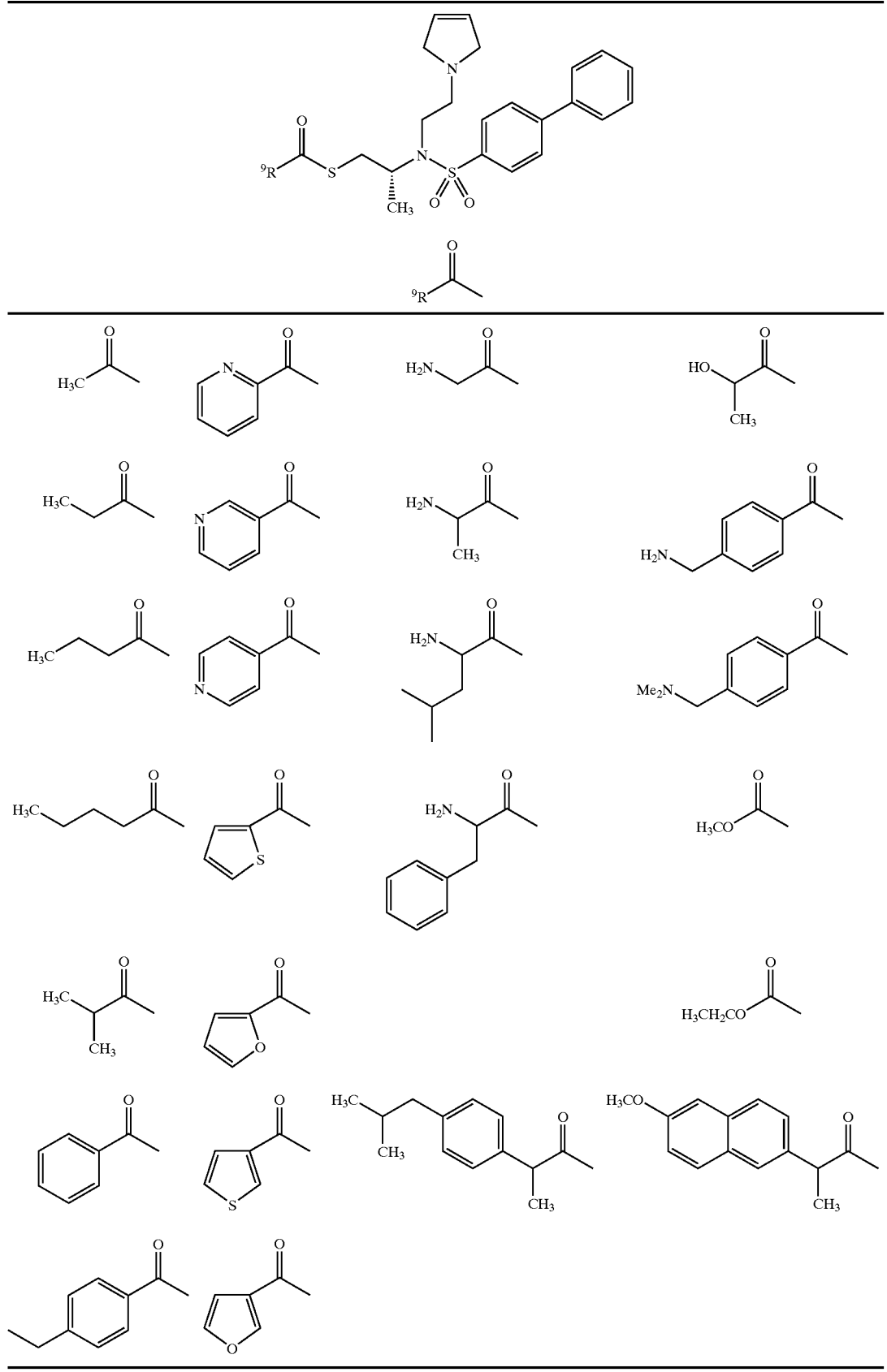

TABLE 70

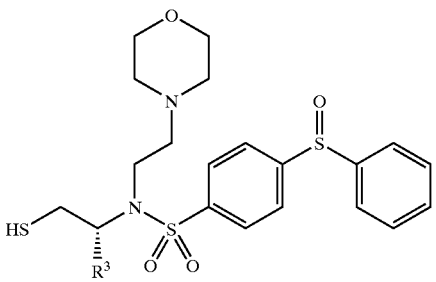

| R³ | | | | |
|---|---|---|---|---|
| CH₃ | HOOC- | imidazol-4-yl-CH₂- | cyclobutyl | CF₃ |
| CH₂CH₃ | H₂NC(O)CH₂- | HOOC-CH₂CH₂- | cyclopropyl | CH₂CF₃ |
| isobutyl | H₃COC(O)CH₂- | H₂NC(O)CH₂CH₂- | cyclopentylmethyl | CH₂OH |
| sec-butyl | HOOC-CH₂CH₂- | H₃COC(O)CH₂CH₂- | cyclobutylmethyl | CH(CH₃)OH |
| isobutyl | H₂NC(O)CH₂CH₂- | cyclohexyl | cyclopropylmethyl | thiazol-4-yl-CH₂- |
| benzyl | H₃COC(O)CH₂CH₂- | cyclopentyl | phenyl | thiazol-2-yl-CH₂- |
| cyclohexylmethyl | | | | thiazol-5-yl-CH₂- |

TABLE 71

[Structure: HS-CH2-CH(C(=O)NH2)-N(R2)-SO2-C6H4-NH-C(=O)-Ph]

—R²

| —R² | | |
|---|---|---|
| —H | morpholino-CH₂CH₂— | piperidino-CH₂CH₂— |
| —CH₃ | | |
| —CH₂CH₃ | pyrrolidino-CH₂CH₂— | (CH₃)₂N-CH₂CH₂— |
| —CH₂CH₂CH₃ | | |
| —CH₂CH₂CH₂CH₃ | cyclopropyl-NH-CH₂CH₂— | cyclopropyl-N(CH₃)-CH₂CH₂— |
| —CH₂CH₂CH₂CH₂CH₃ | | |
| —CH₂CH₂CH₂CH₂CH₂CH₃ | H-piperazino-CH₂CH₂— | PhO-C₆H₄-CH₂CH₂— |
| —CH₂Ph | | |
| —CH₂CH₂Ph | H₃C-piperazino-CH₂CH₂— | PhCH₂-piperazino-CH₂CH₂— |
| —CH₂CH(CH₃)₂ | | |
| —CH₂CF₃ | thiazol-4-yl-CH₂— | thiazol-5-yl-CH₂— | thiazol-2-yl-CH₂— |
| —CH₂CH₂OCH₃ | | | |
| —CH₂CH₂OH | pyridin-2-yl-CH₂— | pyridin-3-yl-CH₂— | pyridin-4-yl-CH₂— |
| —CH₂CO₂H | | | |
| —CH₂CH₂CO₂H | cyclopropyl-CH₂— | cyclobutyl-CH₂— | cyclopentyl-CH₂— | cyclohexyl-CH₂— |
| —CH₂CH₂CH₂CO₂H | | | | |
| —CH₂CH₂CH₂CH₂CO₂H | H₃CO-C₆H₄-CH₂CH₂— | PhCH₂-CH(CO₂H)— | | |
| —CH₂CH₂CH₂CH₂CH₂CO₂H | | | | |

TABLE 72
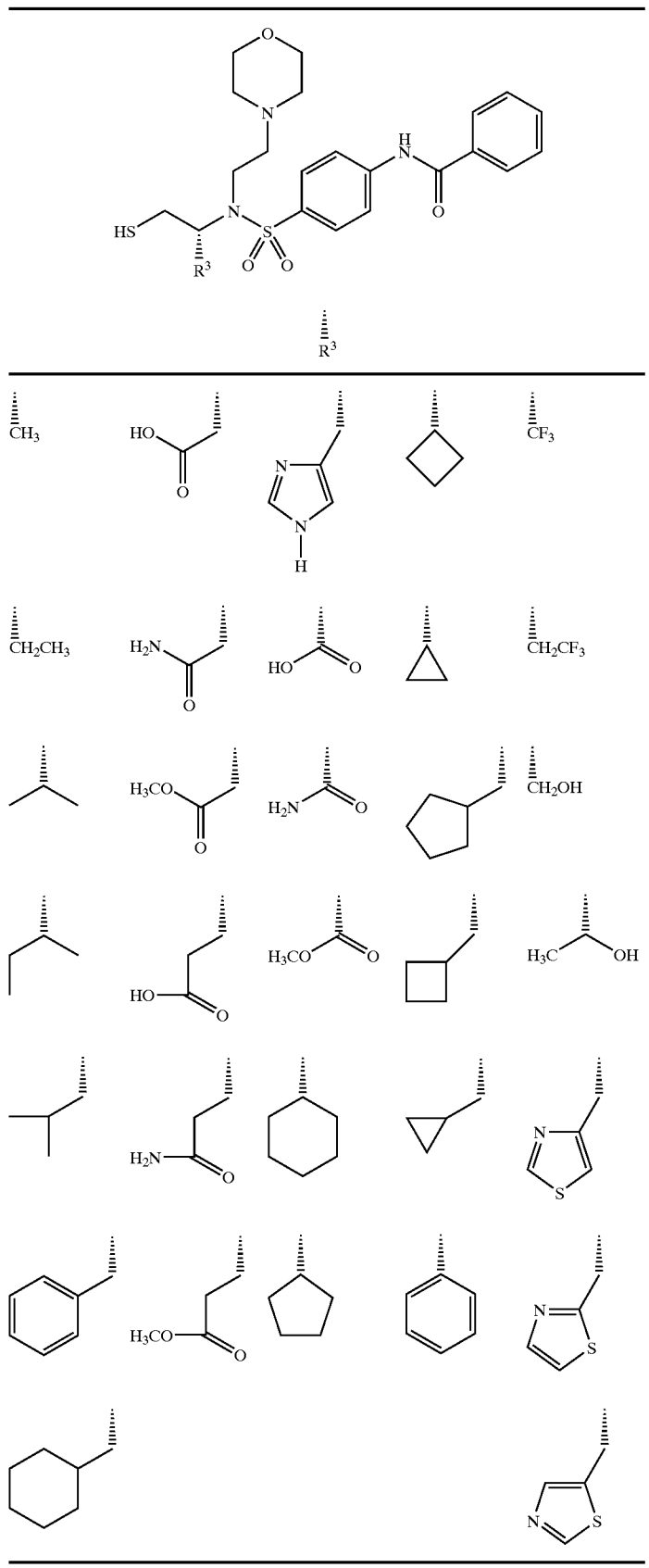

TABLE 73
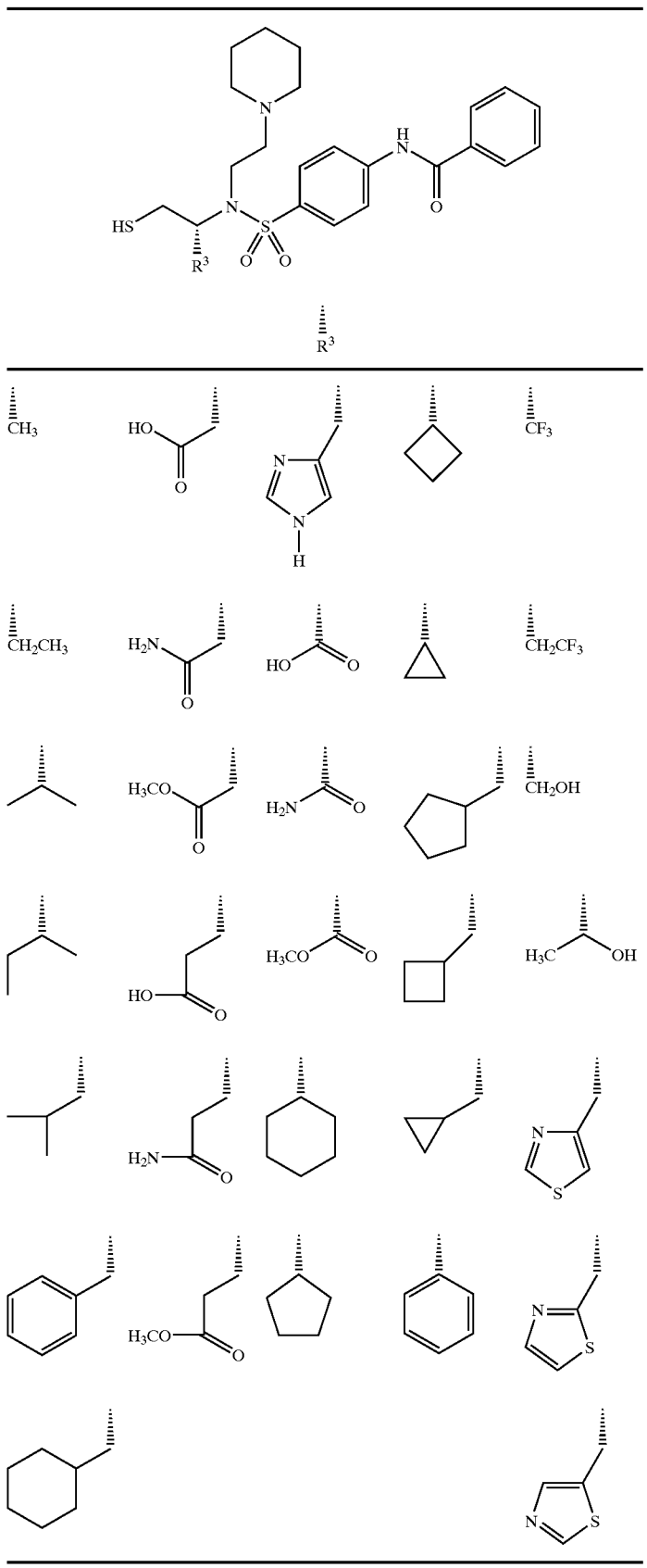

TABLE 74
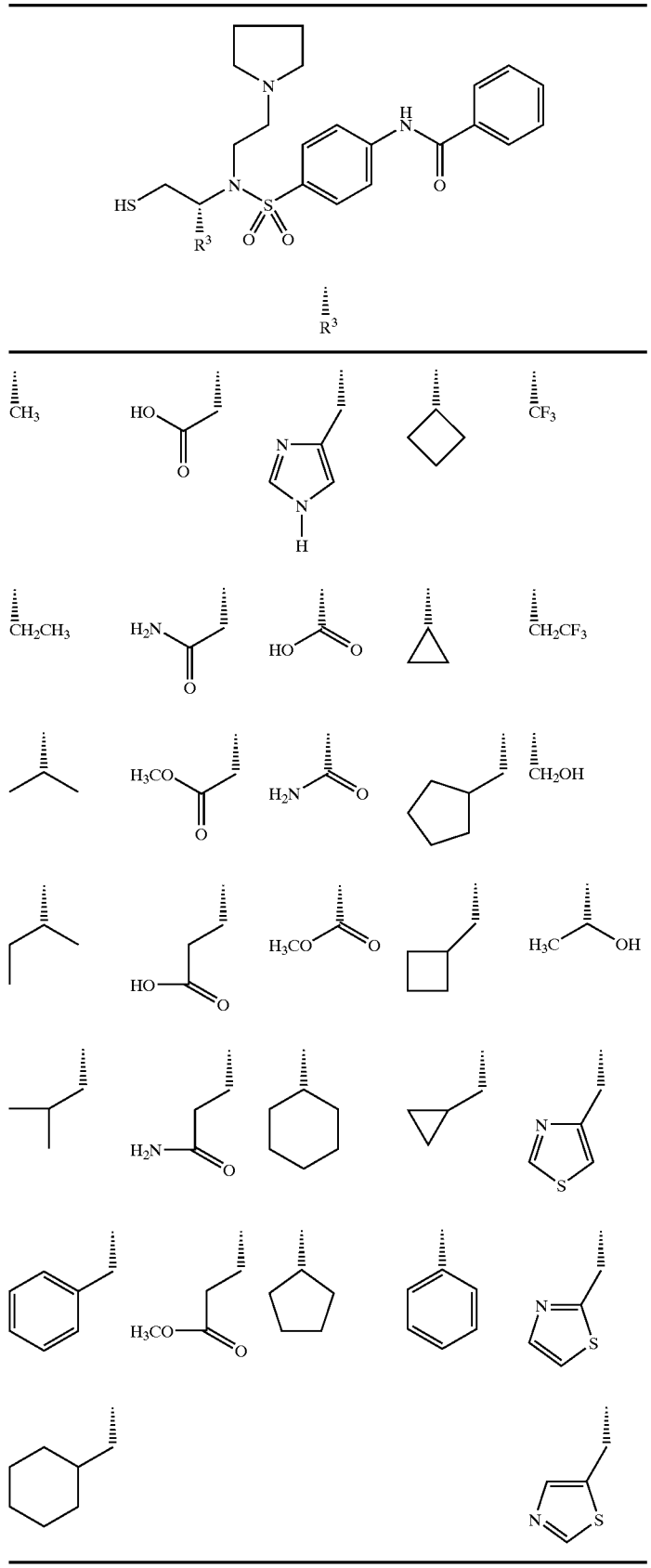

TABLE 75
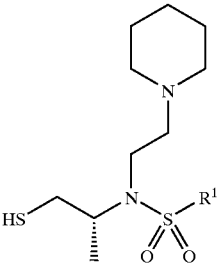
—R¹
| | | |
|---|---|---|
| 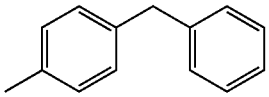 | 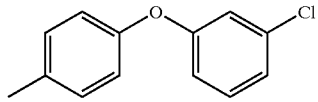 | 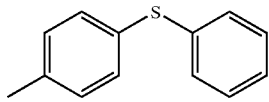 |
| 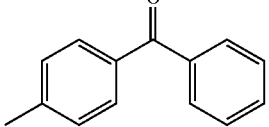 | 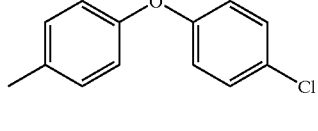 | 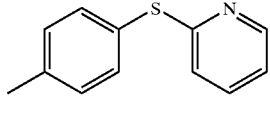 |
| 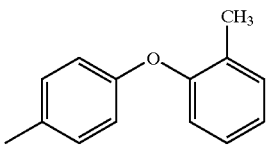 | 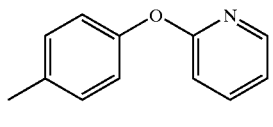 | 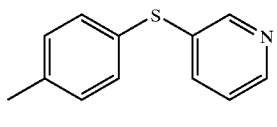 |
| 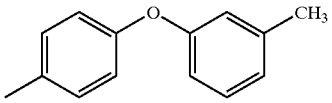 | 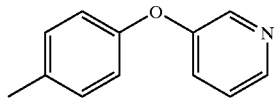 | 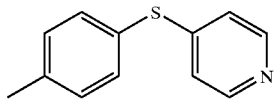 |
| 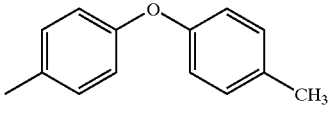 | 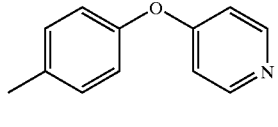 | 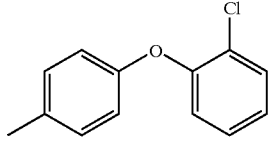 |
| 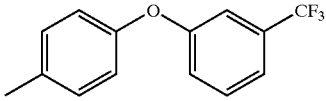 | 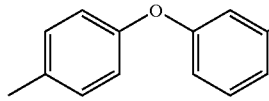 | 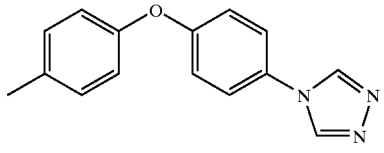 |
| 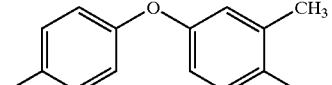 | 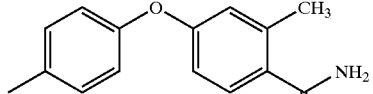 | |

TABLE 76
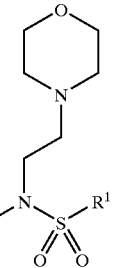
—R¹
| | | |
|---|---|---|
| 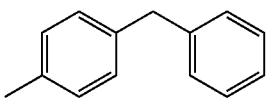 | 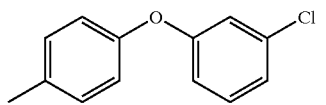 | 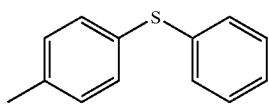 |
| 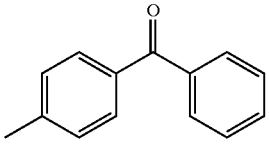 | 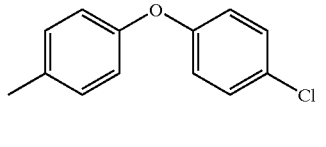 | 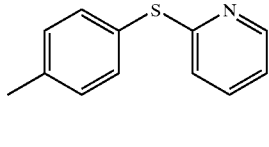 |
| 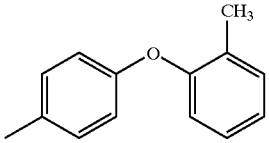 | 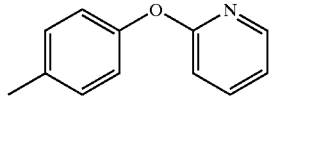 | 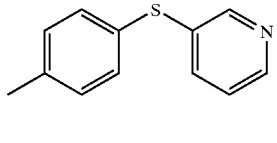 |
| 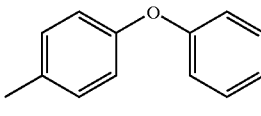 | 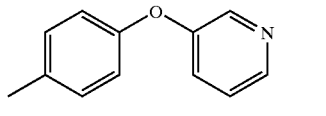 | 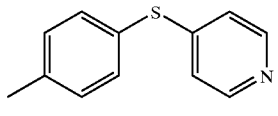 |
| 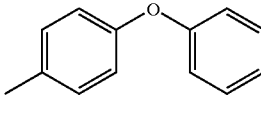 | 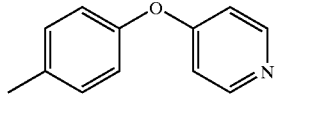 | 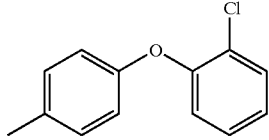 |
| 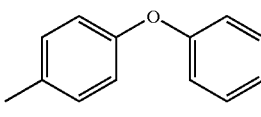 | 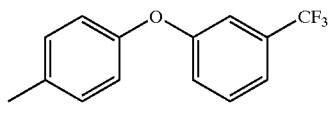 | 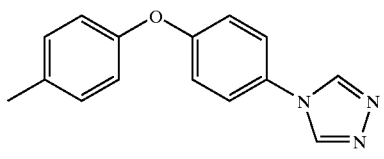 |
| 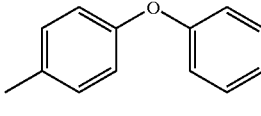 | 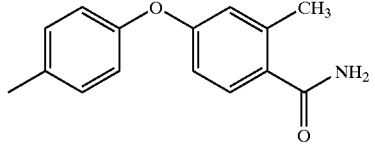 | |

TABLE 77
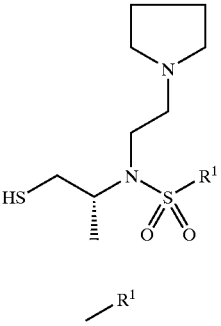
—R¹
| 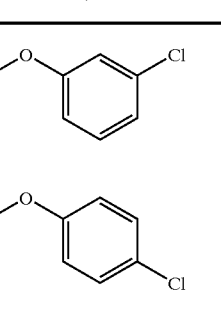 | 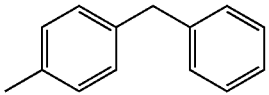 | 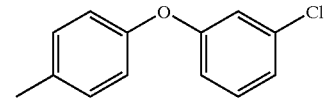 |
| 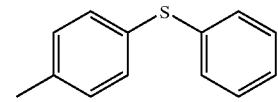 | 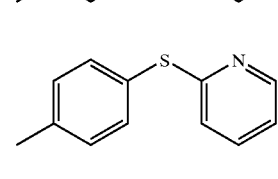 |  |
|  | 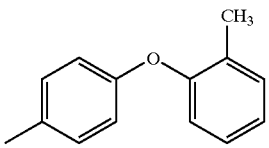 | 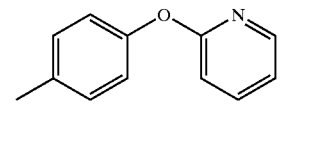 |
| 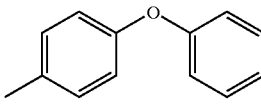 | 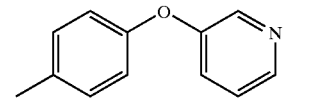 | 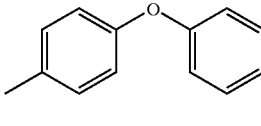 |
| 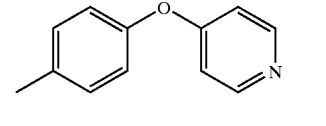 | 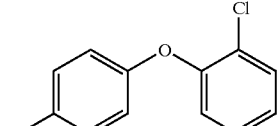 | 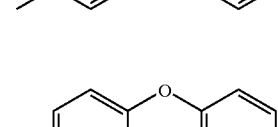 |
| 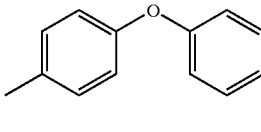 | 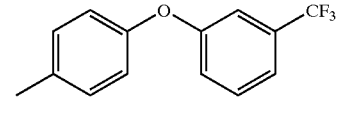 | 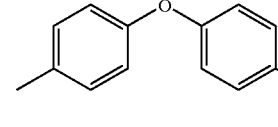 |
|  |  | |

TABLE 78
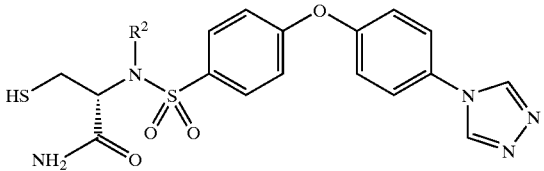
—R²
| —R² | | |
|---|---|---|
| —H | 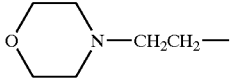 | 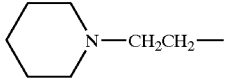 |
| —CH₃ | | |
| —CH₂CH₃ | 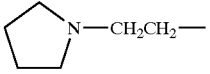 | 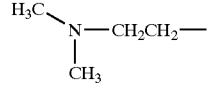 |
| —CH₂CH₂CH₃ | | |
| —CH₂CH₂CH₂CH₃ | 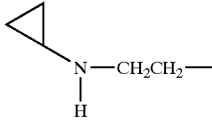 | 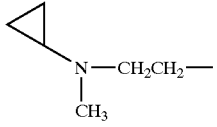 |
| —CH₂CH₂CH₂CH₂CH₃ | | |
| —CH₂CH₂CH₂CH₂CH₂CH₃ | 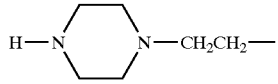 | 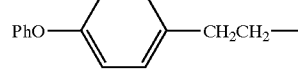 |
| —CH₂Ph | | |
| —CH₂CH₂Ph | 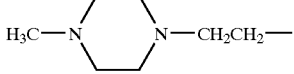 | 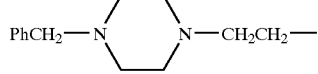 |
| —CH₂CH(CH₃)₂ | | |
| —CH₂CF₃ | 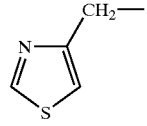 | 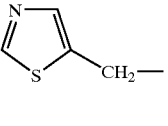 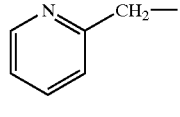 |
| —CH₂CH₂OCH₃ | | |
| —CH₂CH₂OH | 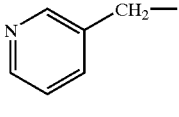 | 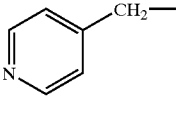 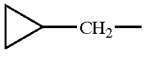 |
| —CH₂CO₂H | | |
| —CH₂CH₂CO₂H | 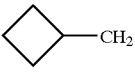 | |
| —CH₂CH₂CH₂CO₂H | | |
| —CH₂CH₂CH₂CH₂CO₂H | 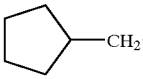 |  |
| —CH₂CH₂CH₂CH₂CH₂CO₂H | | |

TABLE 79

| —R² | | |
|---|---|---|
| —H | morpholine-N-CH₂CH₂— | piperidine-N-CH₂CH₂— |
| —CH₃ | | |
| —CH₂CH₃ | pyrrolidine-N-CH₂CH₂— | (CH₃)₂N-CH₂CH₂— |
| —CH₂CH₂CH₃ | | |
| —CH₂CH₂CH₂CH₃ | cyclopropyl-NH-CH₂CH₂— | cyclopropyl-N(CH₃)-CH₂CH₂— |
| —CH₂CH₂CH₂CH₂CH₃ | | |
| —CH₂CH₂CH₂CH₂CH₂CH₃ | H-N(piperazine)N-CH₂CH₂— | PhO-C₆H₄-CH₂CH₂— |
| —CH₂Ph | | |
| —CH₂CH₂Ph | H₃C-N(piperazine)N-CH₂CH₂— | PhCH₂-N(piperazine)N-CH₂CH₂— |
| —CH₂CH(CH₃)₂ | | |
| —CH₂CF₃ | 4-thiazolyl-CH₂— | 5-thiazolyl-CH₂— | 2-thiazolyl-CH₂— |
| —CH₂CH₂OCH₃ | | | |
| —CH₂CH₂OH | 2-pyridyl-CH₂— | 3-pyridyl-CH₂— | 4-pyridyl-CH₂— |
| —CH₂CO₂H | | | |
| —CH₂CH₂CO₂H | cyclopropyl-CH₂— | cyclobutyl-CH₂— | cyclopentyl-CH₂— | cyclohexyl-CH₂— |
| —CH₂CH₂CH₂CO₂H | | | | |
| —CH₂CH₂CH₂CH₂CO₂H | H₃CO-C₆H₄-CH₂CH₂— | HO₂C-CH(CH₂Ph)— |
| —CH₂CH₂CH₂CH₂CH₂CO₂H | | |

TABLE 80

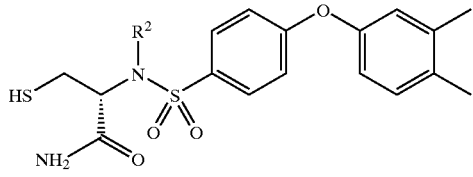

| —R² | | |
|---|---|---|
| —H | | |
| —CH₃ | 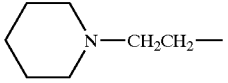 | 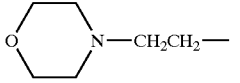 |
| —CH₂CH₃ | | |
| —CH₂CH₂CH₃ | 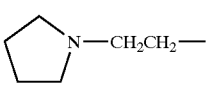 | 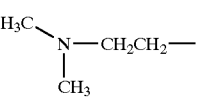 |
| —CH₂CH₂CH₂CH₃ | | |
| —CH₂CH₂CH₂CH₂CH₃ | 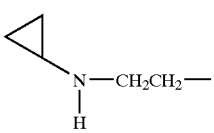 | 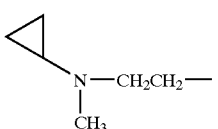 |
| —CH₂CH₂CH₂CH₂CH₂CH₃ | | |
| —CH₂Ph | 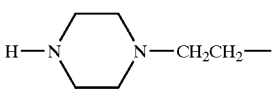 | 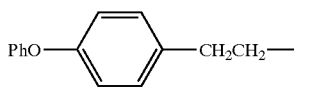 |
| —CH₂CH₂Ph | | |
| —CH₂CH(CH₃)₂ | 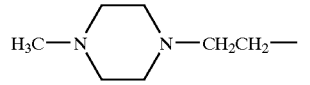 | 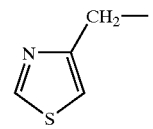 |
| —CH₂CF₃ | | |
| —CH₂CH₂OCH₃ | 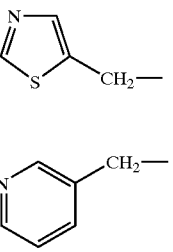 | |
| —CH₂CH₂OH | | |
| —CH₂CO₂H | 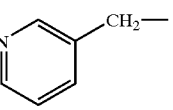 | |
| —CH₂CH₂CO₂H | | |
| —CH₂CH₂CH₂CO₂H | 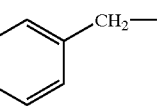 | |
| —CH₂CH₂CH₂CH₂CO₂H | | |
| —CH₂CH₂CH₂CH₂CH₂CO₂H | 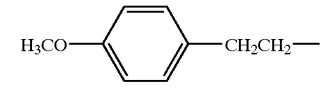 | 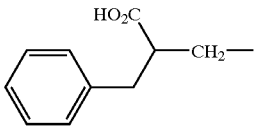 |

In the written descriptions of molecules and groups, molecular descriptors can be combined to produce words or phrases that describe structural groups or are combined to describe structural groups. Such descriptors are used in this document. Common illustrative examples include such terms as aralkyl (or arylalkyl), heteroaralkyl, heterocycloalkyl, cycloalkylalkyl, aralkoxyalkoxycarbonyl and the like. A specific example of a compound encompassed with the latter descriptor aralkoxyalkoxycarbonyl is $C_6H_5$—$CH_2$—$CH_2$—O—$CH_2$—O—(C=O)— wherein $C_6H_5$— is phenyl. It is also to be noted that a structural group can have more than one descriptive word or phrase in the art, for example, heteroaryloxyalkylcarbonyl can also be termed heteroaryloxyalkanoyl. Such combinations are used above in the description of the compounds and compositions of this invention and further examples are described below. The following list is not intended to be exhaustive or drawn out but provide further illustrative examples of such words or phrases.

As utilized herein, the term "alkyl", alone or in combination, means a straight-chain or branched-chain alkyl radical containing 1 to about 12 carbon atoms, preferably 1 to about 10 carbon atoms, and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "alkenyl", alone or in combination, means a straight-chain or branched-chain hydrocarbon radical having one or more double bonds and containing 2 to about 12 carbon atoms preferably 2 to about 10 carbon atoms, and more preferably, 2 to about 6 carbon atoms. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like.

The term "alkynyl", alone or in combination, means a straight-chain hydrocarbon radical having one or more triple bonds and containing 2 to about 12 carbon atoms, preferably 2 to about 10 carbon atoms, and more preferably, 2 to about 6 carbon atoms. Examples of alkynyl radicals include ethynyl, 2-propynyl, 3-propynyl, decynyl, 1-butynyl, 2-butynyl, 3-butynyl, and the like.

The term "carbonyl", alone or in combination, means a —C(=O)— group wherein the remaining two bonds (valences) can be independently substituted. The term "thiol" or "sulfhydryl", alone or in combination, means a —SH group. The term "thio" or "thia", alone or in combination, means a thiaether group; i.e., an ether group wherein the ether oxygen is replaced by a sulfur atom.

The term "amino", alone or in combination, means an amine or —NH$_2$ group whereas the term mono-substituted amino, alone or in combination, means a substituted amine —N(H) (substituent) group wherein one hydrogen atom is replaced with a substituent, and disubstituted amine means a —N(substituent)$_2$ wherein two hydrogen atoms of the amino group are replaced with independently selected substituent groups.

Amines, amino groups and amides are compounds that can be designated as primary (I°), secondary (II°) or tertiary (III°) or unsubstituted, mono-substituted or di-substituted depending on the degree of substitution of the amino nitrogen. Quaternary amine (ammonium)(IV°) means a nitrogen with four substituents [—N$^+$(substituent)$_4$] that is positively charged and accompanied by a counter ion, whereas N-oxide means one substituent is oxygen and the group is represented as [—N$^+$(substituent)$_3$—O$^-$]; i.e., the charges are internally compensated.

The term "cyano", alone or in combination, means a —C-triple bond-N (—C/N) group. The term "azido", alone or in combination, means a —N-triple bond-N (—N/N) group. The term "hydroxyl", alone or in combination, means a —OH group. The term "nitro", alone or in combination, means a —NO$_2$ group. The term "azo", alone or in combination, means a —N=N— group wherein the bonds at the terminal positions can be independently substituted.

The term "hydrazino", alone or in combination, means a —NH—NH— group wherein the depicted remaining two bonds (valences) can be independently substituted. The hydrogen atoms of the hydrazino group can be replaced, independently, with substituents and the nitrogen atoms can form acid addition salts or be quaternized.

The term "sulfonyl", alone or in combination, means a —SO$_2$— group wherein the depicted remaining two bonds (valences) can be independently substituted. The term "sulfoxido", alone or in combination, means a —SO— group wherein the remaining two bonds (valences) can be independently substituted.

The term "sulfonylamide", alone or in combination, means a —SO$_2$—N= group wherein the depicted remaining three bonds (valences) can be independently substituted. The term "sulfinamido", alone or in combination, means a —SON= group wherein the remaining three depicted bonds (valences) can be independently substituted. The term "sulfenamide", alone or in combination, means a —S—N= group wherein the remaining three bonds (valences) can be independently substituted.

The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, isobutoxy, sec-butoxy, tert-butoxy and the like.

The term "cycloalkyl", alone or in combination, means a cyclic alkyl radical that contains 3 to about 8 carbon atoms. The term "cycloalkylalkyl" means an alkyl radical as defined above that is substituted by a cycloalkyl radical containing 3 to about 8, preferably 3 to about 6, carbon atoms. Examples of such cycloalkyl radicals include cyclopropyl, cyclobutyl, cyclopentyl, cyclohexyl and the like.

The term "aryl", alone or in combination, means a 5- or 6-membered aromatic ring-containing moiety or a fused ring system containing two or three rings that have all carbon atoms in the ring; i.e., a carbocyclic aryl radical, or a heteroaryl radical containing one or more heteroatoms such as sulfur, oxygen and nitrogen in the ring(s). Exemplary carbocyclic aryl radicals include phenyl, indenyl and naphthyl radicals. Examples of such heterocyclic or heteroaryl groups are pyrrolidinyl, piperidinyl, piperazinyl, morpholinyl, thiamorpholinyl, pyrrolyl, imidazolyl (e.g., imidazol-4-yl, 1-benzyloxycarbonylimidazol-4-yl, and the like), pyrazolyl, pyridyl, pyrazinyl, pyrimidinyl, furyl, tetrahydrofuryl, thienyl, triazolyl, oxazolyl, oxadiazoyl, thiazolyl, thiadiazoyl, indolyl (e.g., 2-indolyl, and the like), quinolinyl, (e.g., 2-quinolinyl, 3-quinolinyl, 1-oxido-2-quinolinyl, and the like), isoquinolinyl (e.g., 1-isoquinolinyl, 3-isoquinolinyl, and the like), tetrahydroquinolinyl (e.g., 1,2,3,4-tetrahydro-2-quinolyl, and the like), 1,2,3,4-tetrahydroisoquinolinyl (e.g., 1,2,3,4-tetrahydro-1-oxo-isoquinolinyl, and the like), quinoxalinyl, β-carbolinyl, 2-benzofurancarbonyl, benzothiophenyl, 1-, 2-, 4- or 5-benzimidazolyl, and the like.

An aryl ring group optionally carries one or more substituents selected from alkyl, alkoxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like.

The term "aralkyl", alone or in combination, means an alkyl radical as defined above in which one hydrogen atom is replaced by an aryl radical as defined above, such as benzyl, 2-phenylethyl and the like.

The term "aralkoxycarbonyl", alone or in combination, means a radical of the formula —C(O)—O— aralkyl in which the term "aralkyl" has the significance given above. An example of an aralkoxycarbonyl radical is benzyloxycarbonyl.

The term "aryloxy" means a radical of the formula aryl-O— in which the term aryl has the significance given above.

The terms "alkanoyl" or "alkylcarbonyl", alone or in combination, means an acyl radical derived from an alkanecarboxylic acid, examples of which include acetyl, propionyl, butyryl, valeryl, 4-methylvaleryl, and the like.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid that is optionally substituted by, for example, alkanoylamino, such as 1,2,3,4-tetrahydro-2-naphthoyl, 2-acetamido-1,2,3,4-tetrahydro-2-naphthoyl.

The terms "aralkanoyl" or "aralkylcarbonyl" mean an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl and the like.

The terms "aroyl" or "arylcarbonyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl) benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The heterocyclic (heterocyclo) portion of a heterocyclocarbonyl, heterocyclooxycarbonyl, heterocycloalkoxycarbonyl, or heterocycloalkyl group or the like is a saturated or partially unsaturated monocyclic, bicyclic or tricyclic heterocycle that contains one or more hetero atoms selected from nitrogen, oxygen and sulphur. Such a moiety can be optionally substituted on one or more carbon atoms by halogen, alkyl, alkoxy, oxo, and the like, and/or on a secondary nitrogen atom (i.e., —NH—) by alkyl, aralkoxycarbonyl, alkylcarbonyl, aryl or arylalkyl or on a tertiary nitrogen atom (i.e. =N—) by oxido and that is attached via a carbon atom. The tertiary nitrogen atom with three substituents can also attached to form a N-oxide [=N(O)—] group.

The term "cycloalkylalkoxycarbonyl" means an acyl group of the formula cycloalkylalkyl-O—CO— wherein cycloalkylalkyl has the significance given above. The term "aryloxyalkanoyl" means an acyl radical of the formula aryl-O-alkanoyl wherein aryl and alkanoyl have the significance given above. The term "heterocyclooxycarbonyl" means an acyl group having the formula heterocyclo-O—CO— wherein heterocyclo is as defined above. The term "heterocycloalkanoyl" is an acyl radical of the formula heterocyclo-substituted alkane carboxylic acid wherein heterocyclo has the significance given above. The term "heterocycloalkoxycarbonyl" means an acyl radical of the formula heterocyclo-substituted alkane-O—CO— wherein heterocyclo has the significance given above. The term "heteroaryloxycarbonyl" means an acyl radical represented by the formula heteroaryl-O—CO— wherein heteroaryl has the significance given above.

The term "aminocarbonyl" alone or in combination, means an amino-substituted carbonyl (carbamoyl) group derived from an amino-substituted carboxylic acid (carboxamide) wherein the amino group can be a primary or secondary amino (amido nitrogen) group containing substituents selected from hydrogen, and alkyl, aryl, aralkyl, cycloalkyl, cycloalkylalkyl radicals and the like.

The term "aminoalkanoyl" means an acyl group derived from an amino-substituted alkanecarboxylic acid wherein the amino group can be a primary or secondary amino group containing substituents independently selected from hydrogen, alkyl, aryl, aralkyl, cycloalkyl, cycloalkylalkyl radicals and the like.

The term "halogen" means fluoride, chloride, bromide or iodide. The term "haloalkyl" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like.

The term perfluoroalkyl means an alkyl group wherein each hydrogen has been replaced by a fluorine atom.

Examples of such perfluoroalkyl groups, in addition to trifluoromethyl above, are perfluorobutyl, perfluoroisopropyl, perfluorododecyl and perfluorodecyl.

The term "aromatic ring" in combinations such as substituted-aromatic ring sulfonamide, substituted-aromatic ring sulfinamide or substituted-aromatic ring sulfenamide means aryl or heteroaryl as defined above.

M utilized in the reaction Schemes that follow represents a leaving group such as halogen, phosphate ester or sulfate ester.

Preparation of Useful Compounds

Schemes 1 through 5 illustrate chemical processes and transformations that can be useful for the preparation of compounds useful in this invention; i.e., compounds of formulas I–III, Ia–IIIa and Ib–IIIb. The groups $R^1$ through $R^9$ shown in the schemes are defined above.

These reactions can be carried out under a dry inert atmosphere such a nitrogen or argon if desired. Selected reactions known to those skilled in the art, can be carried out under a dry atmosphere such as dry air whereas other synthetic steps, for example, aqueous acid or base ester or amide hydrolysis, can be carried out under laboratory air. In addition, some processes of this invention can be carried out in a pressure apparatus at pressures above, equal to or below atmospheric pressure. The use of such an apparatus aids in the control of gaseous reagents such as hydrogen, ammonia, trimethylamine, methylamine, oxygen and the like. It can also help prevent the leakage of air or humidity into a reaction in progress. This discussion is not intended to be exhaustive as it is readily noted that additional or alternative methods, conditions, reactions or systems can be identified and used by a chemist of ordinary skill.

Step 1 in Scheme 1 illustrates conversion of a hydroxyl group into compound 2 with an activated carbon-M bond via hydroxyl activation or replacement to provide intermediates useful as electrophilic reagents or, when M is —SH, a product of this invention of formula I is formed. M usually represents leaving groups such as halides (Cl, Br, I), fluorides (aromatic) or sulfate esters such as tosylate (OTs), mesylate (OMs), triflate (OTs) and the like, or epoxides. The preparations of epoxides, sulfate esters or organic halides are well known in the art. M can also represent groups such as —SH (thiol) or, following treatment of a thiol with base or with a pre-formed salt, an —S⁻ group. The non-thiols are prepared from the alcohols by standard methods such as treatment with HCl, HBr, thionyl chloride or bromide, phosphorus trihalide, phosphorus pentahalide, trifluoromethylsulfonyl chloride, tosylchloride or methanesulfonyl chloride and the like.

These reactions are usually carried out at a temperature of about −25° C. to solvent reflux under an inert atmosphere such as nitrogen or argon. The solvent or solvent mixture can vary widely depending upon reagents and other conditions and can include polar or dipolar aprotic solvents as listed or mixtures of these solvents.

In some cases, amines such as triethyl amine, pyridine or other non-reactive bases can serve as reagents and/or solvents and/or co-solvents. In some instances, in these reactions and other reactions in these Schemes, protecting groups can be used to maintain or retain groups in other parts of a molecule(s) at locations that is(are) not desired reactive centers. Examples of such groups that the skilled person might want to maintain or retain include, amines, other hydroxyls, thiols, acids and the like. Such protecting groups can include acyl groups, arylalkyl groups, carbamoyl groups, ethers, alkoxyalkyl ethers, cycloalkyloxy ethers, arylalkyl groups, silyl groups including trisubstituted silyl groups, ester groups and the like. Examples of such protecting groups include acetyl, trifluoroacetyl, tetrahydropyran (THP), Benzyl, tert-butoxy carbonyl (BOC or TBOC), benzyloxycarbonyl (Z or CBZ), tert-butyldimethylsilyl (TBDMS) or methoxyethoxymethylene (MEM) groups. The preparation of such protected compounds as well as their removal is well known in the art.

The second step in Scheme 1 illustrates preparation of a sulfonamide 2. Sulfamidation reactions are conveniently carried out by reacting an amine with, for example, a sulfonyl chloride or sulfonic anhydride. A suitable solvent or mixture of solvents includes aprotic or dipolar aprotic solvents as defined below with examples being acetone, methylene chloride DMF, THF, tert-butylmethylether (tBME) or mixtures of such solvents. Usually such reactions are carried out under and inert or dry atmosphere at a temperature of from about −25° C. to 40° C. preferably at about 0° C. A base for the scavenging of acid is usually also present with non-limiting examples being triethyl amine, pyridine, DBU, N-ethyl morpholine (NEM), sodium carbonate and the like. The sulfonyl chlorides are well know in the art and are commercially available or can be prepared by the reaction of a suitable organometallic reagent with sulfuryl chloride or sulfur dioxide followed by oxidation with a halogen such as chlorine. Grignard and alkyl lithium reagents are desirable organometallic reagents.

In addition, thiols can be oxidized to sulfonyl chlorides using chlorine and/or chlorine with water. Sulfonic acids are available by the oxidation of thiols, reaction of sulfur derivatives with organometallic reagents and the like and can be converted into sulfonyl chlorides by treatment with thionyl chloride, $PCl_5$ and the like. They are also commercially available.

Many reactions or processes involve bases that can act as reactants, reagents, deprotonating agents, acid scavengers, salt forming reagents, solvents, co-solvents and the like. Bases that can be used include, for example, metal hydroxides such as sodium, potassium, lithium, cesium or magnesium hydroxide, oxides such as those of sodium, potassium, lithium, calcium or magnesium, metal carbonates such as those of sodium, potassium, lithium, cesium, calcium or magnesium, metal bicarbonates such as sodium bicarbonate or potassium bicarbonate, primary (I°), secondary (II°) or tertiary (III°) organic amines such as alkyl amines, arylalkyl amines, alkylarylalkyl amines, heterocyclic amines or heteroaryl amines, ammonium hydroxides or quaternary ammonium hydroxides. As non-limiting examples, such amines can include triethylamine, trimethylamine, diisopropylamine, methyldiisopropylamine, diazabicyclononane, tribenzylamine, dimethylbenzylamine, morpholine, N-methylmorpholine, N,N'-dimethylpiperazine, N-ethylpiperidine, 1,1,5,5-tetramethylpiperidine, dimethylaminopyridine, pyridine, quinoline, tetramethylethylenediamine, diazabicyclononane and the like. Non-limiting examples of ammonium hydroxides, usually made from amines and water, can include ammonium hydroxide, triethyl ammonium hydroxide, trimethyl ammonium hydroxide, methyldiisopropyl ammonium hydroxide, tribenzyl ammonium hydroxide, dimethylbenzyl ammonium hydroxide, morpholinium hydroxide, N-methylmorpholinium hydroxide, N,N'-dimethylpiperazinium hydroxide, N-ethylpiperidinium hydroxide, and the like. As non-limiting examples, quaternary ammonium hydroxides can include tetraethyl ammonium hydroxide, tetramethyl ammonium hydroxide, dimethyldiisopropyl ammonium hydroxide, benzymethyldiisopropyl ammonium hydroxide, methyldiazabicyclononyl ammonium hydroxide, methyltribenzyl ammonium hydroxide, N,N-dimethylmorpholinium hydroxide, N,N,N',N'-tetramethylpiperazenium hydroxide, and N-ethyl-N'-hexylpiperidinium hydroxide and the like.

Metal hydrides, amides or alcoholates such as calcium hydride, sodium hydride, potassium hydride, lithium hydride, aluminum hydride, diisobutylaluminum hydrice (DIBAL) sodium methoxide, potassium tert-butoxide, calcium ethoxide, magnesium ethoxide, sodium amide, potassium diisopropyl amide and the like can also be suitable reagents. Organometallic deprotonating agents such as alkyl or aryl lithium reagents such as methyl lithium, phenyl lithium, tert-butyl lithium, lithium acetylide or butyl lithium, Grignard reagents such as methylmagnesium bromide or methymagnesium chloride, organocadium reagents such as dimethylcadium and the like can also serve as bases for causing salt formation or catalyzing the reaction. Quaternary ammonium hydroxides or mixed salts are also useful for aiding phase transfer couplings or serving as phase transfer reagents. Pharmaceutically acceptable bases and be reacted with acids to form pharmaceutically acceptable salts of this invention. It should also be noted that optically active bases can be used to make optically active salts which can be used for optical resolutions.

Generally, reaction media can consist of a single solvent, mixed solvents of the same or different classes or serve as a reagent in a single or mixed solvent system. The solvents can be protic, non-protic or dipolar aprotic. Non-limiting examples of protic solvents include water, methanol (MeOH), denatured or pure 95% or absolute ethanol, isopropanol and the like. Typical non-protic solvents include acetone, tetrahydrofurane (THF), dioxane, diethylether, tert-butylmethyl ether (TBME), aromatics such as xylene, toluene, or benzene, ethyl acetate, methyl acetate, butyl acetate, trichloroethane, methylene chloride, ethylenedichloride (EDC), hexane, heptane, isooctane, cyclohexane and the like. Dipolar aprotic solvents include compounds such as dimethylformamide (DMF), dimethylacetamide (DMAc), acetonitrile, DMSO, hexamethylphosphorus triamide (HMPA), nitromethane, tetramethylurea, N-methylpyrrolidone and the like. Non-limiting examples of reagents that might be used as solvents or as part of a mixed solvent system include organic or inorganic mono- or multi-protic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols or amines for making esters or amides or thiols for making the products of this invention and the like.

Step 4 of Scheme 1 is sulfamidation of compound 1 where $R^2$ can be hydrogen or as otherwise defined. The process of sulfamidation is discussed above in reference to Step 2. The product is the alcohol 4.

Scheme 1 shows in Step 5 the direct conversion of an alcohol such as compound 4 into a contemplated sulfur-containing compound, 5. A descriptive term for this process is activated azo coupling. The process can be carried out by reacting a phosphine such as triphenyl phosphine and an azo compound such as diisopropylaziodicarboxylate (DIAD) or diethylazodicarboxylate (DEAD), a starting alcohol and a thiolcarboxylic acid or dithiocarboxylic acid. The reaction is usually carried out under an inert atmosphere such as nitrogen or argon at about −40° C. to about 50° C. in an inert solvent such as methylene chloride, THF or the others listed above.

The thioester or dithioester [R⁹(C=S)—] 5 is a compound of Formula II. Compound 5 can be hydrolyzed to form compound 8 in Scheme 1 or compounds 15 or 16 as shown in Scheme 4. Compound 8 is a compound of formula I. This hydrolysis can be carried out with bases such as a metal hydroxide (LiOH, NaOH, KOH), carbonate ($Na_2CO_3$, $K_2CO_3$) or a bicarbonate ($NaHCO_3$). Examples of other hydrolytic reagents suitable for this reaction include alkoxides such as sodium methoxide, potassium ethoxide and the like, a thiolate such as sodium thiophenolate, potassium methanethiolate and the like or by hydrolytic exchange with an amine or ammonia.

These reactions can be carried out under an inert atmosphere such as helium, nitrogen or argon at temperatures of from about −50° C. to about 100° C. Temperatures from about 0° C. to about 60° C. are preferred. Solvents, pure or mixed, include water, alcohols especially for alcoholate hydrolysis or dipolar aprotic solvents such as acetonitrile, DMSO or DMF. Amine exchanges can occur under conditions as discussed above. In addition, the amine can serve if desired as the solvent or a co-solvent as, for example, when diethylamine, morpholine, dimethyl amine (in a pressure system) or piperidine, are used as exchange agents.

The preparation of compound 8 from compound 5 can also be carried out using reductive processes if desired. Useful reducing agents may include lithium aluminum hydride, aluminum hydride, DIBAL, potassium borohydride, sodium borohydride, lithium borohydride or a metal catalyzed hydrogenation with a system such as the employing a Rosenmund catalyst. Reductions of the hydride type are usually carried out at between 80° C. and −80° C. in non-polar aprotic solvents such as THF or ethers whereas hydrogenations with hydrogen gas require containers (hydrogenation bottles, Parr bombs, pressure kettles and the like) with protic or non-protic solvents or solvent mixtures at temperatures of between −20° C. to 100° C.

Conversion of compound 3 in Scheme 1 into the sulfur-containing compound 5 illustrates displacement of an electrophile by a nucleophile; i.e., the conversion of a intermediate containing our activated leaving group M or a derivative into a sulfur compound of this invention. This method of synthesis is commonly called bimolecular nucleophilic substitution. Solvolysis or $SN_1$ reactions are also possible and, if desired, can be used to provide electrophilic substitutions to produce alcohols, ethers, amines, carboxylate esters and the like. The reagents that provide the above compounds via $SN_1$ ractions are water, alcohols, amines and carboxylic acids.

The nucleophilic displacement ($SN_2$) reaction can be used in Step 3 wherein group M is displaced by a thiol compound or the salt of a thiol compound to produce compounds of formula I (compound 8) or formula II (compound 5) directly or a compound of formula I via conversion of II into I. The diagramatically reverse procedure; i.e., synthesis of a compound of formula I followed by its conversion into a compound of formula II or formula III can also be accomplished. Either compounds of formula I or of formula II can be direct or non-direct intermediates in the preparation of compounds III (e.g. compound 6).

Compounds of formula III can be converted into a compound of either of formulas I or II with a thiol reagent. Non-limiting examples of thiol reagents or their salts useful for nucleophilic displacement reactions are hydrogen sulfide ($H_2S$), sodium sulfide (NaSH), thioacetic acid [HS(C=O)$CH_3$], sodium thiolacetate [NaS(C=O)$CH_3$], dithioacetic acid [HS(C=S)$CH_3$] and sodium dithiolacetate [NaS(C=S)$CH_3$]. A thiolate or other anion can be obtained from a preformed salt such as sodium sulfide or sodium thiolacetate or it can be formed in situ via addition of a base to an acid such as hydrogen sulfide or thiolacetic acid. The bases and solvents are discussed above. Preferred bases are those that are hindered or tertiary such that competition with a sulfur anion as a nucleophile in a two stage reaction is minimized, e.g., triethylamine, pyridine, DBU, DMAP and the like. A strong inorganic base or organometallic base can be used if desired.

The solvents, solvent mixtures or solvent/reagent mixtures discussed above are satisfactory but non-protic or dipolar aprotic solvents such as acetone, acetonitrile, DMF, acetonitrile and the like are examples of a preferred class. Bases can also be used as solvents as well as reagents. Mixtures of the above solvents or with a solvent and a base such as pyridine or triethylamine are also useful. These reactions are usually carried out under an inert atmosphere (nitrogen, argon) at temperatures varying from between about −10° C. to about 80° C. In many cases, room temperature is preferred due to cost or simplicity. Again, procedures involving nucleophilic substitution reactions are well know in the art and sulfur based anions are known to be excellent nucleophiles.

The oxidation/reduction sequence illustrated in Scheme 1 Step 6 and Step 7 is also well known in the art. In addition, in situ hydrolysis of compound 5 by base, preferably protic, reaction of the C=W group with a organometallic reagent or its reductive removal can provide an —SH compound 8. The thiol compound preformed or formed in the reaction, can then be oxidized if desired using, for example, air, oxygen, ozone, hypohalide reagents, sodium plumbite, or other likely oxidation agents. Non-oxidizable solvents and a basic or slightly basic pH value are preferred but not required and the atmosphere of the reaction can be air or another inert gas mentioned above. Preferred temperature is 0° C. to 40° C., but lower or higher temperatures can be used.

Mixed disulfides (heterodimers) can be made if the starting materials have different structures or by reaction of compound 6 (when $R^2$ is H) with different alkylating agents as is discussed below. Reversal of the process ex vivo requires reduction of the disulfide bond to the thiol of formula I (compound 8). Compound 5 is formed by acylation of compound 8 with a reagent such as a derivative of HO(C=W)R⁹. Such a derivative can be an activated carbonyl compounds prepared using reagents well know in the art including the peptide and protein synthesis and amino acid coupling or conjugation art. Examples of such reagents are thionyl chloride, oxalyl chloride, phosphorus oxychloride, HOBT (hydroxybenzotriazole), isobutylchloroformate, carbodimide, azodicarboxylate compounds an the like all of which are well known and established in the art. Reduction of the disulfide to the corresponding thiol can be carried out by, for example, treatment with hydride reagents such as lithium aluminum hydride, aluminum hydride, DIBAL, metal borohydrides ($Li^+$, $Na^+$, $K^+$, $Ca^{++}$), sodium cyanoborohydride and the like.

The aminoalcohol compound 7 in Scheme 2 illustrates a special case example of compound 1 wherein $R^2$ is hydrogen. This series of reactions using, for example, compound 7, permits sulfamidation by processes discussed above wherein one skilled in the art can produce examples of compound 4 where $R^2$ is hydrogen. This intermediate or product can then be alkylated or otherwise substituted to produce compound 4 wherein $R^2$ is other than hydrogen. Alkylating agents include compounds that contain groups that can be displaced by a nucleophile such as a sulfamic acid salt.

Compound 4 with R²=hydrogen is a sulfamic acid and, as such, can be treated with a base to form an anion. This anion can be reacted in an $SN_2$ manner with an intermediate or reagent containing a group that can be displaced with such displaceable groups including such non-limiting examples as epoxide, chloride, bromide, iodide, tosylate, mesylate, triflate, mesylate and the like. Examples of such reagents or intermediates include benzyl bromide, methyl iodide, n-butyl chloride, isoamyl tosylate, N-chloroethylmorpholine, N-bromoethylpiperidine and the like.

The anion can also be reacted (acylated) with a carbonyl compound in an addition-elimination sequence to provide a N-carbonyl compound. Such acylated compounds might be reduced to desired intermediates or serve as protecting groups or both. The anion can be formed with the bases listed and discussed above if the affects of sulfamide structure on pKa are accommodated. Sodium carbonate, potassium carbonate, potassium methoxide or DMAP represent bases sufficiently strong that they can be used to deprotonate a sulfonamide such as 4. In some cases, the use of a strong base such as an organometallic base under argon in a aprotic solvent is desirable.

The reactions are normally carried out under an inert atmosphere at temperatures of from about 0° C. to about 100° C. using either protic or dipolar aprotic solvents or with solvent mixtures. The solvent mixtures can include reagents such as amine bases that can also serve as part of a solvent mixture. An alkylation or acylation reactions involving salt formation are examples of the type reaction wherein a non-participating group such as a hydroxly group hydroxyl group on compound 4 can be protected if desired by the skilled chemist.

A second process that can be used to place an R² group a sulfonamide with at least one hydrogen atom is reductive amination. Treatment of compound 4 containing an active hydrogen on the nitrogen of the sulfamide with an aldehyde or ketone and a reducing agent such as $LiAlH_4$, $NaCNBH_4$, $LiBH_4$, $AlH_4$ or hydrogen in the presence of controlled activity metal catalyst may provide compounds with a R² group. An intermediate in this reductive process can be an sulfimine, sulfimine derivative or a tautomer thereof. The reducing agent can be present in the initial reaction or the intermediate can be subsquently reduced, i.e., the intermdiate carbonylsulfamide compound can be isolatable or it may be reduced further directly. A sulfamide salt can also add to a carbonyl group (acylation) of an ester, amide, anhydride, acid halide, mixed anhydride or similar compound and then be reduced.

Step 4 in Scheme 2 involves the hydroxyl conversion step discussed in with regards to Step 1 in Scheme 1. Here again, protection of a non-reactive group can be desirable. Once the hydroxyl is converted into, for example, a halide or sulfate ester, the sulfamide can be alkylated or reductively alkylated to introduce the R² group (Step 5) if such is desired. This produces compound 3 which can be treated with a nucleophile including —SH to produce compounds 5 or 8. Note, these are the same compounds as can be produced via the methods of Scheme 1.

Scheme 2 also illustrates the conversion of compound 4 into compound 5, compound 4 into compound 9 and compound 9 into compound 3. The former conversion is discussed above per Scheme 1. The preparation of Compound 9 illustrates the preparation of a sulfonamide compound where R² is hydrogen and M is a leaving group (activated intermediate).

The hydroxyl conversion process is well discussed above under Step 1 of Scheme 1. In this case, protection of groups that one does not wish to participate in a reaction or process can be useful. The use of reagents that convert hydroxyl groups into halide type leaving groups is preferred. Examples of such agents include hydrogen bromide, hydrogen chloride, hydrogen iodide, hydrobromic acid, hydrochloric acid or hydriodic acid. Agents that can convert a sulfonamide nitrogen-hydrogen bond into a nitrogen-halogen bond such as sodium hypochlorite can serve as a method of protecting the sulfonamide from further substitution on nitrogen. The halogen is removable when desired by reduction.

Once formed, compound 9 can be alkylated or acylated by processes as discussed for Step 2 in this Scheme to provide compound 3. Compound 3 can be converted into a compound of this invention of formula I or formula II (compound 5) via a nucleophilic or electrophilic substitution process as illustrated in Step 6. These processes and reactions are discussed above.

An alternative synthetic process strategy wherein one starts with an alcohol or protected alcohol intermediate substituted with an M leaving group is illustrated in Scheme 3. Conversion of compound 10 into compound 7 or compound 11 or a protected derivative is accomplished by amination at the carbon-M bond with a ammonia or a I° amine or derivative.

Amination can be a nucleophilic substitution process wherein the nucleophile is an amine, amine anion or other amine derivative. If an amine is the reagent desired, one can treat compound 10 directly with the amine at temperatures of from about −60° C. to reflux temperature in protic, non-protic or dipolar aprotic solvents under an inert atmospheres or air. Protic solvents can include water wherein the reagent is usually an amine hydroxide such as ammonium hydroxide, benzylamine hydroxide and the like. Amine hydroxides are discussed above. Solvents that can react with amines such as ethyl acetate or acetone are not to be used. A pressure containment system or a low temperature system can be used for gaseous amines such as ammonia, methyl amine ethyl amine and the like. For example, reactions with or in ammonia can be run in liquid ammonia at a temperature of about −33° C. The $SN_2$ reaction can also be carried out with an metal-amine salt such as sodium amide, calcium amide, potassium metylamide and the like.

Following synthesis of the alcohol-amine compound 7 or 11 or a protected derivative thereof, one can add the N-substituent R² by reductive amination or alkylation processes as discussed above. Compound 7 represents compounds where R² is hydrogen whereas compound 11 represents compounds wherein R² is any other group described earlier in this specification.

Step 3 in this sequence illustrates conversion of the unprotected alcohol group into the sulfur compound 12, which can then be converted into 5, which is a sulfonamide of this invention if formula II. Step 5 shows conversion of the M-substituted carbinol 10 into the sulfur compound 13 via a before-discussed activated azo procedure as in Step 3. Compound 13 can then be treated in Step 6 as with Step 1 to convert the M-carbon bond in compound 13 into a carbon-nitrogen bond to produce compounds 12 or 14 wherein R² is either hydrogen (compound 14)or not hydrogen (compound 12). When this product is compound 14 and R² is hydrogen, it can be converted into compound 12 by alkylation or reductive alkylation processes of Step 7 using the methods of Step 2.

Scheme 4 presents an alternative synthetic route to the compounds of this invention such as compounds 5, 15 or 16. The amine $R^2NH_2$ is reacted with a sulfonamide forming reagent such as a sulfonyl chloride under sulfamidation conditions to provide a sulfonamide. The sulfonamide can have two hydrogen atoms on the nitrogen of the sulfonamide group or it can have one nitrogen-carbon bond valence be occupied by a group $R^2$. In the latter case, the sulfonamide can be alkylated (Step 3) by processes discussed above using compound 13 as the electrophile. Compound 13 was prepared in Scheme 3.

The product of this alkylation is compound 5, which is a sulfur compound of formula II of this invention. Hydrolysis of compound 5 can provide compound 16, which is a compound of formula I discussed above.

Step three displays the same process as Step 1 except that the amine is replaced by ammonia to provide an unsubstituted sulfonamide. This unsubstituted sulfonamide can be alkylated with, for example, compound 13 or compound 10, to produce sulfonamide compound 14 or sulfonamide compound 4. Alkylation of compound 14 by procedures illustrated above provides compound 5. Hydrolysis of compound 14 (Step 5) can produce compound 15 which is a compound of this invention of formula I.

An extended example Step 3 or Step 2 is provided by the procedure of Example 44. In this case, the amine can be $R^2NH_2$ with $R^2$ being methyl followed by post sulfamidation alkylation with 2-iodobenzylchloride to produce a dialkylated sulfonamide that is subsequently converted into a thiol compound of this invention of formula IV. The inverse procedures can be carried out wherein the product of reaction with iodobenzylchloride or iodobenzylamine is the first sulfonamide that is then alkylated with methyl iodide. Conversion of this intermediate into the sulfur-containing product uses a cobalt complex with thiourea followed by reduction with sodium cyanoborohydride. This process is a useful alternative for the synthesis of aromatic sulfur compounds.

To further illustrate some of the general principles of synthesis of the compounds of this invention, Scheme 5 presents the preparation of the product of Example 41C. The carbinol amine a was treated with the sulfonyl chloride b under sulfamidation conditions to produce sulfonamide compound c. The reaction was carried out under nitrogen in THF and water as co-solvents and with triethylamine as the base to act a the product hydrochloric acid scavenger. The reaction temperature was about 0° C. in an ice bath.

The sulfonamide c in which $R^2$ is H was alkylated with methyl iodide to produce the product d wherein $R^2$ is methyl. The solvent for this reaction was DMF with potassium carbonate base being suspended/dissolved therein under an atmosphere of nitrogen. The reaction mixture including the methyl iodide was maintained at room temperature.

Nucleophilic displacement of fluoride with an (ArS—)⁻ anion from the substituted aryl group on the sulfonamide was the next step carried out to produce compound e. Here, compound d was dissolved in DMF solvent followed by cesium carbonate and thiophenol. The reaction mixture was stirred for about 15 hours at about 70° C. under nitrogen to produce the ArS-substituted aromatic N-methyl sulfonamide compound e.

This alcohol was then converted via the activated azo coupling procedure into the sulfur compound f, which is a compound, useful in a process of this invention. This reaction was carried out at 0° C. in THF under nitrogen. The reagents triphenylphosphine and diethyldiazodicarboxylate were dissolved in the THF and thioacetic acid was added. The reaction was permitted to proceed for about one hour to yield compound f which is the product of Example 41B. Hydrolysis of compound f with sodium methoxide in methanol at room temperature for about one half hour provide compound g which is also the product of Example 41C. This product of this invention is a potent MMP-13 inhibitor with an $IC_{50}=0.002$ $\mu$M (2 nM).

Optically active compound isomers as well as mixed or non-optically active compound isomers are specifically intended to be included in this discussion. Examples of isomers are RS isomers, enantiomers, diastereomers, racemates, cis isomers, trans isomers, E isomers, Z isomers, syn-isomers, anti-isomers, tautomers and the like. Aryl, heterocyclo or heteroaryl tautomers, heteroatom isomers and ortho, meta or para substitution isomers are also included as isomers.

The chemical reactions described above are generally disclosed in terms of their broadest application to the preparation of the compounds useful in this invention. Occasionally, the reactions may not be applicable as described to a particular compound included within the disclosed scope or can be unsafe in a particular instance. In addition, some preparations can be more desirable than the alternatives due to cost or other economic considerations. The compounds for which this occurs are readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

SCHEME 1

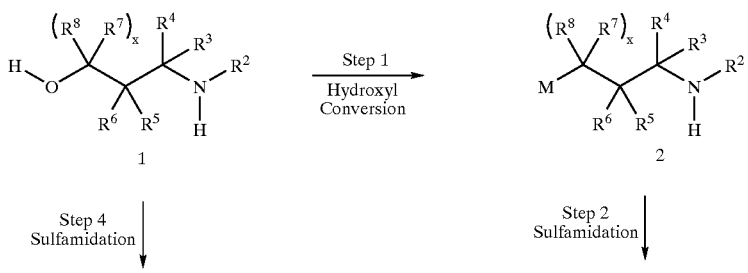

-continued
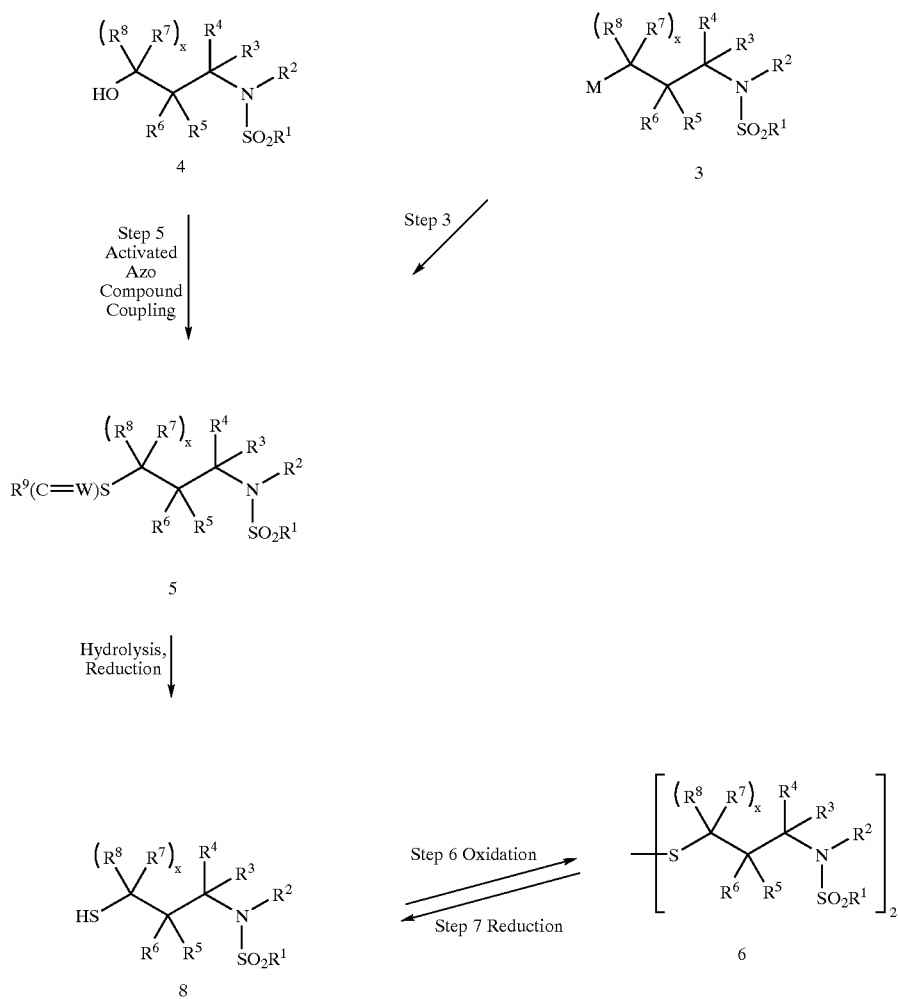
SCHEME 2
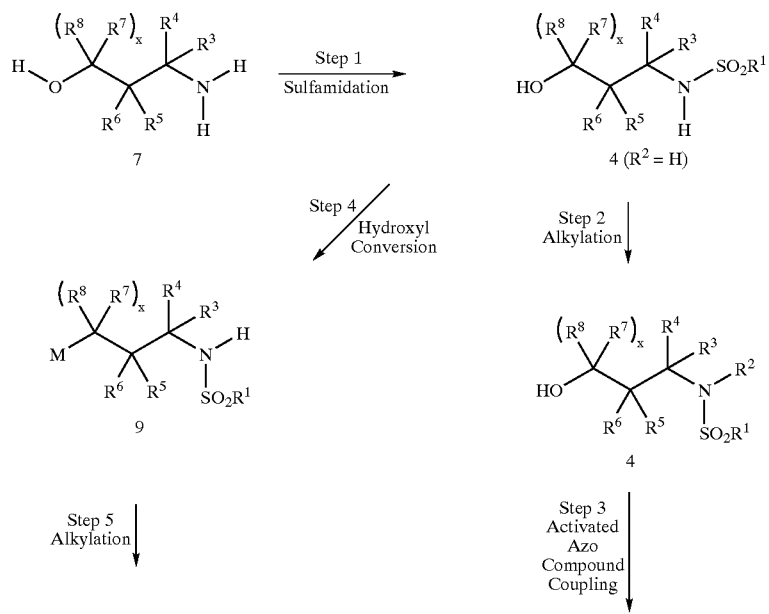

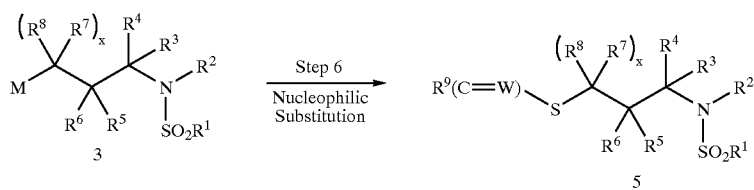
SCHEME 3
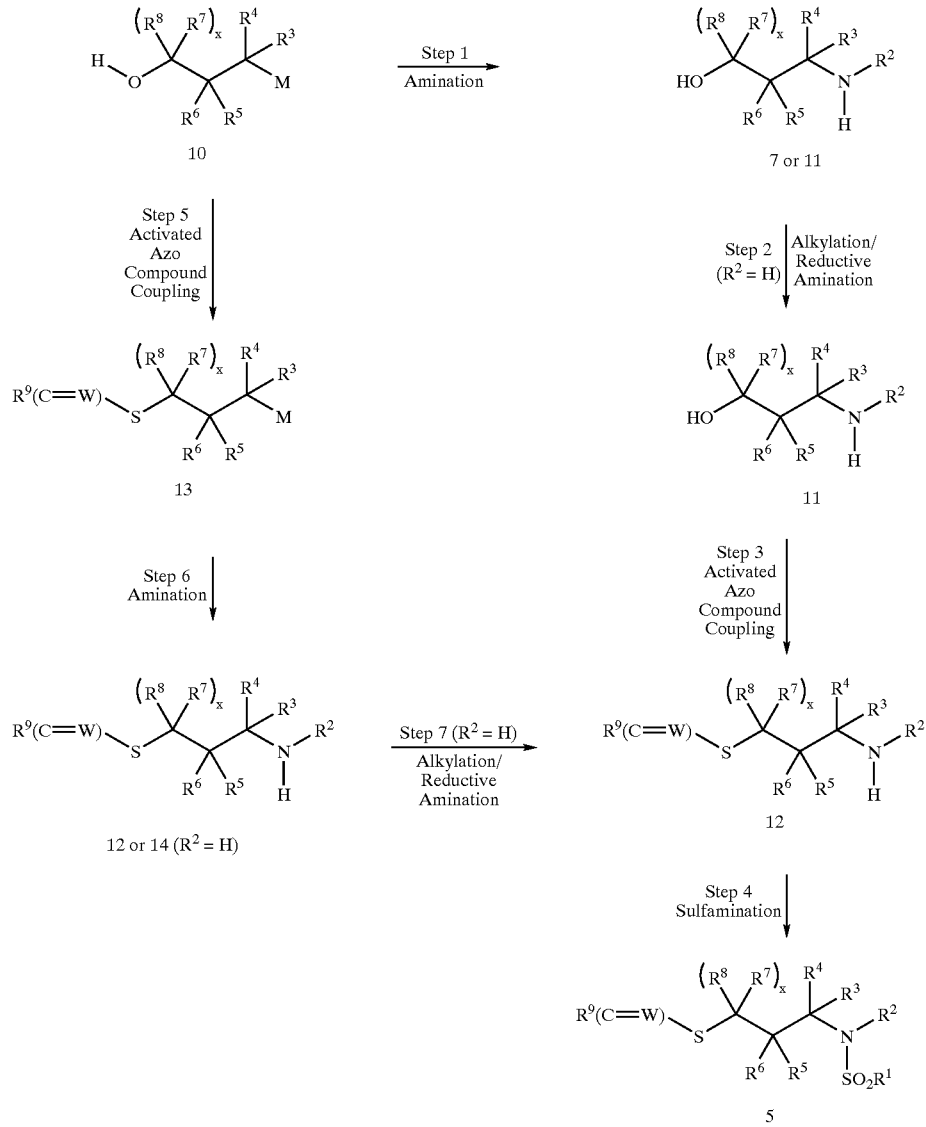
SCHEME 4
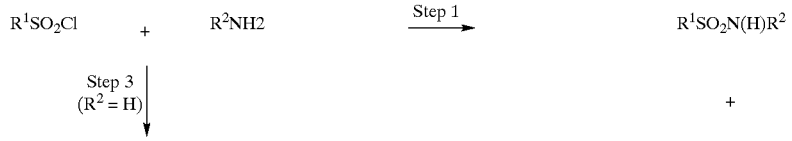

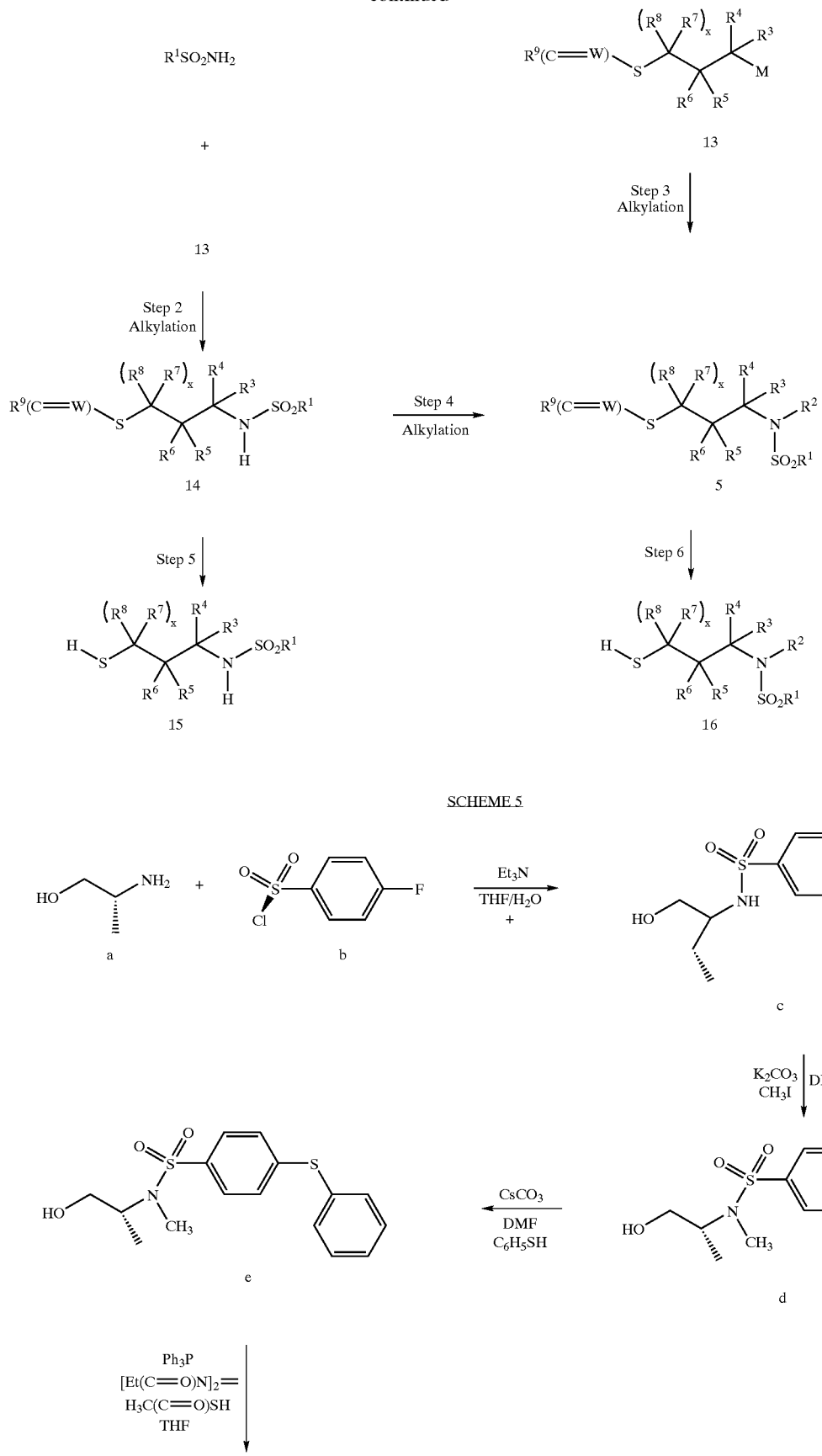

205 206

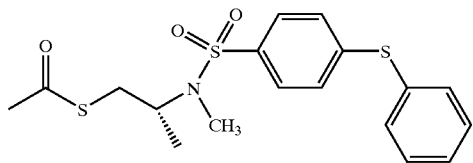
f
Ex 41 B

NaOCH₃ →
H₃COH

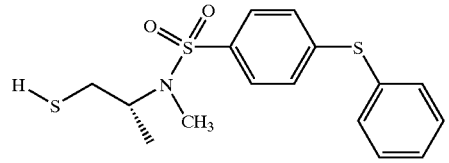
g
Ex 41 C

BEST MODE FOR CARRYING OUT THE INVENTION

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Preparation of N-(2-Hydroxyethyl)-4-methoxybenzenesulfonamide

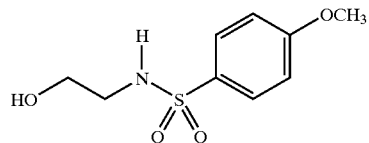

To a solution of 3.5 mL (3.54 g, 58 mmol) of ethanolamine in 20 mL of THF and 5 mL of water, was added 10.7 mL of triethylamine. After cooling in an ice bath, 10.53 g (51 mmol) of para-methoxybenzenesulfonyl chloride was slowly added over ten minutes. After stirring at room temperature for 1 hour, the solvent was removed under reduced pressure and ethyl acetate and water added. The organic layer was separated, washed with 5% KHSO4 and brine, dried over sodium sulfate, filtered and stripped to afford 10.3 g of the desired N-(2-hydroxyethyl)-4-methoxybenzenesulfonamide, m/e=238 (M+Li).

EXAMPLE 2

Preparation of N-(2-Hydroxyethyl)-4-(n-butoxy)benzenesulfonamide

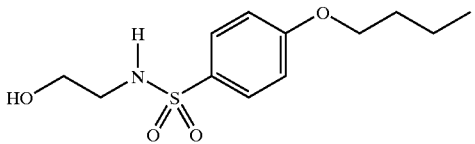

To a solution of 4.0 mL (66 mmol) of ethanolamine in 20 mL of tetrahydrofuran and 5 mL of water, was added 11.3 mL (81 mmol) of triethylamine. The solution was cooled to 0 C, and a solution of 15.0 g (54 mmol) of p-(n-butoxybenzene)sulfonyl chloride in 10 mL of tetrahydrofuran was slowly added. After 2 hours at room temperature, the solution was stripped, ethyl acetate added, washed with 5% KHSO4, saturated sodium bicarbonate, brine and dried over sodium sulfate, filtered and stripped to afford 15.3 g of crude material. This was crystallized from ethyl acetate/hexane to afford 13.4 g of pure N-(2-hydroxyethyl)-4-(n-butoxy) benzenesulfonamide.

EXAMPLE 3

Preparation of N-(2-Hydroxy-1R-methylethyl)-4-methoxybenzenesulfonamide

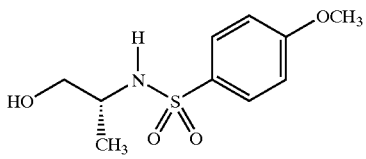

To a solution of 15.5 mL (15.0 g, 200 mmol) of (R)-(–)-2-amino-1-propanol in 140 mL of THF and 47 mL of water, was added 32.9 mL (23.9 g, 236 mmole) of triethylamine. After cooling in an ice bath, 37.5 g (182 mmol) of 4-methoxybenzenesulfonyl chloride was slowly added over 1 hour. After stirring at room temperature for 2 hour, the reaction was concentrated in vacuo, ethyl acetate and water were added, the organic layer was separated and washed with 5% potassium hydrogen sulfate solution, saturated sodium bicarbonate solution and brine, dried over sodium sulfate, filtered and concentrated to afford 44 g of the desired N-(2-hydroxy-1R-methylethyl)-4-methoxybenzenesulfonamide, m/e=252 (M+Li).

EXAMPLE 4

Preparation of N-(2-Hydroxy-1R-methylethyl)-4-(n-butoxy)benzenesulfonamide

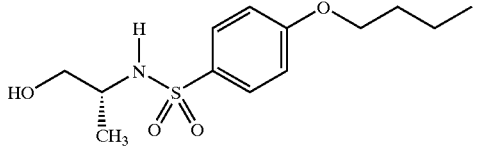

To a solution of 4.83 g (64.3 mmol) of (R)-(–)-2-amino-1-propanol in 22 mL of THF and 6 mL of water, was added 12 mL (83.6 mmol) of triethylamine. After cooling in an ice bath, a solution of 14.4 g (57.9 mmol) of 4-(n-butoxy) benzenesulfonyl chloride in 20 mL of tetrahydrofuran was slowly added over 0.5 hour. After stirring at room temperature for 2 hour, the reaction was concentrated in vacuo, ethyl acetate and water were added, the organic layer was separated and washed with 5% potassium hydrogen sulfate solution, saturated sodium bicarbonate solution and brine, dried over sodium sulfate, filtered and concentrated to afford 16.0 g of the desired N-(2-hydroxy-1R-methylethyl)-4-(n-butoxy)benzenesulfonamide, m/e=288 (M+H).

EXAMPLE 5

Preparation of N-(2-Hydroxy-1R-methylethyl)(3-thiophenylpropyl)sulphonamide

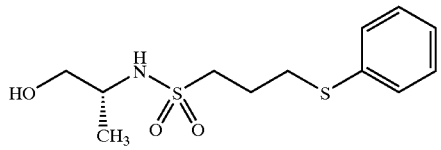

Part A: To a solution of (10.0 g, 133 mmol) 2R-amino-1-propanol in 120 mL of acetone and 50 mL of water, was added 35.8 mL of triethylamine. After cooling in an ice bath, 23.5 g (133 mmol) of 3-chloro propanesulfonyl chloride was slowly added over 15 minutes. After stirring at room temperature for 2 hours, the solvent was removed under reduced pressure and ethyl acetate and water was added. The organic layer was separated; washed with 5% KHSO4 and brine, dried over sodium sulfate, filtered and stripped to afford 8.5 g of the desired N-(2-hydroxy-1R-methylethyl)(3-chloropropyl)sulphonamide, m/e=222 (M+Li).

Part B: To a solution of 4.13 g (20 mmol) of product from part A in (25 mL) of anhydrous acetonitrile, was added (4.4 g, 40 mmol) of triethylamine followed by (3.3 g, 30 mmol) of benzenethiol. After stirring at room temperature for 16 hours, the reaction was diluted with (200 mL) of dichloromethane. Washed with 2x60 mL saturated aqueous sodium bicarbonate and 2x50 mL brine, dried over sodium sulfate, filtered and solvent removed under reduced pressure and the residue chromatographed on 100 g of silica gel using 2:1 ethyl acetate:hexane to afford 2.1 g of the desired N-(2-hydroxy-1R-methylethyl)(3-thiophenylpropyl)sulphonamide, m/e=296 (M+Li).

EXAMPLE 6

Preparation of N-(2-Hydroxy-1R-methylethyl)-4-(n-pentyl)benzenesulfonamide

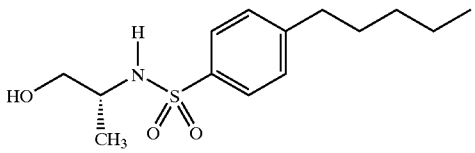

To a ice cooled solution of (2.5 g, 30 mmol) of (R)-(-)-2-amino-1-propanol in 50 mL of acetone, 25 mL of water , and 10 grams of triethylamine was added (7.7 g, 30 mmol) of 4-(n-pentyl)benzenesulfonyl chloride slowly over 10 minutes. After stirring for 3 hours at room temperature, the solution was concentrated by rotory evaporation and the contents were partitioned between 200 mL of ethyl acetate and 200 mL of water. The organic layer was washed with 100 mL of 5% potassium hydrogen sulfate, followed by saturated sodium chloride, dried over magnesium sulfate, filtered and concentrated to yield 8.0 grams of a clear oil, identified as N-(2-hydroxy-1R-methylethyl)-4-(n-pentyl)benzenesulfonamide.

EXAMPLE 7

Preparation of N-(2-Mercaptoethyl)-N-(phenylmethyl)-4-methoxybenzenesulfonamide

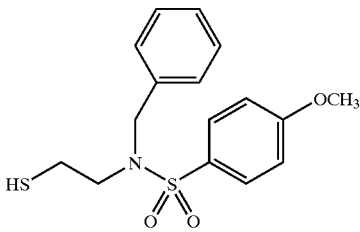

Part A: To a solution of 10.04 g (43 mmol) of N-(2-hydroxyethyl)-4-methoxybenzenesulfonamide from Example 1 in 85 mL of anhydrous DMF, was added 17.8 g (128 mmol) of powdered potassium carbonate and then 8.2 g (48 mmol) of benzyl bromide. After 24 hours, ethyl acetate and water was added, the organic layer separated and washed 3xs with brine, dried with sodium sulfate, filtered and stripped to afford 14.3 g of crude product. This was recrystallized from tert-butylmethyl ether/hexane to afford 9.0 g of the desired N-(hydroxyethyl)-N-(phenylmethyl)-4-methoxybenzenesulfonamide.

Part B: To a solution of 2.0 g (6.2 mmol) of product from Part A and 1.79 g (6.8 mmol) of triphenylphosphine in 31 mL of anhydrous THF at 0 C, was added 1.35 mL (6.8 mmol) of diisopropylazodicarboxylate, followed by 0.50 mL (6.8 mmol) of thiolacetic acid. After stirring at room temperature for 15 hours, the reaction was concentrated and the residue chromatographed on 150 g of silica gel using 20–30% ethyl acetate/hexane to afford 1.48 g of the desired product, which was recrystallized from ethyl acetate/hexane to afford 1.0 g of pure product, identified as the desired product, m/e=380 (M+H).

Part C: To a suspension of 0.57 g (1.5 mmol) of product from Part B above in 4 mL of anhydrous methanol, was added 1.2 mL (5.4 mmol) of 25 weight % sodium methoxide in methanol. After 30 minutes, the solution was cooled in ice and 2% hydrochloric acid added. Ethyl acetate was added and the organic layer separated and washed with saturated sodium bicarbonate, brine, dried over anhydrous magnesium sulfate, filtered and stripped to afford 0.5 g of crude material. This was chromatographed on 50 g of silica gel using 20%–40% ethyl acetate/hexane to yield 0.3 g of pure N-(mercaptoethyl)-N-(phenylmethyl)-4-methoxybenzenesulfonamide.

EXAMPLE 8

Preparation of N-(2-Mercaptoethyl)-N-pentyl-4-methoxybenzenesulfonamide

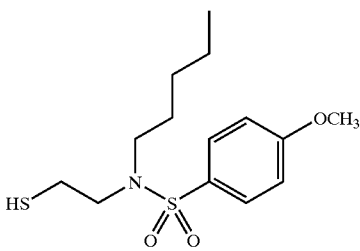

Part A: To a solution of 2.0 g (8.6 mmol) of N-(2-hydroxyethyl)-4-methoxybenzenesulfonamide from Example 1 in 20 mL of anhydrous DMF, was added 3.58 g (25.9 mmol) of powdered potassium carbonate and then 1.96 g (13 mmol) of 1-bromopentane. After 24 hours, ethyl acetate and water was added, the organic layer separated and washed 3×s with brine, dried with sodium sulfate, filtered and stripped to afford 2.3 g of crude product. This was chromatographed on 150 g of silica gel using 20%–50% ethyl acetate/hexane to afford 2.12 g of the desired N-(hydroxyethyl)-N-pentyl-4-methoxybenzenesulfonamide, m/e=302 (M+H).

Part B: To a solution of 2.1 g (7.0 mmol) of product from Part A and 2.03 g (7.7 mmol) of triphenylphosphine in 28 mL of anhydrous THF at 0 C, was added 1.2 mL (7.74 mmol) of diethylazodicarboxylate, followed by 0.56 mL (7.7 mmol) of thiolacetic acid. After stirring at room temperature for 15 minutes, the reaction was concentrated and the residue chromatographed on 150 g of silica gel using 10–50% ethyl acetate/hexane to afford 2.06 g of the desired product, m/e=360 (M+H).

Part C: To a solution of 2.06 g (6.3 mmol) of product from Part B above in 13 mL of anhydrous methanol, was added 5.2 mL (22.6 mmol) of 25 weight % sodium methoxide in methanol. After 30 minutes, the solution was cooled in ice and 2% hydrochloric acid added. Ethyl acetate was added and the organic layer separated and washed with saturated sodium bicarbonate, brine, dried over anhydrous magnesium sulfate, filtered and stripped to afford 1.26 g of pure N-(2-mercaptoethyl)-N-pentyl-4-methoxybenzenesulfonamide, m/e=324 (M+Li).

EXAMPLE 9

Preparation of N-(2-Mercapto-1R-methylethyl)-N-butyl-4-methoxybenzenesulfonamide

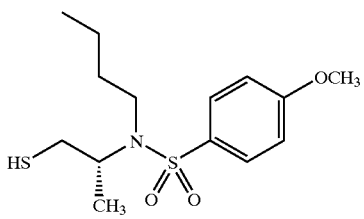

Part A: To a solution of 3.0 g (12 mmol) of N-(2-hydroxy-1R-methylethyl)-4-methoxybenzenesulfonamide from Example 3 in 40 mL of anhydrous DMF, was added 5.1 g (37 mmol) of powdered potassium carbonate, followed by 2.0 mL (2.5 g, 18 mmol) of 1-bromobutane. After 66 hours, and additional 2.5 g (18 mmol) of powdered potassium carbonate and 1.0 mL (1.3 g, 9 mmol) of 1-bromobutane were added, and the reaction heated at 40° C. After 48 hours at 40° C., the reaction was concentrated in vacuo, ethyl acetate and water were added, the organic layer was separated and washed 3×s with brine, dried with magnesium sulfate, filtered and concentrated to afford the crude product. This was chromatographed on silica gel using 30%–40% ethyl acetate/hexane to yield 2.8 g of pure N-(2-hydroxy-1R-methylethyl)-N-butyl-4-methoxybenzenesulfonamide, m/e=302 (M+H).

Part B: To a solution of 2.8 g (9 mmol) of N-(2-hydroxy-1R-methylethyl)-N-butyl-4-methoxybenzenesulfonamide from Part A and 2.7 g (10 mmol) of triphenylphosphine in 50 mL of anhydrous THF at 0° C., was added 1.6 mL (1.8 g, 10 mmol) of diethylazodicarboxylate, followed after 5 min. by 0.7 mL (0.8 g, 10 mM) of thiolacetic acid. After 17 hours, the reaction was concentrated and the residue was chromatographed on silica gel using 10%–20% ethyl acetate/hexane to yield 2.0 g of the desired product, m/e= 366 (M+Li).

Part C: To a solution of 2.0 g (6 mmol) of the product from Part B in 50 mL of anhydrous methanol, was added 0.5 g (21 mmol) of sodium metal. After 1 hour, the reaction was cooled, 1N HCl solution was added, followed by ethyl acetate and water, the organic layer was separated and washed with saturated sodium bicarbonate solution and brine, dried with magnesium sulfate, filtered and concentrated to afford 1.6 g of crude product. This was chromatographed on silica gel using 5%–15% ethyl acetate/hexane to yield 0.9 g of pure N-(2-mercapto-1R-methylethyl)-N-butyl-4-methoxybenzenesulfonamide, m/e=324 (M+Li).

EXAMPLE 10

Preparation of N-(2-Mercaptopropyl)-4-methoxybenzenesulfonamide

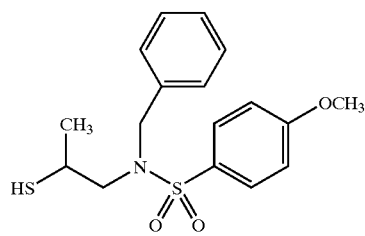

Part A: To a solution of 10.04 g (43 mmol) of N-(2-hydroxyethyl)-4-methoxybenzenesulfonamide from Example 1 in 85 mL of anhydrous DMF, was added 17.8 g (128 mmol) of powdered potassium carbonate and then 8.2 g (48 mmol) of benzyl bromide. After 24 hours, ethyl acetate and water was added, the organic layer separated and washed 3×s with brine, dried with sodium sulfate, filtered and stripped to afford 14.3 g of crude product. This was recrystallized from tert-butylmethyl ether/hexane to afford 9.0 g of the desired N-(hydroxyethyl)-N-(phenylmethyl)-4-methoxybenzene-sulfonamide.

Part B: To a solution of 4.0 g (12.4 mmol) of N-(2-hydroxyethyl)-N-(phenylmethyl)-4-methoxybenzenesulfonamide from Part A in 6 mL of anhydrous methylene chloride and 6 mL of anhydrous dimethyl sulfoxide, was added 17.1 mL of triethylamine, the solution cooled in an ice bath and 7.9 g (50 mmol) of sulfur trioxide/pyridine complex in 38 mL of DMSO was added over 15 minutes. After 1 hour, the reaction mixture was poured into ice, extracted with ethyl acetate, washed with 5% KHSO4, brine, dried over magnesium sulfate, filtered and stripped to afford 4.0 g of N-(2-propanal)-4-methoxybenzenesulfonamide suitable for the next reaction.

Part C: To 8.3 mL (25 mmol) of 3M methyl magnesium bromide in diethyl ether at 0 C under nitrogen, was added a solution of 4 g (12.4 mmol) of crude N-(2-propanal)-4-methoxybenzenesulfonamide from Part B in 10 mL of anhydrous tetrahydrofuran. After 1 hour at room temperature, the reaction was cooled in ice and quenched by the addition of saturated ammonium chloride solution, extracted with ethyl acetate, washed with 5% KHSO4, brine, dried and stripped to afford 4.0 g of crude material. This was chromatographed on silica gel using 20%–40% ethyl acetate/hexane to afford 3.25 g of the desired N-(2-hydroxypropyl)-4-methoxybenzenesulfonamide, m/e=336 (M+H).

Part D: To a solution of 2.0 g (5.9 mmol) of alcohol from Part C and 1.71 g (6.5 mmol) of triphenylphosphine in 30 mL of anhydrous tetrahydrofuran at 0 C, was added 1.28 mL (1.32 g, 6.5 mmol) of diisopropylazodicarboxylate, then 0.47 mL (6.5 mmol) if thioacetic acid. After 15 hours at room temperature, the solution was stripped and chormatographed on 150 g of silica gel using 20%–50% ethyl acetate/hexane to afford 0.43 g of the desired product, m/e=400 (M+Li).

Part E: To a solution of 0.43 g (1.1 mmol) of the product of Part D in 5 mL of anhydrous methanol, was added 0.9 mL (3.9 mmol) of 25 wt % sodium methoxide/methanol. After 15 hours at room temperature, an additional 0.9 mL of sodium methoxide/methanol was added. After 2 hours, the solution was cooled, 1N hydrochloric acid added, extracted with ethyl acetate, washed with saturated sodium bicarbonate, brine, dried and stripped to afford crude product, which was chromatographed over 50 g of silica gel using 100% methylene chloride to afford 117 mg of the desired N-(2-mercaptopropyl)-4-methoxybenzenesulfonamide, m/e=358 (M+Li).

EXAMPLE 11

Preparation of N-(2-Mercapto-1R-methylethyl)-N-methyl-4-methoxybenzenesulfonamide

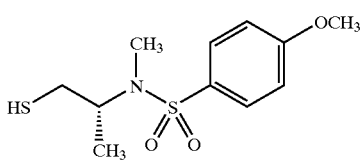

Part A: To a solution of 3.0 g (12.2 mmol) of N-(2-hydroxy-1R-methylethyl)-4-methoxybenzenesulfonamide from example 3, in 20 mL of anhydrous DMF, was added 5.06 g (36.7 mmol) of powdered potassium carbonate, and then 1.1 mL (17.7 mmol) of methyl iodide. After stirring at room temperature for 48 hours, ethyl acetate and water was added, the layers separated and the organic layer washed 3xs with brine, dried with sodium sulfate, filtered and stripped to afford 2.83 g of crude material. This was chromatographed on 200 g of silica gel using 50%–80% ethyl acetate/hexane to afford 2.1 g of pure N-(2-hydroxy-1R-methylethyl)-N-methyl-4-methoxybenzenesulfonamide, m/e=266 (M+Li).

Part B: To a solution of 2.09 g (8.06 mmol) of product from Part A and 2.32 g (8.86 mmol) of triphenylphosphine in 32 mL of anhydrous THF at 0° C., was added 1.4 mL (8.86 mmol) of diethylazodicarboxylate, followed after 5 min. by 0.64 mL (8.86 mmol) of thioacetic acid. After 0.5 hour, the reaction was concentrated and the residue was chromatographed on 200 g of silica gel using 10%–50% ethyl acetate/hexane to yield 1.77 g of the desired product, m/e=324 (M+Li).

Part D: To a solution of 1.77 g (5.58 mmol) of product from Part C in 20 mL of anhydrous methanol, was added 4.6 mL (20 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 1.2 g of pure product, identified as N-(2-mercapto-1R-methylethyl)-4-methoxy-N-methyl-4-methoxybenzenesulfonamide, m/e=282 (M+Li).

EXAMPLE 12

Preparation of N-(2-Mercapto-1R-methylethyl)-N-(phenylmethyl)-4-methoxybenzenesulfonamide

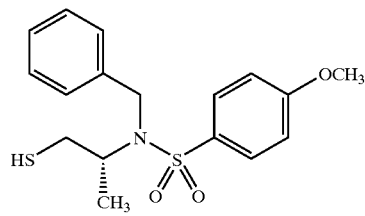

Part A: To a solution of 5.0 g (20 mmol) of N-(2-hydroxy-1R-methylethyl)-4-methoxybenzenesulfonamide from Example 3 in 40 mL of anhydrous DMF, was added 8.5 g (61 mmol) of powdered potassium carbonate, followed by 3.2 mL (4.5 g, 27 mmol) of benzyl bromide. After 16 hours, the reaction was concentrated in vacuo, ethyl acetate and water were added, the organic layer was separated and washed 3xs with brine, dried with magnesium sulfate, filtered and concentrated to afford 7.1 g of crude product. This was chromatographed on silica gel using 30%–50% ethyl acetate/hexane to yield 4.1 g of pure N-(2-hydroxy-1R-methylethyl)-N-(phenylmethyl)-4-methoxybenzenesulfonamide, m/e=342 (M+Li).

Part B: To a solution of 4.1 g (12 mmol) of N-(2-hydroxy-1R-methylethyl)-N-(phenylmethyl)-4-methoxybenzenesulfonamide from Part A and 3.6 g (14 mmole) of triphenylphosphine in 80 mL of anhydrous THF at 0° C., was added 2.1 mL (2.4 g, 14 mmol) of diethylazodicarboxylate, followed after 5 min. by 1.0 mL (1.0 g, 14 mM) of thioacetic acid. After 1 hour, the reaction was concentrated and the residue was chromatographed on silica gel using 20%–40% ethyl acetate/hexane to yield 4.3 g of the desired product, m/e=400 (M+Li).

Part C: To a solution of 4.3 g (11 mmol) of product from Part B in 100 mL of anhydrous methanol, was added 0.9 g (40 mmol) of sodium metal. After 1 hour, the reaction was cooled, 1N HCl solution was added, followed by ethyl acetate and water, the organic layer was separated and washed with saturated sodium bicarbonate solution and brine, dried with magnesium sulfate, filtered and concentrated to afford 3.5 g of crude product. This was chromatographed on silica gel using 15%–25% ethyl acetate/hexane to yield 1.9 g of pure N-(2-mercapto-1R-methylethyl)-N-(phenylmethyl)-4-methoxybenzenesulfonamide, m/e=358 (M+Li).

EXAMPLE 13

Preparation of N-(2-Mercapto-1S-methylethyl)-N-(phenylmethyl)-4-methoxybenzenesulfonamide

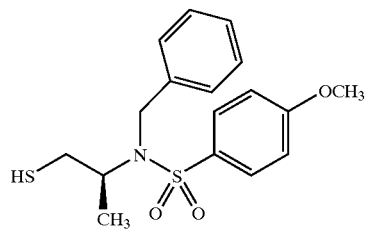

Part A: To a solution of 15.5 mL (15.0 g, 200 mmol) of (S)-(+)-2-amino-1-propanol in 70 mL of THF and 18 mL of water, was added 36 mL (259 mmol) of triethylamine. After cooling in an ice bath, a solution of 37.1 g (179 mmol) of 4-methoxybenzenesulfonyl chloride in 30 mL of tetrahydrofuran was slowly added over 15 minutes. After stirring at room temperature for 2 hour, the reaction was concentrated in vacuo, ethyl acetate and water were added, the organic layer was separated and washed with 5% potassium hydrogen sulfate solution, saturated sodium bicarbonate solution and brine, dried over sodium sulfate, filtered and concentrated to afford 43.3 g of the desired N-(2-hydroxy-1S-methylethyl)-4-methoxybenzenesulfonamide, m/e=246 (M+H).

Part B: To a solution of 5.0 g (20 mmol) of N-(2-hydroxy-1S-methylethyl)-4-methoxybenzenesulfonamide from part A in 40 mL of anhydrous DMF, was added 8.5 g (61 mmol) of powdered potassium carbonate, followed by 3.2 mL (4.5 g, 27 mmol) of benzyl bromide. After 64 hours, the reaction was concentrated in vacuo, ethyl acetate and water were added, the organic layer was separated and washed 3×s with brine, dried with magnesium sulfate, filtered and concentrated to afford 7.0 g of crude product. This was chromatographed on silica gel using 20%–50% ethyl acetate/hexane to yield 4.2 g of pure N-(2-hydroxy-1S-methylethyl)-N-(phenylmethyl)-4-methoxybenzenesulfonamide, m/e=342 (M+Li).

Part C: To a solution of 4.2 g (12.5 mmol) of N-(2-hydroxy-1S-methylethyl)-N-(phenylmethyl)-4-methoxybenzenesulfonamide from Part B and 3.6 g (14 mmole) of triphenylphosphine in 50 mL of anhydrous THF at 0° C., was added 2.2 mL (13.8 mmol) of diethylazodicarboxylate, followed after 5 min. by 1.0 mL (13.8 mmol) of thiolacetic acid. After 0.5 hour, the reaction was concentrated and the residue was chromatographed on silica gel using 20%–40% ethyl acetate/hexane to yield 3.9 g of the desired product, m/e=394 (M+H).

Part D: To a solution of 3.8 g (9.7 mmol) of product from Part C in 20 mL of anhydrous methanol, was added 7.9 mL (34.8 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 2.78 g of pure product, identified as N-(2-mercapto-1R-methylethyl)-N-(phenylmethyl)-4-methoxybenzenesulfonamide, m/e=352 (M+H).

EXAMPLE 14

Preparation of N-(2-Mercapto-1R-methylethyl)-N-(2-methylpropyl)-4-methoxybenzenesulfonamide

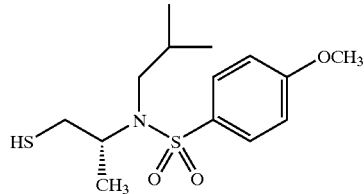

Part A: To a solution of 3.0 g (12.2 mmol) of N-(2-hydroxy-1R-methylethyl)-4-methoxybenzenesulfonamide from example 3, in 20 mL of anhydrous DMF, was added 5.06 g (36.7 mmol) of powdered potassium carbonate, and then 2.0 mL (18.3 mmol) of isobutyl bromide. After stirring at room temperature for 72 hours, ethyl acetate and water was added, the layers separated and the organic layer washed 3×s with brine, dried with sodium sulfate, filtered and stripped to afford 3.35 g of crude material. This was chromatographed on 150 g of silica gel using 30%–70% ethyl acetate/hexane to afford 2.1 g of pure N-(2-hydroxy-1R-methylethyl)-N-(2-methylpropyl)-4-methoxybenzenesulfonamide, m/e=308 (M+Li).

Part B: To a solution of 1.3 g (4.3 mmol) of product from Part A and 1.24 g (4.7 mmol) of triphenylphosphine in 17 mL of anhydrous THF at 0° C., was added 0.75 mL (4.7 mmol) of diethylazodicarboxylate, followed after 5 min. by 0.34 mL (4.7 mmol) of thiolacetic acid. After 0.5 hour, the reaction was concentrated and the residue was chromatographed on 100 g of silica gel using 10%–30% ethyl acetate/hexane to yield 0.73 g of the desired product, m/e=366 (M+Li).

Part C: To a solution of 0.73 g (2.0 mmol) of product from Part B in 10 mL of anhydrous methanol, was added 1.7 mL (7.3 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 10.6 g of crude product. This was chromatographed on 100 g of silica gel to afford 182 mg of pure product, identified as N-(2-mercapto-1R-methylethyl)-N-(2-methylpropyl)-4-methoxybenzenesulfonamide, m/e=324 (M+Li).

EXAMPLE 15

Preparation of N-(2-Mercapto-1R-methylethyl)-4-(n-butoxy)benzenesulfonamide

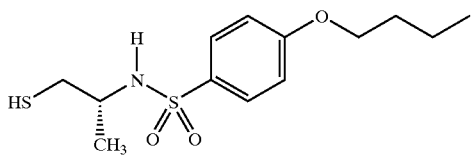

Part A: To a solution of 2.69 g (9.36 mmol) of N-(2-hydroxy-1R-methylethyl)-4-(n-butoxy)benzenesulfonamide from example 4 and 2.7 g (10.3 mmol) of triphenylphosphine in 37 mL of anhydrous THF at 0° C., was added 1.6 mL (10.3 mmol) of diethylazodicarboxylate, followed after 5 minutes by 0.75 mL (10.3 mmol) of thiolacetic acid. After 0.5 hour, the reaction was concentrated and the residue was chromatographed on 150 g of silica gel using 10%–50% ethyl acetate/hexane to yield 1.59 g of impure material, which was carried into the next step.

Part B: To a solution of 1.59 g (4.6 mmol) of product from Part A in 18 mL of anhydrous methanol, was added 3.8 mL (16.6 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 1.4 g of crude product. This was chromatographed on 150 g of silica gel using 1%–20% methanol/methylene chloride to afford 230 mg of pure product, identified as N-(2-mercapto-1R-methylethyl)-4-(n-butoxy)benzenesulfonamide, m/e=304 (M+H).

EXAMPLE 16

Preparation of N-(2-Mercapto-1R-methylethyl)-4-methoxybenzenesulfonamide

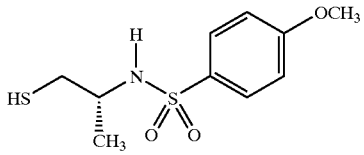

Part A: To a solution of 2.58 g (10.5 mmol) of N-(2-hydroxy-1R-methylethyl)-4-methoxybenzenesulfonamide from example 3 and 3.03 g (11.6 mmol) of triphenylphosphine in 40 mL of anhydrous THF at 1° C., was added 1.8 mL (11.6 mmol) of diethylazodicarboxylate, followed after 5 minutes by 0.83 mL (11.6 mmol) of thiolacetic acid. After 0.5 hour, the reaction was concentrated and the residue was chromatographed on silica gel using 20%–30% ethyl acetate/hexane to yield 1.5 g of pure material, m/e=304 (M+H).

Part B: To a solution of 1.5 g (4.9 mmol) of product from Part A in 20 mL of anhydrous methanol, was added 4.0 mL (17.8 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 1.23 g of pure product, identified as N-(2-mercapto-1R-methylethyl)-4-methoxybenzenesulfonamide, m/e=262 (M+H).

20%–50% ethyl acetate/hexane to yield 3.64 g of pure N-(2-hydroxy-1R-methylethyl)-N-phenylmethyl)-4-(n-butoxy)benzenesulfonamide, m/e=384 (M+Li).

Part B: To a solution of 3.6 g (9.5 mmol) of product from Part A and 2.74 g (10.5 mmol) of triphenylphosphine in 40 mL of anhydrous THF at 0° C., was added 1.7 mL (10.5 mmol) of diethylazodicarboxylate, followed after 5 min. by 0.75 mL (10.5 mmol) of thiolacetic acid. After 0.5 hour, the reaction was concentrated and the residue was chromatographed on 200 g of silica gel using 10%–15% ethyl acetate/hexane to yield 0.99 g of the desired product, m/e=442 (M+Li).

Part C: To a solution of 0.99 g (2.3 mmol) of product from Part B in 10 mL of anhydrous methanol, was added 1.9 mL (8.2 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 0.75 g of pure product, identified as N-(2-mercapto-1R-methylethyl)-N-phenylmethyl)-4-(n-butoxy)benzenesulfonamide, m/e=400 (M+Li).

EXAMPLE 18

Preparation of N-(2-Mercapto-1R-methylethyl)-N-phenylmethyl)-4-(n-butoxy)benzenesulfonamide Disulfide

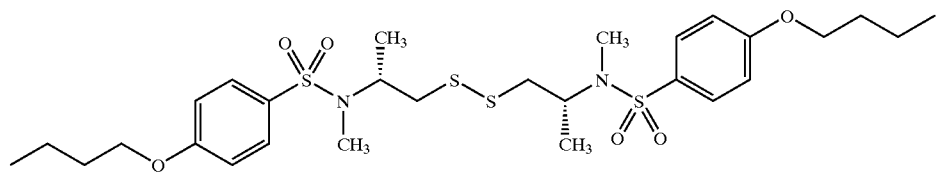

EXAMPLE 17

Preparation of N-(2-Mercapto-1R-methylethyl)-N-phenylmethyl)-4-(n-butoxy)benzenesulfonamide

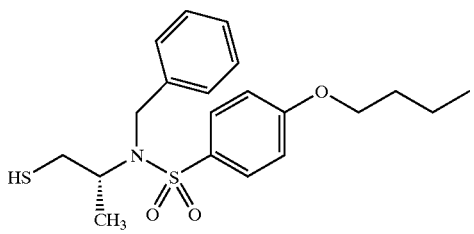

Part A: To a solution of 3.52 g (12.3 mmol) of N-(2-hydroxy-1R-methylethyl)-4-(n-butoxy)benzenesulfonamide from example 4 in 25 mL of anhydrous DMF, was added 5.07 g (36.8 mmol) of powdered potassium carbonate, followed by 1.9 mL (2.7 g, 15.9 mmol) of benzyl bromide. After 63 hours, the reaction was concentrated in vacuo, ethyl acetate and water were added, the organic layer was separated and washed 3×s with brine, dried with magnesium sulfate, filtered and concentrated to afford the crude product. This was chromatographed on 200 g of silica gel using To a solution of 0.42 g (1.32 mmol) of N-(2-mercapto-1R-methylethyl)-N-phenylmethyl)-4-(n-butoxy) benzenesulfonamide in 25 mL of methanol at 0 C, was added 174 mg (0.69 mmol) of iodine crystals. After stirring for 30 minutes, aqueous sodium thiosulfate was added to remove any unreacted iodine and ethyl acetate was added. The organic layer was separated and washed with saturated sodium bicarbonate, brine, dried with magnesium sulfate and stripped to afford 0.40 g of crude product. This was chromatographed on 100 g of silica gel using 20%–50% ethyl acetate/hexane to afford 154 mg of pure N-(2-mercapto-1R-methylethyl)-N-phenylmethyl)-4-(n-butoxy) benzenesulfonamide disulfide, m/e=633 (M+H).

EXAMPLE 19

Preparation of 1,3-Benzodioxole-5-sulfonyl Chloride

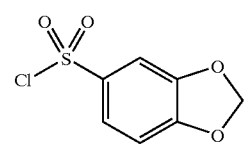

To a 22 liter round bottom flask fitted with a mechanical stirrer, a cooling condenser, a heating mantle and a pressure equalizing dropping funnel was added sulfur trioxide DMF complex (2778 g, 18.1 moles). Dichloroethane (4 liters) was then added and stirring initiated. 1,2-Benzodioxole (1905 g, 15.6 moles) as then added through the dropping funnel over a five minute period. The temperature was then raised to 75° C. and held for 22 hours (NMR indicated that the reaction was done after 9 hours.) The reaction was cooled to 26° and oxalyl chloride (2290 g, 18.1 moles) was added at a rate so as to maintain the temperature below 40° C. (1.5 hours). The mixture was heated to 67° C. for 5 hours followed by cooling to 16° C. with an ice bath. The reaction was quenched with water (5 l) at a rate that kept the temperature below 20° C. After the addition of water was complete, the mixture was stirred for 10 minutes. The layers were separated and the organic layer was washed again twice with water (5 l). The organic layer was dried with magnesium sulfate (500 g) and filtered to remove the drying agent. The solvent was removed under vacuum at 50° C. The resulting warm liquid was permitted to cool at which time a solid began to form. After one hour, the solid was washed with hexane (400 mL), filtered and dried to provide sulfonyl chloride (2823 g). The hexane wash was concentrated and the resulting solid washed with 400 mL hexane to provide additional sulfonyl chloride (464 g). The total yield was 3287 g (95.5% based upon 1,3-benzodioxole).

EXAMPLE 20

Preparation of N-(2-Mercapto-1R-methylethyl)-N-methyl-5-(1,3-benzodioxol-5-yl)sulfonamide

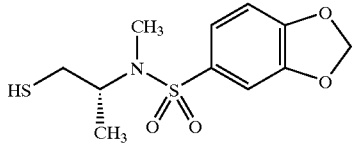

Part A: To a solution of 5.4 g (72 mmol) of (R)-2-amino-1-propanol in 25 mL of tetrahydrofuran and 10 mL of water, was added 13 mL (93 mmol) of triethylamine. The solution was cooled in an ice bath and a solution of 13.3 g (60 mmol) of 1,3-benzodioxole-5-sulfonyl chloride in 20 mL of tetrahydrofuran was added over 20 minutes. The reaction was stirred at room temperature for 21 hours, stripped, ethyl acetate added, washed with 5% KHSO4 and brine, dried with sodium sulfate, filtered and stripped to afford 12 g of crude material. This was triturated with warm methylene chloride, hexane added and the resulting solids collected, washed with hexane and air dried to yield 7.7 g of pure N-(2-hydroxy-1R-methylethyl)-5-(1,3-benzodioxol-5-yl)sulfonamide, m/e=266 (M+Li).

Part B: To a solution of 2.6 g (10 mmol) of N-(2-hydroxy-1R-methylethyl)-5-(1,3-benzodioxol-5-yl)sulfonamide from Part A, in 15 mL of anhydrous DMF, was added 4.15 g (30 mmol) of powdered potassium carbonate, and then 1.25 mL (20 mmol) of methyl iodide. After stirring at room temperature for 17 hours, ethyl acetate and water was added, the layers separated and the organic layer washed 3×s with brine, dried with sodium sulfate, filtered and stripped to afford 2.8 g of crude material. This was chromatographed on 150 g of silica gel using 50%–80% ethyl acetate/hexane to afford 2.0 g of pure N-(2-hydroxy-1R-methylethyl)-N-methyl-5-(1,3-benzodioxol-5-yl)sulfonamide, m/e=280 (M+Li).

Part C: To a solution of 2.0 g (7.3 mmol) of product from Part B and 2.11 g (8.05 mmol) of triphenylphosphine in 30 mL of anhydrous THF at 0° C., was added 1.3 mL (8.05 mmol) of diethylazodicarboxylate, followed after 5 minutes by 0.58 mL (8.05 mmol) of thiolacetic acid. After 0.5 hour, the reaction was concentrated and the residue was chromatographed on 150 g of silica gel using 20%–50% ethyl acetate/hexane to yield 1.86 g of the desired product, m/e= 332 (M+H).

Part D: To a solution of 1.86 g (5.6 mmol) of product from Part C in 20 mL of anhydrous methanol, was added 4.6 mL (20 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 1.53 mg of pure product, identified as N-(2-mercapto-1R-methylethyl)-N-methyl-5-(1,3-benzodioxol-5-yl)sulfonamide, m/e=290 (M+H).

EXAMPLE 21

Preparation of N-(2-Mercapto-1R-methylethyl)-N-(phenylmethyl)-5-(1,3-benzodioxol-5-yl) sulfonamide

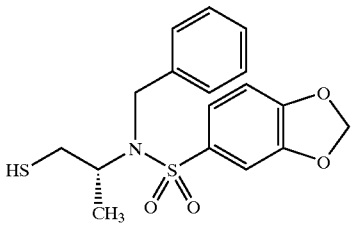

Part A: To a solution of 5.4 g (72 mmol) of (R)-2-amino-1-propanol in 25 mL of tetrahydrofuran and 10 mL of water, was added 13 mL (93 mmol) of triethylamine. The solution was cooled in an ice bath and a solution of 13.3 g (60 mmol) of 1,3-benzodioxole-5-sulfonyl chloride in 20 mL of tetrahydrofuran was added over 20 minutes. The reaction was stirred at room temperature for 21 hours, stripped, ethyl acetate added, washed with 5% KHSO4 and brine, dried with sodium sulfate, filtered and stripped to afford 12 g of crude material. This was triturated with warm methylene chloride, hexane added and the resulting solids collected, washed with hexane and air dried to yield 7.7 g of pure N-(2-hydroxy-1R-methylethyl)-5-(1,3-benzodioxol-5-yl) sulfonamide, m/e=266 (M+Li).

Part B: To a solution of 2.5 g (9.6 mmol) of N-(2-hydroxy-1R-methylethyl)-5-(1,3-benzodioxol-5-yl)sulfonamide from Part A, in 20 mL of anhydrous DMF, was added 3.99 g (29 mmol) of powdered potassium carbonate, and then 1.5 mL (12.5 mmol) of benzyl bromide. After stirring at room temperature for 17 hours, ethyl acetate and water was added, the layers separated and the organic layer washed 3×s with brine, dried with sodium sulfate, filtered and stripped to afford 3.15 g of crude material. This was chromatographed on 150 g of silica gel using 20%.

Part C: To a solution of 1.55 g (4.3 mmol) of product from Part B in 18 mL of anhydrous methanol, was added 3.6 mL (15.5 mmol) of a 25 weight solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 1.3 g of crude product. This was chromatographed on 100 g of silica gel using 1% methanol/methylene chloride to afford 460 mg of pure product, identified as N-(2-mercapto-1R-methylethyl)-N-methyl-4-(n-butoxybenzene)sulfonamide, m/e=324 (M+Li).

EXAMPLE 23

Preparation of N-(1R-Mercaptomethyl)propyl-N-methyl-4-(n-butoxy)benzenesulfonamide

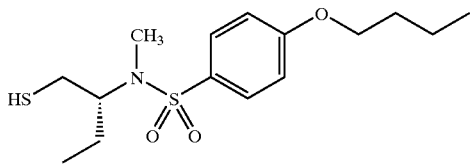

Part A: To a solution of 3.91 g (44 mmol) of (R)-2-amino-1-butanol in 20 mL of tetrahydrofuran and 5 mL of water, was added 9.5 mL (68 mmol) of triethylamine. The solution was cooled in an ice bath and a solution of 9.85 g (40 mmol) of 4-(n-butoxybenzene)sulfonyl chloride in 10 mL of tetrahydrofuran was added over 10 minutes. The reaction was stirred at room temperature for 5 hours, stripped, ethyl acetate added, washed with 5% KHSO4 and brine, dried with sodium sulfate, filtered and stripped to afford 12.1 g of crude material, which was identified as N-(1R-hydroxymethyl)propyl-4-(n-butoxy)benzenesulfonamide, m/e=308 (M+Li).

Part B: To a solution of 3.0 g (9.85 mmol) of N-(1R-hydroxymethyl)propyl-4-(n-butoxy)benzenesulfonamide from Part A, in 12 mL of anhydrous DMF, was added 4.1 g (30 mmol) of powdered potassium carbonate, and then 1.2 mL (20 mmol) of methyl iodide. After stirring at room temperature for 21 hours, ethyl acetate and water was added, the layers separated and the organic layer washed 3xs with brine, dried with sodium sulfate, filtered and stripped to afford 2.9 g of crude material. This was chromatographed on 150 g of silica gel using 20%–80% ethyl acetate/hexane to afford 2.0 g of pure N-(1R-hydroxymethyl)propyl-N-methyl-4-(n-butoxy)benzenesulfonamide, m/e=322 (M+Li).

Part C: To a solution of 2.4 g (7.6 mmol) of product from Part B and 2.19 g (8.37 mmol) of triphenylphosphine in 30 mL of anhydrous THF at 0° C., was added 1.3 mL (8.37 mmol) of diethylazodicarboxylate, followed after 5 minutes by 0.60 mL (8.37 mmol) of thiolacetic acid. After 0.5 hour, the reaction was concentrated and the residue was chromatographed on silica gel using 20%–30% ethyl acetate/hexane to yield 2.12 g of pure material, m/e=374 (M+H).

Part D: To a solution of 2.12 g (5.7 mmol) of product from Part C in 23 mL of anhydrous methanol, was added 4.7 mL (20.4 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 1.32 g of pure product, identified as N-(1R-mercaptomethyl)propyl-N-methyl-4-(n-butoxy)benzenesulfonamide, m/e=332 (M+H).

EXAMPLE 24

Preparation of N-(2-Hydroxy-1R-methylethyl)-N-(propyn-3yl)-4-(n-butoxybenzene)sulfonamide

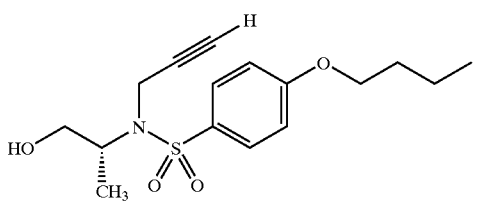

Part A: To a solution of 2.0 g (7 mmol) of N-(2-hydroxy-1R-methylethyl)-4-(n-butoxy)benzenesulfonamide from example 4, in 10 mL of anhydrous DMF, was added 2.9 g (21 mmol) of powdered potassium carbonate, and then 1.6 mL of an 80 wt. % solution of propargyl bromide in toluene (15 mmol). After stirring at room temperature for 24 hours, ethyl acetate and water was added, the layers separated and the organic layer washed 3xs with brine, dried with sodium sulfate, filtered and stripped to afford 2.31 g of crude material. This was chromatographed on 100 g of silica gel using 20%–50% ethyl acetate/hexane to afford 2.1 g of pure N-(2-hydroxy-1R-methylethyl)-(N-propyn-3-yl)-4-(n-butoxy)benzenesulfonamide, m/e=326 (M+H).

EXAMPLE 25

Preparation of N-(Mercapto-1R-methylethyl)-N-(propyn-3-yl)-4-(n-butoxybenzene)sulfonamide Disulfide

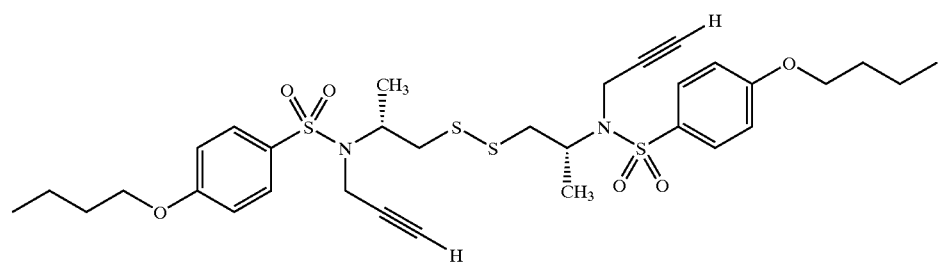

Part A: To a solution of 4.11 g (12.6 mmol) of N-(2-hydroxy-1R-methylethyl)-N-(propyn-3-yl)-4-(n-butoxybenzene)sulfonamide and 3.64 g (13.9 mmol) of triphenylphosphine in 50 mL of anhydrous THF at 0° C., was added 2.2 mL (13.9 mmol) of diethylazodicarboxylate, followed after 5 minutes by 1.0 mL (13.9 mmol) of thiolacetic acid. After 0.5 hour, the reaction was concentrated and the residue was chromatographed on silica gel using 10%–20% ethyl acetate/hexane to yield 3.68 g of pure material, m/e=390 (M+Li).

Part B: To a solution of 1.1 g (2.9 mmol) of product from Part A in 7 mL of anhydrous methanol, was added 7.4 mL of 30% aqueous ammonia. After 1 hour, the reaction was quenched with 1N HCl solution, followed by diethyl ether and water, the organic layer was separated and washed with saturated sodium bicarbonate solution and brine, dried with magnesium sulfate, filtered and concentrated to afford 0.90 g of crude product. This was chromatographed on silica gel using 10%–15% ethyl acetate/hexane to afford 200 mg of pure product, identified as N-(mercapto-1R-methylethyl)-N-(propyn-3-yl)-4-(n-butoxybenzene)sulfonamide disulfide, m/e=687 (M+Li).

EXAMPLE 26

Preparation of 1-[(4-Methoxyphenyl)sulfonyl]-3-mercaptopyrrolidine

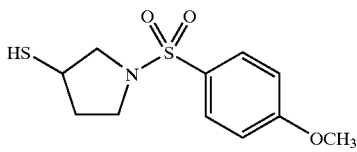

Part A: To a solution of 4.5 g (52 mmol) of racemic 3-pyrrolidinol in 20 mL of tetrahydrofuran and 5 mL of water, was added 10 mL of triethylamine. The solution was cooled to 0 C, and 9.0 g (46 mmol) of 4-(methoxybenzene) sulfonyl chloride was slowly added. After 18 hours at room temperature, the solution was stripped, ethyl acetate added, washed with 5% KHSO4, saturated sodium bicarbonate, brine and dried over sodium sulfate, filtered and stripped to afford the crude material, which was recrystrallized from warm ethyl acetate/hexane to afford 7.0 g of pure 1-[(4-methoxyphenyl)sulfonyl]-3-hydroxypyrrolidine, m/e=258 (M+H).

Part B: To a solution of 2.0 g (7.77 mmol) of product from Part B and 2.24 g (8.54 mmol) of triphenylphosphine in 35 mL of anhydrous THF at 0° C., was added 1.35 mL (8.54 mmol) of diethylazodicarboxylate, followed after 5 minutes by 0.62 mL (8.54 mmol) of thioacetic acid. After 0.5 hour, the reaction was concentrated and the residue was chromatographed on silica gel using 20%–30% ethyl acetate/hexane to yield 1.05 g of pure material, m/e=316 (M+H).

Part C: To a solution of 1.05 g (3.3 mmol) of product from Part C in 6 mL of anhydrous methanol, was added 8.6 mL of 30% aqueous ammonia. After 1 hour, the reaction was quenched with 1N HCl solution, followed by ethyl acetate and water, the organic layer was separated and washed with saturated sodium bicarbonate solution and brine, dried with magnesium sulfate, filtered and concentrated to afford 0.74 g of crude product. This was crystallized from diethyl ether/hexane to afford 220 mg of pure product, identified as 1-[(4-methoxyphenyl)sulfonyl]-3-mercaptopyrrolidine, m/e=274 (M+H).

EXAMPLE 27

Preparation of 1-[(4-Methoxyphenyl)sulfonyl]-3-hydroxypiperidine

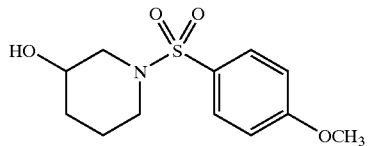

To a solution of 3.44 g (25 mmol) of racemic 3-hydroxypiperidine hydrochloride in 10 mL of tetrahydrofuran and 5 mL of water, was added 14 mL (100 mmol) of triethylamine. The solution was cooled to 0 C, and 4.64 g (22 mmol) of 4-(methoxybenzene)sulfonyl chloride was slowly added. After 21 hours at room temperature, the solution was stripped, ethyl acetate added, washed with 5% KHSO4, saturated sodium bicarbonate, brine and dried over sodium sulfate, filtered and stripped to afford the crude material, which was triturated with hexane to afford 5.39 g of pure 1-[(4-methoxyphenyl)sulfonyl]-3-hydroxypiperidine, m/e= 272 (M+H).

EXAMPLE 28

Preparation of 1-[(4-Methoxyphenyl)sulfonyl] pyrrolidine-2-methanethiol

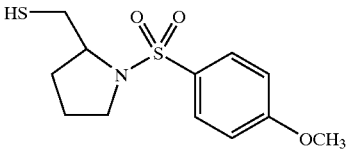

Part A: To a solution of 10.27 g (89 mmol) of D,L-proline in 100 mL of water and 60 mL of acetone, was added 40 mL (287 mmol) of triethylamine. After cooling in an ice bath, 17.6 g (85 mmol) of 4-(methoxybenzene)sulfonyl chloride was slowly added. After stirring at room temperature for 13 hours, the acetone was stripped, the aqueous layer extracted twice with toluene, then acidified with 25 mL of 6N hydrochloric acid and extracted with ethyl acetate. The organic layer was washed with 5% KHSO4, brine, dried with sodium sulfate, filtered and stripped to afford 23.5 g of racemic 1-[(4-methoxyphenyl)sulfonyl]-2-carboxypyrrolidine, m/e=292 (M+Li).

Part B: To a solution of 4.00 g (14 mmol) of 1-[(4-methoxyphenyl)sulfonyl]-2-carboxypyrrolidine from part A in 50 mL of anhydrous tetrahydrofuran at 0 C under a nitrogen atmosphere, was slowly added over 15 minutes, 20 mL (20 mmol) of a 1M solution of lithium aluminum hydride in diethyl ether. After stirring at room temperature for 2 hours, the solution was cooled in an ice bath, and quenched by the slow sequential addition of 0.8 mL of water, 0.8 mL of 10% sodium hydroxide and 2.4 mL of water. The resulting suspension was filtered through celite and the celite washed with ethyl acetate. The combined organic filtrates were stripped, the residue disolved in ethyl acetate, which was washed with 5% KHSO4, saturated sodium bicarbonate, brine, dried with sodium sulfate, filtered and stripped to afford 3.66 g of crude material. This was chromatographed on 200 g of silica gel using 40%–75% ethyl acetate/hexane to yield pure 1-[(4-methoxyphenyl)sulfonyl]-2-(hydroxymethyl)pyrrolidine, m/e=278 (M+Li).

Part C: To a solution of 1.78 g (6.6 mmol) of product from Part B and 1.9 g (7.2 mmol) of triphenylphosphine in 26 mL of anhydrous THF at 0° C., was added 1.14 mL (7.2 mmol) of diethylazodicarboxylate, followed after 5 min. by 0.52 mL (7.2 mmol) of thiolacetic acid. After 0.5 hour, the reaction was concentrated and the residue was chromatographed on 200 g of silica gel using 50%–80% ethyl acetate/hexane to yield 1.5 g of the 54desired product, m/e=336 (M+Li).

Part D: To a solution of 1.5 g (4.6 mmol) of product from Part C in 10 mL of anhydrous methanol, was added 3.7 mL (16.4 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 0.9 g of crude product. This was dissolved in methylene chloride and passed down a short column of silica gel using methylene chloride to afford 0.55 g of pure product, identified as 1-[(4-methoxyphenyl)sulfonyl]pyrrolidine-2-methanethiol, m/e=294 (M+Li).

EXAMPLE 29

Preparation of Racemic N-[1-(Mercaptomethyl)-3-methylbutyl]-N-(phenylmethyl)-4-methoxybenzenesulfonamide

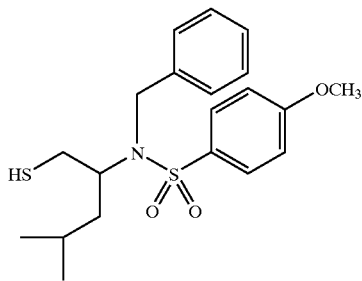

Part A: To a solution of 10.0 g (76.2 mmol) of D,L-leucine in 85 mL of water and 50 mL of acetone, was added 30 mL (215 mmol) of triethylamine. This solution was cooled in an ice bath, and a solution of 15.0 g (72.7 mmol) of 4-methoxybenzenesulfonyl chloride in 50 mL of acetone was slowly added over a 30 minute period. The reaction was stirred at room temperature for 15 hours, concentrated, the remaining aqueous layer extracted twice with toluene, then acidified with 20 mL of 6N hydrochloric acid, extracted with ethyl acetate, which was washed with 5% KHSO4, brine, dried over sodium sulfate, filtered and stripped to afford 19.2 g of crude material, which was triturated with warm hexane to afford 17.5 g of pure material, m/e=308 (M+Li), suitable for use in the next step.

Part B: To a solution of 17.5 g of product from part A in 45 mL of anhydrous methanol at 0 C, was slowly added 5.5 mL (75 mmol) of thionyl chloride over 15 minutes. The solution was then stirred for 15 hours at room temperature, concentrated, ethyl acetate added, washed with water, saturated sodium bicarbonate, brine, dried with sodium sulfate, filtered and stripped to afford 18.6 g of crude material. This was crystallized from ethyl acetate/hexane to afford 13.3 g of the desired product, m/e=322 (M+Li).

Part C: To a solution of 3.00 g (9.5 mmol) of the product from Part B, in 20 mL of anhydrous DMF, was added 4.0 g (29 mmol) of powdered potassium carbonate, and then 1.5 mL (12.6 mmol) of benzyl bromide. After stirring at room temperature for 16 hours, ethyl acetate and water was added, the layers separated and the organic layer washed 3×s with brine, dried with sodium sulfate, filtered and stripped to afford 4.2 g of crude material. This was recrystallized from ethyl acetate/hexane to afford 3.41 g of pure product, m/e= 412 (M+Li).

Part D: To a solution of 3.2 g (7.9 mmol) of the product from part C in 30 mL of anhydrous tetrahydrofuran at 0 C under a nitrogen atmosphere, was slowly added over 15 minutes, 7.9 mL (7.9 mmol) of a 1M solution of lithium aluminum hydride in diethyl ether. After stirring at room temperature for 1 hour, the solution was cooled in an ice bath, and quenched by the slow sequential addition of 0.3 mL of water, 0.3 mL of 10% sodium hydroxide and 0.9 mL of water. The resulting suspension was filtered through celite and the celite washed with ethyl acetate. The combined organic filtrates were stripped, the residue disolved in ethyl acetate, which was washed with 5% KHSO4, saturated sodium bicarbonate, brine, dried with sodium sulfate, filtered and stripped to afford 2.71 g of crude product identified as racemic N-[1-(hydroxymethyl)-3-methylbutyl]-N-(phenylmethyl)-4-methoxybenzenesulfonamide, m/e=384 (M+Li).

Part E: To a solution of 2.7 g (7.2 mmol) of product from Part D and 2.07 g (7.9 mmol) of triphenylphosphine in 30 mL of anhydrous THF at 0° C., was added 1.13 mL (7.2 mmol) of diethylazodicarboxylate, followed after 5 min. by 0.52 mL (7.2 mmol) of thiolacetic acid. After 0.5 hour, the reaction was concentrated and the residue was chromatographed on 200 g of silica gel using 20%–50% ethyl acetate/hexane to yield 2.0 g of pure product, m/e=442 (M+Li).

Part F: To a solution of 2.0 g (4.6 mmol) of product from Part E in 10 mL of anhydrous methanol, was added 3.7 mL (16.4 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 1.8 g of pure product, identified as racemic N-[1-(mercaptomethyl)-3-methylbutyl]-N-(phenylmethyl)-4-methoxybenzenesulfonamide. m/e=400 (M+Li).

EXAMPLE 30

Preparation of N-(4-Methoxybenzenesulfonamide)-D-valine Methyl Ester

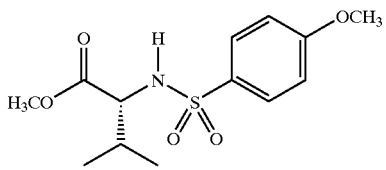

Part A: To a solution of 20.0 g (170 mmol) of D-valine in 170 mL of water and 95 mL of acetone, was added 50 mL (360 mmol) of triethylamine. This solution was cooled in an ice bath, and a solution of 35.2 g (170 mmol) of 4-methoxybenzenesulfonyl chloride in 75 mL of acetone was slowly added over a 20 minute period. The reaction was stirred at room temperature for 21 hours, concentrated, the remaining aqueous layer extracted twice with toluene, then acidified with 25 mL of 6N hydrochloric acid, extracted with ethyl acetate, which was washed with 5% KHSO4, brine, dried over sodium sulfate, filtered and stripped to afford 39.4 g of crude material, m/e=294 (M+Li), suitable for use in the next step.

Part B: To a solution of 35.04 g (122 mmol) of product from part A in 125 mL of anhydrous methanol at 0 C, was slowly added 10.0 mL (137 mmol) of thionyl chloride over 15 minutes. The solution was then stirred for 14 hours at room temperature, concentrated, ethyl acetate added, washed with water, saturated sodium bicarbonate, brine, dried with sodium sulfate, filtered and stripped to afford 37.1 g of crude material. This was triturated with hexane to afford 32.9 g of the desired product, N-(4-methoxybenzenesulfonamide)-D-valine methyl ester, m/e=308 (M+Li).

EXAMPLE 31

Preparation of N-[(1R-Mercaptomethyl)-2-methylpropyl]-4-methoxy-N-(phenylmethyl)benzenesulfonamide

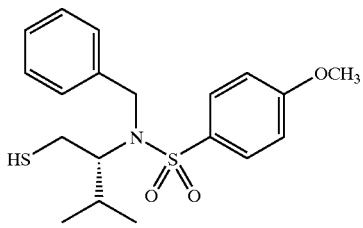

Part A: To a solution of 5.0 g (17 mmol) of product from Example 30 in 40 mL of anhydrous DMF, was added 6.9 g (50 mmol) of powdered potassium carbonate, followed by 2.2 mL (3.1 g, 18 mmol) of benzyl bromide. After 66 hours, ethyl acetate and water were added to the reaction, the organic layer was separated and washed 3×s with brine, dried with magnesium sulfate, filtered and concentrated to afford 7.4 g of crude product. This was chromatographed on silica gel using 15%–20% ethyl acetate/hexane to yield 6.3 g of pure product, m/e=392 (M+H).

Part B: To a solution of 6.3 g (20 mmol) of product from Part A in 60 mL of anhydrous THF at 0° C. under nitrogen, was added 16.1 mL (0.6 g, 16 mmol) of a 1.0 M solution of lithium aluminum hydride in diethyl ether. After 1.5 hours, the reaction mixture was cooled to 0° C. and 0.7 mL of water was added, followed by 0.7 mL of 2.5 N sodium hydroxide solution and 2.1 mL of water, the reaction was filtered, the filtrate concentrated in vacuo, ethyl acetate and citric acid solution were added, the organic layer was separated and washed with saturated sodium bicarbonate solution and brine, dried with magnesium sulfate, filtered and concentrated to afford 5.6 g of pure N-[(1R-hydroxymethyl)-2-methylpropyl]-N-(phenylmethyl)-4-methoxybenzenesulfonamide, m/e=364 (M+H).

Part C: To a solution of 5.6 g (15 mmol) of N-[(1R-hydroxymethyl)-2-methylpropyl]-N-(phenylmethyl)-4-methoxybenzenesulfonamide from Part B and 4.5 g (17 mmole) of triphenylphosphine in 100 mL of anhydrous THF at 0° C., was added 2.7 mL (3.0 g, 17 mmol) of diethylazodicarboxylate, followed after 5 min. by 1.2 mL (1.3 g, 17 mM) of thiolacetic acid. After 16 hours, the reaction was concentrated and the residue was chromatographed on silica gel using 10%–25% ethyl acetate/hexane to yield 4.7 g of pure product, m/e=428 (M+Li).

Part D: To a solution of 4.7 g (11 mmol) of product from Part C in 100 mL of anhydrous methanol, was added 1.0 g (41 mmol) of sodium metal. After 1 hour, the reaction was quenched using dry ice, ethyl acetate and 5% potassium hydrogen sulfate solution were added, the organic layer was separated and washed with saturated sodium bicarbonate solution and brine, dried with magnesium sulfate, filtered and concentrated to afford the crude product. This was chromatographed on silica gel using 10%–20% ethyl acetate/hexane to yield 1.6 g of pure N-[(1R-mercaptomethyl)-2-methylpropyl]-N-(phenylmethyl)-4-methoxybenzenesulfonamide, m/e=386 (M+Li).

EXAMPLE 32

Preparation of N-(4-Methoxybenzenesulfonamide)-L-valine Methyl Ester

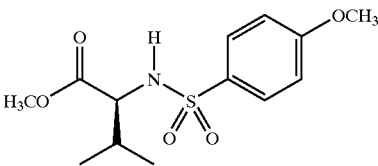

Part A: To a solution of 10.0 g (85 mmol) of L-valine in 85 mL of water and 50 mL of acetone, was added 25 mL (180 mmol) of triethylamine. This solution was cooled in an ice bath, and a solution of 17.6 g (85 mmol) of 4-methoxybenzenesulfonyl chloride in 35 mL of acetone was slowly added over a 20 minute period. The reaction was stirred at room temperature for 21 hours, concentrated, the remaining aqueous layer extracted twice with toluene, then acidified with 25 mL of 6N hydrochloric acid, extracted with ethyl acetate, which was washed with 5% KHSO4, brine, dried over sodium sulfate, filtered and stripped to afford 22 g of crude material, m/e=288 (M+H), suitable for use in the next step.

Part B: To a solution of 18.9 g (65.8 mmol) of product from part A in 60 mL of anhydrous methanol at 0 C, was slowly added 6.0 mL (83 mmol) of thionyl chloride over 15 minutes. The solution was then stirred for 14 hours at room temperature, concentrated, ethyl acetate added, washed with water, saturated sodium bicarbonate, brine, dried with sodium sulfate, filtered and stripped to afford the crude material. This was recrystallized from ethyl acetate/hexane to afford 16.5 g of the desired product, N-(4-methoxybenzenesulfonamide)-L-valine methyl ester, m/e=302 (M+H).

EXAMPLE 33

Preparation of N-[(1S-Mercaptomethyl)-2-methylpropyl]-4-methoxy-N-(phenylmethyl)benzenesulfonamide

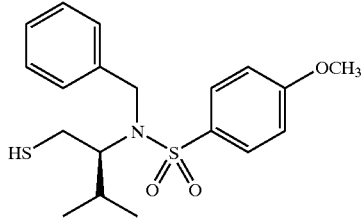

Part A: To a solution of 4.07 g (13.5 mmol) of the product from example 32 in 25 mL of anhydrous DMF, was added 5.6 g (40.5 mmol) of powdered potassium carbonate, followed by 2.0 mL (2.9 g, 17 mmol) of benzyl bromide. After 42 hours, ethyl acetate and water were added to the reaction, the organic layer was separated and washed 3xs with brine, dried with magnesium sulfate, filtered and concentrated to afford 5.85 g of crude product. This was chromatographed on silica gel using 20%–40% ethyl acetate/hexane to yield 4.88 g of pure product, m/e=392 (M+H).

Part B: To a solution of 4.88 g (12.5 mmol) of product from Part A in 50 mL of anhydrous THF at 0° C. under nitrogen, was added 12.5 mL (12.5 mmol) of a 1.0 M solution of lithium aluminum hydride in diethyl ether. After 0.5 hours, the reaction mixture was cooled to 0° C. and 0.5 mL of water was added, followed by 0.5 mL of 2.5 N sodium hydroxide solution and 1.5 mL of water, the reaction was filtered, the filtrate concentrated in vacuo, ethyl acetate and 5% citric acid solution were added, the organic layer was separated and washed with saturated sodium bicarbonate solution and brine, dried with magnesium sulfate, filtered and concentrated to afford 4.0 g of pure N-[(1S-hydroxymethyl)-2-methylpropyl]-N-(phenylmethyl)-4-methoxybenzenesulfonamide, m/e=364 (M+H).

Part C: To a solution of 3.94 g (10.8 mmol) of N-[(1S-hydroxymethyl)-2-methylpropyl]-N-(phenylmethyl)-4-methoxybenzenesulfonamide from Part B and 3.12 g (11.9 mmole) of triphenylphosphine in 50 mL of anhydrous THF at 0° C., was added 1.9 mL (2.1 g, 11.9 mmol) of diethylazodicarboxylate, followed after 5 min. by 0.86 mL (0.91 g, 11.9 mmoles) of thiolacetic acid. After 2 hours, the reaction was concentrated and the residue was chromatographed on silica gel using 20%–40% ethyl acetate/hexane to yield 2.7 g of pure product, m/e=422 (M+H).

Part D: To a solution of 2.7 g (6.4 mmol) of product from Part C in 20 mL of anhydrous methanol, was added 5.3 mL (23 mmol) of 25 weight % sodium methoxide in methanol solution. After 0.5 hour, the reaction was quenched with 1N hydrochloric acid, ethyl acetate added and washed with 5% potassium hydrogen sulfate solution, saturated sodium bicarbonate solution and brine, dried with magnesium sulfate, filtered and concentrated to afford 2.05 g of crude product. This was chromatographed on 100 g of silica gel using 20%–50% ethyl acetate/hexane to yield 1.5 g of pure N-[(1S-mercaptomethyl)-2-methylpropyl]-4-methoxy-N-(phenylmethyl)benzenesulfonamide, m/e=386 (M+Li).

EXAMPLE 34

Preparation of N-(2-Mercaptoethyl)-N-(phenylmethyl)-4-(n-butoxy)benzenesulfonamide

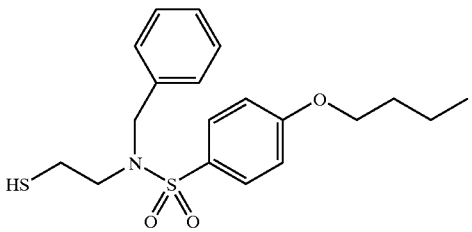

Part A: To a solution of 15.11 g (55 mmol) of N-(2-hydroxyethyl)-4-(n-butoxy)benzenesulfonamide from Example 2 in 100 mL of anhydrous DMF, was added 22.9 g (165 mmol) of powdered potassium carbonate and then 10.3 g (60 mmol) of benzyl bromide. After 16 hours, ethyl acetate and water was added, the organic layer separated and washed 3xs with brine, dried with sodium sulfate, filtered and stripped to afford 20.7 g of crude product. This was recrystallized from ethyl acetate/hexane to afford 13.8 g of the desired N-(hydroxyethyl)-N-(phenylmethyl)-4-(n-butoxy)benzenesulfonamide.

Part B: To a solution of 3.0 g (8.2 mmol) of N-(2-hydroxyethyl)-N-(phenylmethyl)-4-(n-butoxy)benzenesulfonamide from Part A and 2.38 g (9.1 mmol) of triphenylphosphine in 40 mL of anhydrous THF at 0 C, was added 1.4 mL (9.1 mmol) of diisopropylazodicarboxylate, followed by 0.65 mL (9.1 mmol) of thiolacetic acid. After stirring at room temperature for 15 hours, the reaction was concentrated and the residue chromatographed on 150 g of silica gel using 20–50% ethyl acetate/hexane to afford 2.4 g of the desired product, which was recrystallized from ethyl acetate/hexane to afford 1.7 g of pure product, m/e=428 (M+Li).

Part C: To a suspension of 1.7 g (4.1 mmol) of product from Part B above in 20 mL of anhydrous methanol, was added 3.3 mL (14.6 mmol) of 25 weight % sodium methoxide in methanol. After 30 minutes, the solution was cooled in ice and 2% hydrochloric acid added. Ethyl acetate was added and the organic layer separated and washed with saturated sodium bicarbonate, brine, dried over anhydrous magnesium sulfate, filtered and stripped to afford 1.42 g of pure material, identified as N-(2-mercaptoethyl)-N-(phenylmethyl)-4-(n-butoxy)benzenesulfonamide, m/e=386 (M+Li).

EXAMPLE 35

Preparation of 4-(Benzyloxy)benzenesulfonyl Chloride

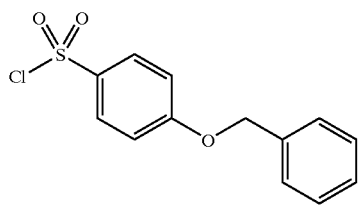

To a suspension of 22.4 g (146 mmol) of sulfur trioxide/DMF complex in 60 mL of anhydrous 1,2-dichloroethane at room temperature, was added a solution of 30 g (162 mmol) of benzylphenyl ether in 30 mL of anhydrous 1,2-dichloroethane. The resulting mixture was warmed to reflux and maintained there for 1 hour, cooled to room temperature and 10.8 mL (146 mmol) of thionyl chloride added. The reaction was then warmed to 75 C for 1 hour, cooled in an ice bath, 50 mL of water slowly added, then ethyl acetate. The layers were separated, washed with saturated sodium bicarbonate, brine, dried with magnesium sulfate, filtered and stripped. The resulting solids were triturated with hexane to afford 24.5 g of pure 4-(Benzyloxy)benzenesulfonyl chloride.

EXAMPLE 36

Preparation of N-(2-Hydroxy-1R-methylethyl)-N-methyl-4-hydroxybenzenesulfonamide

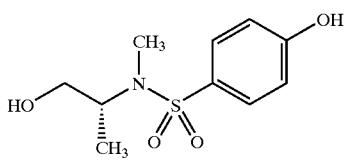

Part A: To a solution of 7.4 mL (95.1 mmol) of (R)-(−)-2-amino-1-propanol in 31 mL of THF and 9 mL of water, was added 17.2 mL (123 mmol) of triethylamine. After cooling in an ice bath, a solution of 24.4 g (86.5 mmol) of 4-(benzyloxy)benzenesulfonyl chloride in 40 mL of tetrahydrofuran was slowly added over 15 minutes. After stirring at room temperature for 16 hours, the reaction was concentrated in vacuo, ethyl acetate and water were added, the organic layer was separated and washed with 5% potassium hydrogen sulfate solution, saturated sodium bicarbonate solution and brine, dried over sodium sulfate, filtered and concentrated to afford a solid, which was triturated with hexane to afford 23.4 g of the desired N-(2-hydroxy-1R-methylethyl)-4-(benzyloxy)benzenesulfonamide, m/e=322 (M+H).

Part B: To a solution of 18.25 g (56.8 mmol) of the product from Part A in 100 mL of anhydrous DMF, was added 23.5 g (170 mmol) of powdered potassium carbonate and then 24.2 g (170 mmol) of methyl iodide. After 22 hours, ethyl acetate and water was added, the organic layer separated and washed 3×s with brine, dried with sodium sulfate, filtered and stripped to afford 18.2 g of crude product, suitable for the next step and identified as the desired N-(2-hydroxy-1R-methylethyl)-N-methyl-4-(benzyloxy)benzenesulfonamide, m/e=333 (M+H).

Part C: A solution of 18.2 g (54 mmol) of the product from Part B in 150 mL of tetrahydrofuran was hydrogenated in the presence of 6.0 g of 4% palladium-on-carbon catalyst under 50 psig of hydrogen at room temperature for 2 hours. The catalyst was removed by filtering through celite and concentrated. The resulting solids were triturated with methylene chloride and hexane, collected and air dried to afford 8.6 g of the desired N-(2-hydroxy-1R-methylethyl)-N-methyl-4-hydroxybenzenesulfonamide, m/e=246 (M+H).

EXAMPLE 37

Preparation of N-(2-Mercapto-1R-methylethyl)-N-methyl-4-(n-propyloxy)benzenesulfonamide

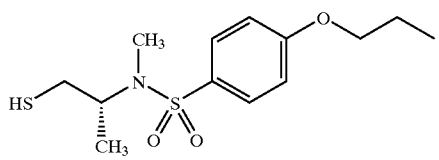

Part A: To a solution of 1.50 g (6.11 mmol) of N-(2-hydroxy-1R-methylethyl)-4-hydroxybenzenesulfonamide from example 36, in 10 mL of anhydrous DMF, was added 2.53 g (18.3 mmol) of powdered potassium carbonate, and then 0.85 mL (9.3 mmol) of bromopropane. After stirring at room temperature for 14 hours, ethyl acetate and water was added, the layers separated and the organic layer washed 3×s with brine, dried with sodium sulfate, filtered and stripped to afford 1.70 g of crude material, suitable for use in the next step and identified as N-(2-hydroxy-1R-methylethyl)-N-methyl-4-(n-propyloxy)benzenesulfonamide, m/e=288 (M+H).

Part B: To a solution of 1.70 g (5.9 mmol) of product from Part A and 1.70 g (6.5 mmol) of triphenylphosphine in 23 mL of anhydrous THF at 0° C., was added 1.0 mL (6.5 mmol) of diethylazodicarboxylate, followed after 5 minutes by 0.47 mL (6.5 mmol) of thiolacetic acid. After 0.5 hour, the reaction was concentrated and the residue was chromatographed on 150 g of silica gel using 20%–50% ethyl acetate/hexane to yield 1.02 g of pure product, m/e=352 (M+Li).

Part C: To a solution of 1.02 g (2.95 mmol) of product from Part B in 10 mL of anhydrous methanol, was added 2.4 mL (10.5 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 0.90 g of the desired product, identified as N-(2-mercapto-1R-methylethyl)-N-methyl-4-(n-propyloxy)benzenesulfonamide, m/e=304 (M+H).

EXAMPLE 38

Preparation of N-(2-Mercapto-1R-methylethyl)-N-methyl-4-ethoxybenzenesulfonamide

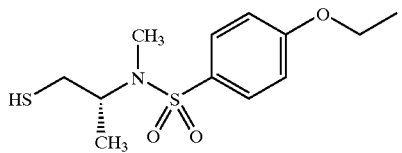

Part A: To a solution of 1.50 g (6.11 mmol) of N-(2-hydroxy-1R-methylethyl)-4-hydroxybenzenesulfonamide from example 36, in 10 mL of anhydrous DMF, was added 2.53 g (18.3 mmol) of powdered potassium carbonate, and then 0.70 mL (9.2 mmol) of bromoethane. After stirring at room temperature for 15 hours, ethyl acetate and water was added, the layers separated and the organic layer washed 3×s with brine, dried with sodium sulfate, filtered and stripped to afford 1.53 g of crude material, suitable for use in the next step and identified as N-(2-hydroxy-1R-methylethyl)-N-methyl-4-ethoxybenzenesulfonamide, m/e=274 (M+H).

Part B: To a solution of 1.53 g (5.6 mmol) of product from Part A and 1.61 g (6.15 mmol) of triphenylphosphine in 20 mL of anhydrous THF at 0° C., was added 0.97 mL (6.15 mmol) of diethylazodicarboxylate, followed after 5 minutes by 0.44 mL (6.15 mmol) of thiolacetic acid. After 0.5 hour, the reaction was concentrated and the residue was chromatographed on 150 g of silica gel using 20%–50% ethyl acetate/hexane to yield 1.59 g of pure product, m/e=332 (M+H).

Part C: To a solution of 1.53 g (4.62 mmol) of product from Part B in 20 mL of anhydrous methanol, was added 3.8 mL (16.6 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 0.90 g of the desired product, identified as N-(2-mercapto-1R-methylethyl)-N-methyl-4-ethoxybenzenesulfonamide, m/e=290 (M+H).

EXAMPLE 39

Preparation of N-(2-Mercapto-1R-methylethyl)-N-methyl-4-(n-pentyloxy)benzenesulfonamide

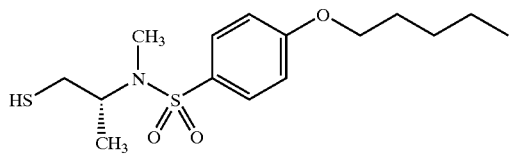

Part A: To a solution of 1.50 g (6.11 mmol) of N-(2-hydroxy-1R-methylethyl)-4-hydroxybenzenesulfonamide from example 36 in 10 mL of anhydrous DMF, was added 2.53 g (18.3 mmol) of powdered potassium carbonate, and then 1.13 mL (9.2 mmol) of 1-bromopentane. After stirring at room temperature for 30 hours, ethyl acetate and water was added, the layers separated and the organic layer washed 3×s with brine, dried with sodium sulfate, filtered and stripped to afford 1.78 g of crude material, suitable for use in the next step and identified as N-(2-hydroxy-1R-methylethyl)-N-methyl-4-(n-pentyloxyoxy)benzenesulfonamide, m/e=316 (M+H).

Part B: To a solution of 1.78 g (5.64 mmol) of product from Part A and 1.63 g (6.20 mmol) of triphenylphosphine in 20 mL of anhydrous THF at 0° C., was added 1.0 mL (6.2 mmol) of diethylazodicarboxylate, followed after 5 minutes by 0.45 mL (6.2 mmol) of thiolacetic acid. After 0.5 hour, the reaction was concentrated and the residue was chromatographed on 150 g of silica gel using 20%–50% ethyl acetate/hexane to yield 1.48 g of pure product, m/e=374 (M+H).

Part C: To a solution of 1.48 g (3.96 mmol) of product from Part B in 15 mL of anhydrous methanol, was added 3.3 mL (14 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 1.14 g of the desired product, identified as N-(2-mercapto-1R-methylethyl)-N-methyl-4-ethoxybenzenesulfonamide, m/e=332 (M+H).

EXAMPLE 40

Preparation of N-(2-Mercapto-1R-methylethyl)-N-methyl-4-(phenoxy)benzenesulfonamide

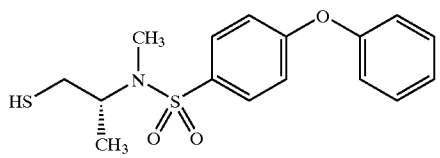

Part A: To a solution of 5.02 g (66.8 mmol) of (R)-(–)-2-amino-1-propanol in 28 mL of THF and 7 mL of water, was added 14.0 mL (100 mmol) of triethylamine. After cooling in an ice bath, 11.7 g (60 mmol) of 4-fluorobenzenesulfonyl chloride was slowly added over 10 minutes. After stirring at room temperature for 2 hour, the reaction was concentrated, ethyl acetate and water were added, the organic layer was separated and washed with 5% potassium hydrogen sulfate solution, saturated sodium bicarbonate solution and brine, dried over sodium sulfate, filtered and concentrated to afford 14.5 g of the desired N-(2-hydroxy-1R-methylethyl)-4-fluorobenzenesulfonamide, m/e=234 (M+H).

Part B: To a solution of 5.14 g (22.0 mmol) of N-(2-hydroxy-1R-methylethyl)-4-fluorobenzenesulfonamide from Part A in 40 mL of anhydrous DMF, was added 9.12 g (66.1 mmol) of powdered potassium carbonate, and then 4.2 mL (66 mmol) of methyl iodide. After stirring at room temperature for 4 hours, ethyl acetate and water was added, the layers separated and the organic layer washed 3×s with brine, dried with sodium sulfate, filtered and stripped to afford 4.64 g of the desired N-(2-hydroxy-1R-methylethyl)-N-methyl-4-fluorobenzenesulfonamide, m/e=247 (M+H).

Part C: To a solution of 3.00 g (12.1 mmol) of the product from Part B in 25 mL of anhydrous DMF, was added 5.02 g (36.4 mmol) of powdered potassium carbonate, and then 2.3 g (24.3 mmol) of phenol. The reaction mixture was heated to 100 C for 48 hours, cooled and tert-butylmethyl ether and water added. The organic layer was separated and washed with 10% sodium hydroxide, brine, dried with sodium sulfate, filtered and stripped to afford 3.0 g of crude material. This was chromatographed on 150 g of silica gel using 20%–30% ethyl acetate/hexane to provide 0.92 g of pure N-(2-hydroxy-1R-methylethyl)-N-methyl-4-(phenoxy)-benzenesulfonamide, m/e=328 (M+Li).

Part D: To a solution of 742 mg (2.3 mmol) of product from Part C and 0.67 g (2.54 mmol) of triphenylphosphine in 10 mL of anhydrous THF at 0° C., was added 0.40 mL (2.54 mmol) of diethylazodicarboxylate, followed after 5 min. by 0.18 mL (2.54 mmol) of thiolacetic acid. After 0.5 hour, the reaction was concentrated and the residue was chromatographed on 100 g of silica gel using 10%–20% ethyl acetate/hexane to yield 0.77 g of the desired product, m/e=380 (M+H).

Part E: To a solution of 0.76 g (2.05 mmol) of product from Part D in 5 mL of anhydrous methanol, was added 1.8 mL (7.4 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford the crude product. This was chromatographed on 100 g of silica gel using 100% methylene chloride to provide the pure N-(2-mercapto-1R-methylethyl)-N-methyl-4-(phenoxy) benzenesulfonamide, m/e=338 (M+H).

EXAMPLE 41

Preparation of N-(2-Mercapto-1R-methylethyl)-N-methyl-4-(thiophenyl)benzenesulfonamide

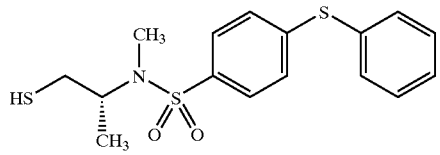

Part A: To a solution of 1.72 g (6.95 mmol) of N-(2-hydroxy-1R-methylethyl)-N-methyl-4-fluorobenzenesulfonamide from Example 40, part B, in 10 mL of anhydrous DMF, was added 7.03 g (21.5 mmol) of cesium carbonate, and then 1.0 mL (1.07 g, 9.73 mmol) of thiophenol. The reaction mixture was heated to 70 C for 15 hours, cooled and ethyl acetate and water added. The organic layer was separated and washed 3×s with brine, dried with sodium sulfate, filtered and stripped to afford 2.5 g of crude material. This was chromatographed on 100 g of silica gel using 20%–60% ethyl acetate/hexane to provide 1.37 g of pure N-(2-hydroxy-1R-methylethyl)-N-methyl-4-(thiophenyl)-benzenesulfonamide, m/e=338 (M+H).

Part B: To a solution of 1.29 g (3.82 mmol) of product from Part A and 1.10 g (4.20 mmol) of triphenylphosphine in 19 mL of anhydrous THF at 0° C., was added 0.60 mL (4.20 mmol) of diethylazodicarboxylate, followed after 5 min. by 0.30 mL (4.20 mmol) of thiolacetic acid. After 1 hour, the reaction was concentrated and the residue was chromatographed on 150 g of silica gel using 100% methylene chloride to yield 1.0 g of the desired product, m/e=402 (M+Li).

Part C: To a solution of 1.0 g (2.53 mmol) of product from Part B in 10 mL of anhydrous methanol, was added 2.1 mL (9.1 mmol) of a 25 weight % solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford the crude product. This was chromatographed on 50 g of silica gel using 100% methylene chloride to provide pure N-(2-mercapto-1R-methylethyl)-N-methyl-4-(thiophenyl) benzene-sulfonamide, m/e=354 (M+H).

EXAMPLE 42

Preparation of N-(2-Hydroxy-1R-methylethyl)-N-methyl-2-(pyrid-2-yl)thiophene-5-sulfonamide

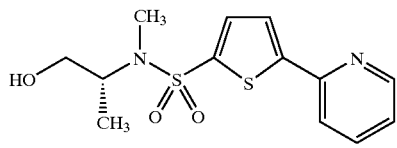

Part A: To a solution of 1.97 g (26.2 mmol) of (R)-(–)-2-amino-1-propanol in 10 mL of THF and 3.5 mL of water, was added 4.5 mL (32 mmol) of triethylamine. After cooling in an ice bath, 5.44 g (20.9 mmol) of 2-(pyrid-2-yl) thiophene-5-sulfonyl chloride was slowly added over 10 minutes. After stirring at room temperature for 3.5 hours, the reaction was concentrated, ethyl acetate and water were added, the organic layer was separated and washed with 5% potassium hydrogen sulfate solution, saturated sodium bicarbonate solution and brine, dried over sodium sulfate, filtered and concentrated to afford 4.1 g crude product. This was crystallized from acetone/diethyl ether to afford 0.96 of pure N-(2-hydroxy-1R-methylethyl)-2-(pyrid-2-yl) thiophene-5-sulfonamide.

Part B: To a solution of 0.94 g (3.15 mmol) of product from Part A in 10 mL of anhydrous DMF, was added 1.31 g (9.45 mmol) of powdered potassium carbonate, and then 0.60 mL (9.5 mmol) of methyl iodide. After stirring at room temperature for 24 hours, ethyl acetate and water was added, the layers separated and the organic layer washed 3×s with brine, dried with sodium sulfate, filtered and stripped to afford 0.93 g of the desired N-(2-hydroxy-1R-methylethyl)-N-methyl-2-(pyrid-2-yl)thiophene-5-sulfonamide.

EXAMPLE 43

Preparation of N-(2-Mercapto-1,1-dimethylethyl)-N-(phenylmethyl)-4-ethoxybenzenesulfonamide

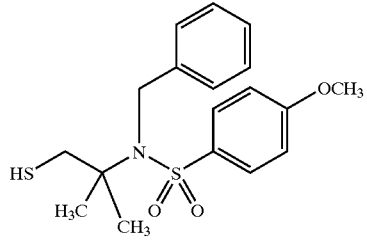

Part A: To a solution of 4.47 g (50 mmol) of 2-amino-2-methyl-1-propanol in 20 mL of THF and 5 mL of water, was added 10 mL (72 mmol) of triethylamine. After cooling in an ice bath, 9.0 g (44 mmol) of 4-methoxybenzenesulfonyl chloride was slowly added over 10 minutes. After stirring at room temperature for 12 hours, the reaction was concentrated, ethyl acetate and water were added, the organic layer was separated and washed with 5% potassium hydrogen sulfate solution, saturated sodium bicarbonate solution and brine, dried over sodium sulfate, filtered and concentrated to afford 9.1 g of the desired N-(2-hydroxy-1,1-dimethylethyl)-4-methoxybenzenesulfonamide.

Part B: To a solution of 3.12 g (12 mmol) of product from Part A in 25 mL of anhydrous DMF, was added 5.0 g (36 mmol) of powdered potassium carbonate, and then 2.2 mL (18 mmol) of benzyl bromide. After stirring at room temperature for 17 hours, ethyl acetate and water was added, the layers separated and the organic layer washed 3×s with brine, dried with sodium sulfate, filtered and stripped to afford 3.2 g of crude product. This was recrystallized from methylene chloride/hexane to afford 1.51 g of the desired N-(2-hydroxy-1,1-dimethylethyl)-N-(phenylmethyl)-4-methoxybenzenesulfonamide, m/e=356 (M+Li).

Part C: To a solution of 1.43 g (4.1 mmol) of product from Part B and 1.18 g (4.5 mmol) of triphenylphosphine in 16 mL of anhydrous THF at zero° C., was added 0.70 mL (4.5 mmol) of diethylazodicarboxylate, followed after 5 min. by 0.32 mL (4.5 mmol) of thiolacetic acid. After 3 hours, the reaction was concentrated and the residue was chromatographed on 150 g of silica gel using 20%–50% ethyl acetate/hexane to yield 0.62 g of the desired product, m/e= 414 (M+Li).

Part D: To a solution of 0.60 g (1.47 mmol) of product from Part C in 10 mL of anhydrous methanol, was added 1.2 mL (5.3 mmol) of a 25 weight percent solution of sodium methoxide in methanol. After 0.5 hour, the reaction was quenched with 1N HCl solution, followed by ethyl acetate and water, the organic layer was separated and washed with saturated sodium bicarbonate solution and brine, dried with magnesium sulfate, filtered and concentrated to afford 0.38 g of pure N-(2-mercapto-1,1-dimethylethyl)-N-(phenylmethyl)-4-methoxybenzenesulfonamide, m/e=366 (M+H).

EXAMPLE 44

Preparation of N-[(2-Mercaptophenyl)methyl]-N-methyl-4-methoxybenzenesulfonamide

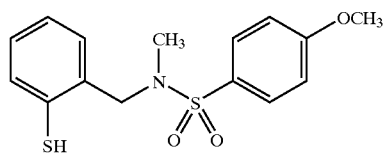

Part A: To a mixture of 50 mL of tetrahydrofuran, 15 mL (108 mmol) of triethylamine and 10 mL (116 mmol) of a 40% aqueous methylamine solution at 0 C, was added 15.0 g (72.6 mmol) of 4-methoxy-benzenesulfonyl chloride over a 15 minutes. After 1 hour, the solvents were removed in vacuo, 5% aqueous KHSO4 and ethyl acetate added, the organic layer separated, washed with saturated aqueous sodium bicarbonate, brine, dried with sodium sulfate, filtered and stripped to afford a white solid. This was recrystallized from hot ethyl acetate/hexane to afford 13.4 g of N-methyl-4-methoxybenzenesulfonamide, m/e=202 (M+H).

Part B: To a solution of 6.32 g (25.0 mmol) of 2-iodobenzyl chloride in 40 mL of anhydrous DMF, was added 5.04 g (25.0 mmol) of the product from Part A, and then 10.4 g (75.3 mmol) of powdered potassium carbonate was added. After stirring at room temperature for 5 hours, ethyl acetate and water were added, the organic layer separated and washed 3×s with brine, dried with sodium sulfate, filtered and stripped to afford 10.6 g of crude product. This was recrystallized from ethyl acetate/hexane to afford 9.0 g of the desired N-[(2-iodophenyl)methyl]-N-methyl-4-methoxybenzenesulfonamide.

Part C: To a mixture of 834 mg (2.0 mmol) of the product from Part B, 236 mg (3.1 mmol) of thiourea and 55 mg (0.10 mmol) of bis(tri-n-butylphosphine)-nickel(II) chloride under a nitrogen atmosphere at room temperature, was added 1 mL of anhydrous DMF, and then 16 mg (0.25 mmol) of sodium cyanoborohydride. The reaction was then warmed to 65 C for 15 hours, cooled to room temperature and 2.0 mL (5 mmol) of 2.5 N sodium hydroxide solution added. After stirring for 15 minutes, 1N hydrochloric acid and ethyl acetate were added, the organic layers separated, washed 3×s with brine, dried with sodium sulfate, filtered and stripped to afford 650 mg of crude product. This was chromatographed on 50 g of silica gel using 20%–30% ethyl acetate/hexane to afford 520 mg of purified product, which was then recrystallized from methylene chloride/hexane to afford 167 mg of the desired N-[(2-mercaptophenyl)methyl]-N-methyl-4-methoxybenzenesulfonamide.

EXAMPLE 45

Preparation of N-(2-Mercapto-1R-methylethyl)-N-[2-(4-morpholino)ethyl]-4-(n-butoxy)benzenesulfonamide

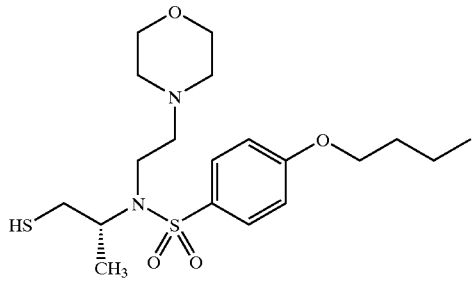

Part A: To a solution of 2.87 g (10 mmol) of N-(2-hydroxy-1R-methylethyl)-4-(n-butoxy)benzenesulfonamide from Example 4 in (10 ml) of anhydrous DMF,was added 4.14 g (30 mmol) of powdered potassium carbonate and then 2.04 g (11 mmol) of 4-(2-Chloroethyl)morpholine hydrochloride. After 12 hours another batch of (2.0 g, mmol) of powdered potassium carbonate and 1.0 g (5.5 mmol) of 4-(2-chloroethyl)-morpholine hydrochloride was added and the reaction mixture stirred at room temperature for an additional 12 hours, ethyl acetate and water was added, the organic layer separated and washed 3×50 mL with brine, dried with sodium sulfate, filtered and solvent removed under reduced pressure and the residue chromatographed on 100 g of silica gel using 3:1 mixture of ethyl acetate:hexane to afford 2.1 g of the desired N-(2-hydroxy-1R-methylethyl)-N-[2-(4-morpholino)-ethyl]-4-(n-butoxy) benzenesulfonamide, m/e=407 (M+Li).

Part B: To a solution of 1.5 g (3.74 mmol) of product from Part A and 983 mg (3.74 mmol) of triphenylphosphine in 15 ml of anhydrous THF at room temperature was added 0.588 mL (3.74 mmol) of diethyl azodicarboxylate,followed by 0.8 mL (11.22 mmol) of thiolacetic acid. After stirring at room temperature for 1.5 hours, the reaction was concentrated and the residue chromatographed on 100 g of silica gel using a 1:1 mixture of ethyl acetate:hexane to afford 718 mg of the desired N-[2-(S-acetyl)mercapto-1R-methylethyl]-N-[2-(4-morpholino)ethyl]-4-(n-butoxy)benzenesulfonamide, m/e= 459 (M+H).

Part C: To a suspension of 0.63 g (1.7 mmol) of product from Part B in 20 mL of anhydrous methanol, was added 0.5 mL (2.3 mmol) of 25 wt. % sodium methoxide in methanol. After 30 minutes at room temperature, ethyl acetate and water was added, the organic layer separated and washed 3×50 ml with water and with brine and dried with sodium sulfate, filtered and solvent removed under reduced pressure and the residue chromatographed on 100 g of silica gel using 3% methanol/dichloromethane to afford 0.38 g of N-(2-mercapto-1R-methylethyl)-N-[2-(4-morpholino)ethyl]-4-(n-butoxy)benzenesulfonamide, m/e=417 (M+H).

EXAMPLE 46
Preparation of N-(2-Mercapto-1R-methylethyl)-N-[2-(1-piperidino)ethyl]-4-(n-butoxy)benzenesulfonamide

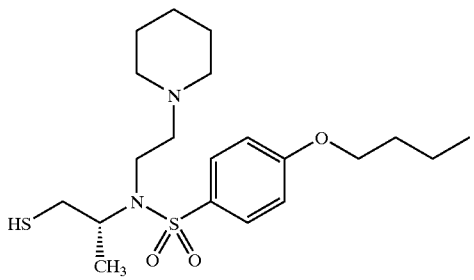

Part A: To a solution of 1.0 g (3.5 mmol) of N-(2-hydroxy-1R-methylethyl)-4-(n-butoxy)-benzenesulfonamide from Example 4 in (30 ml) of anhydrous DMF,was added 2.16 g (15.6 mmol) of powdered potassium carbonate and then 0.96 g (5.2 mmol) of 1-(2-chloroethyl)piperidine hydrochloride. After 20 hours, ethyl acetate and water was added, the organic layer separated and washed 2×50 mL with saturated sodium bicarbonate and 2×50 mL with brine, dried with sodium sulfate, filtered and solvent removed under reduced pressure and the residue chromatographed on 200 g of silica gel using 3:1 mixture of ethyl acetate:hexane to afford 0.98 g of the desired N-(2-hydroxy-1R-methylethyl)-N-[2-(1-piperidino)ethyl]-4-(n-butoxy)-benzenesulfonamide, m/e=399 (M+H).

Part B: To a solution of 0.9 g (2.26 mmol) of product from Part A and 0.6 g (2.3 mmol) of triphenylphosphine in 20 ml of anhydrous THF at room temperature was added 0.36 mL (2.3 mmol) of diethyl azodicarboxylate, followed by 0.48 mL (6.78 mmol) of thiolacetic acid. After stirring at room temperature for 6 hours, the reaction was concentrated and the residue chromatographed on 60 g of silica gel using a 3:1:0.25 mixture of ethyl acetate:hexane:methanol to afford 0.36 g of the desired N-[2-(S-acetyl)mercapto-1R-methylethyl]-N-[2-(1-piperidino)ethyl]-4-(n-butoxy) benzenesulfonamide, m/e=457 (M+H).

Part C: To a suspension of 0.36 g (0.77 mmol) of product from Part B in 20 mL of anhydrous methanol, was added 0.3 mL (1.4 mmol) of 25 wt. % sodium methoxide in methanol. After 30 minutes at room temperature, ethyl acetate and water was added, the organic layer separated and washed 3×50 ml with water and with brine and dried with sodium sulfate, filtered and solvent removed under reduced pressure and the residue chromatographed on 20 g of silica gel using 5% methanol/dichloromethane to afford 0.17 g of N-(2-mercapto-1R-methylethyl)-N-[2-(1-piperidino)ethyl]-4-(n-butoxy)benzenesulfonamide, m/e=415 (M+H).

EXAMPLE 47
Preparation of N-(2-Mercapto-1R-methylethyl)-N-[2-(1-pyrrolidino)ethyl]-4-(n-butoxy)benzenesulfonamide

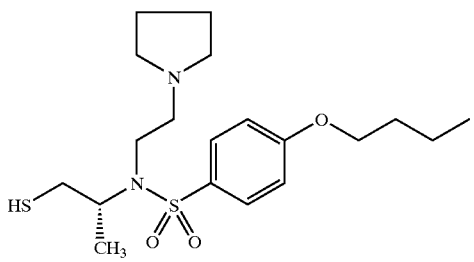

Part A: To a solution of 2.87 g (10 mmol) of N-(2-hydroxy-1R-methylethyl)-4-(n-butoxy)benzenesulfonamide from Example 4 in (10 ml) of anhydrous DMF, was added 4.14 g (30 mmol) of powdered potassium carbonate and then 1.88 g (11 mmol) of 1-(2-chloro-ethyl)pyrrolidine hydrochloride. After 12 hours, ethyl acetate and water was added, the organic layer separated and washed 3×50 mL with brine, dried with sodium sulfate, filtered and solvent removed under reduced pressure and the residue chromatographed on 100 g of silica gel using 3:1:0.5 mixture of ethyl acetate-:hexane:methanol to afford 1.6 g of the desired N-(2-hydroxy-1R-methylethyl)-N-[2-(1-pyrrolidino)-ethyl]-4-(n-butoxy)benzenesulfonamide, m/e=391 (M+Li).

Part B: To a solution of 1.2 g (3 mmol) of product from Part A and 0.79 g (3 mmol) of triphenylphosphine in 15 ml of anhydrous THF at room temperature was added 0.47 mL (3 mmol) of diethyl azodicarboxylate, followed by 0.7 mL (10 mmol) of thiolacetic acid. After stirring at room temperature for 2 hours, the reaction was concentrated and the residue chromatographed on 100 g of silica gel using a 3:1:1 mixture of ethyl acetate:hexane:methanol to afford 0.4 g of the desired N-[2-(S-acetyl)mercapto-1R-methylethyl]-N-[2-(1-pyrrolidino)ethyl]-4-(n-butoxy)benzenesulfonamide, m/e=443 (M+H).

Part C: To a suspension of 0.39 g (0.87 mmol) of product from Part B in 15 mL of anhydrous methanol, was added 0.3 mL (1.4 mmol) of 25 wt. % sodium methoxide in methanol. After 30 minutes at room temperature, ethyl acetate and water was added, the organic layer separated and washed 3×50 ml with water and with brine and dried with sodium sulfate, filtered and solvent removed under reduced pressure and the residue chromatographed on 50 g of silica gel using 5% methanol/dichloromethane to afford 0.18 g of the desired N-(2-mercapto-1R-methylethyl)-N-[2-(1-pyrrolidino)ethyl]-4-(n-butoxy)benzenesulfonamide, m/e=401 (M+H).

EXAMPLE 48
Preparation of N-(2-Mercapto-1R-methylethyl)-N-pentyl-4-(n-butoxy)benzenesulfonamide

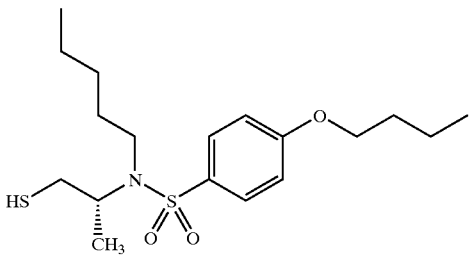

Part A: To a solution of 2.87 g (10 mmol) of N-(2-hydroxy-1R-methylethyl)-4-(n-butoxy)benzenesulfonamide from Example 4 in (20 ml) of anhydrous DMF, was added 4.2 g (30 mmol) of powdered potassium carbonate and then 2.3 g (15 mmol) of 1-Bromopentane. The reaction mixture was stirred at 60° C. for 13 hours, ethyl acetate and water was added, the organic layer separated and washed with water and with brine, dried with sodium sulfate, filtered and solvent removed under reduced pressure and the residue chromatographed on 100 g of silica gel using 2:1 mixture of ethyl acetate:hexane to afford 2.63 g of the desired N-(2-hydroxy-1R-methylethyl)-N-pentyl-4-(n-butoxy)benzenesulphonamide, m/e=364 (M+Li).

Part B: To a solution of 2.0 g (5.6 mmol) of product from Part A and 1.58 g (6 mmol) of triphenylphosphine in 20 ml of anhydrous THF at room temperature was added 0.94 mL (6 mmol) of diethyl azodicarboxylate, followed by 0.86 mL (12 mmol) of thiolacetic acid. After stirring at room temperature for 1 hour, the reaction was concentrated and the residue chromatographed on 100 g of silica gel using a 4:1 mixture of hexane:ethyl acetate to afford 1.2 g of the desired N-[2-(S-acetyl)mercapto-1R-methylethyl]-N-pentyl-4-(n-butoxy)benzenesulfonamide, m/e=416 (M+H).

Part C: To a suspension of 1.0 g (2.4 mmol) of product from Part B in 20 mL of anhydrous methanol, was added 1.0 mL (4.6 mmol) of 25 wt. % sodium methoxide in methanol. After 30 minutes at room temperature, ethyl acetate and water was added, the organic layer separated and washed 3×50 ml with water and with brine and dried with sodium sulfate, filtered and solvent removed under reduced pressure and the residue chromatographed on 50 g of silica gel using dichloromethane to afford g of the desired N-(2-mercapto-1R-methylethyl)-N-pentyl-4-(n-butoxy)benzenesulfonamide, m/e=380 (M+Li).

EXAMPLE 49

N-(2-Mercapto-1-R-methylethyl)-N-(3-pyridylmethyl)-4-methoxybenzenesulfonamide

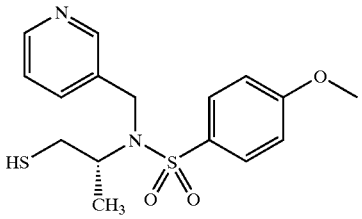

Part A: To a solution of 3.69 g (15 mmol) of N-(2-hydroxy-1R-methylethyl)-4-methoxybenzenesulfonamide from Example 3 in (25 ml) of anhydrous DMF, was added 6.3 g (45 mmol) of powdered potassium carbonate and then 2.7 g (16.5 mmol) of 3-picolyl hydrochloride. The reaction mixture was stirred for 12 hours, ethyl acetate and water was added, the organic layer separated and washed with saturated sodium bicarbonate and with brine, dried with sodium sulfate, filtered and solvent removed under reduced pressure and the residue chromatographed on 100 g of silica gel using 2:1 ethyl acetate:hexane to afford 1.12 g of the desired N-(2-hydroxy-1R-methylethyl)-N-(3-pyridylmethyl)-4-methoxybenzenesulphonamide, m/e=343 (M+Li).

Part B: To a solution of 1.07 g (3.18 mmol) of product from Part A and 0.84 g (3.2 mmol) of triphenylphosphine in 25 ml of anhydrous THF at room temperature was added 0.5 mL (3.18 mmol) of diethyl azodicarboxylate, followed by 0.68 mL (9.5 mmol) of thiolacetic acid. After stirring at room temperature for 1.5 hour, the reaction was concentrated and the residue chromatographed on 80 g of silica gel using 1:2 hexane:ethyl acetate to afford 0.21 g of the desired N-[2-(S-acetyl)mercapto-1R-methylethyl]-N-(3-pyridylmethyl)-4-methoxybenzenesulfonamide, m/e=395 (M+H).

Part C: To a suspension of 0.18 g (0.45 mmol) of product from Part B in 25 mL of anhydrous methanol, was added 0.2 mL (1.2 mmol) of 25 wt. % sodium methoxide in methanol. After 30 minutes at room temperature, ethyl acetate and water was added, the organic layer separated and washed 2×50 ml with water and with brine and dried with sodium sulfate, filtered and solvent removed under reduced pressure and the residue chromatographed on 50 g of silica gel using 1% methanol/dichloromethane to afford 0.1 g of the desired N-(2-mercapto-1R-methylethyl)-N-(3-pyridylmethyl)-4-methoxybenzenesulfonamide, m/e=353 (M+H).

EXAMPLE 50

Preparation of N-(2-Mercapto-1R-methylethyl)-N-methyl(3-thiophenylpropyl)sulphonamide

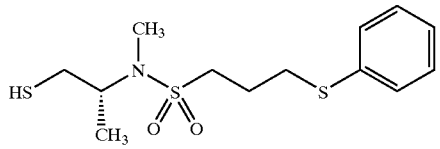

Part A: To a solution of 1.1 g (3.8 mmol) of N-(2-hydroxy-1R-methylethyl)(3-thiophenoxypropyl)sulphonamide from Example 5 in (25 ml) of anhydrous DMF, was added 2.1 g (15 mmol) of powdered potassium carbonate and then 1.1 g (7.6 mmol) of methyl iodide. The reaction mixture was stirred at room temperature for 14 hours, ethyl acetate and water was added, the organic layer separated and washed with saturated sodium bicarbonate and with brine, dried with sodium sulfate, filtered and solvent removed under reduced pressure and the residue chromatographed on 100 g of silica gel using 2:1 ethyl acetate:hexane to afford 0.93 g of the desired N-(2-hydroxy-1R-methylethyl)-N-methyl(3-thiophenylpropyl)sulphonamide, m/e=326 (M+Na).

Part B: To a solution of 0.9 g (2.96 mmol) of product from Part A and 0.78 g (2.96 mmol) of triphenylphosphine in 25 ml of anhydrous THF at room temperature was added 0.47 mL (2.96 mmol) of diethyl azodicarboxylate, followed by 0.63 mL (8.8 mmol) of thiolacetic acid. After stirring at room temperature for 1.5 hour, the reaction was concentrated and the residue chromatographed on 80 g of silica gel using 3:1 hexane:ethyl acetate to afford 0.85 g of the desired N-[2-(S-acetyl)mercapto-1R-methylethyl]-N-methyl(3-thiophenylpropyl)sulfonamide, m/e=368 (M+Li).

Part C: To a suspension of 0.18 g (0.5 mmol) of product from Part B in 15 mL of anhydrous methanol, was added 0.25 mL (1.12 mmol) of 25 wt. % sodium methoxide in methanol. After 25 minutes at room temperature, neutralized with 0.2N hydrochloric acid, ethyl acetate was added, the organic layer separated and washed 2×50 ml with water and with brine and dried over sodium sulfate, filtered and solvent removed under reduced pressure and the residue chromatographed on 50 g of silica gel using dichloromethane to afford 72 mg of the desired N-(2-mercapto-1R-methylethyl)-N-methyl-(3-thiophenylpropyl)sulfonamide, m/e=320 (M+H).

EXAMPLE 51

N-(2-Mercapto-1R-methylethyl)-N-benzyl(3-thiophenylpropyl)sulphonamide

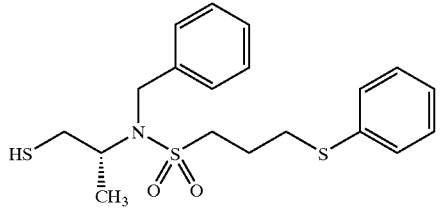

Part A: To a solution of 0.86 g (3 mmol) of N-(2-hydroxy-1R-methylethyl)(3-thiophenoxypropyl)sulphonamide from Example 5 in (25 ml) of anhydrous DMF, was added 1.24 g (8.9 mmol) of powdered potassium carbonate and then 0.62 g (3.6 mmol) of benzyl bromide. The reaction mixture was stirred at room temperature for 14 hours, ethyl acetate and water was added, the organic layer separated and washed with saturated sodium bicarbonate and with brine, dried with sodium sulfate, filtered and solvent removed under reduced pressure and the residue chromatographed on 100 g of silica gel using 1:2 ethyl acetate:hexane to afford 0.64 g of the desired N-(2-hydroxy-1R-methylethyl)-N-benzyl)(3-thiophenylpropyl)sulphonamide, m/e=380 (M+H).

Part B: To a solution of 0.6 g (1.58 mmol) of product from Part A and 0.42 g (1.6 mmol) of triphenylphosphine in 15 ml of anhydrous THF at room temperature was added 0.25 mL (1.6 mmol) of diethyl azodicarboxylate, followed by 0.34 mL (4.8 mmol) of thiolacetic acid. After stirring at room temperature for 1 hour, the reaction was concentrated and the residue chromatographed on 80 g of silica gel using 2:1 hexane:ethyl acetate to afford 0.465 g of the desired N-[2-(S-acetyl)mercapto-1R-methylethyl]-N-benzyl(3-thiophenylpropyl)sulfonamide, m/e=444 (M+Li).

Part C: To a suspension of 0.17 g (0.39 mmol) of product from Part B in 15 mL of anhydrous methanol, was added 0.2 mL (0.92 mmol) of 25 wt. % sodium methoxide in methanol. After 25 minutes at room temperature, neutralized with 0.2N hydrochloric acid, ethyl acetate was added, the organic layer separated and washed 2×50 ml with water and with brine and dried over sodium sulfate,filtered and solvent removed under removed under reduced pressure to afford 72 mg of the desired N-(2-mercapto-1R-methylethyl)-N-benzyl(3-thiophenylpropyl)sulfonamide, m/e=396 (M+H).

EXAMPLE 52

N-(2-Mercapto-1R-methylethyl)-N-[2-(1-piperidino) ethyl](3-thiophenylpropyl)sulphonamide

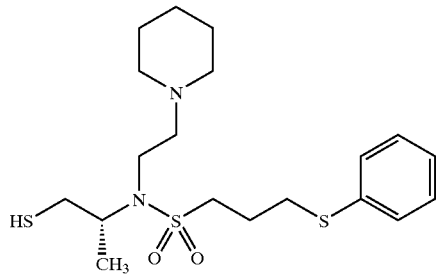

Part A: To a solution of 1.0 g (3.45 mmol) of N-(2-hydroxy-1R-methylethyl)(3-thiophenoxypropy)sulphonamide from Example 5 in (30 ml) of anhydrous DMF, was added 2.16 g (15.6 mmol) of powdered potassium carbonate and then 0.96 g (5.2 mmol) of methyl iodide. The reaction mixture was stirred at room temperature for 10 hours, ethyl acetate and water was added, the organic layer separated and washed with saturated sodium bicarbonate and with brine, dried with sodium sulfate, filtered and solvent removed under reduced pressure and the residue chromatographed on 100 g of silica gel using 3:1:0.5 mixture of ethyl acetate:hexane:methanol to afford 0.9 g of the desired N-(2-hydroxy-1R-methylethyl)-N-[2-(1-piperidino) ethyl]-(3-thiophenylpropyl)sulphonamide, m/e=401 (M+H).

Part B: To a solution of 0.83 g (2.07 mmol) of product from Part A and 0.54 g (2.07 mmol) of triphenylphosphine in 25 ml of anhydrous THF at room temperature was added 0.33 mL (2.07 mmol) of diethyl azodicarboxylate, followed by 0.44 mL (6.21 mmol) of thiolacetic acid. After stirring at room temperature for 1.5 hour, the reaction was concentrated and the residue chromatographed on 100 g of silica gel using a 3:1:0.25 mixture of ethyl acetate:hexane:methanol to afford 0.45 g of the desired N-[2-(S-acetyl)mercapto-1R-methylethyl]-N-[2-(1-piperidino)ethyl](3-thiophenylpropyl)sulfonamide, m/e=465 (M+Li).

Part C: To a suspension of 0.225 g (0.5 mmol) of product from Part B in 15 mL of anhydrous methanol, was added 0.2 mL (0.9 mmol) of 25 wt. % sodium methoxide in methanol. After 25 minutes at room temperature, ethyl acetate and water was added, the organic layer separated and washed 2×50 ml with water and with brine and dried over sodium sulfate,filtered and solvent removed under reduced pressure and the residue chromatographed on 50 g of silica gel using dichloromethane to afford 112 mg of the desired N-(2-mercapto-1R-methylethyl)-N-[2-(1-piperidino)ethyl](3-thiophenylpropyl)sulfonamide, m/e=417 (M+H).

EXAMPLE 53

Preparation of N-(2-Mercapto-1R-methylethyl)-N-methyl-4-(n-pentyl)benzenesulfonamide

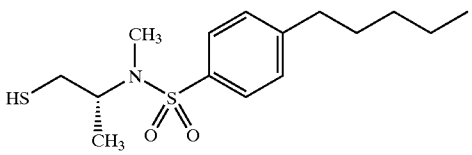

Part A: Preparation of N-(2-Hydroxy-1R-methylethyl)-N-methyl-4-(n-pentyl)benzenesulfonamide. To a stirred solution of (2.85 g, 10 mmol) of N-(2-Hydroxy-1R-methylethyl)-4-(n-pentyl)benzenesulfonamide from example 6, in 30 mL of dry dimethylfomamide was added (4.05 g, 30 mmol) of powdered potassium carbonate followed by (4.23 g, 30 mmol) of methyl iodide and the suspension stirred for 16 hours. The contents were concentrated by rotory evaporation and the residue was partitioned between 200 mL of ethyl acetate and 400 mL of water. The organic phase was washed with saturated sodium chloride, dried over magnesium sulfate, filtered and concentrated to a dark yellow oil. The crude material was purified by silica gel chromatography using an eluant of 30% ethyl acetate in hexane to yield 1.53 grams of a clear oil.

Part B: Preparation of N-(2-Thioacetyl-1R-methylethyl)-N-methyl-4-(n-pentyl)benzenesulfonamide.

To an ice cooled, stirred solution of (1.53 g, 5.1 mmol) of N-(2-hydroxy-1R-methylethyl)-N-methyl-4-(n-pentyl) benzenesulfonamide and (1.46 g, 5.6 mmol) of triphenylphosphine in 20 mL of anhydrous tetrahydrofuran was added (946 mg, 5.6 mmol) of diethylazodicarbocylate, followed by (425 mg, 5.6 mmol) of thioacetic acid. After stirring for 1.5 hours at room temperature the contents were concentrated by rotory evaporation and purified by silica gel chromatography using an eluant of 25% ethyl acetate in hexanes to yield 1.078 grams of a clear oil. N-(2-thioacetyl-1R-methylethyl)-N-methyl-4-(n-pentyl) benzenesulfonamide.

Part C: Preparation of N-(2-Mercapto-1R-methylethyl)-N-methyl-4-(n-pentyl)benzenesulfonamide.

To a stirred solution of (1.07 g, 3 mmol) of N-(2-thioacetyl-1R-methylethyl)-N-methyl-4-(n-pentyl) benzenesulfonamide in 25 mL of dry methanol was added 4.0 mL of 25% sodium methoxide in methanol and the solution stirred for 15 minutes. To the clear solution was added 50 mL of 1 N hydrochloric acid and the milky suspension was extracted with 100 mL of ethyl acetate, dried over magnesium sulfate, filtered and conc. to yield 700 mg of N-(2-mercapto-1R-methylethyl)-N-methyl-4-(n-pentyl) benzenesulfonamide of purified product. m/e=322 (M+Li).

EXAMPLE 54

Preparation of N-(2-Mercapto-1R-methylethyl)-N-[2-(4-morpholino)ethyl]-4-(n-pentyl)benzenesulfonamide

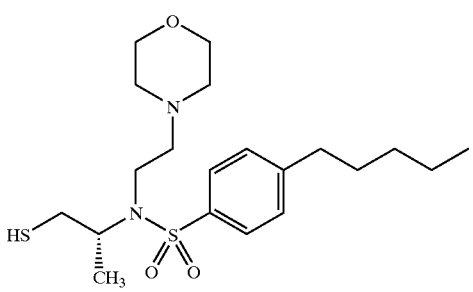

Part A: Preparation of N-(2-Hydroxy-1R-methylethyl)-N-[2-(4-morpholino)ethyl]-4-(n-pentyl)benzenesulfonamide.

To a stirred solution of (2.85 g, 10 mmol) of N-(2-Hydroxy-1R-methylethyl)-4-(n-pentyl)benzenesulfonamide from example 6, in 30 mL of dry dimethylformamide was added (5.40 g, 40 mmol) of powdered potassium carbonate followed by (2.23 g, 12 mmol) of 4-(2-chloroethyl)-morpholine hydrochloride and the suspension stirred for 16 hours. Thin layer chromatography, and H-NMR showed approximately 50% conversion, another 2.23 g of 4-(2-chloroethyl)morpholine hydrochloride was added and the reaction mixture stirred another 16 hours. The contents were concentrated by rotory evaporation and the residue was partitioned between 200 mL of ethyl acetate and 400 mL of water. The organic phase was washed with saturated sodium chloride, dried over magnesium sulfate, filtered and concentrated to a yellow oil. The crude material was purified by silica gel chromatography using an eluant of 30% ethyl acetate in hexane to yield 940 mg of a clear oil.

Part B: Preparation of N-(2-Thioacetyl-1R-methylethyl)-N-[2-(4-morpholino)ethyl]-4-(n-pentyl)benzenesulfonamide.

To a stirred, ice cooled solution of (940 mg, 2.3 mmol) of N-(2-hydroxy-1R-methylethyl)-N-[(4-morpholino)-ethyl]-4-(n-pentyl)benzenesulfonamide and (740 mg, 2.8 mmol) of triphenylphosphine in 30 mL of anhydrous tetrahydrofuran under nitrogen was added (487 mg, 2.8 mmol) of diethylazodicarboxylate, followed by (210 mg, 2.8 mmol) of thioacetic acid. After warming to room temperature over two hours the solution was concentrated by rotory evaporation and subjected to silica gel column chromatography using an eluant of 3:1:0.1 hexane:ethyl acetate: methanol to yield 560 mg of purified product.

Part C: Preparation of N-(2-Mercapto-1R-methylethyl)-N-[2-(4-morpholino)ethyl]-4-(n-pentyl)benzenesulfonamide.

To a stirred solution of (560 mg, 1.2 mmol) of N-(2-thioacetyl-1R-methylethyl)-N[2-(4-morpholino)ethyl]-4-(n-pentyl)benzenesulfonamide in 25 mL of dry methanol was added 4.0 mL of 25% sodium methoxide in methanol and the solution stirred for 15 minutes. To the clear solution was added 1 N hydrochloric acid until pH=7 and the milky suspension was extracted with 100 mL of ethyl acetate, dried over magnesium sulfate, filtered and conc. to yield 480 mg of N-(2-thioacetyl-1R-methylethyl)-N[2-(4-morpholino) ethyl]-4-(n-pentyl)benzenesulfonamide of purified product; m/e=415 (M+H).

EXAMPLE 55

Preparation of N-(2-Mercapto-1R-methylethyl)-N-methyl-4-(phenyl)benzenesulfonamide

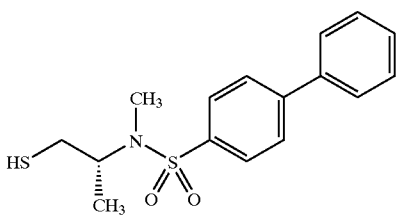

Part A: Preparation of N-(2-Hydroxy-1R-methylethyl)-4-bromo-benzenesulfonamide.

To a ice cooled solution of (5.0 g, 60 mmol) of 2(R)-methyl-ethanolamine in 25 mL of tetrahydrofuran, 10 mL of water, and 8.7 grams of triethylamine was added (15.3 g, 54 mmol) of 4-bromobenzenesulfonyl chloride slowly over 10 minutes. After stirring for 3 hours at room temperature, the solution was concentrated by rotory evaporation and the contents were partitioned between 200 mL of ethyl acetate and 200 mL of water. The organic layer was washed with 100 mL of 5% potassium hydrogen sulfate, followed by saturated sodium chloride, dried over magnesium sulfate, filtered and concentrated to yield 17.5 grams of a clear oil. The crude material was crystallized from ethyl acetate and hexane to yield 13.45 g of purified material.

Part B: Preparation of N-(2-Hydroxy-1R-methylethyl)-4-(phenyl)benzenesulfonamide.

To a stirred solution of (2.54 g, 8.6 mmol) of N-(2-Hydroxy-1R-methylethyl)-4-bromo-benzenesulfonamide in 60 mL of toluene was added 40 mL of ethanol, followed by (1.15 g, 9.0 mmol) of phenylboronic acid, 25 mL of 2M sodium carbonate, and (1.0 g, 0.8 mmol) of tetrakis-(triphenylphosphine)palladium. The subsequent heterogeneous solution was heated to reflux overnight. The solution was cooled and extracted with ethyl acetate. The organic layer was washed with saturated sodium bicarbonate and brine, dried over magnesium sulfate, filtered and concentrated to a dark oil, which contained precipitated catalyst. The crude oil was purified by silical gel chromatography using ethyl acetate hexane as the eluant to yield 1.0 g of purified product.

Part C: Preparation of N-(2-Hydroxy-1R-methylethyl)-N-methyl-4-(phenyl)benzenesulfonamide.

To a solution of (1.0 g, 3.4 mmol) of N-(2-Hydroxy-1R-methylethyl)-4-(phenyl)benzenesulfonamide in 10 mL of dimethylformamide was added (1.35 g, 10 mmol) of potassium carbonate and (1.41 g, 10 mmol) of methyl iodide and the suspension was stirred overnight under nitrogen atmosphere. The contents were concentrated by rotory evaporation and the residue was crystallized from ether hexane to yield 535 mg of purified product.

Part D: Preparation of N-(2-Thioacetyl-1R-methylethyl)-N-methyl-4-(phenyl)benzenesulfonamide.

To an ice cooled solution of (535 mg, 1.8 mmol) of N-(2-Hydroxy-1R-methylethyl)-N-methyl-4-(phenyl) benzenesulfonamide and (524 mg, 2 mmol) of triphenylphosphine in 15 mL of anhydrous tetrahydrofuran was added (348 mg, 2 mmol) of diethyldiazodicarboxylate followed by (152 mg, 2 mmol) of thioacetic acid. The resulting solution was stirred for 1.5 hours to room temperature and then concentrated by rotory evaporation to yield a crude oil which was purified by column chromatography to yield 328 mg of desired product.

Part E: Preparation of N-(2-Mercapto-1R-methylethyl)-N-methyl-4-(phenyl)benzenesulfonamide.

To a stirred solution of (328 mg, 0.9 mmol) of N-(2-thioacetyl-1R-methylethyl)-N-methyl-4-(phenyl)benzenesulfonamide in 5 mL of dry methanol was added 1 mL of 25 wt % sodium methoxide in methanol. After 10 minutes the solution was diluted with 10 mL of 1 N hydrochloric acid and extracted with ethyl acetate. The organic layer was dried and concentrated to yield N-(2-mercapto-1R-methylethyl)-N-methyl-4-(phenyl)-benzenesulfonamide; m/e=328 (M+Li).

EXAMPLE 56

Preparation of N-(2-Mercapto-1R,S-methylethyl)-N-phenylmethyl-4-methoxybenzenesulfonamide benzenesulfonamide

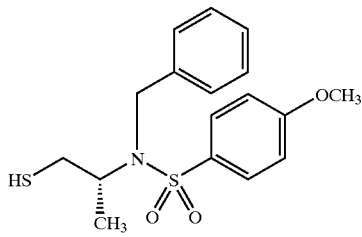

Part A: To a stirred solution (10.0 g, 36.6 mmol) of N-(4-methoxybenzenesulfonyl)-D,L-alanine methyl ester in dimethylformamide in 200 mL of was added (15.17 g, 109 mmol) of powdered potassium carbonate followed by (6.2 g, 36.6 mmol) of benzyl bromide and the solution stirred for 20 hours. The contents were concentrated by rotory evaporation and the residue was partition between 250 mL of ethyl acetate and 250 ml of water.e organic layer was washed with 100 mL 5% aqueous potassium hydrogen sulfate, 100 mL of saturated sodium bicarbonate,and 100 mL of saturated sodium chloride, dried over magnesium sulfate, filtered and concentrated to an oil, which was crystallized from ethyl acetate and hexanes to yield 10.16 g of purified N-phenylmethyl-N-4-methoxybenzenesulfonamide-D,L-alanine methyl ester.

Part B: To an ice cooled, stirred solution of (8.55 g, 23.5 mmol) of N-phenylmethyl-N-4-methoxybenzenesulfonamide-D,L-alanine methyl ester in 100 mL of anhydrous tetrahydrofuran, under nitrogen atmosphere was added (23 mL, 23 mmol) of 1M lithium aluminum hydride in diethyl ether and the solution stirred at 0 C for three hours. The solution was carefully quenched at 0 C by the addition of 2 mL of 10% sodium hydroxide dropwise followed by 2 mL of water. The suspension was filtered through celite and the filtrate was dried over magnesium sulfate, filtered and concentrated to yield 5.67 g of crude N-phenylmethyl-N-4-methoxybenzenesulfonamide-D,L-alaninol which was used without purification.

Part C: To an ice cooled solution of (1.0 g, 3 mmol) of N-phenylmethyl-N-4-methoxybenzenesulfonamide-D,L-alaninol and (860 mg, 3.3 mmol) of triphenylphosphine in 20 mL of anhydrous tetrahydrofuran was added (510 mg, 3.3 mmol) of diethyldiazodicarboxylate followed by (250 mg, 3.3 mmol) of thioacetic acid and the solution stirred to room temperature for 2 hours. The contents were concentrated by rotory evaporation and the crude oil was subjected to silica gel chromatography to yield 730 mg of N-(2-thioacetyl-1R,S-methylethyl)-N-phenylmethyl-4-methoxybenzenesulfonamide benzenesulfonamide.

Part D: To a stirred solution of (730 mg, 1.8 mmol) of N-(2-thioacetyl-1R,S-methylethyl)-N-phenylmethyl-4-methoxybenzenesulfonamide benzenesulfonamide in 10 mL of methanol was added 1.5 mL of 25 wt % sodium methoxide in methanol and the solution stirred for 10 minutes. The contents were diluted with 20 mL of 1 N hydrochloric acid and extracted with ethyl acetate. The organic layer was dried over magnesium sulfate, filtered and concentrated to yield an oil which was crystallized form ether/ethyl acetate/hexane to yield 300 mg of N-(2-mercapto-1R,S-methylethyl)-N-phenylmethyl-4-methoxybenzenesulfonamide benzenesulfonamide. m/e= 358 (M+Li).

EXAMPLE 57

Preparation of N-(2-Mercapto-1R,S-phenylmethyl)-N-phenylmethyl-4-methoxybenzenesulfonamide

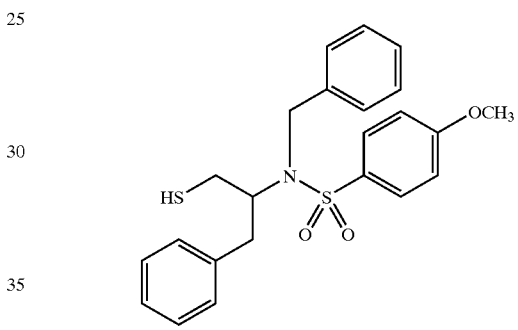

Part A: To a stirred solution (2.03 g, 4.6 mmol) of N-(4-methoxybenzenesulfonyl)-D,L-phenylalanine methyl ester in dimethylformamide in 50 mL of was added (1.8 g, 13 mmol) of powdered potassium carbonate followed by (789 mg, 4.6 mmol) of benzyl bromide and the solution stirred for 20 hours. The contents were concentrated by rotory evaporation and the residue was partition between 50 mL of ethyl acetate and 50 ml of water.e organic layer was washed with 100 mL 5% aqueous potassium hydrogen sulfate, 100 mL of saturated sodium bicarbonate, and 100 mL of saturated sodium chloride, dried over magnesium sulfate, filtered and concentrated to an oil, which was crystallized from ethyl acetate and hexanes to yield 1.55 g of purified N-phenylmethyl-N-4-methoxybenzenesulfonamide-D,L-phenylalanine methyl ester.

Part B: To an ice cooled, stirred solution of (1.55 g, 3.5 mmol) of N-phenylmethyl-N-4-methoxybenzenesulfonamide-D,L-phenylalanine methyl ester in 50 mL of anhydrous tetrahydrofuran, under nitrogen atmosphere was added (4.2 mL) of 1M lithium aluminum hydride in diethyl ether and the solution stirred at 0 C for three hours. The solution was carefully quenched at 0 C by the addition of 2 mL of 10% sodium hydroxide dropwise , followed by 2 mL of water. The suspension was filtered through celite and the filtrate was dried over magnesium sulfate, filtered and concentrated to yield 1.40 g of crude N-phenylmethyl-N-4-methoxy-benzenesulfonamide-D,L-phenylalaninol which was used without purification.

Part C: To an ice cooled solution of (1.24 g, 3.0 mmol) of N-phenylmethyl-N-4-methoxybenzenesulfonamide-D,L-phenylalaninol and (949 mg, 3.6 mmol) of triphenylphosphine in 20 mL of anhydrous tetrahydrofuran was added (630 mg, 3.6 mmol) of diethyldiazodicarboxylate followed by (275 mg, 3.6 mmol) of thioacetic acid and the solution stirred to room temperature for 2 hours. The contents were concentrated by rotory evaporation and the crude oil was subjected to silica gel chromatography to yield 1.10 mg of N-(2-thioacetyl-1R,S-phenylmethyl)-N-phenylmethyl-4-methoxybenzenesulfonamide benzenesulfonamide.

Part D: To a stirred solution of (1.10 g, 2.3 mmol) of N-(2-thioacetyl-1R,S-phenylmethyl)-N-phenylmethyl-4-methoxybenzenesulfonamide benzenesulfonamide in 10 mL of methanol was added 2.0 mL of 25 wt % sodium methoxide in methanol and the solution stirred for 10 minutes. The contents were diluted with 20 mL of 1 N hydrochloric acid and extracted with ethyl acetate. The organic layer was dried over magnesium sulfate, filtered and concentrated to yield an oil which was crystallized form ether/ethyl acetate/hexane to yield 521 mg of N-(2-mercapto-1R,S-phenylmethyl)-N-phenylmethyl-4-methoxybenzenesulfonamide; m/e=434 (M+Li).

EXAMPLE 58

Preparation of N-N'-bis-(4-Methoxybenzenesulfonyl)-L-cystine

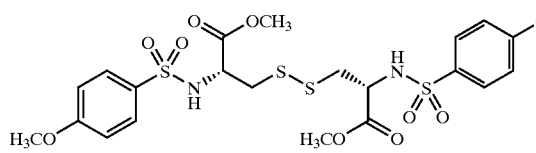

To an ice cooled suspension of (3.41 g, 10 mmol) of L-cystine methyl ester hydrochloride in tetrahydrofuran was added 50 mL of saturated sodium bicarbonate followed by (4.12 g, 20 mmol) of 4-methoxybenzenesulfonyl chloride in 20 mL of tetrahydrofuran and the suspension stirred to room temperature overnight. The contents were acidified with 1N hydrochloric acid and extracted with ethyl acetate to yield 4.13 grams of product. m/e=615 (M+Li).

EXAMPLE 59

Preparation of N-N'-bis-(4-Methoxybenzenesulfonyl)-N,N'-dimethyl-L-cystine

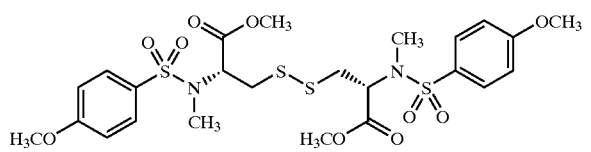

To a stirred solution of (1.3 g, 2.1 mmol) of N-N'-Bis-(4-methoxybenzenesulfonyl)-L-cystine in dimethylformamide was added (635 mg, 4.6 mmol) of potassium carbonate followed by (655 mg, 4.6 mmol) of methyl iodide and the suspension stirred overnight. The contents were concentrated by rotory evaporation and the residue subjected to silica gel chromatography to yield 890 mg of N-N'-Bis-(4-mthoxybenzenesulfonyl)-N,N'-dimethyl-L-cystine as an oil. m/e=643 (M+Li).

EXAMPLE 60

2R-(N-Fluorenylmethoxycarbonyl)aminopropanethiol

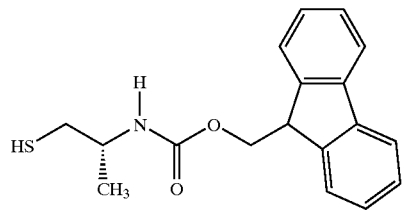

Part A: Preparation of 2R-(N-Fluorenylmethyloxycarbonyl)aminopropanol.

To a stirred solution of (750 mg, 10 mmol) of 2-R-amino propanol in 15 mL dioxane containing 27 mL of 10% aqueous potassium carbonate was added (2.58 g, 10 mmol) of fluorenylmethyl chloroformate and the solution was stirred vigorously for several hours. The contents were diluted with ethyl acetate and the organic layer was washed with 1N hydrochloric acid, dried over magnesium sulfate, filtered and concentrated to yield 2.97 g of crude product which was crystallized from ethyl acetate/hexanes to yield 2.61 g of purified 2R-(N-fluorenylmethyloxycarbonyl)aminopropanol.

Part B: Preparation of 2R-(N-Fluorenylmethyloxycarbonyl)-aminopropanethiol-S-acetate.

To a ice cooled stirred solution of (13.9 g, 47 mmol) of 2R-(N-fluorenylmethyloxycarbonyl)-aminopropanol in 200 mL of anhydrous tetrahydrofuran was added (13.5 g, 51 mmol) of triphenylphosphine, followed by (8.99 g, 51 mmol) of diethylazodicarboxylate, and the (3.92 g, 51 mmol) of thioacetic acid and the reaction stirred overnight to room temperature. The contents were concentrated by rotory evaporation and the residue was chromatographed on silica gel using ethyl acetate/hexane as the eluant. The desired product was crystallized to afford 7.8 g of purified 2R-(N-fluorenylmethyloxycarbonyl)-aminopropanethiol-S-acetate.

Part C: Preparation of 2R-(N-Fluorenylmethyloxycarbonyl)-aminopropanethiol.

To an ice cooled, stirred solution of (355 mg, 1.0 mmol) of 2R-(N-fluorenylmethyloxycarbonyl)-aminopropanethiol-S-acetate in 10 mL of anhydrous methanol was added 1.2 equivalents of 25% sodium hydroxide in methanol and the solution stirred for 30 minutes. The reaction mixture was diluted with 1N hydrochloric acid and concentrated. The residue was partitioned between ethyl acetate and water, and the organic layer was dried over magnesium sulfate, filtered and concentrated to yield 300 mg of mercaptan.

EXAMPLE 61

Preparation of 2R-(N-Fluorenylmethylcarbamoyl)amino-propanethiol—conjugated-chlorotrityl-polystyrene resin with 1 or 2% cross-linking.

A solution of 5% trifluorocacetic acid (40 ml) in methylene chloride was added to dry 2-chlorotrityl-chloride resin (5.84 g, 7 mmoles) and swirled. To this thick slurry was immediately added 14 mmoles (4.4 g) of N-Fmoc-1-methyl-ethyl-2-mercaptan. The suspension was swirled periodically and incubated at RT under nitrogen for 1 hour. Nine volumes methylene chloride were added and incubation continued 30 minutes. Non-bound compound was then removed by vacuum filtration through a centered glass disk funnel and reserved for drying and quantitation. The resin was washed with 300 mls methanol to cap any unreacted sites, followed by 4 dimethylformamide washes, 4 methylene chloride washes and 2 additional methanol washes. The recovered resin was then dried to constant weight under vacuum and loading was quanitated by 1) mass balance 2) Fmoc release and/or 3) elemental analysis. Using this protocol, the desired compound was loaded on approximately 92% of the available sites, as determined by resin manufacturer's data sheet.

Dried resin was washed with methylene chloride (about 250 mls) followed by dimethylformamide (about 250 mls) and the Fmoc protecting group was removed by incubation in a solution of 20% piperidine in dimethylformamide for 30–60 minutes. The resin was washed with dimethylformamide, methanol, dimethylformamide. This procedure was repeated one additional cycle. The final wash included a methylene chloride wash followed by methanol. The resin was dried to constant weight and stored at 4 degrees. Prior to any additional chemistry, the resin was always washed with methylene chloride to ensure good swelling, followed by the solvent of choice for the desired protocol.

Alternatively, instead of loading the resin with two equivalents of mercaptan for each equivalent of resin sites, only 0.9 equivalents of available (monomeric) compound was added. This resulted in loading approximately 90–95% of the target compound, and the excess sites were capped as above. This loading procedure had the advantage that less initial compound had to be synthesized.

EXAMPLE 62
Preparation of N-(2-Mercapto-1R-methylethyl)-4-methoxybenzenesulfonamide To a slurry of 0.12 g (0.14 mmoles) deprotected resin (Example 1) in 6 ml 50% pyridine: $CH_2Cl_2$ under nitrogen was added 0.152 g (0.74 mmoles) 4-methoxybenzene-sulfonylchloride. The reaction was agitated at room temperature for 20 hr. The resin was then filtered and washed four times with 100 ml dimethylformamide and four times with 100 ml $CH_2Cl_2$ The resin was treated with 80% trifluoroacetic acid in $CH_2Cl_2$ for 1 hour. It was then filtered and the eluant stripped. The residue was extracted with ethyl acetate, washed with 1N HCl and dried with $Na_2SO_4$. The extract was stripped to dryness to afford 20 mg of the desired N-(2-mercapto-1R methylethyl)-4-methoxybenzenesulfonamide.

EXAMPLES 63–90
By procedures analogous to Example 62, the following compounds were prepared:

EXAMPLE 63
N-(2-mercapto-1R-methylethyl)-4-fluorobenzenesulfonamide; m/e=256.3 (M+Li).

EXAMPLE 64
N-(2-mercapto-1R-methylethyl)-4-chlorobenzenesulfonamide; m/e=272.7 (M+Li).

EXAMPLE 65
N-(2-mercapto-1R-methylethyl)-4-bromobenzenesulfonamide; m/e=317.2 (M+Li).

EXAMPLE 66
N-(2-mercapto-1R-methylethyl)-4-iodobenzenesulfonamide; m/e=364.2 (M+Li).

EXAMPLE 67
N-(2-mercapto-1R-methylethyl)-4-ethylbenzenesulfonamide; m/e=266.4 (M+Li).

EXAMPLE 68
N-(2-mercapto-1R-methylethyl)-4-methylbenzenesulfonamide; m/e=254.4 (M+Li).

EXAMPLE 69
N-(2-mercapto-1R-methylethyl)-4-(n-butyl) benzenesulfonamide; m/e=292.4 (M+Li).

EXAMPLE 70
N-(2-mercapto-1R-methylethyl)-4-n-propyl) benzenesulfonamide; m/e=280.4 (M+Li).

EXAMPLE 71
N-(2-mercapto-1R-methylethyl)-4-n-pentyl) benzenesulfonamide; m/e=304.4 (M+Li).

EXAMPLE 72
N-(2-mercapto-1R-methylethyl)-4-isopropylbenzenesulfonamide; m/e=280.4 (M+Li).

EXAMPLE 73
N-(2-mercapto-1R-methylethyl)-4-(trifluoromethyl)-benzenesulfonamide; m/e=306.3 (M+Li).

EXAMPLE 74
N-(2-mercapto-1R-methylethyl)-4-(t-butyl) benzenesulfonamide; m/e=294.4 (M+Li).

EXAMPLE 75
N-(2-mercapto-1R-methylethyl)-4-(trifluoromethoxy)-benzenesulfonamide; m/e=322.3 (M+Li).

EXAMPLE 76
N-(2-mercapto-1R-methylethyl)-4-cyanobenzenesulfonamide; m/e=263.3 (M+Li).

EXAMPLE 77
N-(2-mercapto-1R-methylethyl)-2-(trifluoromethyoxy)-benzenesulfonamide; m/e=322.3 (M+Li).

EXAMPLE 78
N-(2-mercapto-1R-methylethyl)-2,4-bis (trifluoromethyoxy)-benzenesulfonamide; m/e=434.4 (M+Li).

EXAMPLE 79
N-(2-mercapto-1R-methylethyl)-2,4,6-trimethyl-benzenesulfonamide; m/e=280.4 (M+Li).

EXAMPLE 80
N-(2-mercapto-1R-methylethyl)-2,4,6-triisopropyl-benzenesulfonamide; m/e=364.6 (M+Li).

EXAMPLE 81
N-(2-mercapto-1R-methylethyl)-3,4-difluoro-benzenesulfonamide; m/e=274.3 (M+Li).

EXAMPLE 82
N-(2-mercapto-1R-methylethyl)-benzenesulfonamide.

EXAMPLE 83
N-(2-mercapto-1R-methylethyl)-2-napthylenesulfonamide; m/e=288.4 (M+Li).

EXAMPLE 84
N-(2-mercapto-1R-methylethyl)-4-N-acetylsulfanilamide; m/e=295.4 (M+Li).

EXAMPLE 85
N-(2-mercapto-1R-methylethyl)-5-bromo-2-thiophenesulfonamide; m/e=323.3 (M+Li).

EXAMPLE 86
N-(2-mercapto-1R-methylethyl)-5-chloro-2-thiophenesulfonamide.

EXAMPLE 87

N-(2-mercapto-1R-methylethyl)-3,5-dibromo-2-thiophenesulfonamide; m/e=403.3 (M+Li).

EXAMPLE 88

N-(2-mercapto-1R-methylethyl)-5-(isoxazol-3-yl)-2-thiophenesulfonamide; m/e=311.4 (M+Li).

EXAMPLE 89

N-(2-mercapto-1R-methylethyl)-4-phenylazobenzenesulfonamide; m/e=342.4 (M+Li).

EXAMPLE 90

N-(2-mercapto-1R-methylethyl)-2-dibenzofuransulfonamide; m/e=328.4 (M+Li).

EXAMPLE 91

Preparation of N-(2-Mercapto-1R-methylethyl)-N-[2-(4-morpholino)ethyl]-4-(thiophenyl)benzenesulfonamide Hydrochloride

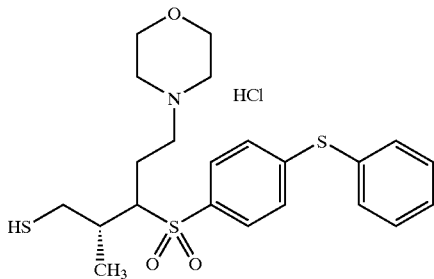

Part A: To a solution of 8.38 g (35.9 mmol) of N-(2-hydroxy-1R-methylethyl)-4-fluorobenzene-sulfonamide from Example 40, part A, in 70 mL of anhydrous DMF, was added 15.38 g (111 mmol) of powdered potassium carbonate, and then 5.2 mL (5.54 g, 50.3 mmol) of thiophenol. The reaction mixture was heated to 70 C for 15 hours, cooled and ethyl acetate and water added. The organic layer was separated and washed 3xs with brine, dried with sodium sulfate, filtered and stripped to afford crude material. This was chromatographed on a Waters Prep 2000 chromatograph over silica gel using 40%–60% ethyl acetate/hexane to provide 9.0 g of pure N-(2-hydroxy-1R-methylethyl)-4-(thiophenyl)benzenesulfonamide, m/e=330 (M+Li).

Part B: To a solution of 3.0 g (9.3 mmol) of N-(2-hydroxy-1R-methylethyl)-4-(thiophenyl)benzene-sulfonamide from part A, in 18 mL of anhydrous DMF, was added 3.85 g (27.8 mmol) of powdered potassium carbonate, and then 2.42 g (13 mmol) of 4-(2-chloroethyl)morpholine hydrochloride. The reaction mixture was stirred for 15 hours, ethyl acetate and water added. The organic layer was separated and washed 3xs with brine, dried with sodium sulfate, filtered and stripped to afford 4.7 g of crude material. This was chromatographed on a Waters Prep 2000 chromatogram over silica gel using 50%–100% ethyl acetate/hexane, then 5% methanol/ethyl acetate, to provide 3.8 g of pure N-(2-hydroxy-1R-methylethyl)-N-[2-(4-morpholino)ethyl]-4-(thiophenyl)benzene-sulfonamide, m/e=437 (M+H).

Part C: To a solution of 3.4 g (7.8 mmol) of product from Part B and 2.25 g (8.6 mmol) of triphenylphosphine in 30 mL of anhydrous THF at 0° C., was added 1.4 mL (8.6 mmol) of diethylazodicarboxylate, followed after 5 min. by 0.62 mL (8.6 mmol) of thiolacetic acid. After 1 hour, the reaction was concentrated and the residue was chromatographed on silica gel using 20%–80% ethyl acetate/hexane to yield 1.4 g of the desired product, m/e=495 (M+H).

Part D: To a solution of 1.4 g (2.83 mmol) of product from Part C in 10 mL of anhydrous methanol, was added 2.3 mL (10.2 mmol) of a 25 weight % solution of sodium methoxide in methanol. After 0.5 hour, the reaction was quenched the addition of dry ice, followed by ethyl acetate and water, the organic layer was separated and washed with brine, dried with magnesium sulfate, filtered and concentrated to afford the crude product. This was chromatographed on 75 g of silica gel using 50% ethyl acetate/hexane to provide 0.86 g of pure N-(2-mercapto-1R-methylethyl)-N-[2-(4-morpholino)ethyl]-4-(thiophenyl)benzenesulfonamide, m/e=453 (M+H).

Part D: To a solution of 0.66 g (1.45 mmol) of the product of Part C in 10 mL of acetonitrile was added 0.24 ml (2.88 mmol) of 12N aqueous hydrochloric acid. After 10 minutes, the solvent was removed in vacuo, acetonitrile added and removed 3xs to afford 0.66 g of the desired N-(2-mercapto-1R-methylethyl)-N-[2-(4-morpholino)ethyl]-4-(thiophenyl)benzene-sulfonamide hydrochloride, m/e=453 (M+H).

EXAMPLE 92

Preparation of N-(2-Mercapto-1R-methylethyl)-N-[2-(1-piperidino)ethyl]-4-(thiophenyl)benzenesulfonamide Hydrochloride

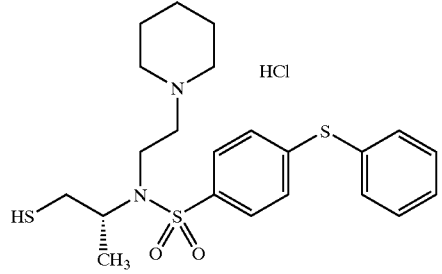

Part A: To a solution of 4.62 g (14.2 mmol) of N-(2-hydroxy-1R-methylethyl)-4-(thiophenyl)benzene-sulfonamide from example 91 part A in 28 mL of anhydrous DMF, was added 5.92 g (42.8 mmol) of powdered potassium carbonate, and then 3.94 g (21.4 mmol) of 1-(2-chloroethyl)piperidine hydrochloride. The reaction mixture was stirred for 17 hours at 50 C, then cooled and ethyl acetate and water added. The organic layer was separated and washed 3xs with brine, dried with sodium sulfate, filtered and stripped to afford crude material. This was chromatographed on 300 g of silica gel using 100% tetrahydrofuran to provide 4.3 g of pure N-(2-hydroxy-1R-methylethyl)-N-[2-(1-piperidinyl)-ethyl]-4-(thiophenyl)benzenesulfonamide, m/e=435 (M+H).

Part B: To a solution of 3.7 g (8.5 mmol) of product from Part A and 2.45 g (9.3 mmol) of triphenylphosphine in 33 mL of anhydrous THF at 0° C., was added 1.47 mL (9.3 mmol) of diethylazodicarboxylate, followed after 5 min. by 0.67 mL (9.3 mmol) of thiolacetic acid. After 1 hour, the reaction was concentrated and the residue was chromatographed on basic alumina using 10%–50% ethyl acetate (5%methanol)/hexane to yield 2.3 g of the desired product, m/e=493 (M+H).

Part C: To a solution of 2.3 g (4.67 mmol) of product from Part B in 10 mL of anhydrous methanol, was added 3.8 mL (16.8 mmol) of a 25 weight % solution of sodium methoxide in methanol. After 0.5 hour, the reaction was quenched the addition of dry ice, followed by ethyl acetate and water, the organic layer was separated and washed with brine, dried with magnesium sulfate, filtered and concentrated to afford the crude product. This was chromatographed on 150 g of silica gel using 50% ethyl acetate (5% methanol)/methylene chloride to provide 1.5 g of pure N-(2-mercapto-1R-methylethyl)-N-[2-(1-piperidino)-ethyl]-4-(thiophenyl) benzenesulfonamide, m/e=451 (M+H).

Part D: To a solution of 1.1 g (2.44 mmol) of the product of Part C in 15 mL of acetonitrile was added 0.40 ml (4.88 mmol) of 12N aqueous hydrochloric acid. After 10 minutes, the solvent was removed in vacuo, acetonitrile added and removed 3×s to afford 1.12 g of the desired N-(2-mercapto-1R-methylethyl)-N-[2-(1-piperidino)ethyl]-4-(thiophenyl) benzenesulfonamide hydrochloride, m/e=451 (M+H).

EXAMPLE 93

Preparation of N-(4-Butoxyphenyl)-L-cysteine-NH$_2$

Part A:

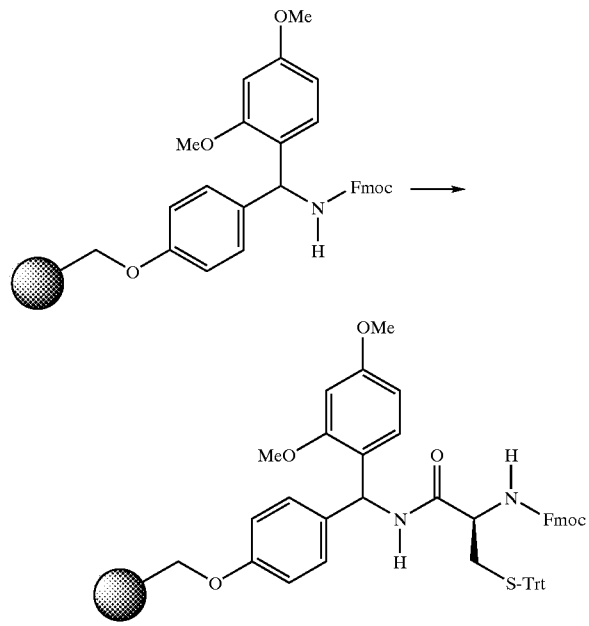

Fmoc-L-Cys(Trt)-Rink resin. Rink resin (0.88 g, 0.44 mmoles) was reacted with 5 mL of:4 piperidine/DMF for 30 min, then washed with DMF (3×5 mL), MeOH (3×5 mL), and CH$_2$Cl$_2$ (3×5 mL). In a separate flask, Fmoc-L-Cys(Trt) OH (0.77 g, 1.3 mmol) in 5 mL anhydrous dimethylacetamide (DMA) was reacted with diisopropylcarbodiimide (0.21 mL, 1.3 mmol) and N-hydroxysuccinimide (0.15 g, 1.3 mmol) for 15 min at rt. Then, this solution was added to the flask containing Rink resin from above. The reaction slurry was agitated using a tabletop shaker overnight (16 h). The resin was then drained, washed with DMF (3×5 mL), MeOH (3×5 mL), CH$_2$Cl$_2$ (3×5 mL), and Et$_2$O (3×5 mL), and dried in vacuo to yield 1.09 g of tan polymeric solid. Theoretical loading of polymer=0.43 mmol/g.

Part B: N-(4-Butoxyphenyl)sulfonyl-L-Cys(Trt)-Rink resin. Fmoc-L-Cys(Trt)-Rink resin from above (50 mg, 0.022 mmol) was reacted with 1 mL of: 4 piperidine/DMF for 30 min, then washed with DMF (3×1 mL), MeOH (3×1 mL), and CH$_2$Cl$_2$ (3×1 mL). Then, 0.5 mL of anhydrous CH$_2$Cl$_2$ was added to the resin followed by 27 mg of 4-butoxyphenylsulfonyl chloride (0.11 mmol), and the reaction slurry was shaken overnight at rt (20 h). The resin was then drained, washed with CH$_2$Cl$_2$ (3×1 mL), MeOH (3×1 mL), CH$_2$Cl$_2$ (3×1 mL), and Et$_2$O (3×1 mL), and dried in vacuo to yield 105 mg brown polymeric solid.

Part C:

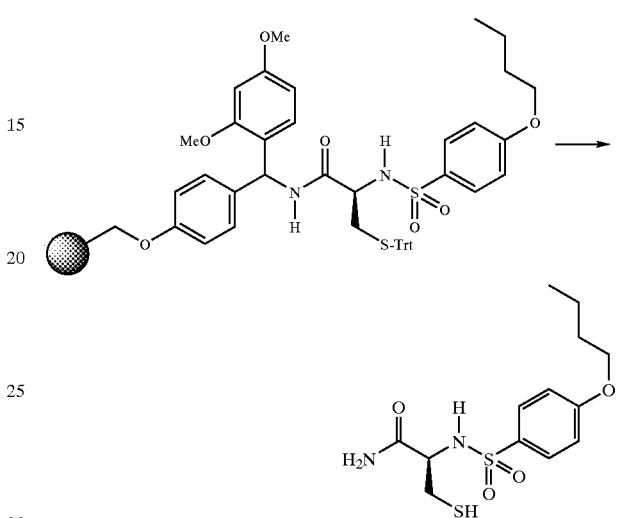

N(4-Butoxyphenyl)sulfonyl-L-Cys-NH$_2$. N-(4-Butoxyphenyl)-sulfonyl-L-Cys(Trt)-Rink resin from above was reacted with 1 mL of a 5:5:95 solution of TFA/triethylsilane/CH$_2$Cl$_2$ at rt for one hour. The resin was drained and washed with CH$_2$Cl$_2$ (3×1 mL). The resin was subsequently reacted with 0.5 mL of a 80:5:15 solution of TFA/triethylsilane/CH$_2$Cl$_2$ at rt for one hour. The resin was drained, and the filtrate collected. The resin was further washed with 1:1 TFA/CH$_2$Cl$_2$ (3×0.5 mL) and CH$_2$Cl$_2$ (3×0.5 mL), again collecting the filtrates. The combined filtrates were concentrated to yield 6.7 mg white solid (92% crude yield). MS (FAB) 333.2 (M+H).

Using procedures analogous to those used in Example 93, Examples 94, 95 and 96 were prepared.

EXAMPLE 94

N-(4-Methoxyphenyl)sulfonyl-L-cysteine-NH$_2$

EXAMPLE 95

N-(4-Iodophenyl)sulfonyl-L-cysteine-NH$_2$

EXAMPLE 96

N-[4-(n-Pentyl)-phenyl]sulfonyl-L-cysteine-NH$_2$

Compounds of Example 97 to Example 223, tabulated below, were prepared by the procedures presented above. Exemplary additional specific syntheses are also provided thereafter.

EXAMPLE TABLE I
97 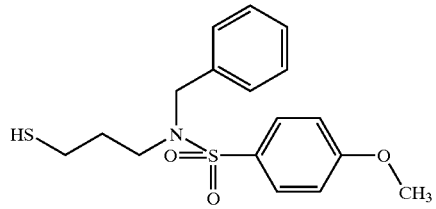
98 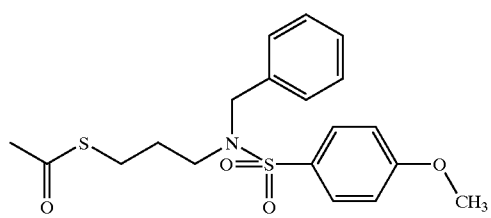
99 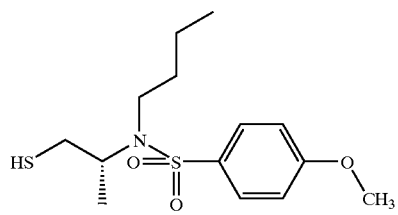
100 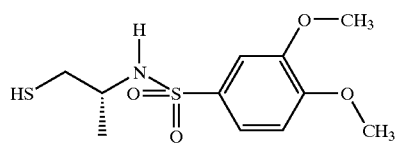
101 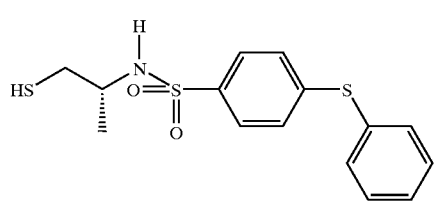
102 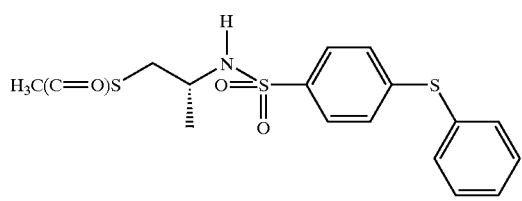
EXAMPLE TABLE I-continued
103 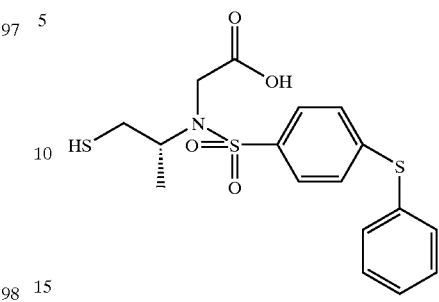
104 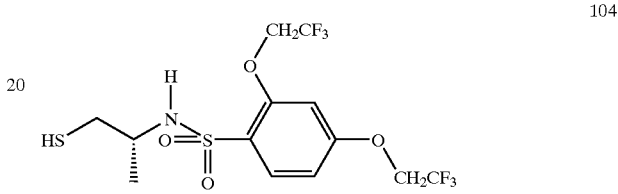
105 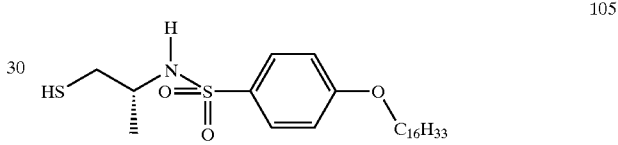
106 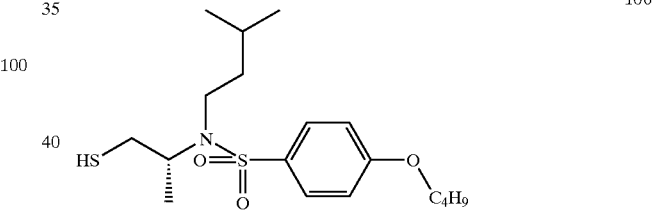
107 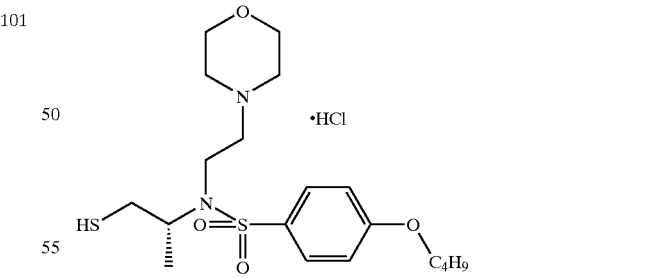
108 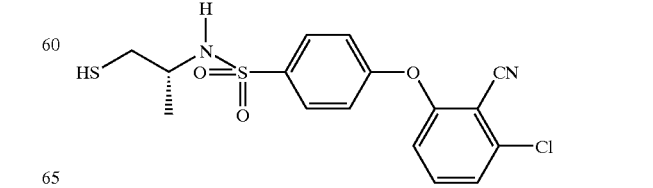

EXAMPLE TABLE II
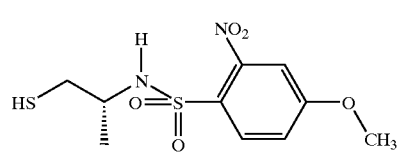
109
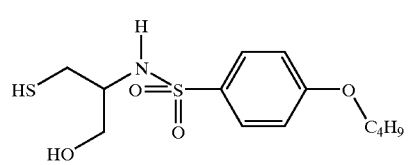
110
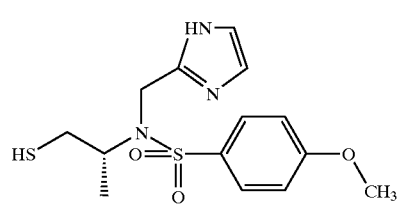
111
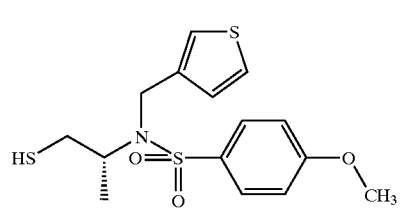
112
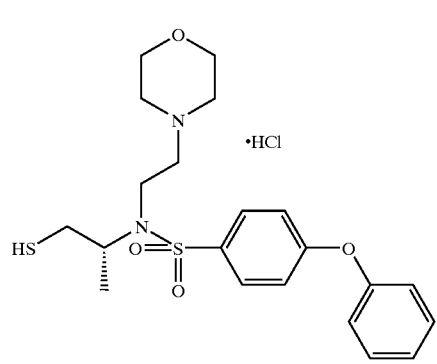
113
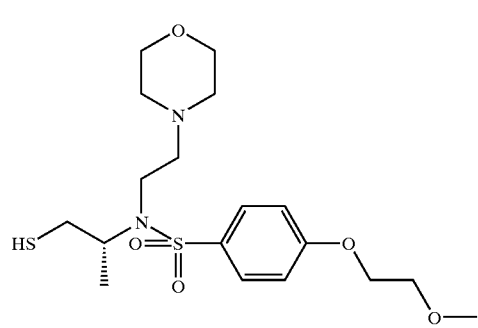
114

EXAMPLE TABLE II-continued
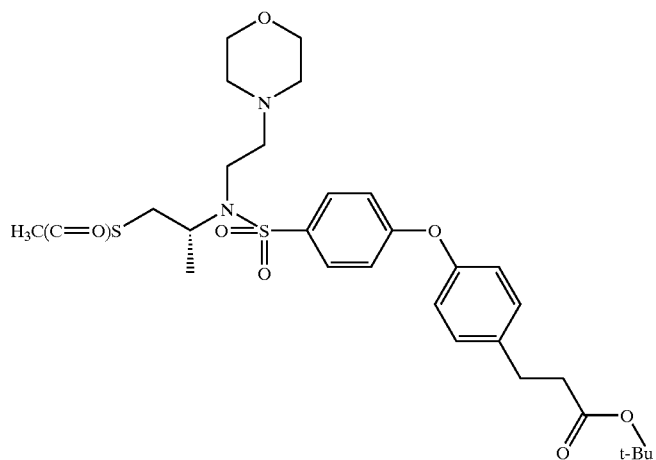
115
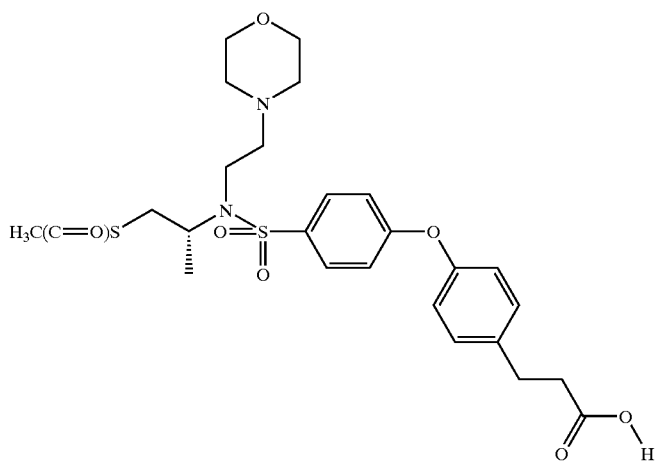
116
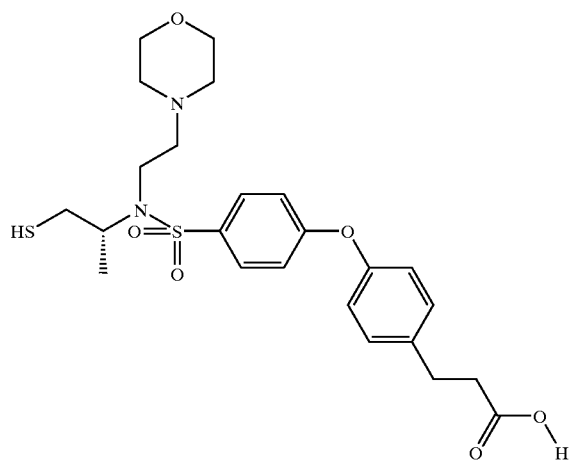
117

EXAMPLE TABLE III
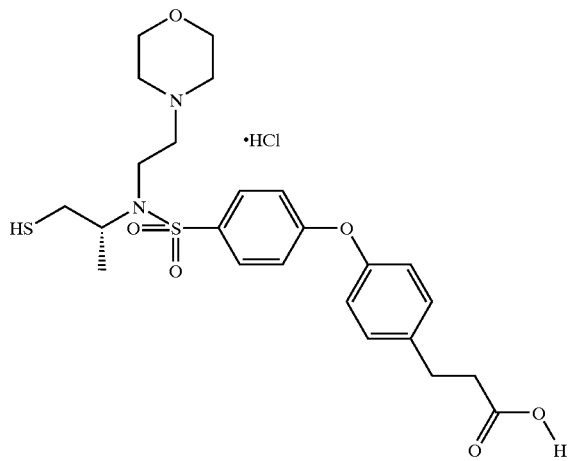
118
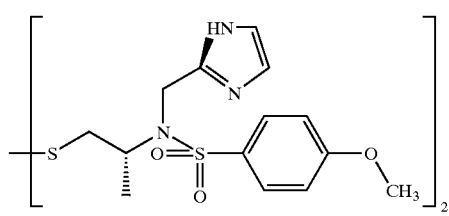
119
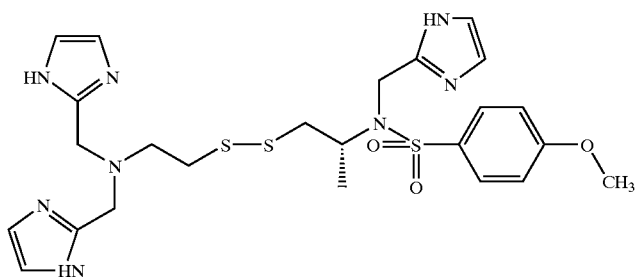
120
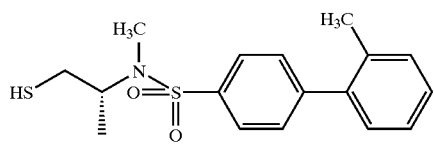
122
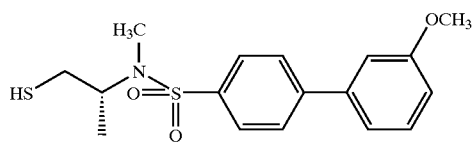
123
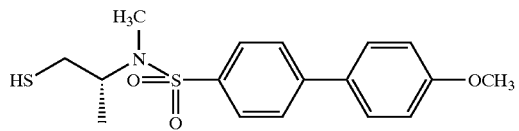
124

EXAMPLE TABLE III-continued
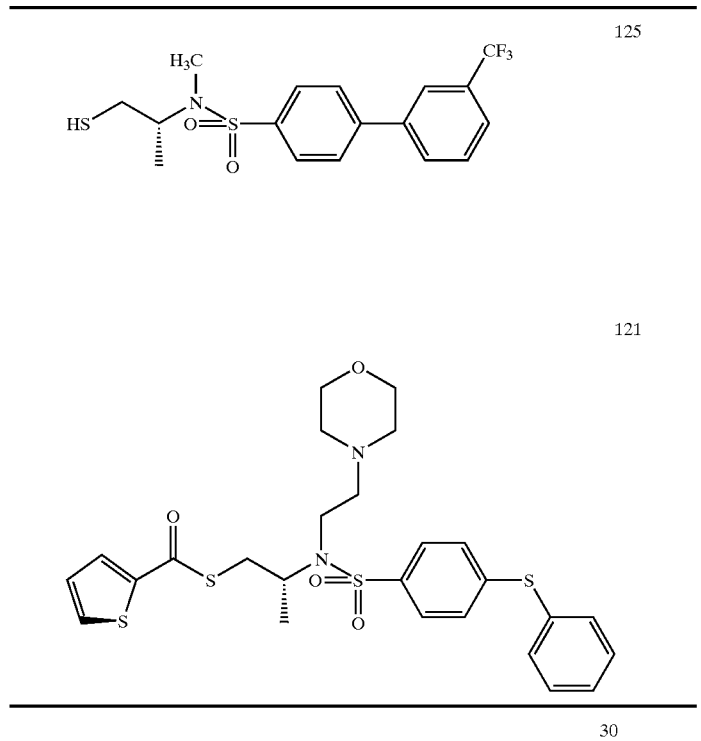
EXAMPLE TABLE IV
EXAMPLE TABLE IV-continued
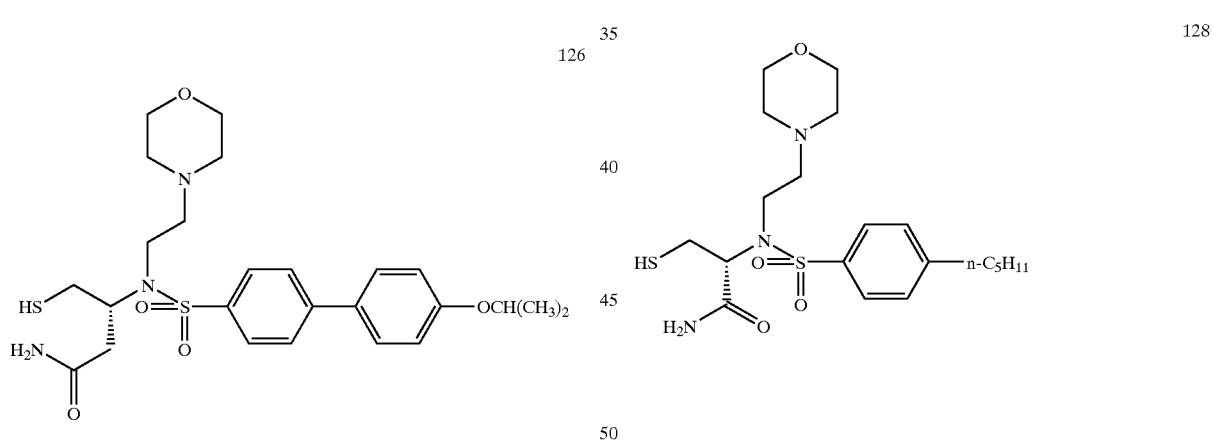

EXAMPLE TABLE IV-continued
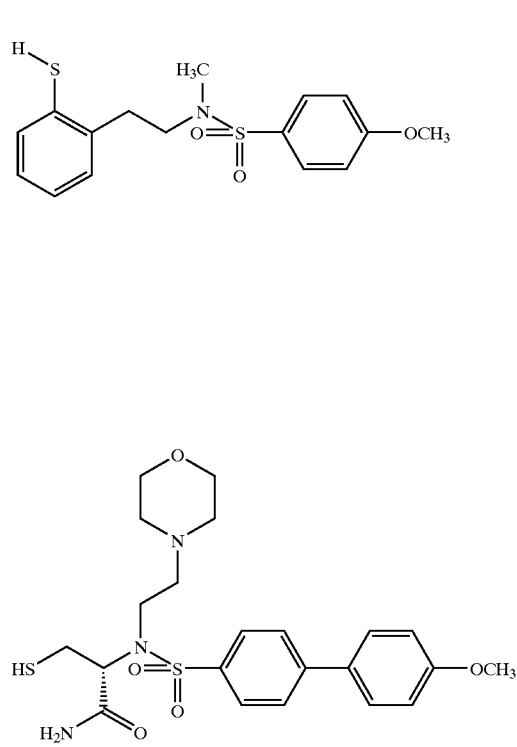
EXAMPLE TABLE IV-continued
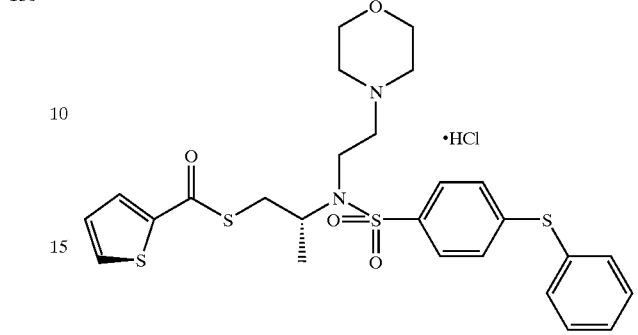
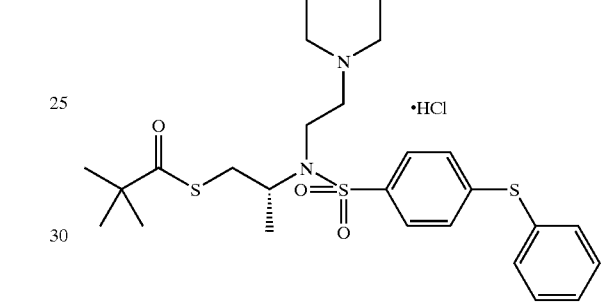
EXAMPLE TABLE V
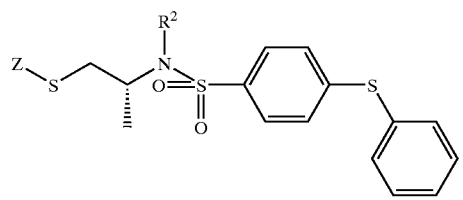
| EXAMPLE | Z | R² |
|---|---|---|
| 134 |  | 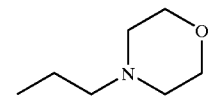 |
| 135 | 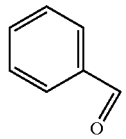 | 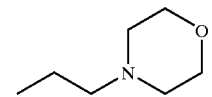 |
| 136 | 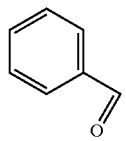 | 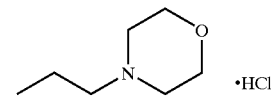 |

EXAMPLE TABLE V-continued

| EXAMPLE | Z | R² |
|---|---|---|
| 137 | t-Bu-O-C(O)-NH-CH(CH₃)-CHO | benzaldehyde |
| 138 | t-Bu-O-C(O)-NH-C(CH₃)₂-CHO | benzaldehyde |
| 139 | H₂N-CH(CH₃)-CHO | 4-(3-propyl)morpholine ·2 HCl |
| 140 | H₂N-C(CH₃)₂-CHO | 4-(3-propyl)morpholine ·2 HCl |

EXAMPLE TABLE VI

| EXAMPLE | Z | R² |
|---|---|---|
| 141 | CH₃CHO | -C(O)-O-t-Bu |
| 142 | CH₃CHO | -C(O)-OH |
| 144 | H— | -CH₂CH₂CH₂-N(CH₃)₂ ·HCl |
| 145 | CH₃CHO | -CH₂CH₂CH₂-N(CH₃)₂ |

EXAMPLE TABLE VII

| EXAMPLE | R¹ | R² | R⁴ |
|---|---|---|---|
| 146 | 5-methyl-2-thienyl-CH₂-NH-C(O)-phenyl | H | CH₃ |
| 147 | 4-(S(O)₂CH₃)-phenyl | H | CH₃ |
| 148 | 2-methyl-5-(CF₃)-pyridin-yl | H | CH₃ |

EXAMPLE TABLE VII-continued

![structure: HS-CH(R4)-CH2-N(R2)-SO2-R1]

| EXAMPLE | R¹ | R² | R⁴ |
|---|---|---|---|
| 149 | 3-methyl-5-CF3-1-methyl-pyrazol-4-yl | H | CH₃ |
| 150 | 4-methyl-2-(SCH3)-pyrimidin-5-yl | H | CH₃ |
| 151 | phenyl | H | CH₃ |
| 152 | 3-bromo-2-chloro-5-methyl-thiophen-4-yl | H | CH₃ |
| 153 | 5-methyl-2-(CH2NHC(O)-(4-Cl-phenyl))-thiophen-yl | H | CH₃ |
| 146 | 5-methyl-2-(CH2NHC(O)-phenyl)-thiophen-yl | H | CH₃ |
| 147 | 4-(S(O)2CH3)-phenyl | H | CH₃ |
| 148 | 6-methyl-3-CF3-pyridin-2-yl | H | CH₃ |
| 149 | 3-methyl-5-CF3-1-methyl-pyrazol-4-yl | H | CH₃ |
| 150 | 4-methyl-2-(SCH3)-pyrimidin-5-yl | H | CH₃ |

EXAMPLE TABLE VII-continued

![structure: HS-CH(R4)-CH2-N(R2)-SO2-R1]

| EXAMPLE | R¹ | R² | R⁴ |
|---|---|---|---|
| 151 | phenyl | H | CH₃ |
| 152 | 3-bromo-2-chloro-5-methyl-thiophen-4-yl | H | CH₃ |
| 153 | 5-methyl-2-(CH2NHC(O)-(4-Cl-phenyl))-thiophen-yl | H | CH₃ |

EXAMPLE TABLE VIII

![structure: HS-CH(R4)-CH2-N(R2)-SO2-R1]

| EXAMPLE | R¹ | R² | R⁴ |
|---|---|---|---|
| 154 | 5-chloro-2,3-dimethyl-benzothiophen-yl | H | CH₃ |
| 155 | 3-chloro-5-CF3-2-((5-methyl-thiophen-2-yl)methyl)-pyridin-yl | H | CH₃ |
| 156 | 2-(5-methyl-thiophen-2-yl)-pyridin-yl | CH₃ | CH₃ |

EXAMPLE TABLE IX
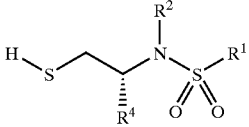
| EXAMPLE | R¹ | R² | R⁴ |
|---|---|---|---|
| 160 | 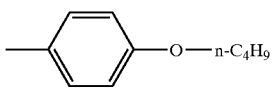 | H |  |
| 161 | 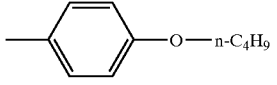 | —(CH₂)₂CH(CH₃)₂ |  |
| 162 | 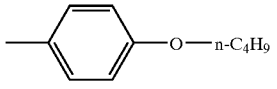 | H | 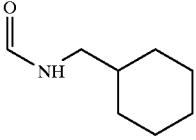 |
| 163 | 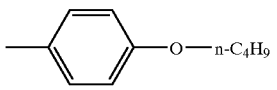 | —CH₃ |  |
| 164 | 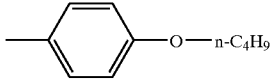 | —(CH₂)C(C=O)OH |  |
| 165 | 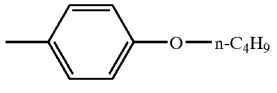 | 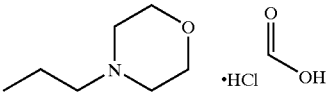 •HCl |  |
| 166 | 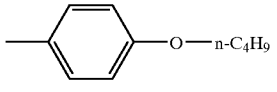 | H | 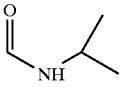 |
EXAMPLE TABLE X
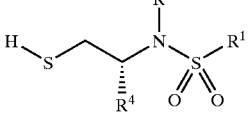
| EXAMPLE | R¹ | R² | R⁴ |
|---|---|---|---|
| 167 | 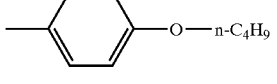 | 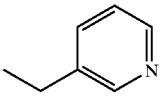 |  |
| 168 | 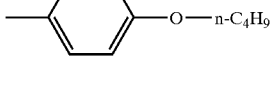 | 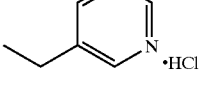 •HCl |  |

EXAMPLE TABLE X-continued

| EXAMPLE | R¹ | R² | R⁴ |
|---|---|---|---|
| 169 | 4-(phenoxy)-4'-methylbiphenyl ether | propyl-morpholine | C(=O)NH₂ |
| 170 | 4-(phenoxy)-4'-methylbiphenyl ether | propyl-morpholine ·HCl | C(=O)NH₂ |
| 171 | 4-(n-C₄H₉O)-phenyl | H | C(=O)NHCH₃ |
| 172 | 4-(n-C₄H₉O)-phenyl | H | C(=O)NH-CH₂CH₂-morpholine |
| 173 | 4-(n-C₄H₉O)-phenyl | H | C(=O)NH-CH₂CH₂-morpholine ·HCl |

EXAMPLE TABLE XI

| EXAMPLE | R¹ | R² | R⁴ |
|---|---|---|---|
| 174 | 4-(n-C₄H₉O)-phenyl | 3-pyridylethyl | C(=O)NH₂ |
| 175 | 4-(n-C₄H₉O)-phenyl | 4-pyridylethyl | C(=O)NH₂ |
| 176 | 4-(n-C₄H₉O)-phenyl | propyl-morpholine | C(=O)NHCH₃ |
| 177 | 4-(n-C₄H₉O)-phenyl | propyl-morpholine | C(=O)NH-CH₂CH₂-morpholine |

EXAMPLE TABLE XI-continued
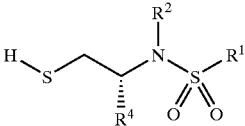
| EXAMPLE | R¹ | R² | R⁴ |
|---|---|---|---|
| 178 | 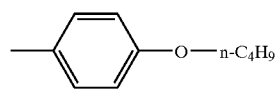 | H | 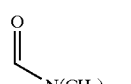 |
| 179 | 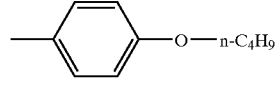 | H | 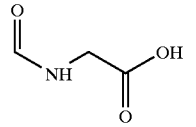 |
| 180 | 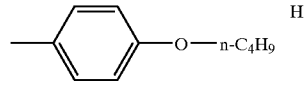 | H | 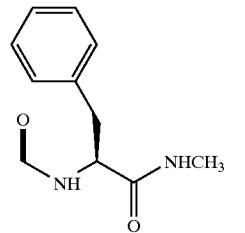 |
EXAMPLE TABLE XII
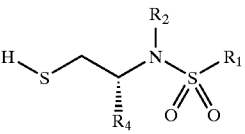
| EXAMPLE | R¹ | R² | R⁴ |
|---|---|---|---|
| 181 | 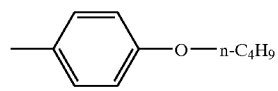 | H |  |
| 182 | 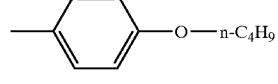 | 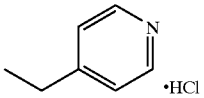 ·HCl |  |
| 183 | 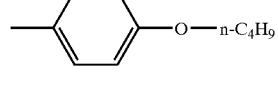 | 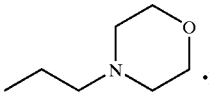 ·HCl | 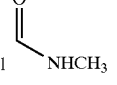 |
| 184 | 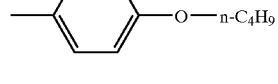 | 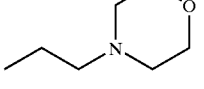 | 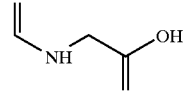 |
| 185 | 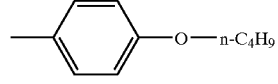 | 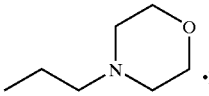 ·HCl | 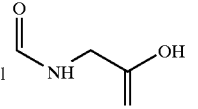 |

EXAMPLE TABLE XII-continued

| EXAMPLE | R¹ | R² | R⁴ |
|---|---|---|---|
| 186 | 4-(n-C₄H₉O)-C₆H₄- | H | -CH₂-CH(NHCHO)-C(O)NH₂ (benzyl side chain) |

EXAMPLE TABLE XIV

| EXAMPLE | R¹ | R² | R⁴ |
|---|---|---|---|
| 192 | 4-NO₂-C₆H₄- | H | CH₃ |
| 193 | 4-(tert-pentyl)-C₆H₄- | H | CH₃ |
| 194 | 4-F-C₆H₄- | H | -C(O)NH₂ |
| 195 | 2-ethyl-4-bromo-C₆H₃- | H | CH₃ |
| 196 | 2-CF₃-C₆H₄- | H | CH₃ |
| 197 | 4-OCH₃-C₆H₄- | H | -C(O)NH₂ |
| 198 | 2-(CO₂CH₃)-C₆H₄- | H | CH₃ |

EXAMPLE TABLE XV
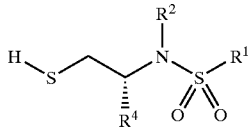
| EXAMPLE | R¹ | R² | R⁴ |
|---|---|---|---|
| 199 | 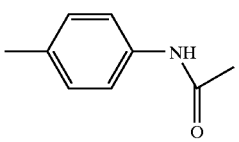 | H |  |
| 200 | 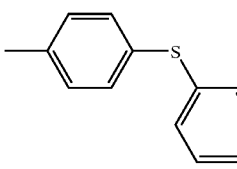 | | 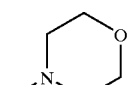 |
| 201 |  | H | 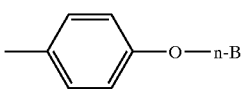 |
| 202 |  •HCl | | 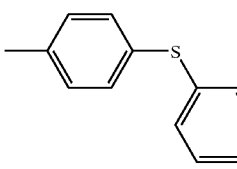 |
| 203 | 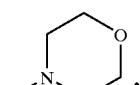 | CH₃ |  |
| 204 | 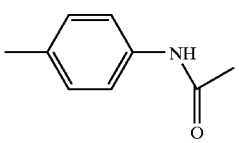 | H | CH₃ |
EXAMPLE TABLE XVI
| EXAMPLE | R¹ | R² | R⁴ |
|---|---|---|---|
| 206 | 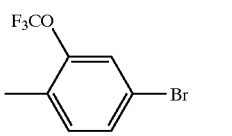 | H | CH₃ |

EXAMPLE TABLE XVI-continued
| EXAMPLE | R¹ | R² | R⁴ |
|---|---|---|---|
| 207 |  | H | CH₃ |
| 208 |  | —(CH₂)₂CH(CH₃)₂ |  |
| 209 | 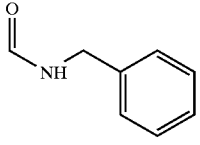 | H |  |
| 210 |  | H |  |
| 211 | 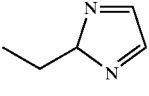 | 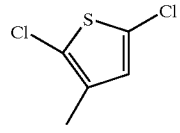 | CH₃ |
| 212 | 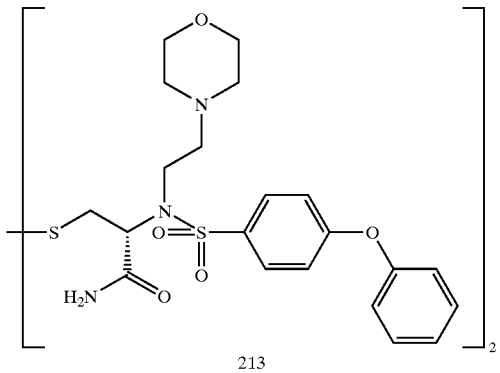 | H | CH₃ |
EXAMPLE TABLE XVII
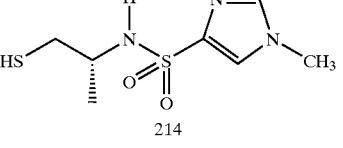
213
EXAMPLE TABLE XVII-continued
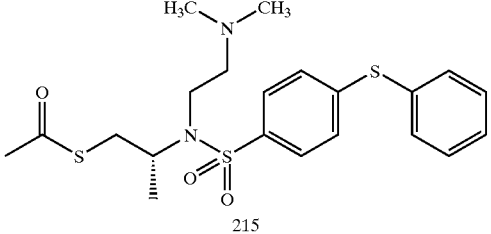
214
215

EXAMPLE TABLE XVII-continued
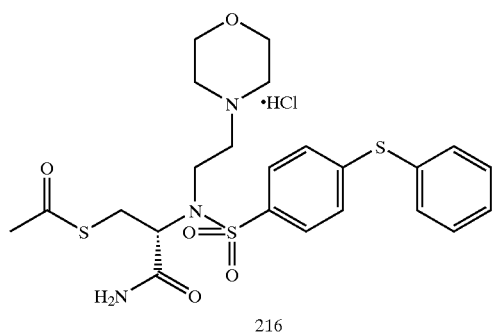
216
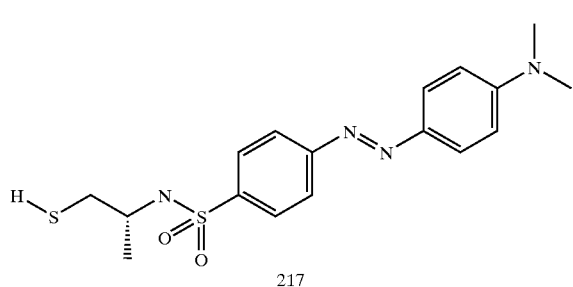
217
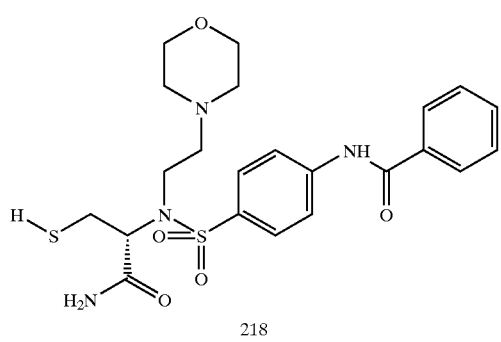
218
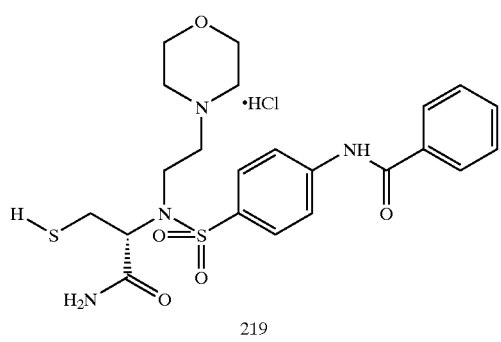
219
EXAMPLE TABLE XVIII
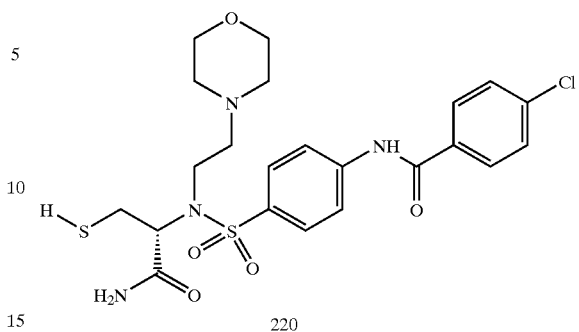
220
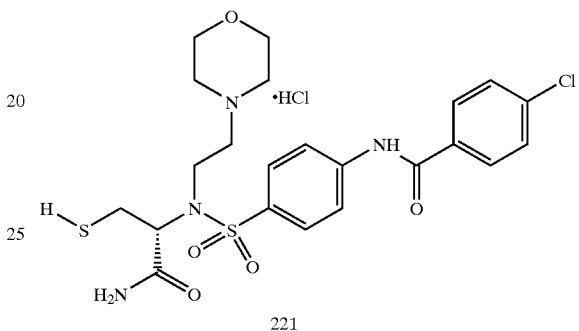
221
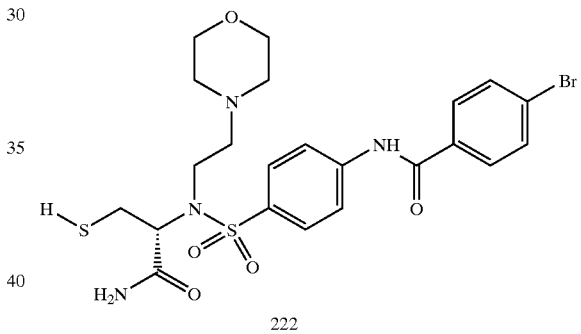
222
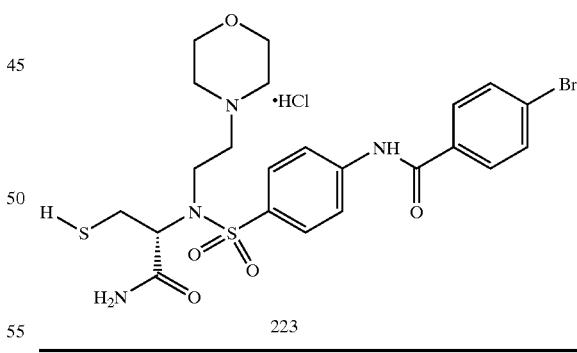
223
EXAMPLE 126
N-(4-(4'-Isopropoxyphenyl)benzenesulfonyl-N-(4-(morpholinoethyl))-L-cysteine Amide
Was prepared in a manner similar to Example 131, by substitution of the sulfonyl chloride to 4-(4-isoproxyphenyl)phenylsulfonyl chloride prepared in an analogous manner. Mass spec. m/z=508.7 (M+H).

EXAMPLE 131

Preparation of N-(4-(4'Methoxyphenyl)-benzenesulfonyl-N-(4-(morpholinoethyl))-L-cysteine Amide

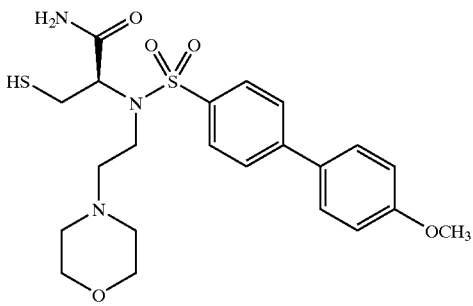

Part A: To a solution of 12.4 grams (5.0 mmol) of 4-(4'-bromophenyl)phenol in 50 mL of dimethylformamide was added 10.1 grams of potassium carbonate followed by 10.51 grams of iodomethane and this stirred at room temperature for 48 hours. The solution was diluted with 400 mL of water and extracted with ethyl acetate. The organics were dried over magnesium sulfate filtered and concentrated to yield 14.1 grams of crude product. Purification by recrystallization from ethyl acetate hexane gave 8.2 grams of 4-(4'-bromophenyl)anisole as a white crystalline solid.

Part B: 5.2 grams (20 mmol) of 4-(4'-bromophenyl)-anisole was dissolved in 100 mL of anhydrous tetrahydrofuran and placed under nitrogen to cool to −78 C. To this flask was added 8.0 mL of 2.5 molar butyl lithium over 10 minutes. In an adjacent flask was added 100 mL of anhydrous tetrahydrofuran which was cooled to −60 C and a stream of sulfur dioxide was added through a dispersion tube while the system is under nitrogen atmosphere. After the addition of approximately 10 mL of liquid sulfur dioxide the dispersion tube was removed and the cold sulfur dioxide solution was transferred by a cannula to the stirred aryl lithium solution over five minutes. After one hour at −70 C the contents were warmed to room temperature and the solution was concentrated to dryness to yield a crude lithium sulfinate. The crude lithium 4-(4'-methoxyphenyl) phenylsulfinic acid was slurried in 100 mL of dry hexanes under nitrogen atmosphere and cooled to 0 C. To this cooled suspension was added 2.45 grams (18.1 mmol) of sulfuryl chloride and the suspension was allowed to warm to room temperature. The contents were concentrated by rotory evaporation to yield 5.1 grams of crude 4-(4'-methoxyphenyl)phenyl-sulfonyl chloride which was purified by recrystallization from chloroform.

Part C: To a solution of 2.93 grams (8.1 mmol) of S-trityl-L-cysteine amide in 50 mL of dry methylene chloride was added 2 equivalents of triethylamine followed by 2.29 grams (8.1 mmol) of 4-(4'-methoxyphenyl) phenylsulfonyl chloride. The solution was stirred at room temperature for one hour, then concentrated on a rotory evaporator. The resulting slurry was partitioned between ethyl acetate and water. The organics were washed with 5% potassium hydrogen sulfate, saturated sodium bicarbonate, and brine, dried over sodium sulfate, filtered and concentrated to give 4.2 grams of crude product. The crude material was purified by silica gel chromatography using 1:1 ethyl acetate:hexane as the eluent to yield 3.36 grams of pure N-(4-(4'methoxyphenyl)-benzenesulfonyl-S-trityl-L-cysteine amide as a white solid.

Part D: To 3.36 grams (5.5 mmol) of N-(4-(4'methoxyphenyl)-benzenesulfonyl-S-trityl-L-cysteine amide in 12 mL of dry dimethylformamide was added 1.50 grams (8.3 mmol) of 4-(2-chloroethylmorpholine) hydrochloride followed by 2.5 grams (17.0 mmol) of powdered potassium carbonate, and the suspension was heated to 60 C in an oil bath under nitrogen atmosphere for 5 hours. The solution is cooled to room temperature and diluted with 100 mL of ethyl acetate and washed with water. The organic layer was washed saturated brine and dried over sodium sulfate, filtered and concentrated to yield 4.5 grams of crude material. Purification by flash chromatography using ethyl acetate as the eluent gave 2.1 grams of purified N-(4-(4'methoxyphenyl)-benzenesulfonyl-N-(4-(morpholinoethyl))-S-trityl-L-cysteine amide.

Part E: 2.1 grams (2.9 mmol) of N-(4-(4'methoxyphenyl)-benzenesulfonyl-N-(4-(morpholinoethyl))-S-trityl-L-cysteine amide was dissolved in 10 mL of methylene chloride and 10 mL of triisopropylsilane was added followed by 40 mL of trifluoroacetic acid and the solution is stirred for 1.5 hours. The contents were concentrated on a rotory evaporator and the resultant material is decanted three times with 50 mL of diethyl ether. The resulting solid is slurried with a mixture of ethyl acetate and sodium bicarbonate until the solids dissolve. The organic layer is washed with saturated sodium bicarbonate, dried over sodium sulfate, filtered and concentrated to yield 1.87 grams of N-(4-(4'methoxyphenyl)-benzenesulfonyl-N-(4-(morpholinoethyl))-L-cysteine amide as a white solid. Mass spec. m/z=480 (M+H).

EXAMPLE 218

Preparation of N-(4-Benzoylamino)-phenylsulfonyl-N-(4-(morpholinoethyl))-S-trityl-L-cysteine Amide Hydrochloride

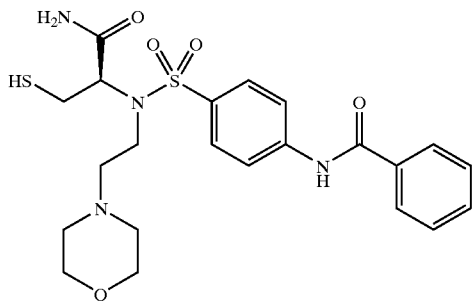

Part A: To a cooled (10 C) solution of 19.4 grams (250 mmol) of chlorosulfonic acid under nitrogen atmosphere was added 10 grams (50.7 mmol) of benzanalide in portions over five minutes. The black solution was heated to 60 C for one hour, then cooled to room temperature and carefully poured over ice slowly. The solid organic material was filtered and dissolved in methylene chloride, washed with water and dried over sodium sulfate. The solution was concentrated on a rotory evaporator to 8.6 grams of a tan solid.

Part B: To a solution of 4.0 grams (11.03 mmol) of S-trityl-L-cysteine amide in 50 mL of dry methylene chloride was added 2.0 mL (14.33 mmol) of triethylamine followed by 2.93 grams (9.93 mmol) of 4-benzoylamino-benzenesulfonyl chloride. The solution was stirred at room temperature for one hour, then concentrated on a rotory evaporator. The resulting slurry was partitioned between ethyl acetate and water. The organics were washed with 5% potassium hydrogen sulfate, saturated sodium bicarbonate, and brine, dried over sodium sulfate, filtered and concentrated to give 7.0 grams of crude product. The crude material was purified by silica gel chromatography using 1:1 ethyl acetate:hexane as the eluent to yield 3.5 grams of pure N-(4-benzoylamino)-phenylsulfonyl-S-trityl-L-cysteine as a white solid.

Part C: To 3.5 grams (5.74 mmol) of N-(4-benzoylamino) phenylsulfonyl-S-trityl-L-cysteine amide in 12 mL of dry dimethylformamide was added 1.60 grams (8.61 mmol) of 4-(2-chloroethylmorpholine)hydrochloride followed by 2.38 grams (17.22 mmol) of powdered potassium carbonate, and the suspension was heated to 60 C in an oil bath under nitrogen atmosphere for 5 hours. The solution is cooled to room temperature and diluted with 100 mL of ethyl acetate and washed with water. The organic layer was washed saturated brine and dried over sodium sulfate, filtered and concentrated to yield 4.4 grams of crude material. Purification by flash chromatography using ethyl acetate as the eluent gave 3.5 grams of purified N-(4-benzoylamino)-phenylsulfonyl-N-(4-(morpholinoethyl))-S-trityl-L-cysteine amide.

Part D: 3.5 grams (4.8 mmol) of N-(4-benzoylamino)-phenylsulfonyl-N-(4-(morpholinoethyl))-S-trityl-L-cysteine amide was dissolved in 10 mL of methylene chloride and 10 mL of triisopropylsilane was added followed by 40 mL of trifluoroacetic acid and the solution is stirred for 1.5 hours. The contents were concentrated on a rotory evaporator and the resultant material is decanted three times with 50 mL of diethyl ether. The resulting solid is slurried with a mixture of ethyl acetate and sodium bicarbonate until the solids dissolve. The organic layer is washed with saturated sodium bicarbonate, dried over sodium sulfate, filtered and concentrated to yield 1.87 grams of N-(4-benzoylamino) phenylsulfonyl-N-(4-(morpholino-ethyl))-L-cysteine amide as a white solid. Mass spec. m/z=493 (M+H).

EXAMPLE 219

1.87 grams of N-(4-benzoylamino)-phenylsulfonyl-N-(4-(morpholinoethyl))-S-trityl-L-cysteine amide was dissolved in 20 mL of dry acetonitrile and to this was added 630 uL of concentrated HCl and the resulting solution was concentrated to give a white foam solid which was dried extensively under vacuum to obtain N-(4-benzoylamino)-phenylsulfonyl-N-(4-(morpholinoethyl))-L-cysteine amide hydrochloride.

EXAMPLE 220

N-(4-(4'-chlorobenzoyl)amino)phenylsulfonyl-N-(4-(morpholinoethyl))-L-cysteine amide. Preparation similar to Example 218, by substitution of chlorobenzanalide in part a.

EXAMPLE 221

N-(4-(4'-chlorobenzoyl)amino)phenylsulfonyl-N-(4-(morpholinoethyl))-L-cysteine amide. Preparation similar to Example 219.

EXAMPLE 222

N-(4-(4'-bromobenzoyl)amino)phenylsulfonyl-N-(4-(morpholinoethyl))-L-cysteine amide. Prepared in a similar manner as Example 218, by substitution of bromobenzanalide in part a.

EXAMPLE 223

N-(4-(4'-bromobenzoyl)amino)phenylsulfonyl-N-(4-(morpholinoethyl))-L-cysteine amide hydrochloride. Prepared in a similar manner as Example 219.

EXAMPLE 224

In vitro Metalloprotease Inhibition

Certain of the compounds prepared in the manner described in Examples 1 to 223 were tested for activity by an in vitro assay. Following the procedures of Knight et al., FEBS Lett. 296(3):263 (1992). Briefly, 4-aminophenylmercuric acetate (APMA) or trypsin activated MMPs were incubated with various concentrations of the inhibitor compound at room temperature for 5 minutes (0.02% 2-mercapto-ethanol added to buffer for thiol compounds with 5 minutes or overnight incubation). More specifically, recombinant human MMP-13 and MMP-1 enzymes were prepared in laboratories of the inventors' employer. MMP-13 was expressed in baculovirus as a proenzyme, and purified first over a heparin agarose column and then over a chelating zinc chloride column. The proenzyme was activated by APMA for use in the assay. MMP-1 expressed in transfected HT-1080 was provided by Dr. Howard Welgus of Washington University, St. Louis, Mo. The enzyme was also activated using APMA and was then purified over a hydroxamic acid column.

The enzyme substrate is a methoxycoumarin-containing polypeptide having the following sequence:

MCA-ProLeuGlyLeuDpaAlaArgNH$_2$, wherein MCA is methoxycoumarin and Dpa is 3-(2,4-dinitrophenyl)-L-2,3-diaminopropionyl alanine. This substrate is commercially available from Baychem as product M-1895.

The buffer used for assays contained 100 mM Tris-HCl, 100 mM NaCl, 10 mM CaCl$_2$ and 0.05 percent polyethyleneglycol(23) lauryl ether at a pH value of 7.5. Assays were carried out at room temperature, and dimethyl sulfoxide (DMSO) at a final concentration of 1 percent was used to dissolve inhibitor compound.

The assayed inhibitor compound in DMSO/buffer solution was compared to an equal amount of DMSO/buffer with no inhibitor as control using microfluor™ white plates (Dynatech). The inhibitor or control solution was maintained in the plate for 10 minutes and the substrate was added to provide a final concentration of 4 uM.

In the absence of inhibitor activity, a fluorogenic peptide is cleaved at the gly-leu peptide bond, separating the highly fluorogenic peptide from a 2.4-dinitrophenyl quencher, resulting in an increase of fluorescence intensity (excitation at 328 nm/emmission at 415 nm). Inhibition was measured as a reduction in fluorescent intensity as a function of inhibitor concentration, using a Perkin Elmer L550 plate reader. The IC$_{50}$ values were calculated from those values. The results are set forth in the Inhibition Table below, reported in terms of IC$_{50}$ to three significant figures.

Inhibition Table

| Example Number | MMP-1 IC$_{50}$ (nanomolar) | MMP-13 IC$_{50}$ (nanomolar) |
|---|---|---|
| 7B | >10000 | >10000 |
| 7C | 4000 | 300 |
| 8 | 4200 | 65 |
| 10 |  | 550 |
| 11D | 300 | 32.5 |
| 12C | 1300 | 38.5 |
| 13C | >10000 | 2000 |
| 14C | 1060 | 46 |
| 15 | >10000 | 75 |

Inhibition Table

| Example Number | MMP-1 IC$_{50}$ (nanomolar) | MMP-13 IC$_{50}$ (nanomolar) |
| --- | --- | --- |
| 16B | 7000 | 245 |
| 17C | >10000 | 260 |
| 18 | >10000 | 390 |
| 20C | 3000 | 110 |
| 21C | 7000 | 200 |
| 22C | 3400 | 13 |
| 23C | 4000 | 150 |
| 26 | >10000 | 250 |
| 28 | >10000 | 800 |
| 29F | 8000 | 1800 |
| 31D | 2500 | 600 |
| 33C | >10000 | 345 |
| 33D | >10000 | >10000 |
| 37C | 1500 | 5.0 |
| 38C | 2500 | 31.0 |
| 39C | >10000 | 21.5 |
| 40E | 309 | 0.61 |
| 41C | >10000 | 1.8 |
| 42D | >10000 | 1800 |
| 44 | >10000 | 400 |
| 45C | 3200 | 3.0 |
| 46 | 3500 | 4.0 |
| 47C | 4830 | 4.47 |
| 48C | >10000 | 45.0 |
| 49 | 300 | 17.5 |
| 51 | >10000 | 340 |
| 52 | >10000 | 45 |
| 53 | >10000 | 11.0 |
| 54 | 9000 | 7.0 |
| 55 | 313 | 0.71 |
| 56 | 2000 | 67.5 |
| 57 | >10000 | 5000 |
| 58 | 6000 | 200 |
| 59 | 1000 | 13 |
| 63 | 300 | 2500 |
| 64 |  | 900 |
| 65 | 1000 | 445 |
| 66 |  | 38 |
| 67 |  | 570 |
| 68 | >10000 | 1720 |
| 69 |  | 175 |
| 70 | >10000 | 440 |
| 71 | >10000 | 40 |
| 72 |  | 2300 |
| 73 |  | 2100 |
| 74 |  | >10000 |
| 75 | 5000 | 1000 |
| 76 | 3500 | 8800 |
| 77 |  | >10000 |
| 79 |  | >10000 |
| 80 |  | >10000 |
| 81 |  | 6500 |
| 82 | >10000 | 1200 |
| 83 |  | 1150 |
| 84 | >10000 | >10000 |
| 85 |  | 9000 |
| 86 |  | 1700 |
| 87 |  | 8500 |
| 88 |  | 365 |
| 89 | >10000 | 90 |
| 90 |  | 600 |
| 91C | >10000 | 0.6 |
| 91D | >10000 | 0.7 |
| 91E | need | need |
| 92C | need | need |
| 92D | 6000 | 0.7 |
| 94 | 4400 | 34.0 |
| 95 | 800 | 20 |
| 96 | >10000 | 17 |
| 97 |  | 4000 |
| 98 |  | >10000 |
| 99 | 900 | 31.3 |
| 100 | >10000 | >10000 |
| 101 | >10000 | 30 |
| 103 | >10000 | 17 |
| 104 |  | >10000 |
| 105 |  | 3500 |
| 107 | 4000 | 2.7 |
| 108 |  | 500 |
| 109 |  | >10000 |
| 110 | >10000 | 1600 |
| 111 | 2000 | 40.0 |
| 112 | 4000 | 150 |
| 113 | 125 | 0.25 |
| 114 | >10000 | 45 |
| 115 | >10000 | 220 |
| 117 | 8000 | 15.0 |
| 118 | 7000 | 14.0 |
| 122 | >10000 | 4250 |
| 123 | >10000 | 115 |
| 124 | 2100 | <0.5 |
| 125 | >10000 | 770 |
| 126 | >100 | 3.5 |
| 128 | 5000 | 1.1 |
| 130 | >10000 | 3300 |
| 131 | 70 | <0.1 |
| 132 | >10000 | 47.0 |
| 133 | >10000 | 4200 |
| 141 |  | >10000 |
| 142 |  | >10000 |
| 146 |  | >10000 |
| 147 | <10000 | >10000 |
| 148 |  | >10000 |
| 149 |  | >10000 |
| 150 |  | 9000 |
| 151 |  | >10000 |
| 152 |  | 3000 |
| 153 |  | >10000 |
| 154 |  | 9000 |
| 155 | >10000 | >10000 |
| 156 | 1070 | 7.3 |
| 163 | 500 | 0.3 |
| 164 | >10000 | 40 |
| 165 | 1100 | 0.15 |
| 166 | >10000 | 880 |
| 168 | 540 | 0.45 |
| 170 | 30 | 0.2 |
| 171 | >10000 | 30 |
| 172 | >10000 | 250 |
| 174 | 1700 | 2.5 |
| 175 | 400 | 0.7 |
| 176 | 2900 | 2.5 |
| 177 | 10000 | 20 |
| 178 | >10000 | 300 |
| 179 | 2000 | 23.5 |
| 180 | >10000 | 700 |
| 181 | >10000 | 3000 |
| 184 | 210 | 1.4 |
| 185 | 300 | 2.2 |
| 186 | >10000 | 1100 |
| 187 | >10000 | 1000 |
| 188 |  | >10000 |
| 189 |  | >10000 |
| 190 |  | 6500 |
| 191 | >10000 | >10000 |
| 192 | >10000 | >10000 |
| 193 | >10000 | >10000 |
| 195 |  | 464 |
| 196 |  | >10000 |
| 197 | 4600 | 100 |
| 198 |  | 2300 |
| 199 | >10000 | 350 |
| 200 | 2060 | <0.1 |
| 201 | 7000 | 3.3 |
| 203 | >10000 | 170 |
| 204 |  | >10000 |
| 206 |  | >10000 |
| 207 |  | >10000 |

-continued

Inhibition Table

| Example Number | MMP-1 IC$_{50}$ (nanomolar) | MMP-13 IC$_{50}$ (nanomolar) |
|---|---|---|
| 208 | >10000 | 190 |
| 209 | >10000 | 50 |
| 210 | >10000 | 1320 |
| 213 | >10000 | 1.5 |
| 214 |  | >10000 |
| 216 | >10000 | 200 |
| 217 | >10000 | 1.5 |
| 218 | >10000 | 1.1 |
| 219 |  |  |
| 220 | 7000 | 1.4 |
| 221 |  |  |
| 222 | 5300 | 1.1 |
| 223 |  |  |

IN VIVO ANGIOGENESIS ASSAY

The study of angiogenesis depends on a reliable and reproducible model for the stimulation and inhibition of a neovascular response. The corneal micropocket assay provides such a model of angiogenesis in the cornea of a mouse. See, *A Model of Angiogenesis in the Mouse Cornea*; Kenyon, B M, et al., Investigative Ophthalmology & Visual Science, July 1996, Vol. 37, No. 8.

In this assay, uniformly sized Hydron™ pellets containing bFGF and sucralfate were prepared and surgically implanted into the stroma mouse cornea adjacent to the temporal limbus. The pellets were formed by making a suspension of 20 μl sterile saline containing 10 μg recombinant bFGF, 10 mg of sucralfate and 10 μl of 12 percent Hydron™ in ethanol. The slurry was then deposited on a 10×10 mm piece of sterile nylon mesh. After drying, the nylon fibers of the mesh was separated to release the pellets.

The corneal pocket was made by anesthetizing a 7 week old C57Bl/6 female mouse, then proptosing the eye with a jeweler's forceps. Using a dissecting microscope, a central, intrastromal linear keratotomy of approximately 0.6 mm in length was performed with a #15 surgical blade, parallel to the insertion of the lateral rectus muscle. Using a modified cataract knife, a lamellar micropocket was dissected toward the temporal limbus. The pocket was extended to within 1.0 mm of the temporal limbus. A single pellet was placed on the corneal surface at the base of the pocket with a jeweler's forceps. The pellet was then advanced to the temporal end of the pocket. Antibiotic ointment was then applied to the eye.

Mice were dosed on a daily basis for the duration of the assay. Dosing of the animals was based on bioavailability and overall potency of the compound. In the case of the compound of Example 218, dosing was 50 mg/kg bid, po. Neovascularization of the corneal stroma began at about day three and was permitted to continue under the influence of the assayed compound until day five. At day five, the degree of angiogenic inhibition was scored by viewing the neovascular progression with a slit lamp microscope.

The mice were anesthetized and the studied eye was once again proptosed. The maximum vessel length of neovascularization, extending from the limbal vascular plexus toward the pellet was measured. In addition, the contiguous circumferential zone of neovascularization was measured as clock hours, where 30 degrees of arc equals 1 clock hour. The area of angiogenesis was calculated as $$\text{area} = \frac{(0.4 \times \text{clock hours} \times 3.14 \times \text{vessel length (in mm)})}{2}$$

where the vessel length is measured in millimeters.

The studied mice were thereafter compared to control mice and the difference in the area of neovascularization was recorded. The compound of Example 218 exhibited 37 percent inhibition, whereas the vehicle control exhibited zero percent inhibition.

From the foregoing, it will be observed that numerous modifications and variations can be effectuated without departing from the true spirit and scope of the novel concepts of the present invention. It is to be understood that no limitation with respect to the specific example presented is intended or should be inferred. The disclosure is intended to cover by the appended claims all such modifications as fall within the scope of the claims.

What is claimed is:

1. A compound or a salt thereof, wherein:
   the compound or salt is characterizeable in that the compound or salt selectively inhibits in vitro activity of human MMP-13 over in vitro activity of human MMP-1;
   the compound corresponds in structure to a formula selected from the group consisting of:

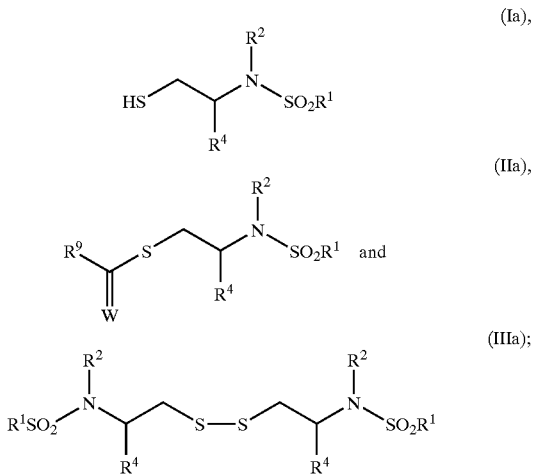

$R^1$ is a substituted 5- or 6-member ring structure and has a length greater than that of a saturated four carbon chain, and shorter than that of a saturated eighteen carbon chain, and when rotated about an axis drawn through the SO$_2$-bonded 1-position and the 4-position of a 6-member ring or the SO$_2$-bonded 1-position and substituent-bonded 3- or 5-position of a 5-member ring, defines a three-dimensional volume whose widest dimension has the width of from about one phenyl ring to about three phenyl rings in a direction transverse to the axis of rotation;

$R^2$ is selected from the group consisting of hydrogen, $C_1$–$C_6$-alkyl, phenyl-$C_1$–$C_4$-alkyl, single-ring heteroaryl-$C_1$–$C_4$-alkyl, and $C_2$–$C_4$-alkyl substituted by amino, wherein the amino nitrogen optionally is substituted with:
   up to two substituents independently selected from the group consisting of $C_1$–$C_6$-alkyl, arylalkyl, $C_5$–$C_8$-cycloalkyl, and $C_1$–$C_6$-alkylcarbonyl, or two substituents such that the two substituents, together with the amino nitrogen, form a 5- to 8-member heterocyclo or heteroaryl ring, wherein:
one ring atom of the heterocyclo or heteroaryl is nitrogen,
one ring atom of the heterocyclo or heteroaryl is selected from the group consisting of carbon, nitrogen, oxygen, and sulfur, and
the remaining ring atoms of the heterocyclo or heteroaryl are carbon;
$R^4$ is $C_1$–$C_6$-alkyl;
W is selected from the group consisting of oxygen and sulfur;
$R^9$ is selected from the group consisting of $C_1$–$C_6$-alkyl, $C_1$–$C_6$-alkoxy, phenyl, and single-ring heteroaryl;
$R^9$ may be hydrogen only when $R^1$ is 4-(phenylazo)phenyl; and
the compound comprises at least one heterocyclic ring.

2. The compound or salt according to claim 1, wherein $R^1$ has a length greater than that of a pentyl group and less than that of a lauryl group.

3. The compound or salt according to claim 1, wherein $R^1$ is substituted phenyl or substituted heteroaryl.

4. The compound or salt according to claim 3, wherein:
except to the extent otherwise stated in claims 1 and 3, each said aryl is independently selected from the group consisting of phenyl, indenyl, and naphthyl;
except to the extent otherwise stated in claims 1 and 3, each said heteroaryl is independently selected from the group consisting of pyrrolyl, imidazolyl, pyrazolyl, pyridyl, pyrazinyl, pyrimidinyl, furyl, thienyl, triazolyl, oxazolyl, oxadiazolyl, thiazolyl, and thiadiazolyl; and
said heterocyclo is selected from the group consisting of pyrrolidinyl, piperidinyl, piperazinyl, morpholinyl, and thiamorpholinyl.

5. The compound or salt according to claim 3, wherein $R^1$ is phenyl or heteroaryl, wherein:
the phenyl or heteroaryl is substituted at its own 4-position when a 6-member ring or at its own 3-position when a 5-member ring with a substituent selected from the group consisting of phenyl, single-ring heteroaryl, alkyl comprising an unbranched chain of from 3 to about 7 carbon atoms, alkoxy comprising an unbranched chain of from 3 to about 7 carbon atoms, phenoxy, phenylthio, phenylazo, and benzamido.

6. The compound or salt according to claim 1, wherein the compound corresponds in structure to Formula (Ia):

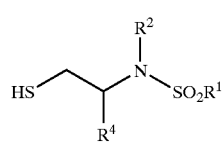
(Ia).

7. A compound or a salt thereof wherein:
the compound or salt is characterizeable in that the compound or salt selectively inhibits in vitro activity of human MMP-13 over in vitro activity of human MMP-1;

the compound corresponds in structure to a formula selected from the group consisting of:

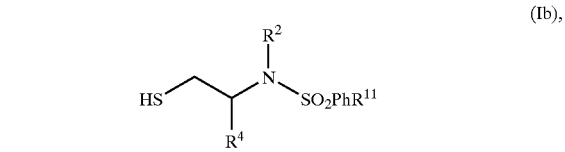
(Ib),

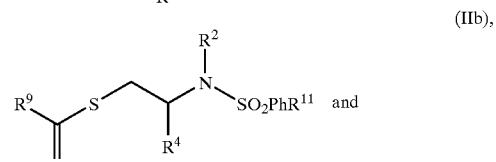
(IIb),

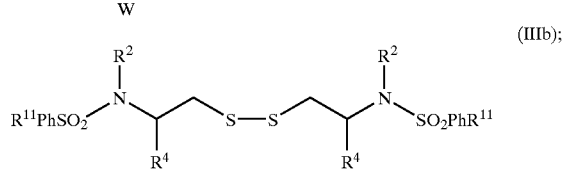
(IIIb);

$PhR^{11}$ is phenyl substituted with $R^{11}$ at the 4-position;
$R^{11}$ is selected from the group consisting of $C_3$–$C_8$-alkoxy, $C_3$–$C_8$-alkyl, phenoxy, phenylthio, benzamido, phenylazo, and phenyl;
$R^2$ is selected from the group consisting of:
hydrogen,
$C_1$–$C_6$-alkyl,
5- to 6-member heterocyclo-$C_2$–$C_3$-alkyl, wherein:
one ring atom of the heterocyclo is nitrogen,
one ring atom of the heterocyclo is selected from the group consisting of nitrogen, carbon, and oxygen, and
the remaining ring atoms of the heterocyclo are carbon, and single-ring heteroaryl-$C_1$–$C_4$-alkyl, wherein:
one ring atom of the heteroaryl is nitrogen,
one ring atom of the heteroaryl is selected from the group consisting of nitrogen and carbon, and
the remaining ring atoms of the heteroaryl are carbon;
$R^4$ is $C_1$–$C_6$-alkyl;
$R^9$ is selected from the group consisting of $C_1$–$C_6$-alkyl, $C_1$–$C_6$-alkoxy, phenyl, and single-ring heteroaryl;
$R^2$ may be hydrogen only when $R^{11}$ is phenylazo; and
the compound comprises at least one heterocyclic ring.

8. The compound or salt according to claim 7, wherein, except to the extent otherwise stated in claim 7, each said heteroaryl of $R^9$ is independently selected from the group consisting of pyrrolyl, imidazolyl, pyrazolyl pyridyl, pyrazinyl, pyrimidinyl, furyl, thienyl, triazolyl, oxazolyl, oxadiazolyl, thiazolyl, and thiadiazolyl.

9. The compound or salt according to claim 7, wherein the compound corresponds in structure to Formula (Ib):

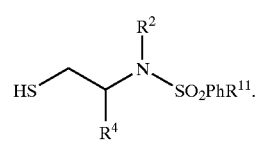
(Ib)

10. The compound or salt according to claim 9, wherein the compound corresponds in structure to the following formula:

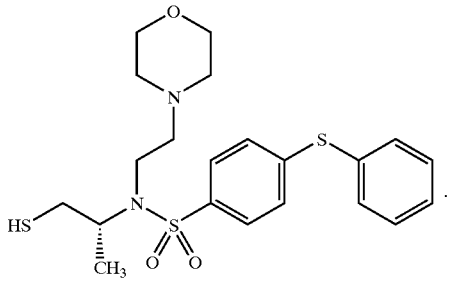

11. A compound or a salt thereof, wherein:
the compound or salt is characterizeable in that the compound or salt selectively inhibits in vitro activity of human MMP-13 over in vitro activity of human MMP-1;
the compound corresponds in structure to a formula selected from the group consisting of:

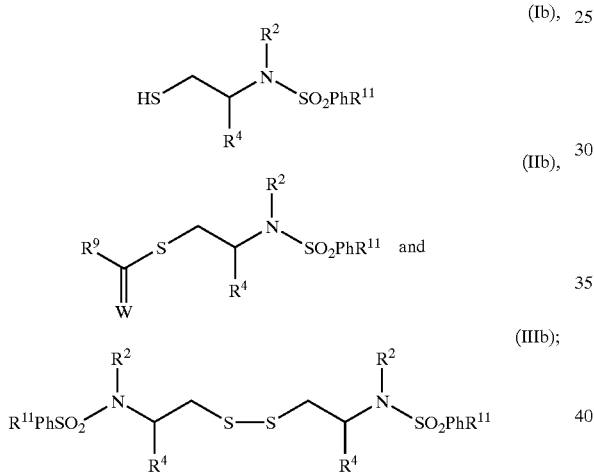

$PhR^{11}$ is phenyl substituted with $R^{11}$ at the 4-position;
$R^{11}$ is selected from the group consisting of phenoxy, phenylthio, benzamido, phenylazo, and phenyl, wherein:
the phenoxy, phenylthio, benzamido, phenylazo, or phenyl is substituted at the 3-position, 4-position, or both with a single atom or a substituent composing a longest chain of up to five atoms, not counting any hydrogen in the substituent;
$R^2$ is selected from the group consisting of:
hydrogen,
$C_1$–$C_6$-alkyl,
5- to 6-member heterocyclo-$C_2$–$C_3$-alkyl, wherein:
one of the ring atoms of the heterocyclo is nitrogen,
one of the ring atoms of the heterocyclo is selected from the group consisting of nitrogen, carbon, and oxygen, and
the remaining ring atoms of the heterocyclo are carbon, and single-ring heteroaryl-$C_1$–$C_4$-alkyl, wherein:
one ring atom of the heteroaryl is nitrogen,
one ring atom of the heteroaryl is selected from the group consisting of nitrogen and carbon, and
the remaining ring atoms of the heteroaryl are carbon;
$R^4$ $C_1$–$C_6$-alkyl;
$R^9$ is selected from the group consisting of $C_1$–$C_6$-alkyl, $C_1$–$C_6$-alkoxy, phenyl and single-ring heteroaryl;
$R^2$ may be hydrogen only when $R^{11}$ is phenylazo; and the compound comprises at least one heterocyclic ring.

12. The compound or salt according to claim 11, wherein the compound corresponds in structure to Formula (Ib):

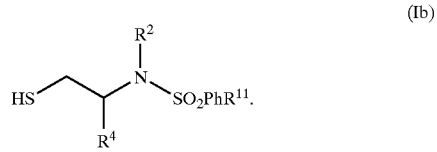

13. The compound or salt according to claim 11, wherein $R^{11}$ is selected from the group consisting of phenoxy, phenylthio, benzamido, phenylazo, and phenyl, wherein the phenoxy, phenylthio, benzamido, phenylazo, or phenyl is substituted with:
a substituent at the 4-position selected from the group consisting of halogen, $C_1$–$C_4$-alkoxy, $C_1$–$C_4$-alkyl, carboxy-$C_1$–$C_2$-alkyl, and amino, wherein the amino optionally is substituted with up to two substituents independently selected from the group consisting of $C_1$–$C_4$-alkyl; or
a 3,4-methylenedioxy group.

14. A compound or a salt thereof, wherein:
the compound or salt is characterizeable in that the compound or salt selectively inhibits in vitro activity of human MMP-13 over in vitro activity of human MMP-1;
the compound corresponds in structure to a formula selected from the group consisting of:

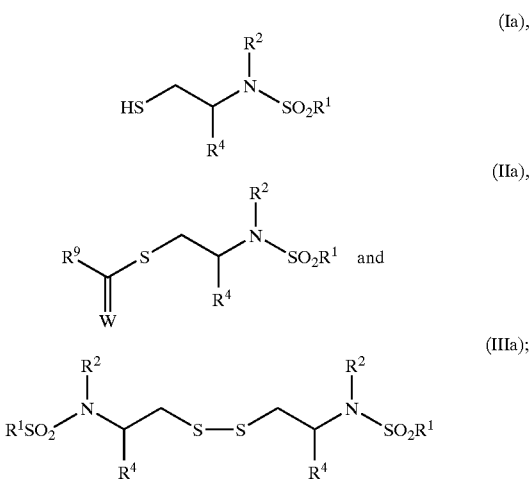

W is selected from the group consisting of oxygen and sulfur;
$R^9$ is selected from the group consisting of alkyl, aryl, alkoxy, cycloalkyl, aryloxy, arylalkoxy, arylalkyl, heteroaryl, and aminoalkyl, wherein the aminoalkyl nitrogen optionally is substituted with:
up to two substituents independently selected from the group consisting of alkyl, aryl, arylalkyl, cycloalkyl, arylalkoxycarbonyl, alkoxycarbonyl, and alkylcarbonyl, or two substituents such that the two substituents, together with the aminoalkyl nitrogen, form a 5- to 8-member heterocyclo or heteroaryl ring;

$R^1$ is selected from the group consisting of alkyl, cycloalkyl, heterocyclo, arylalkyl, heteroarylalkyl, arylalkoxyalkyl, aryloxyalkyl, hydroxyalkyl, alkylcarbonylalkyl, arylalkylcarbonylalkyl, arylcarbonylalkyl, haloalkyl, arylalkylaryl, aryloxyalkylaryl, arylalkoxyaryl, arylazoaryl, arylhydrazinoaryl, alkylthioalkyl, alkythioaryl, arylthioalkyl, alkylthioarylalkyl, arylalkylthioalkyl, arylalylthioaryl, a sulfoxide of any of said thio substituents, a sulfone of any of said thio substituents, aryl; heteroaryl, and a fused ring structure comprising at least two 5- to 6-member rings selected from the group consisting of aryl, heteroaryl, cycloalkyl, and heterocyclo, wherein:

any aryl or heteroaryl in $R^1$ optionally is substituted with one or more substituents independently selected from the group consisting of halo, $C_1$–$C_{10}$-alkyl, $C_1$–$C_{10}$-alkoxy, nitro, cyano, perfluoroalkyl, trifluoromethylalkyl, hydroxy, thiol, hydroxycarbonyl, aryloxy, arylthio, arylamino, arylalkyl, aryl, heteroaryloxy, heteroarylthio, heteroarylamino, heteroarylalkyl, cycloalkyl, heterocyclooxy, heterocyclothio, heterocycloamino, cycloalkyloxy, cycloalkylthio, cycloalkylamino, heteroarylalkoxy, heteroarylalkylthio, heteroarylalkylamino, arylalkoxy, arylalkylthio, arylalkylamino, heterocyclic, heteroaryl, arylazo, hydroxycarbonylalkoxy, alkoxycarbonylalkoxy, alkylcarbonyl, arylcarbonyl, arylalkylcarbonyl, alkylcarbonyloxy, arylalkylcarbonyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylakylthio, amino, alkylcarbonylamino, arylcarbonylamino, arylalkylcarbonylamino, heteroarylcarbonylamino, heteroarylalkylcarbonylamino, N-monosubstituted aminoalkyl, and N,N-disubstituted aminoalkyl, wherein:
the substituent(s) on the monosubstituted or disubstituted aminoalkyl nitrogen is/are independently selected from the group consisting of alkyl, aryl, arylalkyl, cycloalkyl, arylalkoxycarbonyl, alkoxycarbonyl, and alkylcarbonyl, or
the disubstituted aminoalkyl nitrogen and its two substituents form a 5 to 8 member heterocyclo or heteroaryl ring;

as to $R^2$:
$R^2$ is selected from the group consisting of hydrogen, alkyl, aryl, arylalkyl, heteroaryl, heteroarylalkyl, alkynylalkyl, alkenylalkyl, thioalkyl, cycloalkyl, cycloalkylalkyl, heterocycloalkyl, alkoxyalkyl, arylalkoxyalkyl, alkoxyalkoxyalkyl, aryloxyalkyl, hydroxyalkyl, hydroxycarbonyl, hydroxycarbonylalkyl, hydroxycarbonylarylalkyl, and aminoalkyl, wherein the aminoalkyl nitrogen optionally is substituted with:
up to two substituents independently selected from the group consisting of alkyl, arylalkyl, cycloalkyl, and alkylcarbonyl, or
two substituents such that the two substituents, together with the aminoalkyl nitrogen, form a 5- to 8-member heterocyclo or heteroaryl ring, or
$R^2$ and $R^4$, together with the atoms to which they are bonded, form a 4- to 8-member ring;

as to $R^4$:
$R^4$ is selected from the group consisting of alkyl, cycloalkyl, cycloalkylalkyl, alkoxyalkyl, hydroxyalkyl, aryloxyalkyl, arylalkoxyalkyl, arylalkyl, aryl, heteroaryl, heteroarylalkyl, hydroxycarbonylalkyl alkoxycarbonylalkyl, arylalkoxycarbonylalkyl, alkoxycarbonyl, perfluoroalkyl, trifluoromethylalkyl, thioalkyl, alkylthioalkyl, arylthioalkyl, arylalkylthioalkyl, heteroarylalkyl thioalkyl, a sulfoxide of any of said thio substituents, a sulfone of any of said thio substituents, and aminocarbonylalkyl, wherein the nitrogen of the aminocarbonylalkyl optionally is substituted with:
up to two substituents independently selected from the group consisting of alkyl arylalkyl, cycloalkyl, and alkylcarbonyl, or
two substituents such that the two substituents, together with the amino nitrogen, form a 5- to 8-member heterocyclo or heteroaryl ring, or
$R^2$ and $R^4$, together with the atoms to which they are bonded, form a 4- to 8-member ring;
$R^2$ may be hydrogen only when $R^1$ is 4-(phenylazo)phenyl; and
the compound comprises at least one heterocyclic ring.

15. The compound or salt according to claim 14, wherein $R^4$ is $C_1$–$C_6$-alkyl.

16. The compound or salt according to claim 14, wherein the compound corresponds in structure to Formula (Ia):

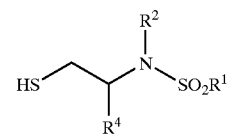

(Ia).

17. The compound or salt according to claim 14, wherein;
except to the extent otherwise stated in claim 14, each said aryl is independently selected from the group consisting of phenyl, indenyl, and naphthyl;
except to the extent otherwise stated in claim 14, each said heteroaryl is independently selected from the group consisting of pyrrolyl, imidazolyl, pyrazolyl, pyridyl, pyrazinyl, pyrimidinyl, furyl, thienyl, triazolyl, oxazolyl, oxadiazolyl, thiazolyl, thiadiazolyl, indolyl, quinolinyl isoquinolinyl, quinoxalinyl, benzothiophenyl, β-carbolinyl, 2-benzofurancarbonyl, 1-benzimidazolyl, 2-benzimidazolyl, 3-benzimidazolyl, 4-benzimidazolyl, and 5-benzimidazolyl; and
except to the extent otherwise stated in claim 14, each said heterocyclo is independently selected from the group consisting of pyrrolidinyl, piperidinyl, piperazinyl, morpholinyl, thiamorpholinyl, tetrahydrofuryl, tetrahydroquinolinyl, and 1,2,3,4-tetrahydroisoquinolinyl.

18. A pharmaceutical composition, wherein the composition comprises a compound according to claim 1 (or a pharmaceutically acceptable salt thereof) dissolved or dispersed in a pharmaceutically acceptable carrier.

19. A pharmaceutical composition, wherein the composition comprises a compound according to claim 7 (or a pharmaceutically acceptable salt thereof) dissolved or dispersed in a pharmaceutically acceptable carrier.

20. A pharmaceutical composition, wherein the composition comprises a compound according to claim 11 (or a pharmaceutically acceptable salt thereof) dissolved or dispersed in a pharmaceutically acceptable carrier.

21. A pharmaceutical composition, wherein the composition comprises a compound according to claim 14 (or a pharmaceutically acceptable salt thereof) dissolved or dispersed in a pharmaceutically acceptable carrier.

22. A process for treating a mammal having a condition associated with pathological matrix metalloprotease activity, wherein the process comprises administering to the mammal an effective amount of the compound or salt of claim 1.

23. A process for treating a mammal having a condition associated with pathological matrix metalloprotease activity, wherein the process comprises administering to the mammal an effective amount of the compound or salt of claim 7.

24. A process for treating a mammal having a condition associated with pathological matrix metalloprotease activity, wherein the process comprises administering to the mammal an effective amount of the compound or salt of claim 10.

25. A process for treating a mammal having a condition associated with pathological matrix metalloprotease activity, wherein the process comprises administering to the mammal an effective amount of the compound or salt of claim 11.

26. A process for treating a mammal having a condition associated with pathological matrix metalloprotease activity, wherein the process comprises administering to the mammal an effective amount of the compound or salt of claim 14.

* * * * *

UNITED STATES PATENT AND TRADEMARK OFFICE
CERTIFICATE OF CORRECTION

PATENT NO.    : 6,747,027 B1
DATED         : June 8, 2004
INVENTOR(S)   : Gary DeCrescenzo It is certified that error appears in the above-identified patent and that said Letters Patent is hereby corrected as shown below:

Column 292,
Lines 23 and 24, replace "in vitro" with -- *in vitro* --;

Column 293,
Line 19, replace "$R^9$" with -- $R^2$ --;
Lines 65 and 66, replace "in vitro" with -- *in vitro* --;

Column 295,
Lines 19 and 20, replace "in vitro" with -- *in vitro* --;
Lines 50-51, replace "composing" with -- comprising --;

Column 296,
Line 3, replace "$R^4$ $C_1$-$C_6$-alkyl" with -- $R^4$ is $C_1$-$C_6$-alkyl --.
Lines 32 and 33, replace "in vitro" with -- *in vitro* --;

Column 297,
Line 13, replace "aryl; heteroaryl" with -- aryl, heteroaryl --;

Column 298,
Lines 10-11, replace "hydroxycarbonylalkyl alkoxycarbonylalkyl" with
-- hydroxycarbonylalkyl, alkoxycarbonylalkyl --;
Line 21, replace "alkyl arylalkyl" with -- alkyl, arylalkyl --; and
Line 53, replace "quinolonyl isoquinolinyl" with -- quinolinyl, isoquinolinyl --.

Signed and Sealed this

Fourteenth Day of September, 2004

JON W. DUDAS
*Director of the United States Patent and Trademark Office*